(12) United States Patent
Toporik et al.

(10) Patent No.: US 9,428,574 B2
(45) Date of Patent: Aug. 30, 2016

(54) POLYPEPTIDES AND USES THEREOF FOR TREATMENT OF AUTOIMMUNE DISORDERS AND INFECTION

(75) Inventors: Amir Toporik, Holon (IL); Avi Yeshah Rosenberg, Kfar Saba (IL); Galit Rotman, Herzliyya (IL); Iris Hecht, Tel Aviv-Yafo (IL); Zurit Levine, Herzliyya (IL)

(73) Assignee: COMPUGEN LTD., Holon (IL)

( * ) Notice: Subject to any disclaimer, the term of this patent is extended or adjusted under 35 U.S.C. 154(b) by 94 days.

(21) Appl. No.: 14/129,974

(22) PCT Filed: Jul. 1, 2012

(86) PCT No.: PCT/IB2012/053342
§ 371 (c)(1),
(2), (4) Date: Dec. 29, 2013

(87) PCT Pub. No.: WO2013/001517
PCT Pub. Date: Jan. 3, 2013

(65) Prior Publication Data
US 2014/0170141 A1    Jun. 19, 2014

Related U.S. Application Data

(60) Provisional application No. 61/502,880, filed on Jun. 30, 2011, provisional application No. 61/581,201, filed on Dec. 29, 2011.

(51) Int. Cl.
| | | |
|---|---|---|
| C07K 16/18 | (2006.01) | |
| C07K 14/705 | (2006.01) | |
| A61K 39/395 | (2006.01) | |
| A61K 45/06 | (2006.01) | |
| A61K 38/00 | (2006.01) | |

(52) U.S. Cl.
CPC ............ *C07K 16/18* (2013.01); *A61K 39/395* (2013.01); *A61K 45/06* (2013.01); *C07K 14/70503* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,366,241 A | 12/1982 | Tom |
| 4,376,110 A | 3/1983 | David |
| 4,399,216 A | 8/1983 | Axel |
| 4,439,196 A | 3/1984 | Higuchi |
| 4,447,224 A | 5/1984 | DeCant, Jr. |
| 4,447,233 A | 5/1984 | Mayfield |
| 4,469,863 A | 9/1984 | Paul |
| 4,475,196 A | 10/1984 | La Zor |
| 4,476,301 A | 10/1984 | Imbach |
| 4,486,194 A | 12/1984 | Ferrara |
| 4,487,603 A | 12/1984 | Harris |
| 4,517,288 A | 5/1985 | Giegel |
| 4,522,811 A | 6/1985 | Eppstein |
| 4,596,556 A | 6/1986 | Morrow |
| 4,634,665 A | 1/1987 | Axel |
| 4,790,824 A | 12/1988 | Morrow |
| 4,816,567 A | 3/1989 | Cabilly |
| 4,837,168 A | 6/1989 | De Jaeger |
| 4,837,306 A | 6/1989 | Ling et al. |
| 4,873,316 A | 10/1989 | Meade |
| 4,881,175 A | 11/1989 | Ladner |
| 4,941,880 A | 7/1990 | Burns |
| 4,946,778 A | 8/1990 | Ladner |
| 4,954,617 A | 9/1990 | Fanger |
| 5,013,653 A | 5/1991 | Huston |
| 5,023,243 A | 6/1991 | Tullis |
| 5,034,506 A | 7/1991 | Summerton |
| 5,064,413 A | 11/1991 | McKinnon |
| 5,091,513 A | 2/1992 | Huston |
| 5,132,405 A | 7/1992 | Huston |
| 5,166,315 A | 11/1992 | Summerton |
| 5,177,196 A | 1/1993 | Meyer, Jr. |
| 5,179,017 A | 1/1993 | Axel |
| 5,185,444 A | 2/1993 | Summerton |
| 5,188,897 A | 2/1993 | Suhadolnik |
| 5,214,134 A | 5/1993 | Weis |
| 5,216,141 A | 6/1993 | Benner |
| 5,223,409 A | 6/1993 | Ladner |
| 5,225,538 A | 7/1993 | Capon et al. |
| 5,225,539 A | 7/1993 | Winter |
| 5,235,033 A | 8/1993 | Summerton |
| 5,258,498 A | 11/1993 | Huston |
| 5,260,203 A | 11/1993 | Ladner |
| 5,264,423 A | 11/1993 | Cohen |
| 5,264,562 A | 11/1993 | Matteucci |

(Continued)

FOREIGN PATENT DOCUMENTS

| | | |
|---|---|---|
| EP | 0154316 | 9/1985 |
| EP | 0264166 | 4/1988 |

(Continued)

OTHER PUBLICATIONS

Sequence alignments, 2015, 2 pages.*
Declaration by Eyal Neria filed on Oct. 20, 2012 in U.S. Appl. No. 12/676,359, 47 pages.*
Michels et al. (Seminars in Immunology 23 (2011) 214-219).*
Gillard et al. (Expert Opin. Biol. Ther. (2011) 11(5): 609-621).*
Bluestone et al. (Cold Spring Harb Perspect Biol 2012;4:a007542, p. 1-23).*
von Herrath et al. (Clinical and Experimental Immunology, 2013, 172: 186-202).*

(Continued)

*Primary Examiner* — Ilia Ouspenski
(74) *Attorney, Agent, or Firm* — Graeser Associates International Inc; Dvorah Graeser

(57) ABSTRACT

This invention relates to C1ORF32 protein and its variants and fragments and fusion proteins thereof, pharmaceutical composition comprising same and methods of use thereof for treatment of immune related disorders and infections.

21 Claims, 3 Drawing Sheets

(56) References Cited

U.S. PATENT DOCUMENTS

| | | |
|---|---|---|
| 5,264,564 A | 11/1993 | Matteucci |
| 5,276,019 A | 1/1994 | Cohen |
| 5,278,302 A | 1/1994 | Caruthers |
| 5,286,717 A | 2/1994 | Cohen |
| 5,312,335 A | 5/1994 | McKinnon |
| 5,321,131 A | 6/1994 | Agrawal |
| 5,374,548 A | 12/1994 | Caras |
| 5,383,851 A | 1/1995 | McKinnon, Jr. |
| 5,399,163 A | 3/1995 | Peterson |
| 5,399,331 A | 3/1995 | Loughrey |
| 5,399,676 A | 3/1995 | Froehler |
| 5,403,484 A | 4/1995 | Ladner |
| 5,405,938 A | 4/1995 | Summerton et al. |
| 5,405,939 A | 4/1995 | Suhadolnik et al. |
| 5,416,016 A | 5/1995 | Low |
| 5,427,908 A | 6/1995 | Dower |
| 5,434,257 A | 7/1995 | Matteucci |
| 5,453,496 A | 9/1995 | Caruthers |
| 5,455,030 A | 10/1995 | Ladner |
| 5,455,233 A | 10/1995 | Spielvogel |
| 5,466,677 A | 11/1995 | Baxter |
| 5,470,967 A | 11/1995 | Huie |
| 5,476,786 A | 12/1995 | Huston |
| 5,476,925 A | 12/1995 | Letsinger |
| 5,476,996 A | 12/1995 | Wilson |
| 5,482,858 A | 1/1996 | Huston |
| 5,489,677 A | 2/1996 | Sanghvi |
| 5,519,126 A | 5/1996 | Hecht |
| 5,530,101 A | 6/1996 | Queen |
| 5,536,821 A | 7/1996 | Agrawal |
| 5,539,082 A | 7/1996 | Nielsen |
| 5,541,306 A | 7/1996 | Agrawal |
| 5,541,307 A | 7/1996 | Cook |
| 5,545,806 A | 8/1996 | Lonberg |
| 5,545,807 A | 8/1996 | Surani |
| 5,550,111 A | 8/1996 | Suhadolnik |
| 5,561,225 A | 10/1996 | Maddry |
| 5,563,253 A | 10/1996 | Agrawal |
| 5,569,825 A | 10/1996 | Lonberg |
| 5,571,698 A | 11/1996 | Ladner |
| 5,571,799 A | 11/1996 | Tkachuk |
| 5,580,717 A | 12/1996 | Dower |
| 5,585,089 A | 12/1996 | Queen |
| 5,587,361 A | 12/1996 | Cook |
| 5,596,086 A | 1/1997 | Matteucci |
| 5,602,240 A | 2/1997 | De Mesmaeker |
| 5,608,046 A | 3/1997 | Cook |
| 5,610,289 A | 3/1997 | Cook |
| 5,618,704 A | 4/1997 | Sanghvi |
| 5,623,070 A | 4/1997 | Cook |
| 5,624,821 A | 4/1997 | Winter |
| 5,625,050 A | 4/1997 | Beaton |
| 5,625,126 A | 4/1997 | Lonberg |
| 5,625,825 A | 4/1997 | Rostoker |
| 5,633,360 A | 5/1997 | Bischofberger |
| 5,633,425 A | 5/1997 | Lonberg |
| 5,648,260 A | 7/1997 | Winter |
| 5,661,016 A | 8/1997 | Lonberg |
| 5,663,312 A | 9/1997 | Chaturvedula |
| 5,677,425 A | 10/1997 | Bodmer |
| 5,677,437 A | 10/1997 | Teng |
| 5,677,439 A | 10/1997 | Weis |
| 5,693,762 A | 12/1997 | Queen |
| 5,698,767 A | 12/1997 | Wilson |
| 5,714,331 A | 2/1998 | Buchardt |
| 5,714,350 A | 2/1998 | Co |
| 5,719,262 A | 2/1998 | Buchardt |
| 5,770,429 A | 6/1998 | Lonberg |
| 5,789,650 A | 8/1998 | Lonberg |
| 5,814,318 A | 9/1998 | Lonberg |
| 5,869,046 A | 2/1999 | Presta |
| 5,874,299 A | 2/1999 | Lonberg |
| 5,877,397 A | 3/1999 | Lonberg |
| 5,885,793 A | 3/1999 | Griffiths |
| 5,939,598 A | 8/1999 | Kucherlapati |
| 5,969,108 A | 10/1999 | McCafferty |
| 6,075,181 A | 6/2000 | Kucherlapati |
| 6,114,598 A | 9/2000 | Kucherlapati |
| 6,121,022 A | 9/2000 | Presta |
| 6,150,584 A | 11/2000 | Kucherlapati |
| 6,162,963 A | 12/2000 | Kucherlapati |
| 6,165,745 A | 12/2000 | Ward |
| 6,172,197 B1 | 1/2001 | McCafferty |
| 6,180,370 B1 | 1/2001 | Queen |
| 6,194,551 B1 | 2/2001 | Idusogie |
| 6,277,375 B1 | 8/2001 | Ward |
| 6,303,374 B1 | 10/2001 | Zhang |
| 6,350,861 B1 | 2/2002 | Co |
| 6,521,404 B1 | 2/2003 | Griffiths |
| 6,544,731 B1 | 4/2003 | Griffiths |
| 6,555,313 B1 | 4/2003 | Griffiths |
| 6,582,915 B1 | 6/2003 | Griffiths |
| 6,593,081 B1 | 7/2003 | Griffiths |
| 6,709,654 B1 | 3/2004 | Anderson et al. |
| 7,189,507 B2 | 3/2007 | Mack |
| 7,745,391 B2 | 6/2010 | Mintz et al. |
| 7,829,084 B2 | 11/2010 | Ledbetter et al. |
| 7,842,665 B2 | 11/2010 | Levin et al. |
| 7,982,017 B2 | 7/2011 | Lin et al. |
| 8,043,616 B2 | 10/2011 | Anderson et al. |
| 8,080,246 B2 | 12/2011 | Lin et al. |
| 8,183,207 B2 | 5/2012 | Lin et al. |
| 8,293,883 B2 | 10/2012 | Presta |
| 8,318,159 B2 | 11/2012 | Adam et al. |
| 8,318,168 B2 | 11/2012 | Sass et al. |
| 8,415,455 B2* | 4/2013 | Levine et al. ............... 530/350 |
| 2002/0037286 A1 | 3/2002 | Krause et al. |
| 2002/0193567 A1 | 12/2002 | Jacobs |
| 2004/0110704 A1 | 6/2004 | Yamane |
| 2006/0034852 A1 | 2/2006 | Rixon |
| 2008/0299042 A1 | 12/2008 | Bechtel et al. |
| 2011/0151515 A1 | 6/2011 | Heifetz et al. |
| 2011/0281302 A1 | 11/2011 | Williams et al. |
| 2012/0128672 A1 | 5/2012 | Keer |
| 2012/0141573 A1 | 6/2012 | Ling et al. |
| 2012/0219559 A1 | 8/2012 | Chen |
| 2013/0160150 A1 | 6/2013 | Leibel et al. |
| 2014/0363446 A1* | 12/2014 | Toporik et al. ............ 424/158.1 |

FOREIGN PATENT DOCUMENTS

| | | |
|---|---|---|
| EP | 0338841 | 10/1989 |
| EP | 0401384 | 12/1990 |
| EP | 1176195 | 1/2002 |
| EP | 2116259 A1 | 11/2009 |
| EP | 2190469 A2 | 6/2010 |
| WO | WO 87/04462 | 7/1987 |
| WO | WO 87/05330 | 9/1987 |
| WO | WO 88/00052 | 1/1988 |
| WO | WO 89/01036 | 2/1989 |
| WO | WO 92/03918 | 3/1992 |
| WO | WO 93/12227 | 6/1993 |
| WO | WO 94/10332 | 5/1994 |
| WO | WO 94/25585 | 5/1994 |
| WO | WO 94/29351 | 12/1994 |
| WO | WO 97/13852 | 4/1997 |
| WO | WO 98/24884 | 6/1998 |
| WO | WO 99/26972 | 6/1999 |
| WO | WO 99/45962 | 9/1999 |
| WO | WO 99/54342 | 10/1999 |
| WO | WO 99/60020 | 11/1999 |
| WO | WO 00/42072 | 7/2000 |
| WO | WO 01/09187 | 2/2001 |
| WO | WO 01/14424 | 3/2001 |
| WO | WO 02/26930 | 4/2002 |
| WO | WO 02/43478 | 6/2002 |
| WO | WO 02/092780 | 11/2002 |
| WO | WO 03/000012 | 1/2003 |
| WO | WO 03/027228 | 4/2003 |
| WO | WO 03/035835 | 5/2003 |
| WO | WO 03/074679 | 9/2003 |
| WO | WO 03/101283 | 12/2003 |
| WO | WO 2004/037999 | 5/2004 |
| WO | WO 2004/048550 | 6/2004 |

(56) References Cited

FOREIGN PATENT DOCUMENTS

| WO | WO 2004/100774 | | 11/2004 |
|---|---|---|---|
| WO | WO 2005/108415 | | 11/2005 |
| WO | WO 2006/050247 | | 5/2006 |
| WO | WO 2006/050262 | | 5/2006 |
| WO | 2007014123 | A2 | 2/2007 |
| WO | 2007106056 | A1 | 9/2007 |
| WO | 2008049070 | A2 | 4/2008 |
| WO | 2008131242 | A1 | 10/2008 |
| WO | 2009032845 | | 3/2009 |
| WO | 2009055074 | A2 | 4/2009 |
| WO | 2009076651 | | 6/2009 |
| WO | 2010017198 | A2 | 2/2010 |
| WO | 2012001647 | | 1/2012 |
| WO | 2012006027 | A1 | 1/2012 |

OTHER PUBLICATIONS

Coppieters et al. (Clinical Immunology (2013) 149, 345-355).*
Search Report and Written Opinion for parent PCT Application No. PCT/IB2012/053342, mailed Sep. 23, 2012.
Heidi Schultz, Towards a Comprehensive Description of the Human Retinal Transcriptome:Identification and Characterization of Differentially Expressed Genes, [Online], 2003, PhD Thesis—Würzburg University.
Crawford et al., Curr Opin Immunol. 2009;21:179-186.
Kaufmann et al., J Immunol 2009;182:5891-5897.
Sharpe et al., Nat Immunol 2007;8:239-245.
Rivas et al., J Immunol. 2009 ;183:4284-91.
Golden-Mason et al., J Virol. 2009;83:9122-30.
Hofmeyer et al, J. Biomed. & Biotech. 2011, vol. 2011, The PD-1/PD-L1 (B7-H1) Pathway in Chronic Infection-Induced Cytotoxic T Lymphocyte Exhaustion, Art. ID 451694, pp. 1-9.
Ha et al, Immunol Rev. Jun. 2008;223:317-33.
Diepolder and Obst, Expert Rev Vaccines. Mar. 2010;9(3):243-7.
Velu et al., Nature 2009;458:206-210, Enhancing SIV-specific immunity in vivo by PD-1 blockade.
Restoring function in exhausted CD8 T cells during chronic viral infection, Barber et al., Nature. 2006;439:682-7.
Target-Dependent B7-H1 Regulation Contributes to Clearance of Central Nervous Sysyem Infection and Dampens Morbidity, Phares et al., J Immunol. 2009: 182; 5430-5438.
Follicular Helper CD4 T Cells (TFH), Crotty, Annu. Rev. Immunol. 29: 621-663, 2011.
International Search Report and Written Opinion for PCT/US2008/ 075122 dated Apr. 9, 2009.
Supplementary European Search Report for EP08829443.4 dated Dec. 14, 2010.
Database UniProt [Online], Jul. 5, 2004, "RecName: Full=Immunoglobin-like-domain-containing receptor 2;" XP002614181 retrieved from EPI Database accession No. Q71H61.
Valeria Roni et al., Mapping of transcription start sites of human retina expressed genes, BMC Genomics, 2007, vol. 8:42.
Office Action for EP08829443.4 dated Feb. 7, 2011.
Markomichelakis, et al., Regression of neovascular age-related macular degeneration following infliximab therapy, American Journal of Ophthalmology, 2005, vol. 139, Issue 3.
Nussenblatt et al., Perspectives: Age Related Macular Degeneration and the Immune Response—Implications for Therapy, American Journal of Ophthalmology, 2007, vol. 144, Issue 4.
Altschul, et al., Basic Local Allignment Search Tool, J Mol. Biol.; 1990; 215:403-10.
Arimochi et al., Interaction of Mat-8 (FXYD-3) with Na/K-ATPase in Colorectal Cancer Cells, Biol. Pharm. Bull., 2007; 30(4) 648-654.
Bibert et al.; Structural and Functional Properties of Two Human FXYD3 (Mat-8) Isoforms; The Journal of Biological Chemistry; 2006; vol. 281, 51:39142-39151.
Crambert et al.; FXYD3 (Mat-8), a New Regulator of Na,K-ATPase; Molecular Biology of the Cell; 2005; 16:2363-2371.
Fahrlander, P.D. and Klausner A., Amplifying DNA Probe Signals: A 'Christmas Tree' Approach; Bio/Technology; 1988; 6:1165.

Geering; FXYD proteins: new regulators of Na-K-ATPase; AJP—Renal Physiology; 2006; 290:F241-F250.
Gregory SG et al.; The DNA sequence and biological annotation of human chromosome 1; Nature; 2006, 441 (7091):315-321.
Grzmil et al.; Up-regulated expression of the MAT-8 gene in prostate cancer and its siRNA-mediated inhibition of expression induces a decrease in proliferation of human prostate carcinoma cells; International Journal of Oncology; 2004; 24:97-105.
Huston et al.; Protein engineering of antibody binding sites: Recovery of specific activity in an anti-digoxin single-chain Fv analogue produced in *Escherichia coli*; Proc. Natl. Acad. Sci. USA; 1988; 85:5879-5883.
Kayed et al.; FXYD3 is overexpressed in pancreatic ductal adenocarcinoma and influences pancreatic cancer cell growth; Int. J. Cancer:; 2006; 118:43-54.
M. Clark; Chemical Immunol and Antibody Engineering; 1991 Cambridge; pp. 1-31.
Morrison et al.; Mat-8, a Novel Phospholemman-like Protein Expressed in Human Breast Tumors, Induces a Chloride Conductance in Xenopus Oocytes; The Journal of Biological Chemistry ; 1995; 270:2176-2182.
Needleman and Wunsch; A general method applicable to the search for similarities in the amino acid sequence of two proteins; J. Mol. Biol.; 1970; 48:444-453.
Scanlan et al.; Glycoprotein A34, a novel target for antibody-based cancer immunotherapy; Cancer Immunotherapy; 2006; 6:2.
Shields et al.; High Resolution Mapping of the Binding Site on Human IgG1 for FcgRI, FcgRll, FcgRIII, and FcRn and Design of IgG1 Variants with Improved Binding to the FcgR*; The Journal of Biological Chemistry; 2001; 276:6591-6604.
Takebe Y. et al.; SR alpha promoter: an efficient and versatile mammalian cDNA expression system composed of the simian virus 40 early promoter and the R-U5 segment of human T-cell leukemia virus type 1 long terminal repeat; Mol. Cell. Biol.; 1988; 8:466-472.
Umana et al.; Engineered glycoforms of an antineuroblastoma IgG1 with optimized antibodydependent cellular cytotoxic activity; Nat. Biotech.; 1999; 17:176-180.
Urlaub and Chasin; Isolation of Chinese hamster cell mutants deficient in dihydrofolate reductase activity; Proc. Natl. Acad. Sci. USA; 1980; 77:4216-4220.
Altschul et al., Gapped BLAST and PSI-BLAST: a new generation of protein database search programs; Nucleic Acids Res.; 1997; 25(17):3389-3402.
Baldari, et al.; A novel leader peptide which allows efficient secretion of a fragment of human interleukin 1 beta in *Saccharomyces cerevisiae*; EMBO J.; 1987; 6:229-234.
Byrne et al.; Multiplex gene regulation: A two-tiered approach to transgene regulation in transgenic mice; Proc. Natl. Acad. Sci. USA; 1989; 86:5473-5477.
Chen, J. et al.; B cell development in mice that lack one or both immunoglobulin x light chain genes; EMBO J.; 1993; 12:821-830.
Clark et al; The Secreted Protein Discovery Initiative (SPDI), a Large-Scale Effort to Identify Novel Human Secreted and Transmembrane Proteins: A Bioinformatics Assessment;Genome Res.; 2003; 13: 2265-2270.
Coruzzi et al.; Tissue-specific and light-regulated expression of a pea nuclear gene encoding the small subunit of ribulose-1,5-bisphosphate carboxylase; EMBO J.; 1984; 3:1671-1680.
Karpovsky et al.; Production of Target-Specific Effector Cells Using Hetero-Cross-Linked Aggregates Containing Anti-Target Cell and Anti-Fc3, Receptor Antibodies; J. Exp. Med.; 1984; 160:1686-1701.
Kaufman, et al., Translational efficiency of polycistronic mRNAs and their utilization to express heterologous genes in mammalian cells; EMBO J.; 1987; 6:187-195.
Kwoh et al., Transcription-based amplification system and detection of amplified human immunodeficiency virus type 1 with a bead-based sandwich hybridization format; Proc. Natl. Acad. Sci. USA; 1989; 86:1173-1177.
Liu, M A et al.; Heteroantibody duplexes target cells for lysis by cytotoxic T lymphocytes; Proc. Natl. Acad. Sci. USA; 1985; 82:8648-8652.
Owais et al.; Chloroquine Encapsulated in Malaria-Infected Erythrocyte-Specific Antibody-Bearing Liposomes Effectively Controls

(56) References Cited

OTHER PUBLICATIONS

Chloroquine- Resistant Plasmodium berghei Infections in Mice†; Antimicrob. Agents Chemother.; 1995; 39:180-184.
Pinkert et al., An albumin enhancer located 10 kb upstream functions along with its promoter to direct efficient, liver-specific expression in transgenic mice; Genes and Development; 1987; 1:268-277.
Queen, C. et al.; A humanized antibody that binds to the interleukin 2 receptor; Proc. Natl. Acad. See. U.S.A.; 1989 86:10029-10033.
Shields, R. L. et al.; Lack of Fucose on Human IgG1 N-Linked Oligosaccharide Improves Binding to Human Fc.GAMA. RIII and Antibody-dependent Cellular Toxicity*; J. Biol. Chem.; 2002; 277:26733-26740.
Singhal et al.; Glutathione, a first line of defense against cadmium toxicity; FASEB J.; 1987; 1:220-223.
Smith, et al., Production of Human Beta Interferon in Insect Cells Infected with a Baculovirus Expression Vector; Mol. Cell. Biol.; 1983; 3:2156-2165.
Takamatsu et al.; Expression of bacterial chloramphenicol acetyltransferase gene in tobacco plants mediated by TMV-RNA; EMBO J.; 1987; 6:307-311.
Taylor, L. et al.; A transgenic mouse that expresses a diversity of human sequence heavy and light chain immunoglobulins; Nucleic Acids Research; 1992; 20:6287-6295.
Tomizuka et al.; Double trans-chromosomic mice: Maintenance of two individual human chromosome fragments containing Ig heavy and k loci and expression of fully human antibodies; Proc. Natl. Acad Sci. USA; 2000; 97:722-727.
Tuaillon et al.; Human immunoglobulin heavy-chain minilocus recombination in transgenic mice: Gene-segment use in ,u and y transcripts; Proc. Natl. Acad. Sci. USA; 1993; 90:3720-3724.
Winoto and Baltimore; A novel, inducible and T cell-specific enhancer located at the 3' end of the T cell receptor alpha locus; EMBO J.; 1989; 8:729-733.
Office Action for IL 204255 dated Jan. 30, 2013.
"Compugen Announces Positive Therapeutic Effects of CGEN 15001 in Aminal Model of Rheumatoid Arthritis", published Dec. 14, 2010, retrieved through the Internet, www.cgen.com.
Database Uniprot[Online](Jul. 5, 2004), Accession No:Q71H61.
Taylor et al, Human chromosome 11 DNA sequence and analysis including novel gene identification, Nature, 2006, 440(7083), 497-500.
Yan et al, Genome sequencing and comparison of two nonhuman primate animal models, the cynomolgus and Chinese rhesus macaques, Nature Biotechnology, 2011, 29(11), 1019-1023.
Zimin et al, A whole-genome assembly of the domestic cow, Bos Taurus, Genome Biology, 2009, 10(4), R42.
Strausberg et al, Generation and initial analysis of more than 15,000 full-length human and mouse cDNA sequences, Proceedings of the National Academy of Sciences, 2002, 99(26), 16899-16903.
Li et al, The sequence and de novo assembly of the giant panda genome, Nature, 2010, 463(7279), 311-317.
Skarnes et al, A conditional knockout resource for the genome-wide study of mouse gene function, Nature, 2011, 474 (7351), 337-342.
Kim et al, Genome sequencing reveals insights into physiology and longevity of the naked mole rat, Nature, 2011, 479 (7372), 223-227.
OA for JP2011-505792 mailed Jul. 2, 2013.
GenBank Accession EAW90779, Dec. 2006.
Riches et al. 2009. Recent insights into the pathogenesis of hyperuricaemia and gout. Hum Mol Genet.; 18:R177-84.
Masseoud et al. 2005. Overview of hyperuricaemia and gout. Curr Pharm Des.; 11(32):4117-24.
Bencardino and Hassankhani. 2003. Calcium pyrophosphate dihydrate crystal deposition disease. Semin Musculoskelet Radiol.; 7(3):175-85.
Zaka R. and Williams C.J. 2005. Genetics of chondrocalcinosis. OsteoArthritis and Cartilage; 13,745-750.
Langford CA. 2010. Vasculitis. J Allergy Clin Immunol; 125:S216-225.
Khasnis and Langford. 2009. Update on vasculitis. J Allergy Clin Immunol; 123:1226-36.
Miller et al. 2010. An approach to the diagnosis and management of systemic vasculitis. Clinical and Experimental Immunology, 160: 143-160.
Gonzalez et al. 2009. Pediatric Henoch—Schönlein purpura. International Journal of Dermatology; 48: 1157-1165.
Pillebout et al. 2002. Henoch-Schönlein Purpura in Adults: Outcome and Prognostic Factors. J Am Soc Nephrol.; 13: 1271-1278.
Genta et al. 2006. Systemic rheumatoid vasculitis: a review. Semin Arthritis Rheum; 36:88-98.
Olivencia-Simmons I. 2007. Wegener's granulomatosis: Symptoms, diagnosis, and treatment. J. of the American Academy of Nurse Practitioners 19:315-320.
Hua et al. 2009. T-Lymphocytes and Disease Mechanisms in Wegener's Granulomatosis. Kidney Blood Press Res; 32:389-398.
Moosig et al. 2008. Wegener's Granulomatosis: The Current View. Clinic Rev Allerg Immunol; 35:19-21.
Khan MA. 2002. Update on spondyloarthropathies. Ann Intern Med.; 136(12):896-907.
Rostom et al. 2010. New tools for diagnosing spondyloarthropathy. Joint Bone Spine; 77:108-114.
FitzGerald and McInnes. 2006. Spondyloarthropathy: disease at the crossroads of immunity. Best Practice & Research Clinical Rheumatology; 20(5): 949-967.
Brown, 2008. Breakthroughs in genetic studies of ankylosing spondylitis. Rheumatology, vol. 47(2): 132-137.
Brionez and Reveille. 2008. The contribution of genes outside the major histocompatibility complex to susceptibility to ankylosing spondylitis. Curr Opin Rheumatol.; 20(4):384-91.
Kwiatkowska B. and Filipowicz?Sosnowska A. 2009. Reactive arthritis. Pol Arch Med Wewn; 119 (1?2): 60-65.
Rohekar S. and Pope J. 2009. Epidemiologic approaches to infection and immunity: the case of reactive arthritis. Curr Opin Rheumatol.; 21(4):386-90.
Kim et al. 2009. Reactive arthritis: a review. J Adolesc Health; 44(4):309-15.
Gladman et al. 2005. Psoriatic arthritis: epidemiology, clinical features, course, and outcome. Ann Rheum Dis.; 64 (Suppl 2): ii14-ii17.
Leung et al. 2007. Psoriatic arthritis as a distinct disease entity. J Postgrad Med.; 53(1):63-71.
Ho et al. 2008. Investigating the role of the HLA-Cw*06 and HLA-DRB1 genes in susceptibility to psoriatic arthritis: comparison with psoriasis and undifferentiated inflammatory arthritis. Ann Rheum Dis 67(5):677-682.
Wollheim FA. 2001. Enteropathic arthritis: how do the joints talk with the gut? Curr Opin Rheumatol; 13:305-309.
Colombo et al. 2009. Enteropathic spondyloarthropathy: a common genetic background with inflammatory bowel disease? World J Gastroenterol.; 15(20):2456-62.
Nade S. 2003. Septic arthritis. Best Practice & Research Clinical Rheumatology; 17(2): 183-200.
Mathews CJ. and Coakley G. 2008. Septic arthritis: current diagnostic and therapeutic algorithm. Current Opinion in Rheumatology; 20:457-462.
Tarkowski A. 2006. Infectious arthritis. Best Practice & Research Clinical Rheumatology; 20(6): 1029-1044.
Marques AR. 2010. Lyme disease: A Review. Curr Allergy Asthma Rep; 10:13-20.
Murray TS. and Shapiro ED. 2010. Lyme disease. Clin Lab Med.; 30(1):311-28.
Bratton et al. 2008. Diagnosis and treatment of Lyme disease. Mayo Clinic Proceedings; 83(5):566-571.
Iannuzzi et al. 2007. Sarcoidosis. N Engl J Med; 357:2153-2165.
Chen and Moller. 2008. Etiology of sarcoidosis. Clin Chest Med. ;29(3):365-77.
Ben-Chetrit and Touitou I. 2009. Familial Mediterranean fever in the world. Arthritis Rheum.; 61(10):1447-53.
Chae et al. 2009. Advances in the understanding of familial Mediterranean fever and possibilities for targeted therapy. Br J Haematol.; 146(5):467-78.

(56) References Cited

OTHER PUBLICATIONS van der Hilst et al. 2008. Long-term follow-up, clinical features, and quality of life in a series of 103 patients with hyperimmunoglobulinemia D syndrome. Medicine; 87(6):301-310.
Simon et al. 2001. Molecular analysis of the mevalonate kinase gene in a cohort of patients with the hyper-IgD and periodic fever syndrome: its application as a diagnostic tool. Ann Intern Med.; 135:338-343.
Rezaei N. 2006. TNF-receptor-associated periodic syndrome (TRAPS): an autosomal dominant multisystem disorder. Clin Rheumatol.; 25(6):773-7.
Kimberley et al. 2007. Falling into TRAPS—receptor misfolding in the TNF receptor 1-associated periodic fever syndrome. Arthritis Research & Therapy; 9(4):217.
Hull et al. 2002. The TNF receptor-associated periodic syndrome (TRAPS): emerging concepts of an autoinflammatory disorder. Medicine (Baltimore); 81(5):349-368.
Mason and Reed. 2005. Update in Juvenile Rheumatoid Arthritis. Arthritis & Rheumatism.; 53 (5): 796-799.
Stastny and Fink. 1979. Different HLA-D associations in adult and juvenile rheumatoid arthritis. J. Clin. Invest.; 63:124-130.
Thomson et al. 2002. Juvenile idiopathic arthritis classi?ed by the ILAR criteria: HLA associations in UK patients. Rheumatology; 41:1183-1189.
Woo P. 2006. Systemic juvenile idiopathic arthritis: Diagnosis, management, and outcome. Nat Clin Pract Rheumatol.;2:28-34.
Buckwalter and Martin. 2006. Osteoarthritis. Adv Drug Deliv Rev.; 20;58(2):150-67.
Brandt et al. 2009. Etiopathogenesis of osteoarthritis. Med Clin North Am.; 93(1):1-24.
Ayonrinde et al. 2008. Clinical perspectives on hereditary hemochromatosis. Critical Reviews in Clinical Laboratory Sciences; 45(5):451-484.
Brissot et al. 2008. Current approach to hemochromatosis. Blood Reviews; 22: 195-210.
Adams PC and Barton JC. 2007. Haemochromatosis. Lancet; 370: 1855-1860.
Teufel et al. 2009. Update on autoimmune hepatitis. World J Gastroenterol; 15(9): 1035-1041.
Foster GR. 2009. Recent advances in viral hepatitis. Clinical Medicine; 9(6): 613-616.
Rizzetto M. 2010. Hepatitis D: clinical features and therapy. Dig Dis.; 28:139-143.
Lucey et al. 2009. Alcoholic Hepatitis. N. Engl J Med; 360:2758-2769.
Krasnokutski et al, Osteoarthritis and Cartilage (2008) 16, S1-S3.
Fillatreau et al.: "B cells regulate autoimmunity by provision of IL-10" Nature Immunology 3, 944-950 (2002).
Lowes at al.: "Psoriasis vulgaris lesions contain discrete populations of Th1 and Th17 T cells" Jour. of investigative dermatology (2008) vol. 128 p. 1207-1211.
Marija Dokmanovic-Chouinard et al.: "Positional Cloning of "Lisch-like", a Candidate Modifier of Susceptibility to Type 2 Diabetes in Mice", PLoS Genetics, Jul. 25, 2008, vol. 4, Issue 7, e1000137.
Search report from the Singaporean Patent Office, mailed Jun. 12, 2015.
Rentero, Inmaculada, and Christian Heinis. "Screening of large molecule diversities by phage display." CHIMIA International Journal for Chemistry 65.11 (2011): 843-845.
Blast Search results from related U.S. Appl. 13/767,891—Oct. 2014.
Colman, Peter M. "Effects of amino acid sequence changes on antibody-antigen interactions." Research in Immunology 145.1 (1994): 33-36.
Blast Search results from related U.S. Appl. 13/845,420—Dec. 2014.
Lederman, Seth, et al. "A single amino acid substitution in a common African allele of the CD4 molecule ablates binding of the monoclonal antibody, OKT4." Molecular immunology 28.11 (1991): 1171-1181.
Dong, Haidong, et al. "B7-H1, a third member of the B7 family, co-stimulates T-cell proliferation and interleukin-10 secretion." Nature medicine 5.12 (1999): 1365-1369.
Freeman, Gordon J., et al. "Engagement of the PD-1 immunoinhibitory receptor by a novel B7 family member leads to negative regulation of lymphocyte activation." The Journal of experimental medicine 192.7 (2000): 1027-1034.
Tamura, Hideto, et al. "B7-H1 costimulation preferentially enhances CD28-independent T-helper cell function." Blood 97.6 (2001): 1809-1816.
Latchman, Yvette, et al. "PD-L2 is a second ligand for PD-1 and inhibits T cell activation." Nature immunology 2.3 (2001): 261-268.
Greaves, Paul, and John G. Gribben. "The role of B7 family molecules in hematologic malignancy." Blood 121.5 (2013): 734-744.
Li, Yili, Qian Wang, and Roy A. Mariuzza. "Structure of the human activating natural cytotoxicity receptor NKp30 bound to its tumor cell ligand B7-H6." The Journal of experimental medicine 208.4 (2011): 703-714.

\* cited by examiner

MDRVLLRWISLFWLTAMVEGLQVTVPDKKKVAMLFQPTVLRCHFSTSSHQ
PAVVQWKFKSYCQDRMGESLGMSSTRAQSLSKRNLEWDPYLDCLDSRRTV
RVVASKQGSTVTLGDFYRGREITIVHDADLQIGKLMWGDSGLYYCIITTP
DDLEGKNEDSVELLVLG|RTGLLA|DLLPS|FAVEIM|PE|WVFVGLVLLGVFLF
FVLVGICWCQCCPHSCCCYVRCPCCPDSCWCPQACEYSDRWGDRAIERNV
YLST

SEQUENCE LISTING

```
<160> NUMBER OF SEQ ID NOS: 190

<210> SEQ ID NO 1
<211> LENGTH: 1407
<212> TYPE: DNA
<213> ORGANISM: Homo Sapiens

<400> SEQUENCE: 1
ccggcggcgc gatccagccc ccggccccgc ctgcgcggcc ggcccggcgg gcgctgcgcc      60
cagggacgcc cggtgcccgc cgctccgccg ccgcccgctg ccgcggggtg acagcgatcc     120
ttctgttcca gccatttccc actttcctca ctccgtaatt cggctgggaa gttggggaag    180
atggataggg tcttgctgag gtggatttct ctcttctggc taacagccat ggtcgaaggc    240
cttcaggtca cagtgcccga caagaagaag gtggccatgc tcttccagcc cactgtgctt    300
cgctgccact tctcaacatc ctcccatcag cctgcagttg tgcagtggaa gttcaagtcc    360
tactgccagg atcgcatggg agaatccttg ggcatgtcct ctacccgggc ccaatctctc    420
agcaagagaa acctggaatg ggaccccctac ttggattgtt tggacagcag gaggactgtt    480
```

| | |
|---|---|
| cgagtagtag cttcaaaaca gggctcgact gtcaccctgg gagatttcta caggggcaga | 540 |
| gagatcacga ttgttcatga tgcagatctt caaattggaa agcttatgtg gggagacagc | 600 |
| ggactctatt actgtattat caccacccca gatgacctgg aggggaaaaa tgagggctca | 660 |
| ctgggactgc tggtgttggg caggacaggg ctgcttgctg atctcttgcc cagttttgct | 720 |
| gtggagatta tgccagagtg ggtgtttgtt ggcctggtgc tcctgggcgt cttcctcttc | 780 |
| ttcgtcctgg tggggatctg ctggtgccag tgctgccctc acagctgctg ctgctatgtc | 840 |
| cgctgcccat gctgcccaga ttcctgctgg tgccctcaag cctgtgagta cagtgaccgc | 900 |
| tggggagaca gagcgatcga gagaaatgtc tacctctcta cctgacagct gtgtgcgctg | 960 |
| ggttcctcct ccacctcctg tcctgccacc cccaagattg gtcattccag actcttctcc | 1020 |
| gctgggtgcc cctggcctca gggatgacca ttctcatttg ccttttcacc tacatacacc | 1080 |
| tctccacact tcttatccat atctatcact ccatgcattt ggaattctca tggacactat | 1140 |
| tgataaaatg aagggcaggt ttggcgtggt gaggttgtg tgtaagact gttccctctc | 1200 |
| cctgggcat tcaaactaga ggaaaccttc tctggtcgtt cccttcccat gcagagaagt | 1260 |
| tccttttat atgagaagag tgtgcaaact gtggcctttg ggcacccacc cagccacaga | 1320 |
| tttgttttat ttactcccat gatgacatgg gccacaatag ggcctagttc ttatttgagg | 1380 |
| attcacaatt tttaccttac tggccaa | 1407 |

<210> SEQ ID NO 2
<211> LENGTH: 1350
<212> TYPE: DNA
<213> ORGANISM: Homo Sapiens

<400> SEQUENCE: 2

| | |
|---|---|
| ccggcggcgc gatccagccc ccggccccgc ctgcgcggcc ggcccggcgg gcgctgcgcc | 60 |
| cagggacgcc cggtgcccgc cgctccgccg ccgcccgctg ccgcggggtg acagcgatcc | 120 |
| ttctgttcca gccatttccc actttcctca ctccgtaatt cggctgggaa gttggggaag | 180 |
| atggataggg tcttgctgag gtggatttct ctcttctggc taacagccat ggtcgaaggc | 240 |
| cttcaggtca cagtgcccga caagaagaag gtggccatgc tcttccagcc cactgtgctt | 300 |
| cgctgccact tctcaacatc ctcccatcag cctgcagttg tgcagtggaa gttcaagtcc | 360 |
| tactgccagg atcgcatggg agaatccttg gcatgtcct ctacccgggc caatctctc | 420 |
| agcaagagaa acctggaatg ggaccctac ttggattgtt tggacagcag gaggactgtt | 480 |
| cgagtagtag cttcaaaaca gggctcgact gtcaccctgg gagatttcta caggggcaga | 540 |
| gagatcacga ttgttcatga tgcagatctt caaattggaa agcttatgtg gggagacagc | 600 |
| ggactctatt actgtattat caccacccca gatgacctgg aggggaaaaa tgagggctca | 660 |
| ctgggactgc tggtgttgga gtgggtgttt gttggcctgg tgctcctggg cgtcttcctc | 720 |
| ttcttcgtcc tggtggggat ctgctggtgc cagtgctgcc ctcacagctg ctgctgctat | 780 |
| gtccgctgcc catgctgccc agattcctgc tggtgccctc aagcctgtga gtacagtgac | 840 |
| cgctggggag acagagcgat cgagagaaat gtctacctct ctacctgaca gctgtgtgcg | 900 |
| ctgggttcct cctccacctc ctgtcctgcc accccaaga ttggtcattc agactcttc | 960 |
| tccgctgggt gccctggcc tcagggatga ccattctcat tgccttttc acctacatac | 1020 |
| acctctccac acttcttatc catatctatc actccatgca tttggaattc tcatggacac | 1080 |
| tattgataaa atgaagggc aggtttggcg tggtgaggtt gtggtgtaag actgttccct | 1140 |

```
ctccctgggg cattcaaact agaggaaacc ttctctggtc gttcccttcc catgcagaga    1200
agttcctttt tatatgagaa gagtgtgcaa actgtggcct ttgggcaccc acccagccac    1260
agatttgttt tatttactcc catgatgaca tgggccacaa tagggcctag ttcttatttg    1320
aggattcaca attttacct tactggccaa                                      1350
```

<210> SEQ ID NO 3
<211> LENGTH: 639
<212> TYPE: PRT
<213> ORGANISM: Homo Sapiens

<400> SEQUENCE: 3

```
Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
                20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Ala Ser Lys Gln Gly Ser Thr Val Thr
            100                 105                 110

Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
        130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
            180                 185                 190

Val Leu Leu Gly Val Phe Leu Phe Phe Val Leu Val Gly Ile Cys Trp
        195                 200                 205

Cys Gln Cys Cys Pro His Ser Cys Cys Cys Tyr Val Arg Cys Pro Cys
        210                 215                 220

Cys Pro Asp Ser Cys Cys Cys Pro Gln Ala Leu Tyr Glu Ala Gly Lys
225                 230                 235                 240

Ala Ala Lys Ala Gly Tyr Pro Pro Ser Val Ser Gly Val Pro Gly Pro
                245                 250                 255

Tyr Ser Ile Pro Ser Val Pro Leu Gly Gly Ala Pro Ser Ser Gly Met
            260                 265                 270

Leu Met Asp Lys Pro His Pro Pro Leu Ala Pro Ser Asp Ser Thr
        275                 280                 285

Gly Gly Ser His Ser Val Arg Lys Gly Tyr Arg Ile Gln Ala Asp Lys
290                 295                 300

Glu Arg Asp Ser Met Lys Val Leu Tyr Tyr Val Glu Lys Glu Leu Ala
305                 310                 315                 320

Gln Phe Asp Pro Ala Arg Arg Met Arg Gly Arg Tyr Asn Asn Thr Ile
                325                 330                 335
```

Ser Glu Leu Ser Ser Leu His Glu Glu Asp Ser Asn Phe Arg Gln Ser
                340                 345                 350

Phe His Gln Met Arg Ser Lys Gln Phe Pro Val Ser Gly Asp Leu Glu
            355                 360                 365

Ser Asn Pro Asp Tyr Trp Ser Gly Val Met Gly Gly Ser Ser Gly Ala
        370                 375                 380

Ser Arg Gly Pro Ser Ala Met Glu Tyr Asn Lys Glu Asp Arg Glu Ser
385                 390                 395                 400

Phe Arg His Ser Gln Pro Arg Ser Lys Ser Glu Met Leu Ser Arg Lys
                405                 410                 415

Asn Phe Ala Thr Gly Val Pro Ala Val Ser Met Asp Glu Leu Ala Ala
            420                 425                 430

Phe Ala Asp Ser Tyr Gly Gln Arg Pro Arg Arg Ala Asp Gly Asn Ser
        435                 440                 445

His Glu Ala Arg Gly Gly Ser Arg Phe Glu Arg Ser Glu Ser Arg Ala
    450                 455                 460

His Ser Gly Phe Tyr Gln Asp Asp Ser Leu Glu Glu Tyr Tyr Gly Gln
465                 470                 475                 480

Arg Ser Arg Ser Arg Glu Pro Leu Thr Asp Ala Asp Arg Gly Trp Ala
                485                 490                 495

Phe Ser Pro Ala Arg Arg Pro Ala Glu Asp Ala His Leu Pro Arg
            500                 505                 510

Leu Val Ser Arg Thr Pro Gly Thr Ala Pro Lys Tyr Asp His Ser Tyr
        515                 520                 525

Leu Gly Ser Ala Arg Glu Arg Gln Ala Arg Pro Glu Gly Ala Ser Arg
    530                 535                 540

Gly Gly Ser Leu Glu Thr Pro Ser Lys Arg Ser Ala Gln Leu Gly Pro
545                 550                 555                 560

Arg Ser Ala Ser Tyr Tyr Ala Trp Ser Pro Pro Gly Thr Tyr Lys Ala
                565                 570                 575

Gly Ser Ser Gln Asp Asp Gln Glu Asp Ala Ser Asp Ala Leu Pro
            580                 585                 590

Pro Tyr Ser Glu Leu Glu Leu Thr Arg Gly Pro Ser Tyr Arg Gly Arg
        595                 600                 605

Asp Leu Pro Tyr His Ser Asn Ser Glu Lys Lys Arg Lys Lys Glu Pro
    610                 615                 620

Ala Lys Lys Thr Asn Asp Phe Pro Thr Arg Met Ser Leu Val Val
625                 630                 635

<210> SEQ ID NO 4
<211> LENGTH: 254
<212> TYPE: PRT
<213> ORGANISM: Homo Sapiens

<400> SEQUENCE: 4

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

```
Ser Lys Arg Asn Leu Glu Trp Asp Pro Tyr Leu Asp Cys Leu Asp Ser
            85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
            130                 135                 140

Cys Ile Ile Thr Thr Pro Asp Asp Leu Glu Gly Lys Asn Glu Gly Ser
145                 150                 155                 160

Leu Gly Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
                180                 185                 190

Val Leu Leu Gly Val Phe Leu Phe Phe Val Leu Val Gly Ile Cys Trp
                195                 200                 205

Cys Gln Cys Cys Pro His Ser Cys Cys Cys Tyr Val Arg Cys Pro Cys
        210                 215                 220

Cys Pro Asp Ser Cys Trp Cys Pro Gln Ala Cys Glu Tyr Ser Asp Arg
225                 230                 235                 240

Trp Gly Asp Arg Ala Ile Glu Arg Asn Val Tyr Leu Ser Thr
                245                 250

<210> SEQ ID NO 5
<211> LENGTH: 254
<212> TYPE: PRT
<213> ORGANISM: Homo Sapiens

<400> SEQUENCE: 5

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
            85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
            130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Pro Glu Trp Val Phe Val Gly Leu
                180                 185                 190

Val Leu Leu Gly Val Phe Leu Phe Phe Val Leu Val Gly Ile Cys Trp
```

```
                    195                 200                 205
Cys Gln Cys Cys Pro His Ser Cys Cys Cys Tyr Val Arg Cys Pro Cys
    210                 215                 220
Cys Pro Asp Ser Cys Cys Cys Pro Gln Ala Cys Glu Tyr Ser Asp Arg
225                 230                 235                 240
Trp Gly Asp Arg Ala Ile Glu Arg Asn Val Tyr Leu Ser Thr
                245                 250

<210> SEQ ID NO 6
<211> LENGTH: 235
<212> TYPE: PRT
<213> ORGANISM: Homo Sapiens

<400> SEQUENCE: 6

Met Asp Arg Val Leu Leu Arg Trp Ile Ser Leu Phe Trp Leu Thr Ala
1               5                   10                  15
Met Val Glu Gly Leu Gln Val Thr Val Pro Asp Lys Lys Val Ala
                20                  25                  30
Met Leu Phe Gln Pro Thr Val Leu Arg Cys His Phe Ser Thr Ser Ser
            35                  40                  45
His Gln Pro Ala Val Val Gln Trp Lys Phe Lys Ser Tyr Cys Gln Asp
    50                  55                  60
Arg Met Gly Glu Ser Leu Gly Met Ser Ser Thr Arg Ala Gln Ser Leu
65                  70                  75                  80
Ser Lys Arg Asn Leu Glu Trp Asp Pro Tyr Leu Asp Cys Leu Asp Ser
                85                  90                  95
Arg Arg Thr Val Arg Val Ala Ser Lys Gln Gly Ser Thr Val Thr
                100                 105                 110
Leu Gly Asp Phe Tyr Arg Gly Arg Glu Ile Thr Ile Val His Asp Ala
            115                 120                 125
Asp Leu Gln Ile Gly Lys Leu Met Trp Gly Asp Ser Gly Leu Tyr Tyr
    130                 135                 140
Cys Ile Ile Thr Thr Pro Asp Asp Leu Glu Gly Lys Asn Glu Gly Ser
145                 150                 155                 160
Leu Gly Leu Leu Val Leu Glu Trp Val Phe Val Gly Leu Val Leu Leu
                165                 170                 175
Gly Val Phe Leu Phe Phe Val Leu Val Gly Ile Cys Trp Cys Gln Cys
            180                 185                 190
Cys Pro His Ser Cys Cys Cys Tyr Val Arg Cys Pro Cys Pro Asp
    195                 200                 205
Ser Cys Trp Cys Pro Gln Ala Cys Glu Tyr Ser Asp Arg Trp Gly Asp
    210                 215                 220
Arg Ala Ile Glu Arg Asn Val Tyr Leu Ser Thr
225                 230                 235

<210> SEQ ID NO 7
<211> LENGTH: 1287
<212> TYPE: DNA
<213> ORGANISM: Artificial Sequence
<220> FEATURE:
<223> OTHER INFORMATION: Synthetic polynucleotide

<400> SEQUENCE: 7
atggataggg tcttgctgag gtggatttct ctcttctggc taacagccat ggtcgaaggc     60
cttcaggtca cagtgcccga caagaagaag gtggccatgc tcttccagcc cactgtgctt    120
cgctgccact tctcaacatc ctcccatcag cctgcagttg tgcagtggaa gttcaagtcc    180
```

```
tactgccagg atcgcatggg agaatccttg ggcatgtcct ctacccgggc ccaatctctc      240
agcaagagaa acctggaatg ggaccccta c ttgattgtt tggacagcag gaggactgtt      300
cgagtagtag cttcaaaaca gggctcgact gtcaccctgg agatttcta caggggcaga      360 gagatcacga ttgttcatga tgcagatctt caaattggaa agcttatgtg gggagacagc      420
ggactctatt actgtattat caccacccca gatgacctgg aggggaaaaa tgaggactca      480
gtggaactgc tggtgttggg caggacaggg ctgcttgctg atctcttgcc cagttttgct      540
gtggagatta tgggatccga gaacctgtac tttcagggca gcggcgagcc cagaggcccc      600
accatcaagc cctgcccccc ctgcaagtgc ccagccccta acctgctggg cggacccagc      660
gtgttcatct ccccccccaa gatcaaggac gtgctgatga tcagcctgag ccccatcgtg      720
acctgcgtgg tggtggacgt gagcgaggac gaccccgacg tgcagatcag ctggttcgtg      780
aacaacgtgg aggtgcacac cgcccagacc cagacccacc gggaggacta caacagcacc      840
ctgcgggtgg tgtccgccct gcccatccag caccaggact ggatgagcgg caaagaattc      900
aagtgcaagg tgaacaacaa ggacctgcct gcccccatcg agcggaccat cagcaagccc      960
aagggcagcg tgagagcccc ccaggtgtac gtgctgcccc ctcccgagga agagatgacc     1020
aagaaacagg tgaccctgac ctgcatggtg accgacttca tgcccgagga catctacgtg     1080
gagtggacca acaacggcaa gaccgagctg aactacaaga caccgagcc cgtgctggac     1140 agcgacggca gctacttcat gtatagcaag ctgagagtcg agaagaaaaa ctgggtggag     1200
cggaacagct acagctgcag cgtggtgcac gagggcctgc acaaccacca caccaccaag     1260
agcttcagcc ggaccccgg caagtga                                          1287

<210> SEQ ID NO 8
<211> LENGTH: 428
<212> TYPE: PRT
<213> ORGANISM: Artificial Sequence
<220> FEATURE:
<223> OTHER INFORMATION: Synthetic polypeptide

<400> SEQUENCE: 8

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160
```

Val Glu Leu Leu Val Leu Gly Arg Thr Gly Leu Leu Ala Asp Leu Leu
            165                 170                 175

Pro Ser Phe Ala Val Glu Ile Met Gly Ser Glu Asn Leu Tyr Phe Gln
        180                 185                 190

Gly Ser Gly Glu Pro Arg Gly Pro Thr Ile Lys Pro Cys Pro Pro Cys
        195                 200                 205

Lys Cys Pro Ala Pro Asn Leu Leu Gly Gly Pro Ser Val Phe Ile Phe
        210                 215                 220

Pro Pro Lys Ile Lys Asp Val Leu Met Ile Ser Leu Ser Pro Ile Val
225                 230                 235                 240

Thr Cys Val Val Val Asp Val Ser Glu Asp Asp Pro Asp Val Gln Ile
                245                 250                 255

Ser Trp Phe Val Asn Asn Val Glu Val His Thr Ala Gln Thr Gln Thr
            260                 265                 270

His Arg Glu Asp Tyr Asn Ser Thr Leu Arg Val Val Ser Ala Leu Pro
        275                 280                 285

Ile Gln His Gln Asp Trp Met Ser Gly Lys Glu Phe Lys Cys Lys Val
        290                 295                 300

Asn Asn Lys Asp Leu Pro Ala Pro Ile Glu Arg Thr Ile Ser Lys Pro
305                 310                 315                 320

Lys Gly Ser Val Arg Ala Pro Gln Val Tyr Val Leu Pro Pro Pro Glu
                325                 330                 335

Glu Glu Met Thr Lys Lys Gln Val Thr Leu Thr Cys Met Val Thr Asp
            340                 345                 350

Phe Met Pro Glu Asp Ile Tyr Val Glu Trp Thr Asn Asn Gly Lys Thr
        355                 360                 365

Glu Leu Asn Tyr Lys Asn Thr Glu Pro Val Leu Asp Ser Asp Gly Ser
    370                 375                 380

Tyr Phe Met Tyr Ser Lys Leu Arg Val Glu Lys Lys Asn Trp Val Glu
385                 390                 395                 400

Arg Asn Ser Tyr Ser Cys Ser Val Val His Glu Gly Leu His Asn His
                405                 410                 415

His Thr Thr Lys Ser Phe Ser Arg Thr Pro Gly Lys
            420                 425

<210> SEQ ID NO 9
<211> LENGTH: 524
<212> TYPE: DNA
<213> ORGANISM: Artificial Sequence
<220> FEATURE:
<223> OTHER INFORMATION: Synthetic polynucleotide

<400> SEQUENCE: 9
gtgagtacag tgaccgctgg ggagacagag cgatcgagag aaatgtctac ctctctacct      60
gacagctgtg tgcgctgggt tcctcctcca cctcctgtcc tgccacccc aagattggtc     120 attccagact cttctccgct gggtgcccct ggcctcaggg atgaccattc tcatttgcct     180
tttcacctac atacacctct ccacacttct tatccatatc tatcactcca tgcatttgga     240
attctcatgg acactattga taaaatggaa gggcaggttt ggcgtggtga ggttgtggtg     300
taagactgtt ccctctccct ggggcattca aactagagga aaccttctct ggtcgttccc     360
ttcccatgca gagaagttcc ttttatatg agaagagtgt gcaaactgtg gcctttgggc      420
acccacccag ccacagattt gttttattta ctcccatgat gacatgggcc acaatagggc     480
ctagttctta tttgaggatt cacaattttt accttactgg ccaa                       524

<210> SEQ ID NO 10
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 10
gcaggacagg gctgcttgct gatctcttgc ccagttttgc tgtggagatt atgccag    57

<210> SEQ ID NO 11
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 11
agtgggtgtt tgttggcctg gtgctcctgg gcgtcttcct cttcttcgtc ctggtgggga    60
t                                                                     61

<210> SEQ ID NO 12
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 12
ctgctggtgc cagtgctgcc ctcacagctg ctgctgctat gtccgctgcc catgctgccc    60
agattc                                                                66

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
ctgctggtgc cctcaagcct                                                20

<210> SEQ ID NO 14
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 14

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Gly Ser Leu Gly Leu Leu
    130                 135                 140

Val Leu Gly Arg Thr Gly Leu Leu Ala Asp Leu Leu Pro Ser Phe Ala
145                 150                 155                 160

Val Glu Ile Met

<210> SEQ ID NO 15
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 15

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Gly Ser Leu Gly Leu Leu
    130                 135                 140

Val Leu Glu Trp Val
145

<210> SEQ ID NO 16
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 16
ctagctagcc accatggata gggtcttgct gag                                    33

<210> SEQ ID NO 17
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 17
cgcggatccc ataatctcca cagcaaaac                                         29

<210> SEQ ID NO 18
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 18

Cys Glu Tyr Ser Asp Arg Trp Gly Asp Arg Ala Ile Glu Arg Asn Val
1               5                   10                  15

Tyr Leu Ser Thr
            20

<210> SEQ ID NO 19
<211> LENGTH: 184
<212> TYPE: PRT
<213> ORGANISM: Artificial Sequence
<220> FEATURE:
<223> OTHER INFORMATION: Synthetic polypeptide

<400> SEQUENCE: 19

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Val Ala
                20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
                100                 105                 110

Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
        130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met
            180

<210> SEQ ID NO 20
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 20

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val

```
            35                  40                  45
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 21
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 21

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
```

165                 170                 175
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
            210                 215

<210> SEQ ID NO 22
<211> LENGTH: 416
<212> TYPE: PRT
<213> ORGANISM: Artificial Sequence
<220> FEATURE:
<223> OTHER INFORMATION: Synthetic polypeptide

<400> SEQUENCE: 22

Met Asp Arg Val Leu Arg Trp Ile Ser Leu Phe Trp Leu Thr Ala
1               5                   10                  15

Met Val Glu Gly Leu Gln Val Thr Val Pro Asp Lys Lys Val Ala
            20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Glu Pro Lys Ser Cys Asp Lys Thr
            180                 185                 190

His Thr Cys Pro Pro Cys Pro Ala Pro Glu Leu Leu Gly Gly Pro Ser
            195                 200                 205

Val Phe Leu Phe Pro Pro Lys Pro Lys Asp Thr Leu Met Ile Ser Arg
    210                 215                 220

Thr Pro Glu Val Thr Cys Val Val Val Asp Val Ser His Glu Asp Pro
225                 230                 235                 240

Glu Val Lys Phe Asn Trp Tyr Val Asp Gly Val Glu Val His Asn Ala
                245                 250                 255

Lys Thr Lys Pro Arg Glu Glu Gln Tyr Asn Ser Thr Tyr Arg Val Val
            260                 265                 270

Ser Val Leu Thr Val Leu His Gln Asp Trp Leu Asn Gly Lys Glu Tyr
            275                 280                 285

Lys Cys Lys Val Ser Asn Lys Ala Leu Pro Ala Pro Ile Glu Lys Thr
    290                 295                 300

Ile Ser Lys Ala Lys Gly Gln Pro Arg Glu Pro Gln Val Tyr Thr Leu

```
305                 310                 315                 320
Pro Pro Ser Arg Asp Glu Leu Thr Lys Asn Gln Val Ser Leu Thr Cys
                325                 330                 335

Leu Val Lys Gly Phe Tyr Pro Ser Asp Ile Ala Val Glu Trp Glu Ser
                340                 345                 350

Asn Gly Gln Pro Glu Asn Asn Tyr Lys Thr Thr Pro Pro Val Leu Asp
                355                 360                 365

Ser Asp Gly Ser Phe Phe Leu Tyr Ser Lys Leu Thr Val Asp Lys Ser
    370                 375                 380

Arg Trp Gln Gln Gly Asn Val Phe Ser Cys Ser Val Met His Glu Ala
385                 390                 395                 400

Leu His Asn His Tyr Thr Gln Lys Ser Leu Ser Leu Ser Pro Gly Lys
                405                 410                 415

<210> SEQ ID NO 23
<211> LENGTH: 411
<212> TYPE: PRT
<213> ORGANISM: Artificial Sequence
<220> FEATURE:
<223> OTHER INFORMATION: Synthetic polypeptide

<400> SEQUENCE: 23

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
                20                  25                  30

Met Leu Phe Gln Pro Thr Val Leu Arg Cys His Phe Ser Thr Ser Ser
                35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
                100                 105                 110

Leu Gly Asp Phe Tyr Arg Gly Arg Glu Ile Thr Ile Val His Asp Ala
                115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Asp Leu Leu
                165                 170                 175

Pro Ser Phe Ala Val Glu Ile Met Asp Lys Thr His Thr Cys Pro Pro
                180                 185                 190

Cys Pro Ala Pro Glu Leu Leu Gly Gly Pro Ser Val Phe Leu Phe Pro
                195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
```

```
                260                 265                 270
Leu His Gln Asp Trp Leu Asn Gly Lys Glu Tyr Lys Cys Lys Val Ser
            275                 280                 285

Asn Lys Ala Leu Pro Ala Pro Ile Glu Lys Thr Ile Ser Lys Ala Lys
        290                 295                 300

Gly Gln Pro Arg Glu Pro Gln Val Tyr Thr Leu Pro Pro Ser Arg Asp
305                 310                 315                 320

Glu Leu Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
370                 375                 380

Asn Val Phe Ser Cys Ser Val Met His Glu Ala Leu His Asn His Tyr
                385                 390                 395                 400

Thr Gln Lys Ser Leu Ser Leu Ser Pro Gly Lys
            405                 410
```

<210> SEQ ID NO 24
<211> LENGTH: 2
<212> TYPE: PRT
<213> ORGANISM: Artificial Sequence
<220> FEATURE:
<223> OTHER INFORMATION: Synthetic polypeptide

<400> SEQUENCE: 24

Gly Ser
1

<210> SEQ ID NO 25
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 25

Gly Ser Gly Ser
1

<210> SEQ ID NO 26
<211> LENGTH: 2
<212> TYPE: PRT
<213> ORGANISM: Artificial Sequence
<220> FEATURE:
<223> OTHER INFORMATION: Synthetic polypeptide

<400> SEQUENCE: 26

Ala Ser
1

<210> SEQ ID NO 27
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 27

Gly Gly Gly Ser

<210> SEQ ID NO 28
<211> LENGTH: 169
<212> TYPE: PRT
<213> ORGANISM: Artificial Sequence
<220> FEATURE:
<223> OTHER INFORMATION: Synthetic polypeptide

<400> SEQUENCE: 28

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Val Ala
            20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Leu Glu Gly Lys Asn Glu Gly Ser
145                 150                 155                 160

Leu Gly Leu Leu Val Leu Glu Trp Val
                165

<210> SEQ ID NO 29
<211> LENGTH: 147
<212> TYPE: PRT
<213> ORGANISM: Artificial Sequence
<220> FEATURE:
<223> OTHER INFORMATION: Synthetic polypeptide

<400> SEQUENCE: 29

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

```
Thr Pro Asp Asp Leu Glu Gly Lys Asn Glu Asp Ser Val Glu Leu Leu
    130                 135                 140

Val Leu Gly
145
```

<210> SEQ ID NO 30
<211> LENGTH: 104
<212> TYPE: PRT
<213> ORGANISM: Artificial Sequence
<220> FEATURE:
<223> OTHER INFORMATION: Synthetic polypeptide

<400> SEQUENCE: 30

```
Cys His Phe Ser Thr Ser Ser His Gln Pro Ala Val Val Gln Trp Lys
1               5                   10                  15

Phe Lys Ser Tyr Cys Gln Asp Arg Met Gly Glu Ser Leu Gly Met Ser
            20                  25                  30

Ser Thr Arg Ala Gln Ser Leu Ser Lys Arg Asn Leu Glu Trp Asp Pro
        35                  40                  45

Tyr Leu Asp Cys Leu Asp Ser Arg Arg Thr Val Arg Val Ala Ser
    50                  55                  60

Lys Gln Gly Ser Thr Val Thr Leu Gly Asp Phe Tyr Arg Gly Arg Glu
65                  70                  75                  80

Ile Thr Ile Val His Asp Ala Asp Leu Gln Ile Gly Lys Leu Met Trp
                85                  90                  95

Gly Asp Ser Gly Leu Tyr Tyr Cys
            100
```

<210> SEQ ID NO 31
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 31

```
Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175
```

-continued

Tyr Lys Asn Thr Glu Pro Val Leu Asp Ser Asp Gly Ser Tyr Phe Met
            180                 185                 190

Tyr Ser Lys Leu Arg Val Glu Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230

<210> SEQ ID NO 32
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 32

Gly Gly Gly Gly Ser Gly Gly Gly Gly Ser Gly Gly Gly Gly Ser
1               5                   10                  15

<210> SEQ ID NO 33
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 33

Gly Gly Gly Gly Ser Gly Gly Gly Gly Ser Gly Gly Gly Gly Ser Gly
1               5                   10                  15

Gly Gly Gly Ser
            20

<210> SEQ ID NO 34
<211> LENGTH: 235
<212> TYPE: PRT
<213> ORGANISM: Artificial Sequence
<220> FEATURE:
<223> OTHER INFORMATION: Synthetic polypeptide

<400> SEQUENCE: 34

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

```
Cys Ile Ile Thr Thr Pro Asp Asp Leu Glu Gly Lys Asn Glu Asp Ser
145                 150                 155                 160

Val Glu Leu Leu Val Leu Glu Trp Val Phe Val Gly Leu Val Leu Leu
                165                 170                 175

Gly Val Phe Leu Phe Phe Val Leu Val Gly Ile Cys Trp Cys Gln Cys
                180                 185                 190

Cys Pro His Ser Cys Cys Cys Tyr Val Arg Cys Pro Cys Cys Pro Asp
            195                 200                 205

Ser Cys Cys Cys Pro Gln Ala Cys Glu Tyr Ser Asp Arg Trp Gly Asp
    210                 215                 220

Arg Ala Ile Glu Arg Asn Val Tyr Leu Ser Thr
225                 230                 235

<210> SEQ ID NO 35
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 35

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Gly Arg Thr Gly Leu Leu Ala Asp Leu Leu Pro Ser Phe Ala
145                 150                 155                 160

Val Glu Ile Met

<210> SEQ ID NO 36
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 36

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45
```

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
 65                  70                  75                  80

Arg Val Val Ala Ser Lys Gln Gly Ser Thr Val Thr Leu Gly Asp Phe
                 85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Glu Trp Val
145

<210> SEQ ID NO 37
<211> LENGTH: 184
<212> TYPE: PRT
<213> ORGANISM: Artificial Sequence
<220> FEATURE:
<223> OTHER INFORMATION: Synthetic polypeptide

<400> SEQUENCE: 37

Met Asp Arg Val Leu Leu Arg Trp Ile Ser Leu Phe Trp Leu Thr Ala
 1               5                  10                  15

Met Val Glu Gly Leu Gln Val Thr Val Pro Asp Lys Lys Val Ala
                 20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
 65                  70                  75                  80

Ser Lys Arg Asn Leu Glu Trp Asp Pro Tyr Leu Asp Cys Leu Asp Ser
                 85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
130                 135                 140

Cys Ile Ile Thr Thr Pro Asp Asp Leu Glu Gly Lys Asn Glu Gly Ser
145                 150                 155                 160

Leu Gly Leu Leu Val Leu Gly Arg Thr Gly Leu Leu Ala Asp Leu Leu
                165                 170                 175

Pro Ser Phe Ala Val Glu Ile Met
            180

<210> SEQ ID NO 38
<211> LENGTH: 416
<212> TYPE: PRT
<213> ORGANISM: Artificial Sequence
<220> FEATURE:
<223> OTHER INFORMATION: Synthetic polypeptide

<400> SEQUENCE: 38

Met Asp Arg Val Leu Leu Arg Trp Ile Ser Leu Phe Trp Leu Thr Ala
 1               5                  10                  15

Met Val Glu Gly Leu Gln Val Thr Val Pro Asp Lys Lys Val Ala
              20                  25                  30

Met Leu Phe Gln Pro Thr Val Leu Arg Cys His Phe Ser Thr Ser Ser
          35                  40                  45

His Gln Pro Ala Val Val Gln Trp Lys Phe Lys Ser Tyr Cys Gln Asp
 50                  55                  60

Arg Met Gly Glu Ser Leu Gly Met Ser Ser Thr Arg Ala Gln Ser Leu
 65                  70                  75                  80

Ser Lys Arg Asn Leu Glu Trp Asp Pro Tyr Leu Asp Cys Leu Asp Ser
              85                  90                  95

Arg Arg Thr Val Arg Val Ala Ser Lys Gln Gly Ser Thr Val Thr
             100                 105                 110

Leu Gly Asp Phe Tyr Arg Gly Arg Glu Ile Thr Ile Val His Asp Ala
         115                 120                 125

Asp Leu Gln Ile Gly Lys Leu Met Trp Gly Asp Ser Gly Leu Tyr Tyr
 130                 135                 140

Cys Ile Ile Thr Thr Pro Asp Asp Leu Glu Gly Lys Asn Glu Gly Ser
145                 150                 155                 160

Leu Gly Leu Leu Val Leu Gly Arg Thr Gly Leu Leu Ala Asp Leu Leu
             165                 170                 175

Pro Ser Phe Ala Val Glu Ile Met Glu Pro Lys Ser Cys Asp Lys Thr
         180                 185                 190

His Thr Cys Pro Pro Cys Pro Ala Pro Glu Leu Leu Gly Gly Pro Ser
     195                 200                 205

Val Phe Leu Phe Pro Pro Lys Pro Lys Asp Thr Leu Met Ile Ser Arg
 210                 215                 220

Thr Pro Glu Val Thr Cys Val Val Val Asp Val Ser His Glu Asp Pro
225                 230                 235                 240

Glu Val Lys Phe Asn Trp Tyr Val Asp Gly Val Glu Val His Asn Ala
             245                 250                 255

Lys Thr Lys Pro Arg Glu Glu Gln Tyr Asn Ser Thr Tyr Arg Val Val
         260                 265                 270

Ser Val Leu Thr Val Leu His Gln Asp Trp Leu Asn Gly Lys Glu Tyr
     275                 280                 285

Lys Cys Lys Val Ser Asn Lys Ala Leu Pro Ala Pro Ile Glu Lys Thr
 290                 295                 300

Ile Ser Lys Ala Lys Gly Gln Pro Arg Glu Pro Gln Val Tyr Thr Leu
305                 310                 315                 320

Pro Pro Ser Arg Asp Glu Leu Thr Lys Asn Gln Val Ser Leu Thr Cys
             325                 330                 335

Leu Val Lys Gly Phe Tyr Pro Ser Asp Ile Ala Val Glu Trp Glu Ser
         340                 345                 350

Asn Gly Gln Pro Glu Asn Asn Tyr Lys Thr Thr Pro Pro Val Leu Asp
     355                 360                 365

Ser Asp Gly Ser Phe Phe Leu Tyr Ser Lys Leu Thr Val Asp Lys Ser
 370                 375                 380

Arg Trp Gln Gln Gly Asn Val Phe Ser Cys Ser Val Met His Glu Ala
385                 390                 395                 400

Leu His Asn His Tyr Thr Gln Lys Ser Leu Ser Leu Ser Pro Gly Lys
             405                 410                 415

<210> SEQ ID NO 39
<211> LENGTH: 411

<212> TYPE: PRT
<213> ORGANISM: Artificial Sequence
<220> FEATURE:
<223> OTHER INFORMATION: Synthetic polypeptide

<400> SEQUENCE: 39

```
Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Val Ala
            20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Ala Ser Lys Gln Gly Ser Thr Val Thr
            100                 105                 110

Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Gly Ser
145                 150                 155                 160

Leu Gly Leu Leu Val Leu Gly Arg Thr Gly Leu Leu Ala Asp Leu Leu
                165                 170                 175

Pro Ser Phe Ala Val Glu Ile Met Asp Lys Thr His Thr Cys Pro Pro
            180                 185                 190

Cys Pro Ala Pro Glu Leu Leu Gly Gly Pro Ser Val Phe Leu Phe Pro
            195                 200                 205

Pro Lys Pro Lys Asp Thr Leu Met Ile Ser Arg Thr Pro Glu Val Thr
    210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
    275                 280                 285

Asn Lys Ala Leu Pro Ala Pro Ile Glu Lys Thr Ile Ser Lys Ala Lys
290                 295                 300

Gly Gln Pro Arg Glu Pro Gln Val Tyr Thr Leu Pro Pro Ser Arg Asp
305                 310                 315                 320

Glu Leu Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
    355                 360                 365

Phe Leu Tyr Ser Lys Leu Thr Val Asp Lys Ser Arg Trp Gln Gln Gly
370                 375                 380
```

Asn Val Phe Ser Cys Ser Val Met His Glu Ala Leu His Asn His Tyr
385                 390                 395                 400

Thr Gln Lys Ser Leu Ser Leu Ser Pro Gly Lys
            405                 410

<210> SEQ ID NO 40
<211> LENGTH: 169
<212> TYPE: PRT
<213> ORGANISM: Artificial Sequence
<220> FEATURE:
<223> OTHER INFORMATION: Synthetic polypeptide

<400> SEQUENCE: 40

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Val Ala
            20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Ala Ser Lys Gln Gly Ser Thr Val Thr
            100                 105                 110

Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
130                 135                 140

Cys Ile Ile Thr Thr Pro Asp Asp Leu Glu Gly Lys Asn Glu Asp Ser
145                 150                 155                 160

Val Glu Leu Leu Val Leu Glu Trp Val
                165

<210> SEQ ID NO 41
<211> LENGTH: 147
<212> TYPE: PRT
<213> ORGANISM: Artificial Sequence
<220> FEATURE:
<223> OTHER INFORMATION: Synthetic polypeptide

<400> SEQUENCE: 41

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

```
Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Gly Ser Leu Gly Leu Leu
        130                 135                 140

Val Leu Gly
145

<210> SEQ ID NO 42
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 42

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

<210> SEQ ID NO 43
<211> LENGTH: 145
<212> TYPE: PRT
<213> ORGANISM: Artificial Sequence
<220> FEATURE:
<223> OTHER INFORMATION: Synthetic polypeptide

<400> SEQUENCE: 43

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
```

```
                 115                 120                 125
Thr Pro Asp Asp Leu Glu Gly Lys Asn Glu Asp Ser Val Glu Leu Leu
    130                 135                 140
Val
145

<210> SEQ ID NO 44
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 44

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
    130                 135                 140

Val Leu
145

<210> SEQ ID NO 45
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 45

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110
```

```
Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Leu Leu Ala Asp Leu Leu Pro Ser Gly Gly
145                 150                 155                 160

Val Glu Ile Met

<210> SEQ ID NO 46
<211> LENGTH: 148
<212> TYPE: PRT
<213> ORGANISM: Artificial Sequence
<220> FEATURE:
<223> OTHER INFORMATION: Synthetic polypeptide

<400> SEQUENCE: 46

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg
145

<210> SEQ ID NO 47
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 47

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95
```

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr
145

<210> SEQ ID NO 48
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 48

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly
145                 150

<210> SEQ ID NO 49
<211> LENGTH: 151
<212> TYPE: PRT
<213> ORGANISM: Artificial Sequence
<220> FEATURE:
<223> OTHER INFORMATION: Synthetic polypeptide

<400> SEQUENCE: 49

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu
145                 150

<210> SEQ ID NO 50
<211> LENGTH: 152
<212> TYPE: PRT
<213> ORGANISM: Artificial Sequence
<220> FEATURE:
<223> OTHER INFORMATION: Synthetic polypeptide

<400> SEQUENCE: 50

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu
145                 150

<210> SEQ ID NO 51
<211> LENGTH: 153
<212> TYPE: PRT
<213> ORGANISM: Artificial Sequence
<220> FEATURE:
<223> OTHER INFORMATION: Synthetic polypeptide

<400> SEQUENCE: 51

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe

```
                    85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Gly Arg Thr Gly Leu Leu Ala
145                 150

<210> SEQ ID NO 52
<211> LENGTH: 154
<212> TYPE: PRT
<213> ORGANISM: Artificial Sequence
<220> FEATURE:
<223> OTHER INFORMATION: Synthetic polypeptide

<400> SEQUENCE: 52

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Gly Arg Thr Gly Leu Leu Ala Asp
145                 150

<210> SEQ ID NO 53
<211> LENGTH: 155
<212> TYPE: PRT
<213> ORGANISM: Artificial Sequence
<220> FEATURE:
<223> OTHER INFORMATION: Synthetic polypeptide

<400> SEQUENCE: 53

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80
```

```
Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu
145                 150                 155

<210> SEQ ID NO 54
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 54

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu
145                 150                 155

<210> SEQ ID NO 55
<211> LENGTH: 157
<212> TYPE: PRT
<213> ORGANISM: Artificial Sequence
<220> FEATURE:
<223> OTHER INFORMATION: Synthetic polypeptide

<400> SEQUENCE: 55

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80
```

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro
145                 150                 155

<210> SEQ ID NO 56
<211> LENGTH: 158
<212> TYPE: PRT
<213> ORGANISM: Artificial Sequence
<220> FEATURE:
<223> OTHER INFORMATION: Synthetic polypeptide

<400> SEQUENCE: 56

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser
145                 150                 155

<210> SEQ ID NO 57
<211> LENGTH: 159
<212> TYPE: PRT
<213> ORGANISM: Artificial Sequence
<220> FEATURE:
<223> OTHER INFORMATION: Synthetic polypeptide

<400> SEQUENCE: 57

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val

```
                65                  70                  75                  80
Arg Val Val Ala Ser Lys Gln Gly Ser Thr Val Thr Leu Gly Asp Phe
                    85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
                115                 120                 125

Thr Pro Asp Asp Leu Glu Gly Lys Asn Glu Asp Ser Val Glu Leu Leu
            130                 135                 140

Val Leu Gly Arg Thr Gly Leu Leu Ala Asp Leu Leu Pro Ser Phe
145                 150                 155

<210> SEQ ID NO 58
<211> LENGTH: 160
<212> TYPE: PRT
<213> ORGANISM: Artificial Sequence
<220> FEATURE:
<223> OTHER INFORMATION: Synthetic polypeptide

<400> SEQUENCE: 58

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                    85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
                115                 120                 125

Thr Pro Asp Asp Leu Glu Gly Lys Asn Glu Asp Ser Val Glu Leu Leu
            130                 135                 140

Val Leu Gly Arg Thr Gly Leu Leu Ala Asp Leu Leu Pro Ser Phe Ala
145                 150                 155                 160

<210> SEQ ID NO 59
<211> LENGTH: 161
<212> TYPE: PRT
<213> ORGANISM: Artificial Sequence
<220> FEATURE:
<223> OTHER INFORMATION: Synthetic polypeptide

<400> SEQUENCE: 59

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
50                  55                  60
```

```
Leu Glu Trp Asp Pro Tyr Leu Asp Cys Leu Asp Ser Arg Arg Thr Val
 65                  70                  75                  80

Arg Val Val Ala Ser Lys Gln Gly Ser Thr Val Thr Leu Gly Asp Phe
                 85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Ala
145                 150                 155                 160

Val

<210> SEQ ID NO 60
<211> LENGTH: 162
<212> TYPE: PRT
<213> ORGANISM: Artificial Sequence
<220> FEATURE:
<223> OTHER INFORMATION: Synthetic polypeptide

<400> SEQUENCE: 60

Leu Gln Val Thr Val Pro Asp Lys Lys Val Ala Met Leu Phe Gln
 1               5                  10                  15

Pro Thr Val Leu Arg Cys His Phe Ser Thr Ser Ser His Gln Pro Ala
                 20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
 65                  70                  75                  80

Arg Val Val Ala Ser Lys Gln Gly Ser Thr Val Thr Leu Gly Asp Phe
                 85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Ala
145                 150                 155                 160

Val Glu

<210> SEQ ID NO 61
<211> LENGTH: 163
<212> TYPE: PRT
<213> ORGANISM: Artificial Sequence
<220> FEATURE:
<223> OTHER INFORMATION: Synthetic polypeptide

<400> SEQUENCE: 61

Leu Gln Val Thr Val Pro Asp Lys Lys Val Ala Met Leu Phe Gln
 1               5                  10                  15

Pro Thr Val Leu Arg Cys His Phe Ser Thr Ser Ser His Gln Pro Ala
                 20                  25                  30

Val Val Gln Trp Lys Phe Lys Ser Tyr Cys Gln Asp Arg Met Gly Glu
```

```
                35                  40                  45
Ser Leu Gly Met Ser Ser Thr Arg Ala Gln Ser Leu Ser Lys Arg Asn
 50                  55                  60

Leu Glu Trp Asp Pro Tyr Leu Asp Cys Leu Asp Ser Arg Arg Thr Val
 65                  70                  75                  80

Arg Val Val Ala Ser Lys Gln Gly Ser Thr Val Thr Leu Gly Asp Phe
                 85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
                115                 120                 125

Thr Pro Asp Asp Leu Glu Gly Lys Asn Glu Asp Ser Val Glu Leu Leu
                130                 135                 140

Val Leu Gly Arg Thr Gly Leu Leu Ala Asp Leu Leu Pro Ser Phe Ala
145                 150                 155                 160

Val Glu Ile

<210> SEQ ID NO 62
<211> LENGTH: 166
<212> TYPE: PRT
<213> ORGANISM: Artificial Sequence
<220> FEATURE:
<223> OTHER INFORMATION: Synthetic polypeptide

<400> SEQUENCE: 62

Leu Gln Val Thr Val Pro Asp Lys Lys Val Ala Met Leu Phe Gln
  1               5                  10                  15

Pro Thr Val Leu Arg Cys His Phe Ser Thr Ser Ser His Gln Pro Ala
                 20                  25                  30

Val Val Gln Trp Lys Phe Lys Ser Tyr Cys Gln Asp Arg Met Gly Glu
                 35                  40                  45

Ser Leu Gly Met Ser Ser Thr Arg Ala Gln Ser Leu Ser Lys Arg Asn
 50                  55                  60

Leu Glu Trp Asp Pro Tyr Leu Asp Cys Leu Asp Ser Arg Arg Thr Val
 65                  70                  75                  80

Arg Val Val Ala Ser Lys Gln Gly Ser Thr Val Thr Leu Gly Asp Phe
                 85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
                115                 120                 125

Thr Pro Asp Asp Leu Glu Gly Lys Asn Glu Asp Ser Val Glu Leu Leu
                130                 135                 140

Val Leu Gly Arg Thr Gly Leu Leu Ala Asp Leu Leu Pro Ser Phe Ala
145                 150                 155                 160

Val Glu Ile Met Pro Glu
                165

<210> SEQ ID NO 63
<211> LENGTH: 165
<212> TYPE: PRT
<213> ORGANISM: Artificial Sequence
<220> FEATURE:
<223> OTHER INFORMATION: Synthetic polypeptide

<400> SEQUENCE: 63

Leu Gln Val Thr Val Pro Asp Lys Lys Val Ala Met Leu Phe Gln
```

```
            1               5                   10                  15
        Pro Thr Val Leu Arg Cys His Phe Ser Thr Ser Ser His Gln Pro Ala
                        20                  25                  30
        Val Val Gln Trp Lys Phe Lys Ser Tyr Cys Gln Asp Arg Met Gly Glu
                        35                  40                  45
        Ser Leu Gly Met Ser Ser Thr Arg Ala Gln Ser Leu Ser Lys Arg Asn
                        50                  55                  60
        Leu Glu Trp Asp Pro Tyr Leu Asp Cys Leu Asp Ser Arg Arg Thr Val
        65                  70                  75                  80
        Arg Val Val Ala Ser Lys Gln Gly Ser Thr Val Thr Leu Gly Asp Phe
                        85                  90                  95
        Tyr Arg Gly Arg Glu Ile Thr Ile Val His Asp Ala Asp Leu Gln Ile
                        100                 105                 110
        Gly Lys Leu Met Trp Gly Asp Ser Gly Leu Tyr Tyr Cys Ile Ile Thr
                        115                 120                 125
        Thr Pro Asp Asp Leu Glu Gly Lys Asn Glu Asp Ser Val Glu Leu Leu
                        130                 135                 140
        Val Leu Gly Arg Thr Gly Leu Leu Ala Asp Leu Leu Pro Ser Phe Ala
        145                 150                 155                 160
        Val Glu Ile Met Pro
                        165

<210> SEQ ID NO 64
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 64

Leu Gln Val Thr Val Pro Asp Lys Lys Lys Val Ala Met Leu Phe Gln
        1               5                   10                  15
        Pro Thr Val Leu Arg Cys His Phe Ser Thr Ser Ser His Gln Pro Ala
                        20                  25                  30
        Val Val Gln Trp Lys Phe Lys Ser Tyr Cys Gln Asp Arg Met Gly Glu
                        35                  40                  45
        Ser Leu Gly Met Ser Ser Thr Arg Ala Gln Ser Leu Ser Lys Arg Asn
                        50                  55                  60
        Leu Glu Trp Asp Pro Tyr Leu Asp Cys Leu Asp Ser Arg Arg Thr Val
        65                  70                  75                  80
        Arg Val Val Ala Ser Lys Gln Gly Ser Thr Val Thr Leu Gly Asp Phe
                        85                  90                  95
        Tyr Arg Gly Arg Glu Ile Thr Ile Val His Asp Ala Asp Leu Gln Ile
                        100                 105                 110
        Gly Lys Leu Met Trp Gly Asp Ser Gly Leu Tyr Tyr Cys Ile Ile Thr
                        115                 120                 125
        Thr Pro Asp Asp Leu Glu Gly Lys Asn Glu Asp Ser Val Glu Leu Leu
                        130                 135                 140
        Val Leu Gly Arg Thr Gly Leu Leu Ala Asp Leu Leu Pro Ser Gly Ala
        145                 150                 155                 160
        Val Glu Ile Met

<210> SEQ ID NO 65
<211> LENGTH: 167
<212> TYPE: PRT
<213> ORGANISM: Artificial Sequence
```

```
<220> FEATURE:
<223> OTHER INFORMATION: Synthetic polypeptide

<400> SEQUENCE: 65

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Leu Leu Ala Asp Leu Leu Pro Ser Phe Ala
145                 150                 155                 160

Val Glu Ile Met Pro Glu Trp
                165

<210> SEQ ID NO 66
<211> LENGTH: 168
<212> TYPE: PRT
<213> ORGANISM: Artificial Sequence
<220> FEATURE:
<223> OTHER INFORMATION: Synthetic polypeptide

<400> SEQUENCE: 66

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Leu Leu Ala Asp Leu Leu Pro Ser Phe Ala
145                 150                 155                 160

Val Glu Ile Met Pro Glu Trp Val
```

<210> SEQ ID NO 67
<211> LENGTH: 169
<212> TYPE: PRT
<213> ORGANISM: Artificial Sequence
<220> FEATURE:
<223> OTHER INFORMATION: Synthetic polypeptide

<400> SEQUENCE: 67

```
Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Leu Leu Ala Asp Leu Leu Pro Ser Phe Ala
145                 150                 155                 160

Val Glu Ile Met Pro Glu Trp Val Phe
                165
```

<210> SEQ ID NO 68
<211> LENGTH: 138
<212> TYPE: PRT
<213> ORGANISM: Artificial Sequence
<220> FEATURE:
<223> OTHER INFORMATION: Synthetic polypeptide

<400> SEQUENCE: 68

```
Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
            115                 120                 125
```

Gly Lys Asn Glu Asp Ser Val Glu Leu Leu
    130                 135

<210> SEQ ID NO 69
<211> LENGTH: 139
<212> TYPE: PRT
<213> ORGANISM: Artificial Sequence
<220> FEATURE:
<223> OTHER INFORMATION: Synthetic polypeptide

<400> SEQUENCE: 69

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val
    130                 135

<210> SEQ ID NO 70
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 70

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu
    130                 135                 140

<210> SEQ ID NO 71

<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 71

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly
    130                 135                 140

<210> SEQ ID NO 72
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 72

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg
    130                 135                 140

<210> SEQ ID NO 73
<211> LENGTH: 143
<212> TYPE: PRT
<213> ORGANISM: Artificial Sequence
<220> FEATURE:
<223> OTHER INFORMATION: Synthetic polypeptide

<400> SEQUENCE: 73

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr
    130                 135                 140

<210> SEQ ID NO 74
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 74

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

<210> SEQ ID NO 75
<211> LENGTH: 145
<212> TYPE: PRT
<213> ORGANISM: Artificial Sequence
<220> FEATURE:
<223> OTHER INFORMATION: Synthetic polypeptide

<400> SEQUENCE: 75

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu
145

<210> SEQ ID NO 76
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 76

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu
145

<210> SEQ ID NO 77
<211> LENGTH: 147
<212> TYPE: PRT
<213> ORGANISM: Artificial Sequence
<220> FEATURE:
<223> OTHER INFORMATION: Synthetic polypeptide

<400> SEQUENCE: 77

Asp Lys Lys Lys Val Ala Met Leu Phe Gln Pro Thr Val Leu Arg Cys

```
                  1               5                  10                  15
His Phe Ser Thr Ser Ser His Gln Pro Ala Val Val Gln Trp Lys Phe
                 20                  25                  30

Lys Ser Tyr Cys Gln Asp Arg Met Gly Glu Ser Leu Gly Met Ser Ser
             35                  40                  45

Thr Arg Ala Gln Ser Leu Ser Lys Arg Asn Leu Glu Trp Asp Pro Tyr
         50                  55                  60

Leu Asp Cys Leu Asp Ser Arg Arg Thr Val Arg Val Val Ala Ser Lys
 65                  70                  75                  80

Gln Gly Ser Thr Val Thr Leu Gly Asp Phe Tyr Arg Gly Arg Glu Ile
                 85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
                115                 120                 125

Gly Lys Asn Glu Asp Ser Val Glu Leu Leu Val Leu Gly Arg Thr Gly
            130                 135                 140

Leu Leu Ala
145

<210> SEQ ID NO 78
<211> LENGTH: 148
<212> TYPE: PRT
<213> ORGANISM: Artificial Sequence
<220> FEATURE:
<223> OTHER INFORMATION: Synthetic polypeptide

<400> SEQUENCE: 78

Asp Lys Lys Val Ala Met Leu Phe Gln Pro Thr Val Leu Arg Cys
1               5                  10                  15

His Phe Ser Thr Ser Ser His Gln Pro Ala Val Val Gln Trp Lys Phe
                 20                  25                  30

Lys Ser Tyr Cys Gln Asp Arg Met Gly Glu Ser Leu Gly Met Ser Ser
             35                  40                  45

Thr Arg Ala Gln Ser Leu Ser Lys Arg Asn Leu Glu Trp Asp Pro Tyr
         50                  55                  60

Leu Asp Cys Leu Asp Ser Arg Arg Thr Val Arg Val Val Ala Ser Lys
 65                  70                  75                  80

Gln Gly Ser Thr Val Thr Leu Gly Asp Phe Tyr Arg Gly Arg Glu Ile
                 85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
                115                 120                 125

Gly Lys Asn Glu Asp Ser Val Glu Leu Leu Val Leu Gly Arg Thr Gly
            130                 135                 140

Leu Leu Ala Asp
145

<210> SEQ ID NO 79
<211> LENGTH: 149
<212> TYPE: PRT
<213> ORGANISM: Artificial Sequence
<220> FEATURE:
<223> OTHER INFORMATION: Synthetic polypeptide

<400> SEQUENCE: 79
```

```
Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
        50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
        130                 135                 140

Leu Leu Ala Asp Leu
145
```

<210> SEQ ID NO 80
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 80

```
Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
        50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
        130                 135                 140

Leu Leu Ala Asp Leu Leu
145                 150
```

<210> SEQ ID NO 81
<211> LENGTH: 151
<212> TYPE: PRT
<213> ORGANISM: Artificial Sequence
<220> FEATURE:
<223> OTHER INFORMATION: Synthetic polypeptide

<400> SEQUENCE: 81

-continued

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
        50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
        130                 135                 140

Leu Leu Ala Asp Leu Leu Pro
145                 150

<210> SEQ ID NO 82
<211> LENGTH: 152
<212> TYPE: PRT
<213> ORGANISM: Artificial Sequence
<220> FEATURE:
<223> OTHER INFORMATION: Synthetic polypeptide

<400> SEQUENCE: 82

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
        50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
        130                 135                 140

Leu Leu Ala Asp Leu Leu Pro Ser
145                 150

<210> SEQ ID NO 83
<211> LENGTH: 153
<212> TYPE: PRT
<213> ORGANISM: Artificial Sequence
<220> FEATURE:
<223> OTHER INFORMATION: Synthetic polypeptide

<400> SEQUENCE: 83

```
Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
        50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
        130                 135                 140

Leu Leu Ala Asp Leu Leu Pro Ser Phe
145                 150
```

<210> SEQ ID NO 84
<211> LENGTH: 154
<212> TYPE: PRT
<213> ORGANISM: Artificial Sequence
<220> FEATURE:
<223> OTHER INFORMATION: Synthetic polypeptide

<400> SEQUENCE: 84

```
Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
        50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
        130                 135                 140

Leu Leu Ala Asp Leu Leu Pro Ser Phe Ala
145                 150
```

<210> SEQ ID NO 85
<211> LENGTH: 155
<212> TYPE: PRT
<213> ORGANISM: Artificial Sequence
<220> FEATURE:
<223> OTHER INFORMATION: Synthetic polypeptide

<400> SEQUENCE: 85

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val
145                 150                 155

<210> SEQ ID NO 86
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 86

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu
145                 150                 155

<210> SEQ ID NO 87
<211> LENGTH: 157
<212> TYPE: PRT
<213> ORGANISM: Artificial Sequence
<220> FEATURE:

<223> OTHER INFORMATION: Synthetic polypeptide

<400> SEQUENCE: 87

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu Ile
145                 150                 155

<210> SEQ ID NO 88
<211> LENGTH: 158
<212> TYPE: PRT
<213> ORGANISM: Artificial Sequence
<220> FEATURE:
<223> OTHER INFORMATION: Synthetic polypeptide

<400> SEQUENCE: 88

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu Ile Met
145                 150                 155

<210> SEQ ID NO 89
<211> LENGTH: 159
<212> TYPE: PRT
<213> ORGANISM: Artificial Sequence
<220> FEATURE:
<223> OTHER INFORMATION: Synthetic polypeptide

<400> SEQUENCE: 89

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu Ile Met Pro
145                 150                 155

<210> SEQ ID NO 90
<211> LENGTH: 160
<212> TYPE: PRT
<213> ORGANISM: Artificial Sequence
<220> FEATURE:
<223> OTHER INFORMATION: Synthetic polypeptide

<400> SEQUENCE: 90

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu Ile Met Pro Glu
145                 150                 155                 160

<210> SEQ ID NO 91
<211> LENGTH: 161
<212> TYPE: PRT

<213> ORGANISM: Artificial Sequence
<220> FEATURE:
<223> OTHER INFORMATION: Synthetic polypeptide

<400> SEQUENCE: 91

```
Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu Ile Met Pro Glu
145                 150                 155                 160

Trp
```

<210> SEQ ID NO 92
<211> LENGTH: 162
<212> TYPE: PRT
<213> ORGANISM: Artificial Sequence
<220> FEATURE:
<223> OTHER INFORMATION: Synthetic polypeptide

<400> SEQUENCE: 92

```
Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu Ile Met Pro Glu
145                 150                 155                 160

Trp Val
```

<210> SEQ ID NO 93
<211> LENGTH: 163
<212> TYPE: PRT
<213> ORGANISM: Artificial Sequence
<220> FEATURE:
<223> OTHER INFORMATION: Synthetic polypeptide

<400> SEQUENCE: 93

```
Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu Ile Met Pro Glu
145                 150                 155                 160

Trp Val Phe
```

<210> SEQ ID NO 94
<211> LENGTH: 147
<212> TYPE: PRT
<213> ORGANISM: Artificial Sequence
<220> FEATURE:
<223> OTHER INFORMATION: Synthetic polypeptide

<400> SEQUENCE: 94

```
Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140
```

Val Leu Glu
145

<210> SEQ ID NO 95
<211> LENGTH: 148
<212> TYPE: PRT
<213> ORGANISM: Artificial Sequence
<220> FEATURE:
<223> OTHER INFORMATION: Synthetic polypeptide

<400> SEQUENCE: 95

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
    130                 135                 140

Val Leu Glu Trp
145

<210> SEQ ID NO 96
<211> LENGTH: 164
<212> TYPE: PRT
<213> ORGANISM: Artificial Sequence
<220> FEATURE:
<223> OTHER INFORMATION: Synthetic polypeptide

<400> SEQUENCE: 96

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu

```
                130                 135                 140
Val Leu Gly Arg Thr Gly Leu Ala Asp Leu Leu Pro Ser Ala Ala
145                 150                 155                 160

Val Glu Ile Met

<210> SEQ ID NO 97
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 97

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Glu Trp Val Phe
145                 150

<210> SEQ ID NO 98
<211> LENGTH: 151
<212> TYPE: PRT
<213> ORGANISM: Artificial Sequence
<220> FEATURE:
<223> OTHER INFORMATION: Synthetic polypeptide

<400> SEQUENCE: 98

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
```

```
                    115                 120                 125
Thr Pro Asp Asp Leu Glu Gly Lys Asn Glu Asp Ser Val Glu Leu Leu
    130                 135                 140

Val Leu Glu Trp Val Phe Val
145                 150

<210> SEQ ID NO 99
<211> LENGTH: 152
<212> TYPE: PRT
<213> ORGANISM: Artificial Sequence
<220> FEATURE:
<223> OTHER INFORMATION: Synthetic polypeptide

<400> SEQUENCE: 99

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Glu Trp Val Phe Val Gly
145                 150

<210> SEQ ID NO 100
<211> LENGTH: 141
<212> TYPE: PRT
<213> ORGANISM: Artificial Sequence
<220> FEATURE:
<223> OTHER INFORMATION: Synthetic polypeptide

<400> SEQUENCE: 100

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110
```

```
Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Glu
        130                 135                 140
```

<210> SEQ ID NO 101
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 101

```
Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Glu Trp
        130                 135                 140
```

<210> SEQ ID NO 102
<211> LENGTH: 143
<212> TYPE: PRT
<213> ORGANISM: Artificial Sequence
<220> FEATURE:
<223> OTHER INFORMATION: Synthetic polypeptide

<400> SEQUENCE: 102

```
Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Glu Trp Val
        130                 135                 140
```

<210> SEQ ID NO 103
<211> LENGTH: 144
<212> TYPE: PRT
<213> ORGANISM: Artificial Sequence
<220> FEATURE:
<223> OTHER INFORMATION: Synthetic polypeptide

<400> SEQUENCE: 103

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Glu Trp Val Phe
    130                 135                 140

<210> SEQ ID NO 104
<211> LENGTH: 145
<212> TYPE: PRT
<213> ORGANISM: Artificial Sequence
<220> FEATURE:
<223> OTHER INFORMATION: Synthetic polypeptide

<400> SEQUENCE: 104

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Glu Trp Val Phe
    130                 135                 140

Val
145

-continued

<210> SEQ ID NO 105
<211> LENGTH: 146
<212> TYPE: PRT
<213> ORGANISM: Artificial Sequence
<220> FEATURE:
<223> OTHER INFORMATION: Synthetic polypeptide

<400> SEQUENCE: 105

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Pro Asp Asp Leu Glu
        115                 120                 125

Gly Lys Asn Glu Asp Ser Val Glu Leu Leu Val Leu Glu Trp Val Phe
    130                 135                 140

Val Gly
145

<210> SEQ ID NO 106
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 106

Gly Gly Gly Gly Ser
1               5

<210> SEQ ID NO 107
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 107

Gly Gly Gly Gly Ser Gly Gly Gly Gly Ser
1               5                   10

<210> SEQ ID NO 108
<211> LENGTH: 408
<212> TYPE: PRT
<213> ORGANISM: Artificial Sequence
<220> FEATURE:
<223> OTHER INFORMATION: Synthetic polypeptide

<400> SEQUENCE: 108

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala

```
            20                  25                  30
Val Val Gln Trp Lys Phe Lys Ser Tyr Cys Gln Asp Arg Met Gly Glu
        35                  40                  45
Ser Leu Gly Met Ser Ser Thr Arg Ala Gln Ser Leu Ser Lys Arg Asn
    50                  55                  60
Leu Glu Trp Asp Pro Tyr Leu Asp Cys Leu Asp Ser Arg Arg Thr Val
65                  70                  75                  80
Arg Val Val Ala Ser Lys Gln Gly Ser Thr Val Thr Leu Gly Asp Phe
                85                  90                  95
Tyr Arg Gly Arg Glu Ile Thr Ile Val His Asp Ala Asp Leu Gln Ile
            100                 105                 110
Gly Lys Leu Met Trp Gly Asp Ser Gly Leu Tyr Tyr Cys Ile Ile Thr
            115                 120                 125
Thr Pro Asp Asp Leu Glu Gly Lys Asn Glu Asp Ser Val Glu Leu Leu
            130                 135                 140
Val Leu Gly Arg Thr Gly Leu Leu Ala Asp Leu Leu Pro Ser Phe Ala
145                 150                 155                 160
Val Glu Ile Met Gly Ser Glu Asn Leu Tyr Phe Gln Gly Ser Gly Glu
                165                 170                 175
Pro Arg Gly Pro Thr Ile Lys Pro Cys Pro Pro Cys Lys Cys Pro Ala
            180                 185                 190
Pro Asn Leu Leu Gly Gly Pro Ser Val Phe Ile Phe Pro Pro Lys Ile
            195                 200                 205
Lys Asp Val Leu Met Ile Ser Leu Ser Pro Ile Val Thr Cys Val Val
    210                 215                 220
Val Asp Val Ser Glu Asp Asp Pro Asp Val Gln Ile Ser Trp Phe Val
225                 230                 235                 240
Asn Asn Val Glu Val His Thr Ala Gln Thr Gln Thr His Arg Glu Asp
                245                 250                 255
Tyr Asn Ser Thr Leu Arg Val Val Ser Ala Leu Pro Ile Gln His Gln
            260                 265                 270
Asp Trp Met Ser Gly Lys Glu Phe Lys Cys Lys Val Asn Asn Lys Asp
            275                 280                 285
Leu Pro Ala Pro Ile Glu Arg Thr Ile Ser Lys Pro Lys Gly Ser Val
    290                 295                 300
Arg Ala Pro Gln Val Tyr Val Leu Pro Pro Glu Glu Glu Met Thr
305                 310                 315                 320
Lys Lys Gln Val Thr Leu Thr Cys Met Val Thr Asp Phe Met Pro Glu
                325                 330                 335
Asp Ile Tyr Val Glu Trp Thr Asn Asn Gly Lys Thr Glu Leu Asn Tyr
            340                 345                 350
Lys Asn Thr Glu Pro Val Leu Asp Ser Asp Gly Ser Tyr Phe Met Tyr
            355                 360                 365
Ser Lys Leu Arg Val Glu Lys Lys Asn Trp Val Glu Arg Asn Ser Tyr
            370                 375                 380
Ser Cys Ser Val Val His Glu Gly Leu His Asn His His Thr Thr Lys
385                 390                 395                 400
Ser Phe Ser Arg Thr Pro Gly Lys
                405
```

<210> SEQ ID NO 109
<211> LENGTH: 417
<212> TYPE: PRT
<213> ORGANISM: Artificial Sequence
<220> FEATURE:
<223> OTHER INFORMATION: Synthetic polypeptide

<400> SEQUENCE: 109

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Arg Thr Gly Leu Leu Ala Gly Ser Glu
                165                 170                 175

Asn Leu Tyr Phe Gln Gly Ser Gly Glu Pro Arg Gly Pro Thr Ile Lys
            180                 185                 190

Pro Cys Pro Pro Cys Lys Cys Pro Ala Pro Asn Leu Leu Gly Gly Pro
        195                 200                 205

Ser Val Phe Ile Phe Pro Pro Lys Ile Lys Asp Val Leu Met Ile Ser
    210                 215                 220

Leu Ser Pro Ile Val Thr Cys Val Val Asp Val Ser Glu Asp Asp
225                 230                 235                 240

Pro Asp Val Gln Ile Ser Trp Phe Val Asn Asn Val Glu Val His Thr
                245                 250                 255

Ala Gln Thr Gln Thr His Arg Glu Asp Tyr Asn Ser Thr Leu Arg Val
            260                 265                 270

Val Ser Ala Leu Pro Ile Gln His Gln Asp Trp Met Ser Gly Lys Glu
        275                 280                 285

Phe Lys Cys Lys Val Asn Asn Lys Asp Leu Pro Ala Pro Ile Glu Arg
    290                 295                 300

Thr Ile Ser Lys Pro Lys Gly Ser Val Arg Ala Pro Gln Val Tyr Val
305                 310                 315                 320

Leu Pro Pro Pro Glu Glu Glu Met Thr Lys Lys Gln Val Thr Leu Thr
                325                 330                 335

Cys Met Val Thr Asp Phe Met Pro Glu Asp Ile Tyr Val Glu Trp Thr
            340                 345                 350

Asn Asn Gly Lys Thr Glu Leu Asn Tyr Lys Asn Thr Glu Pro Val Leu
        355                 360                 365

Asp Ser Asp Gly Ser Tyr Phe Met Tyr Ser Lys Leu Arg Val Glu Lys
    370                 375                 380

Lys Asn Trp Val Glu Arg Asn Ser Tyr Ser Cys Ser Val Val His Glu
385                 390                 395                 400

```
Gly Leu His Asn His His Thr Thr Lys Ser Phe Ser Arg Thr Pro Gly
                405                 410                 415
Lys

<210> SEQ ID NO 110
<211> LENGTH: 397
<212> TYPE: PRT
<213> ORGANISM: Artificial Sequence
<220> FEATURE:
<223> OTHER INFORMATION: Synthetic polypeptide

<400> SEQUENCE: 110

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Gly Ser Glu Asn Leu Tyr Phe
145                 150                 155                 160

Gln Gly Ser Gly Glu Pro Arg Gly Pro Thr Ile Lys Pro Cys Pro Pro
                165                 170                 175

Cys Lys Cys Pro Ala Pro Asn Leu Leu Gly Gly Pro Ser Val Phe Ile
            180                 185                 190

Phe Pro Pro Lys Ile Lys Asp Val Leu Met Ile Ser Leu Ser Pro Ile
        195                 200                 205

Val Thr Cys Val Val Asp Val Ser Glu Asp Asp Pro Asp Val Gln
    210                 215                 220

Ile Ser Trp Phe Val Asn Asn Val Glu Val His Thr Ala Gln Thr Gln
225                 230                 235                 240

Thr His Arg Glu Asp Tyr Asn Ser Thr Leu Arg Val Val Ser Ala Leu
                245                 250                 255

Pro Ile Gln His Gln Asp Trp Met Ser Gly Lys Glu Phe Lys Cys Lys
            260                 265                 270

Val Asn Asn Lys Asp Leu Pro Ala Pro Ile Glu Arg Thr Ile Ser Lys
        275                 280                 285

Pro Lys Gly Ser Val Arg Ala Pro Gln Val Tyr Val Leu Pro Pro Pro
    290                 295                 300

Glu Glu Glu Met Thr Lys Lys Gln Val Thr Leu Thr Cys Met Val Thr
305                 310                 315                 320

Asp Phe Met Pro Glu Asp Ile Tyr Val Glu Trp Thr Asn Asn Gly Lys
                325                 330                 335
```

Thr Glu Leu Asn Tyr Lys Asn Thr Glu Pro Val Leu Asp Ser Asp Gly
                340                 345                 350

Ser Tyr Phe Met Tyr Ser Lys Leu Arg Val Glu Lys Lys Asn Trp Val
            355                 360                 365

Glu Arg Asn Ser Tyr Ser Cys Ser Val Val His Glu Gly Leu His Asn
        370                 375                 380

His His Thr Thr Lys Ser Phe Ser Arg Thr Pro Gly Lys
385                 390                 395

<210> SEQ ID NO 111
<211> LENGTH: 411
<212> TYPE: PRT
<213> ORGANISM: Artificial Sequence
<220> FEATURE:
<223> OTHER INFORMATION: Synthetic polypeptide

<400> SEQUENCE: 111

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
        35                  40                  45

His Gln Pro Ala Val Val Gln Trp Lys Phe Lys Ser Tyr Cys Gln Asp
    50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
        115                 120                 125

Asp Leu Gln Ile Gly Lys Leu Met Trp Gly Asp Ser Gly Leu Tyr Tyr
    130                 135                 140

Cys Ile Ile Thr Thr Pro Asp Asp Leu Glu Gly Lys Asn Glu Asp Ser
145                 150                 155                 160

Val Glu Leu Leu Val Leu Gly Gly Ser Glu Asn Leu Tyr Phe Gln Gly
                165                 170                 175

Ser Gly Glu Pro Arg Gly Pro Thr Ile Lys Pro Cys Pro Pro Cys Lys
            180                 185                 190

Cys Pro Ala Pro Asn Leu Leu Gly Gly Pro Ser Val Phe Ile Phe Pro
        195                 200                 205

Pro Lys Ile Lys Asp Val Leu Met Ile Ser Leu Ser Pro Ile Val Thr
    210                 215                 220

Cys Val Val Val Asp Val Ser Glu Asp Asp Pro Asp Val Gln Ile Ser
225                 230                 235                 240

Trp Phe Val Asn Asn Val Glu Val His Thr Ala Gln Thr Gln Thr His
                245                 250                 255

Arg Glu Asp Tyr Asn Ser Thr Leu Arg Val Val Ser Ala Leu Pro Ile
            260                 265                 270

Gln His Gln Asp Trp Met Ser Gly Lys Glu Phe Lys Cys Lys Val Asn
        275                 280                 285

Asn Lys Asp Leu Pro Ala Pro Ile Glu Arg Thr Ile Ser Lys Pro Lys
    290                 295                 300

```
Gly Ser Val Arg Ala Pro Gln Val Tyr Val Leu Pro Pro Glu Glu
305                 310                 315                 320

Glu Met Thr Lys Lys Gln Val Thr Leu Thr Cys Met Val Thr Asp Phe
                325                 330                 335

Met Pro Glu Asp Ile Tyr Val Glu Trp Thr Asn Asn Gly Lys Thr Glu
            340                 345                 350

Leu Asn Tyr Lys Asn Thr Glu Pro Val Leu Asp Ser Asp Gly Ser Tyr
                355                 360                 365

Phe Met Tyr Ser Lys Leu Arg Val Glu Lys Lys Asn Trp Val Glu Arg
        370                 375                 380

Asn Ser Tyr Ser Cys Ser Val Val His Glu Gly Leu His Asn His His
385                 390                 395                 400

Thr Thr Lys Ser Phe Ser Arg Thr Pro Gly Lys
                405                 410

<210> SEQ ID NO 112
<211> LENGTH: 391
<212> TYPE: PRT
<213> ORGANISM: Artificial Sequence
<220> FEATURE:
<223> OTHER INFORMATION: Synthetic polypeptide

<400> SEQUENCE: 112

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Gly Ser Glu Asn Leu Tyr Phe Gln Gly Ser Gly Glu Pro
145                 150                 155                 160

Arg Gly Pro Thr Ile Lys Pro Cys Pro Pro Cys Lys Cys Pro Ala Pro
                165                 170                 175

Asn Leu Leu Gly Gly Pro Ser Val Phe Ile Phe Pro Pro Lys Ile Lys
            180                 185                 190

Asp Val Leu Met Ile Ser Leu Ser Pro Ile Val Thr Cys Val Val Val
        195                 200                 205

Asp Val Ser Glu Asp Asp Pro Asp Val Gln Ile Ser Trp Phe Val Asn
    210                 215                 220

Asn Val Glu Val His Thr Ala Gln Thr Gln Thr His Arg Glu Asp Tyr
225                 230                 235                 240

Asn Ser Thr Leu Arg Val Val Ser Ala Leu Pro Ile Gln His Gln Asp
                245                 250                 255
```

```
Trp Met Ser Gly Lys Glu Phe Lys Cys Lys Val Asn Asn Lys Asp Leu
                260                 265                 270

Pro Ala Pro Ile Glu Arg Thr Ile Ser Lys Pro Lys Gly Ser Val Arg
            275                 280                 285

Ala Pro Gln Val Tyr Val Leu Pro Pro Glu Glu Glu Met Thr Lys
290                 295                 300

Lys Gln Val Thr Leu Thr Cys Met Val Thr Asp Phe Met Pro Glu Asp
305                 310                 315                 320

Ile Tyr Val Glu Trp Thr Asn Asn Gly Lys Thr Glu Leu Asn Tyr Lys
                325                 330                 335

Asn Thr Glu Pro Val Leu Asp Ser Asp Gly Ser Tyr Phe Met Tyr Ser
            340                 345                 350

Lys Leu Arg Val Glu Lys Lys Asn Trp Val Glu Arg Asn Ser Tyr Ser
            355                 360                 365

Cys Ser Val Val His Glu Gly Leu His Asn His His Thr Lys Ser
370                 375                 380

Phe Ser Arg Thr Pro Gly Lys
385                 390

<210> SEQ ID NO 113
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 113

Gly Ser Glu Asn Leu Tyr Phe Gln Gly Ser Gly
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 114

Ala Glu Ala Ala Ala Lys Glu Ala Ala Ala Lys Ala
1               5                   10

<210> SEQ ID NO 115
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 115

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
```

```
                    85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Ala Lys Gly Gln Pro
            115                 120                 125
Arg Glu Pro Gln Val Tyr Thr Leu Pro Pro Ser Arg Asp Glu Leu Thr
        130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
210                 215                 220
Ser Leu Ser Leu Ser Pro Gly Lys
225                 230

<210> SEQ ID NO 116
<211> LENGTH: 396
<212> TYPE: PRT
<213> ORGANISM: Artificial sequence
<220> FEATURE:
<223> OTHER INFORMATION: Synthetic polypeptide

<400> SEQUENCE: 116

Leu Gln Val Thr Val Pro Asp Lys Lys Val Ala Met Leu Phe Gln
1               5                   10                  15
Pro Thr Val Leu Arg Cys His Phe Ser Thr Ser Ser His Gln Pro Ala
            20                  25                  30
Val Val Gln Trp Lys Phe Lys Ser Tyr Cys Gln Asp Arg Met Gly Glu
        35                  40                  45
Ser Leu Gly Met Ser Ser Thr Arg Ala Gln Ser Leu Ser Lys Arg Asn
    50                  55                  60
Leu Glu Trp Asp Pro Tyr Leu Asp Cys Leu Asp Ser Arg Arg Thr Val
65                  70                  75                  80
Arg Val Val Ala Ser Lys Gln Gly Ser Thr Val Thr Leu Gly Asp Phe
                85                  90                  95
Tyr Arg Gly Arg Glu Ile Thr Ile Val His Asp Ala Asp Leu Gln Ile
                100                 105                 110
Gly Lys Leu Met Trp Gly Asp Ser Gly Leu Tyr Tyr Cys Ile Ile Thr
            115                 120                 125
Thr Pro Asp Asp Leu Glu Gly Lys Asn Glu Gly Ser Leu Gly Leu Leu
        130                 135                 140
Val Leu Gly Arg Thr Gly Leu Leu Ala Asp Leu Leu Pro Ser Phe Ala
145                 150                 155                 160
Val Glu Ile Met Glu Pro Lys Ser Ser Asp Lys Thr His Thr Cys Pro
                165                 170                 175
Pro Cys Pro Ala Pro Glu Leu Leu Gly Gly Pro Ser Val Phe Leu Phe
            180                 185                 190
Pro Pro Lys Pro Lys Asp Thr Leu Met Ile Ser Arg Thr Pro Glu Val
        195                 200                 205
Thr Cys Val Val Val Asp Val Ser His Glu Asp Pro Glu Val Lys Phe
```

210                 215                 220
Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                    245                 250                 255

Val Leu His Gln Asp Trp Leu Asn Gly Lys Glu Tyr Lys Cys Lys Val
                260                 265                 270

Ser Asn Lys Ala Leu Pro Ala Pro Ile Glu Lys Thr Ile Ser Lys Ala
            275                 280                 285

Lys Gly Gln Pro Arg Glu Pro Gln Val Tyr Thr Leu Pro Pro Ser Arg
        290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                    325                 330                 335

Glu Asn Asn Tyr Lys Thr Thr Pro Pro Val Leu Asp Ser Asp Gly Ser
                340                 345                 350

Phe Phe Leu Tyr Ser Lys Leu Thr Val Asp Lys Ser Arg Trp Gln Gln
            355                 360                 365

Gly Asn Val Phe Ser Cys Ser Val Met His Glu Ala Leu His Asn His
        370                 375                 380

Tyr Thr Gln Lys Ser Leu Ser Leu Ser Pro Gly Lys
385                 390                 395

<210> SEQ ID NO 117
<211> LENGTH: 381
<212> TYPE: PRT
<213> ORGANISM: Artificial sequence
<220> FEATURE:
<223> OTHER INFORMATION: Synthetic polypeptide

<400> SEQUENCE: 117

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Gly Ser Leu Gly Leu Leu
        130                 135                 140

Val Leu Glu Trp Val Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu

```
              180             185             190
Val Thr Cys Val Val Asp Val Ser His Glu Asp Pro Glu Val Lys
            195             200             205
Phe Asn Trp Tyr Val Asp Gly Val Glu Val His Asn Ala Lys Thr Lys
    210             215             220
Pro Arg Glu Glu Gln Tyr Asn Ser Thr Tyr Arg Val Val Ser Val Leu
225             230             235             240
Thr Val Leu His Gln Asp Trp Leu Asn Gly Lys Glu Tyr Lys Cys Lys
            245             250             255
Val Ser Asn Lys Ala Leu Pro Ala Pro Ile Glu Lys Thr Ile Ser Lys
            260             265             270
Ala Lys Gly Gln Pro Arg Glu Pro Gln Val Tyr Thr Leu Pro Pro Ser
            275             280             285
Arg Asp Glu Leu Thr Lys Asn Gln Val Ser Leu Thr Cys Leu Val Lys
            290             295             300
Gly Phe Tyr Pro Ser Asp Ile Ala Val Glu Trp Glu Ser Asn Gly Gln
305             310             315             320
Pro Glu Asn Asn Tyr Lys Thr Thr Pro Pro Val Leu Asp Ser Asp Gly
            325             330             335
Ser Phe Phe Leu Tyr Ser Lys Leu Thr Val Asp Lys Ser Arg Trp Gln
            340             345             350
Gln Gly Asn Val Phe Ser Cys Ser Val Met His Glu Ala Leu His Asn
            355             360             365
His Tyr Thr Gln Lys Ser Leu Ser Leu Ser Pro Gly Lys
            370             375             380

<210> SEQ ID NO 118
<211> LENGTH: 416
<212> TYPE: PRT
<213> ORGANISM: Artificial sequence
<220> FEATURE:
<223> OTHER INFORMATION: Synthetic polypeptide

<400> SEQUENCE: 118

Met Asp Arg Val Leu Leu Arg Trp Ile Ser Leu Phe Trp Leu Thr Ala
1               5                   10                  15
Met Val Glu Gly Leu Gln Val Thr Val Pro Asp Lys Lys Lys Val Ala
            20                  25                  30
Met Leu Phe Gln Pro Thr Val Leu Arg Cys His Phe Ser Thr Ser Ser
        35                  40                  45
His Gln Pro Ala Val Val Gln Trp Lys Phe Lys Ser Tyr Cys Gln Asp
    50                  55                  60
Arg Met Gly Glu Ser Leu Gly Met Ser Ser Thr Arg Ala Gln Ser Leu
65                  70                  75                  80
Ser Lys Arg Asn Leu Glu Trp Asp Pro Tyr Leu Asp Cys Leu Asp Ser
                85                  90                  95
Arg Arg Thr Val Arg Val Val Ala Ser Lys Gln Gly Ser Thr Val Thr
            100                 105                 110
Leu Gly Asp Phe Tyr Arg Gly Arg Glu Ile Thr Ile Val His Asp Ala
        115                 120                 125
Asp Leu Gln Ile Gly Lys Leu Met Trp Gly Asp Ser Gly Leu Tyr Tyr
    130                 135                 140
Cys Ile Ile Thr Thr Pro Asp Asp Leu Glu Gly Lys Asn Glu Asp Ser
145                 150                 155                 160
Val Glu Leu Leu Val Leu Gly Arg Thr Gly Leu Leu Ala Asp Leu Leu
```

```
                165                 170                 175
Pro Ser Phe Ala Val Glu Ile Met Glu Pro Lys Ser Ser Asp Lys Thr
            180                 185                 190

His Thr Cys Pro Pro Cys Pro Ala Pro Glu Leu Leu Gly Gly Pro Ser
            195                 200                 205

Val Phe Leu Phe Pro Pro Lys Pro Lys Asp Thr Leu Met Ile Ser Arg
210                 215                 220

Thr Pro Glu Val Thr Cys Val Val Val Asp Val Ser His Glu Asp Pro
225                 230                 235                 240

Glu Val Lys Phe Asn Trp Tyr Val Asp Gly Val Glu Val His Asn Ala
            245                 250                 255

Lys Thr Lys Pro Arg Glu Glu Gln Tyr Asn Ser Thr Tyr Arg Val Val
            260                 265                 270

Ser Val Leu Thr Val Leu His Gln Asp Trp Leu Asn Gly Lys Glu Tyr
            275                 280                 285

Lys Cys Lys Val Ser Asn Lys Ala Leu Pro Ala Pro Ile Glu Lys Thr
            290                 295                 300

Ile Ser Lys Ala Lys Gly Gln Pro Arg Glu Pro Gln Val Tyr Thr Leu
305                 310                 315                 320

Pro Pro Ser Arg Asp Glu Leu Thr Lys Asn Gln Val Ser Leu Thr Cys
            325                 330                 335

Leu Val Lys Gly Phe Tyr Pro Ser Asp Ile Ala Val Glu Trp Glu Ser
            340                 345                 350

Asn Gly Gln Pro Glu Asn Asn Tyr Lys Thr Thr Pro Pro Val Leu Asp
            355                 360                 365

Ser Asp Gly Ser Phe Phe Leu Tyr Ser Lys Leu Thr Val Asp Lys Ser
            370                 375                 380

Arg Trp Gln Gln Gly Asn Val Phe Ser Cys Ser Val Met His Glu Ala
385                 390                 395                 400

Leu His Asn His Tyr Thr Gln Lys Ser Leu Ser Leu Ser Pro Gly Lys
            405                 410                 415

<210> SEQ ID NO 119
<211> LENGTH: 400
<212> TYPE: PRT
<213> ORGANISM: Artificial sequence
<220> FEATURE:
<223> OTHER INFORMATION: Synthetic polypeptide

<400> SEQUENCE: 119

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
            20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
        50                  55                  60

Arg Met Gly Glu Ser Leu Gly Met Ser Ser Thr Arg Ala Gln Ser Leu
65                  70                  75                  80

Ser Lys Arg Asn Leu Glu Trp Asp Pro Tyr Leu Asp Cys Leu Asp Ser
                85                  90                  95

Arg Arg Thr Val Arg Val Val Ala Ser Lys Gln Gly Ser Thr Val Thr
            100                 105                 110

Leu Gly Asp Phe Tyr Arg Gly Arg Glu Ile Thr Ile Val His Asp Ala
```

```
                 115                 120                 125
Asp Leu Gln Ile Gly Lys Leu Met Trp Gly Asp Ser Gly Leu Tyr Tyr
            130                 135                 140
Cys Ile Ile Thr Thr Pro Asp Leu Glu Gly Lys Asn Glu Gly Ser
145                 150                 155                 160
Leu Gly Leu Leu Val Leu Glu Trp Glu Pro Lys Ser Ser Asp Lys Thr
                165                 170                 175
His Thr Cys Pro Pro Cys Pro Ala Pro Glu Leu Leu Gly Gly Pro Ser
            180                 185                 190
Val Phe Leu Phe Pro Pro Lys Pro Lys Asp Thr Leu Met Ile Ser Arg
                195                 200                 205
Thr Pro Glu Val Thr Cys Val Val Val Asp Val Ser His Glu Asp Pro
            210                 215                 220
Glu Val Lys Phe Asn Trp Tyr Val Asp Gly Val Glu Val His Asn Ala
225                 230                 235                 240
Lys Thr Lys Pro Arg Glu Glu Gln Tyr Asn Ser Thr Tyr Arg Val Val
                245                 250                 255
Ser Val Leu Thr Val Leu His Gln Asp Trp Leu Asn Gly Lys Glu Tyr
            260                 265                 270
Lys Cys Lys Val Ser Asn Lys Ala Leu Pro Ala Pro Ile Glu Lys Thr
                275                 280                 285
Ile Ser Lys Ala Lys Gly Gln Pro Arg Glu Pro Gln Val Tyr Thr Leu
            290                 295                 300
Pro Pro Ser Arg Asp Glu Leu Thr Lys Asn Gln Val Ser Leu Thr Cys
305                 310                 315                 320
Leu Val Lys Gly Phe Tyr Pro Ser Asp Ile Ala Val Glu Trp Glu Ser
                325                 330                 335
Asn Gly Gln Pro Glu Asn Asn Tyr Lys Thr Thr Pro Pro Val Leu Asp
            340                 345                 350
Ser Asp Gly Ser Phe Phe Leu Tyr Ser Lys Leu Thr Val Asp Lys Ser
            355                 360                 365
Arg Trp Gln Gln Gly Asn Val Phe Ser Cys Ser Val Met His Glu Ala
            370                 375                 380
Leu His Asn His Tyr Thr Gln Lys Ser Leu Ser Leu Ser Pro Gly Lys
385                 390                 395                 400

<210> SEQ ID NO 120
<211> LENGTH: 379
<212> TYPE: PRT
<213> ORGANISM: Artificial sequence
<220> FEATURE:
<223> OTHER INFORMATION: Synthetic polypeptide

<400> SEQUENCE: 120

Leu Gln Val Thr Val Pro Asp Lys Lys Val Ala Met Leu Phe Gln
1               5                   10                  15
Pro Thr Val Leu Arg Cys His Phe Ser Thr Ser Ser His Gln Pro Ala
                20                  25                  30
Val Val Gln Trp Lys Phe Lys Ser Tyr Cys Gln Asp Arg Met Gly Glu
            35                  40                  45
Ser Leu Gly Met Ser Ser Thr Arg Ala Gln Ser Leu Ser Lys Arg Asn
            50                  55                  60
Leu Glu Trp Asp Pro Tyr Leu Asp Cys Leu Asp Ser Arg Arg Thr Val
65                  70                  75                  80
Arg Val Val Ala Ser Lys Gln Gly Ser Thr Val Thr Leu Gly Asp Phe
```

```
                    85                  90                  95
Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Glu Pro Lys Ser Ser Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
        195                 200                 205

Trp Tyr Val Asp Gly Val Glu Val His Asn Ala Lys Thr Lys Pro Arg
    210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Asp
        275                 280                 285

Glu Leu Thr Lys Asn Gln Val Ser Leu Thr Cys Leu Val Lys Gly Phe
    290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
        355                 360                 365

Thr Gln Lys Ser Leu Ser Leu Ser Pro Gly Lys
    370                 375

<210> SEQ ID NO 121
<211> LENGTH: 336
<212> TYPE: PRT
<213> ORGANISM: Artificial sequence
<220> FEATURE:
<223> OTHER INFORMATION: Synthetic polypeptide

<400> SEQUENCE: 121

Cys His Phe Ser Thr Ser Ser His Gln Pro Ala Val Val Gln Trp Lys
1               5                   10                  15

Phe Lys Ser Tyr Cys Gln Asp Arg Met Gly Glu Ser Leu Gly Met Ser
            20                  25                  30

Ser Thr Arg Ala Gln Ser Leu Ser Lys Arg Asn Leu Glu Trp Asp Pro
        35                  40                  45

Tyr Leu Asp Cys Leu Asp Ser Arg Arg Thr Val Arg Val Val Ala Ser
    50                  55                  60

Lys Gln Gly Ser Thr Val Thr Leu Gly Asp Phe Tyr Arg Gly Arg Glu
```

```
                65                  70                  75                  80
Ile Thr Ile Val His Asp Ala Asp Leu Gln Ile Gly Lys Leu Met Trp
                    85                  90                  95
Gly Asp Ser Gly Leu Tyr Tyr Cys Glu Pro Lys Ser Ser Asp Lys Thr
                    100                 105                 110
His Thr Cys Pro Pro Cys Pro Ala Pro Glu Leu Leu Gly Gly Pro Ser
                    115                 120                 125
Val Phe Leu Phe Pro Pro Lys Pro Lys Asp Thr Leu Met Ile Ser Arg
                    130                 135                 140
Thr Pro Glu Val Thr Cys Val Val Val Asp Val Ser His Glu Asp Pro
145                 150                 155                 160
Glu Val Lys Phe Asn Trp Tyr Val Asp Gly Val Glu Val His Asn Ala
                    165                 170                 175
Lys Thr Lys Pro Arg Glu Glu Gln Tyr Asn Ser Thr Tyr Arg Val Val
                    180                 185                 190
Ser Val Leu Thr Val Leu His Gln Asp Trp Leu Asn Gly Lys Glu Tyr
                    195                 200                 205
Lys Cys Lys Val Ser Asn Lys Ala Leu Pro Ala Pro Ile Glu Lys Thr
                    210                 215                 220
Ile Ser Lys Ala Lys Gly Gln Pro Arg Glu Pro Gln Val Tyr Thr Leu
225                 230                 235                 240
Pro Pro Ser Arg Asp Glu Leu Thr Lys Asn Gln Val Ser Leu Thr Cys
                    245                 250                 255
Leu Val Lys Gly Phe Tyr Pro Ser Asp Ile Ala Val Glu Trp Glu Ser
                    260                 265                 270
Asn Gly Gln Pro Glu Asn Asn Tyr Lys Thr Thr Pro Pro Val Leu Asp
                    275                 280                 285
Ser Asp Gly Ser Phe Phe Leu Tyr Ser Lys Leu Thr Val Asp Lys Ser
                    290                 295                 300
Arg Trp Gln Gln Gly Asn Val Phe Ser Cys Ser Val Met His Glu Ala
305                 310                 315                 320
Leu His Asn His Tyr Thr Gln Lys Ser Leu Ser Leu Ser Pro Gly Lys
                    325                 330                 335

<210> SEQ ID NO 122
<211> LENGTH: 396
<212> TYPE: PRT
<213> ORGANISM: Artificial sequence
<220> FEATURE:
<223> OTHER INFORMATION: Synthetic polypeptide

<400> SEQUENCE: 122

Leu Gln Val Thr Val Pro Asp Lys Lys Val Ala Met Leu Phe Gln
1                   5                   10                  15
Pro Thr Val Leu Arg Cys His Phe Ser Thr Ser Ser His Gln Pro Ala
                    20                  25                  30
Val Val Gln Trp Lys Phe Lys Ser Tyr Cys Gln Asp Arg Met Gly Glu
                    35                  40                  45
Ser Leu Gly Met Ser Ser Thr Arg Ala Gln Ser Leu Ser Lys Arg Asn
                    50                  55                  60
Leu Glu Trp Asp Pro Tyr Leu Asp Cys Leu Asp Ser Arg Arg Thr Val
65                  70                  75                  80
Arg Val Val Ala Ser Lys Gln Gly Ser Thr Val Thr Leu Gly Asp Phe
                    85                  90                  95
Tyr Arg Gly Arg Glu Ile Thr Ile Val His Asp Ala Asp Leu Gln Ile
```

```
                100             105             110
Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Ala
145                 150                 155                 160

Val Glu Ile Met Glu Pro Lys Ser Ser Asp Lys Thr His Thr Cys Pro
                165                 170                 175

Pro Cys Pro Ala Pro Glu Leu Leu Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
    290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
        355                 360                 365

Gly Asn Val Phe Ser Cys Ser Val Met His Glu Ala Leu His Asn His
    370                 375                 380

Tyr Thr Gln Lys Ser Leu Ser Leu Ser Pro Gly Lys
385                 390                 395

<210> SEQ ID NO 123
<211> LENGTH: 381
<212> TYPE: PRT
<213> ORGANISM: Artificial sequence
<220> FEATURE:
<223> OTHER INFORMATION: Synthetic polypeptide

<400> SEQUENCE: 123

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
```

```
            65                  70                  75                  80
        Arg Val Val Ala Ser Lys Gln Gly Ser Thr Val Thr Leu Gly Asp Phe
                        85                  90                  95

Tyr Arg Gly Arg Glu Ile Thr Ile Val His Asp Ala Asp Leu Gln Ile
                    100                 105                 110

Gly Lys Leu Met Trp Gly Asp Ser Gly Leu Tyr Tyr Cys Ile Ile Thr
                115                 120                 125

Thr Pro Asp Asp Leu Glu Gly Lys Asn Glu Asp Ser Val Glu Leu Leu
            130                 135                 140

Val Leu Glu Trp Val Glu Pro Lys Ser Ser Asp Lys Thr His Thr Cys
        145                 150                 155                 160

Pro Pro Cys Pro Ala Pro Glu Leu Leu Gly Gly Pro Ser Val Phe Leu
                        165                 170                 175

Phe Pro Pro Lys Pro Lys Asp Thr Leu Met Ile Ser Arg Thr Pro Glu
                    180                 185                 190

Val Thr Cys Val Val Val Asp Val Ser His Glu Asp Pro Glu Val Lys
                195                 200                 205

Phe Asn Trp Tyr Val Asp Gly Val Glu Val His Asn Ala Lys Thr Lys
            210                 215                 220

Pro Arg Glu Glu Gln Tyr Asn Ser Thr Tyr Arg Val Val Ser Val Leu
        225                 230                 235                 240

Thr Val Leu His Gln Asp Trp Leu Asn Gly Lys Glu Tyr Lys Cys Lys
                        245                 250                 255

Val Ser Asn Lys Ala Leu Pro Ala Pro Ile Glu Lys Thr Ile Ser Lys
                    260                 265                 270

Ala Lys Gly Gln Pro Arg Glu Pro Gln Val Tyr Thr Leu Pro Pro Ser
                275                 280                 285

Arg Asp Glu Leu Thr Lys Asn Gln Val Ser Leu Thr Cys Leu Val Lys
            290                 295                 300

Gly Phe Tyr Pro Ser Asp Ile Ala Val Glu Trp Glu Ser Asn Gly Gln
        305                 310                 315                 320

Pro Glu Asn Asn Tyr Lys Thr Thr Pro Pro Val Leu Asp Ser Asp Gly
                        325                 330                 335

Ser Phe Phe Leu Tyr Ser Lys Leu Thr Val Asp Lys Ser Arg Trp Gln
                    340                 345                 350

Gln Gly Asn Val Phe Ser Cys Ser Val Met His Glu Ala Leu His Asn
                355                 360                 365

His Tyr Thr Gln Lys Ser Leu Ser Leu Ser Pro Gly Lys
            370                 375                 380

<210> SEQ ID NO 124
<211> LENGTH: 416
<212> TYPE: PRT
<213> ORGANISM: Artificial sequence
<220> FEATURE:
<223> OTHER INFORMATION: Synthetic polypeptide

<400> SEQUENCE: 124

Met Asp Arg Val Leu Leu Arg Trp Ile Ser Leu Phe Trp Leu Thr Ala
1               5                   10                  15

Met Val Glu Gly Leu Gln Val Thr Val Pro Asp Lys Lys Lys Val Ala
                20                  25                  30

Met Leu Phe Gln Pro Thr Val Leu Arg Cys His Phe Ser Thr Ser Ser
            35                  40                  45

His Gln Pro Ala Val Val Gln Trp Lys Phe Lys Ser Tyr Cys Gln Asp
```

```
                50              55              60
Arg Met Gly Glu Ser Leu Gly Met Ser Ser Thr Arg Ala Gln Ser Leu
 65                      70                  75                  80

Ser Lys Arg Asn Leu Glu Trp Asp Pro Tyr Leu Asp Cys Leu Asp Ser
                 85                  90                  95

Arg Arg Thr Val Arg Val Val Ala Ser Lys Gln Gly Ser Thr Val Thr
                100                 105                 110

Leu Gly Asp Phe Tyr Arg Gly Arg Glu Ile Thr Ile Val His Asp Ala
            115                 120                 125

Asp Leu Gln Ile Gly Lys Leu Met Trp Gly Asp Ser Gly Leu Tyr Tyr
        130                 135                 140

Cys Ile Ile Thr Thr Pro Asp Asp Leu Glu Gly Lys Asn Glu Gly Ser
145                 150                 155                 160

Leu Gly Leu Leu Val Leu Gly Arg Thr Gly Leu Leu Ala Asp Leu Leu
                165                 170                 175

Pro Ser Phe Ala Val Glu Ile Met Glu Pro Lys Ser Ser Asp Lys Thr
            180                 185                 190

His Thr Cys Pro Pro Cys Pro Ala Pro Glu Leu Leu Gly Gly Pro Ser
        195                 200                 205

Val Phe Leu Phe Pro Pro Lys Pro Lys Asp Thr Leu Met Ile Ser Arg
210                 215                 220

Thr Pro Glu Val Thr Cys Val Val Val Asp Val Ser His Glu Asp Pro
225                 230                 235                 240

Glu Val Lys Phe Asn Trp Tyr Val Asp Gly Val Glu Val His Asn Ala
                245                 250                 255

Lys Thr Lys Pro Arg Glu Glu Gln Tyr Asn Ser Thr Tyr Arg Val Val
            260                 265                 270

Ser Val Leu Thr Val Leu His Gln Asp Trp Leu Asn Gly Lys Glu Tyr
        275                 280                 285

Lys Cys Lys Val Ser Asn Lys Ala Leu Pro Ala Pro Ile Glu Lys Thr
290                 295                 300

Ile Ser Lys Ala Lys Gly Gln Pro Arg Glu Pro Gln Val Tyr Thr Leu
305                 310                 315                 320

Pro Pro Ser Arg Asp Glu Leu Thr Lys Asn Gln Val Ser Leu Thr Cys
                325                 330                 335

Leu Val Lys Gly Phe Tyr Pro Ser Asp Ile Ala Val Glu Trp Glu Ser
            340                 345                 350

Asn Gly Gln Pro Glu Asn Asn Tyr Lys Thr Thr Pro Pro Val Leu Asp
        355                 360                 365

Ser Asp Gly Ser Phe Phe Leu Tyr Ser Lys Leu Thr Val Asp Lys Ser
370                 375                 380

Arg Trp Gln Gln Gly Asn Val Phe Ser Cys Ser Val Met His Glu Ala
385                 390                 395                 400

Leu His Asn His Tyr Thr Gln Lys Ser Leu Ser Leu Ser Pro Gly Lys
                405                 410                 415

<210> SEQ ID NO 125
<211> LENGTH: 401
<212> TYPE: PRT
<213> ORGANISM: Artificial sequence
<220> FEATURE:
<223> OTHER INFORMATION: Synthetic polypeptide

<400> SEQUENCE: 125

Met Asp Arg Val Leu Leu Arg Trp Ile Ser Leu Phe Trp Leu Thr Ala
```

```
          1               5                   10                  15
        Met Val Glu Gly Leu Gln Val Thr Val Pro Asp Lys Lys Val Ala
                        20                  25                  30
        Met Leu Phe Gln Pro Thr Val Leu Arg Cys His Phe Ser Thr Ser Ser
                        35                  40                  45
        His Gln Pro Ala Val Val Gln Trp Lys Phe Lys Ser Tyr Cys Gln Asp
                        50                  55                  60
        Arg Met Gly Glu Ser Leu Gly Met Ser Ser Thr Arg Ala Gln Ser Leu
        65                      70                  75                  80
        Ser Lys Arg Asn Leu Glu Trp Asp Pro Tyr Leu Asp Cys Leu Asp Ser
                        85                  90                  95
        Arg Arg Thr Val Arg Val Ala Ser Lys Gln Gly Ser Thr Val Thr
                        100                 105                 110
        Leu Gly Asp Phe Tyr Arg Gly Arg Glu Ile Thr Ile Val His Asp Ala
                        115                 120                 125
        Asp Leu Gln Ile Gly Lys Leu Met Trp Gly Asp Ser Gly Leu Tyr Tyr
                        130                 135                 140
        Cys Ile Ile Thr Thr Pro Asp Asp Leu Glu Gly Lys Asn Glu Asp Ser
        145                     150                 155                 160
        Val Glu Leu Leu Val Leu Glu Trp Val Glu Pro Lys Ser Ser Asp Lys
                        165                 170                 175
        Thr His Thr Cys Pro Pro Cys Pro Ala Pro Glu Leu Leu Gly Gly Pro
                        180                 185                 190
        Ser Val Phe Leu Phe Pro Pro Lys Pro Lys Asp Thr Leu Met Ile Ser
                        195                 200                 205
        Arg Thr Pro Glu Val Thr Cys Val Val Asp Val Ser His Glu Asp
                        210                 215                 220
        Pro Glu Val Lys Phe Asn Trp Tyr Val Asp Gly Val Glu Val His Asn
        225                     230                 235                 240
        Ala Lys Thr Lys Pro Arg Glu Glu Gln Tyr Asn Ser Thr Tyr Arg Val
                        245                 250                 255
        Val Ser Val Leu Thr Val Leu His Gln Asp Trp Leu Asn Gly Lys Glu
                        260                 265                 270
        Tyr Lys Cys Lys Val Ser Asn Lys Ala Leu Pro Ala Pro Ile Glu Lys
                        275                 280                 285
        Thr Ile Ser Lys Ala Lys Gly Gln Pro Arg Glu Pro Gln Val Tyr Thr
                        290                 295                 300
        Leu Pro Pro Ser Arg Asp Glu Leu Thr Lys Asn Gln Val Ser Leu Thr
        305                     310                 315                 320
        Cys Leu Val Lys Gly Phe Tyr Pro Ser Asp Ile Ala Val Glu Trp Glu
                        325                 330                 335
        Ser Asn Gly Gln Pro Glu Asn Asn Tyr Lys Thr Thr Pro Pro Val Leu
                        340                 345                 350
        Asp Ser Asp Gly Ser Phe Phe Leu Tyr Ser Lys Leu Thr Val Asp Lys
                        355                 360                 365
        Ser Arg Trp Gln Gln Gly Asn Val Phe Ser Cys Ser Val Met His Glu
                        370                 375                 380
        Ala Leu His Asn His Tyr Thr Gln Lys Ser Leu Ser Leu Ser Pro Gly
        385                     390                 395                 400
        Lys

<210> SEQ ID NO 126
<211> LENGTH: 379
```

```
<212> TYPE: PRT
<213> ORGANISM: Artificial sequence
<220> FEATURE:
<223> OTHER INFORMATION: Synthetic polypeptide

<400> SEQUENCE: 126

Leu Gln Val Thr Val Pro Asp Lys Lys Val Ala Met Leu Phe Gln
1               5                   10                  15

Pro Thr Val Leu Arg Cys His Phe Ser Thr Ser His Gln Pro Ala
                20                  25                  30

Val Val Gln Trp Lys Phe Lys Ser Tyr Cys Gln Asp Arg Met Gly Glu
                35                  40                  45

Ser Leu Gly Met Ser Ser Thr Arg Ala Gln Ser Leu Ser Lys Arg Asn
50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
                115                 120                 125

Thr Pro Asp Asp Leu Glu Gly Lys Asn Glu Asp Ser Val Glu Leu Leu
130                 135                 140

Val Leu Gly Glu Pro Lys Ser Ser Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
                180                 185                 190

Cys Val Val Val Asp Val Ser His Glu Asp Pro Glu Val Lys Phe Asn
                195                 200                 205

Trp Tyr Val Asp Gly Val Glu Val His Asn Ala Lys Thr Lys Pro Arg
210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
                260                 265                 270

Gly Gln Pro Arg Glu Pro Gln Val Tyr Thr Leu Pro Pro Ser Arg Asp
                275                 280                 285

Glu Leu Thr Lys Asn Gln Val Ser Leu Thr Cys Leu Val Lys Gly Phe
290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
                340                 345                 350

Asn Val Phe Ser Cys Ser Val Met His Glu Ala Leu His Asn His Tyr
                355                 360                 365

Thr Gln Lys Ser Leu Ser Leu Ser Pro Gly Lys
                370                 375
```

```
<210> SEQ ID NO 127
<211> LENGTH: 376
<212> TYPE: PRT
<213> ORGANISM: Artificial sequence
<220> FEATURE:
<223> OTHER INFORMATION: Synthetic polypeptide

<400> SEQUENCE: 127

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65              70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Glu Pro Lys Ser Ser Asp Lys Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Ser Arg Asp Glu Leu Thr
        275                 280                 285

Lys Asn Gln Val Ser Leu Thr Cys Leu Val Lys Gly Phe Tyr Pro Ser
    290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365
```

Ser Leu Ser Leu Ser Pro Gly Lys
    370                 375

<210> SEQ ID NO 128
<211> LENGTH: 377
<212> TYPE: PRT
<213> ORGANISM: Artificial sequence
<220> FEATURE:
<223> OTHER INFORMATION: Synthetic polypeptide

<400> SEQUENCE: 128

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
130                 135                 140

Val Glu Pro Lys Ser Ser Asp Lys Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Asp Glu Leu
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

```
Phe Ser Cys Ser Val Met His Glu Ala Leu His Asn His Tyr Thr Gln
            355                 360                 365
Lys Ser Leu Ser Leu Ser Pro Gly Lys
    370                 375

<210> SEQ ID NO 129
<211> LENGTH: 378
<212> TYPE: PRT
<213> ORGANISM: Artificial sequence
<220> FEATURE:
<223> OTHER INFORMATION: Synthetic polypeptide

<400> SEQUENCE: 129

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
    130                 135                 140

Val Leu Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
                180                 185                 190

Val Val Val Asp Val Ser His Glu Asp Pro Glu Val Lys Phe Asn Trp
            195                 200                 205

Tyr Val Asp Gly Val Glu Val His Asn Ala Lys Thr Lys Pro Arg Glu
    210                 215                 220

Glu Gln Tyr Asn Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
                260                 265                 270

Gln Pro Arg Glu Pro Gln Val Tyr Thr Leu Pro Pro Ser Arg Asp Glu
            275                 280                 285

Leu Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335
```

-continued

Leu Tyr Ser Lys Leu Thr Val Asp Lys Ser Arg Trp Gln Gln Gly Asn
              340                 345                 350

Val Phe Ser Cys Ser Val Met His Glu Ala Leu His Asn His Tyr Thr
            355                 360                 365

Gln Lys Ser Leu Ser Leu Ser Pro Gly Lys
        370                 375

<210> SEQ ID NO 130
<211> LENGTH: 396
<212> TYPE: PRT
<213> ORGANISM: Artificial sequence
<220> FEATURE:
<223> OTHER INFORMATION: Synthetic polypeptide

<400> SEQUENCE: 130

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Leu Leu Ala Asp Leu Leu Pro Ser Gly Gly
145                 150                 155                 160

Val Glu Ile Met Glu Pro Lys Ser Ser Asp Lys Thr His Thr Cys Pro
                165                 170                 175

Pro Cys Pro Ala Pro Glu Leu Leu Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
    290                 295                 300

Asp Glu Leu Thr Lys Asn Gln Val Ser Leu Thr Cys Leu Val Lys Gly
305                 310                 315                 320

```
Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
            355                 360                 365

Gly Asn Val Phe Ser Cys Ser Val Met His Glu Ala Leu His Asn His
370                 375                 380

Tyr Thr Gln Lys Ser Leu Ser Leu Ser Pro Gly Lys
385                 390                 395

<210> SEQ ID NO 131
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 131

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Gly Arg Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
            195                 200                 205

Asn Trp Tyr Val Asp Gly Val Glu Val His Asn Ala Lys Thr Lys Pro
210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
            275                 280                 285
```

Asp Glu Leu Thr Lys Asn Gln Val Ser Leu Thr Cys Leu Val Lys Gly
            290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 132
<211> LENGTH: 381
<212> TYPE: PRT
<213> ORGANISM: Artificial sequence
<220> FEATURE:
<223> OTHER INFORMATION: Synthetic polypeptide

<400> SEQUENCE: 132

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
130                 135                 140

Val Leu Gly Arg Thr Glu Pro Lys Ser Ser Asp Lys Thr His Thr Cys
145                 150                 155                 160

Pro Pro Cys Pro Ala Pro Glu Leu Leu Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

```
Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
        290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
                340                 345                 350

Gln Gly Asn Val Phe Ser Cys Ser Val Met His Glu Ala Leu His Asn
            355                 360                 365

His Tyr Thr Gln Lys Ser Leu Ser Leu Ser Pro Gly Lys
        370                 375                 380

<210> SEQ ID NO 133
<211> LENGTH: 382
<212> TYPE: PRT
<213> ORGANISM: Artificial sequence
<220> FEATURE:
<223> OTHER INFORMATION: Synthetic polypeptide

<400> SEQUENCE: 133

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Glu Pro Lys Ser Ser Asp Lys Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
                180                 185                 190

Glu Val Thr Cys Val Val Val Asp Val Ser His Glu Asp Pro Glu Val
            195                 200                 205

Lys Phe Asn Trp Tyr Val Asp Gly Val Glu Val His Asn Ala Lys Thr
210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255
```

```
Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
        275                 280                 285

Ser Arg Asp Glu Leu Thr Lys Asn Gln Val Ser Leu Thr Cys Leu Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
        340                 345                 350

Gln Gln Gly Asn Val Phe Ser Cys Ser Val Met His Glu Ala Leu His
    355                 360                 365

Asn His Tyr Thr Gln Lys Ser Leu Ser Leu Ser Pro Gly Lys
        370                 375                 380

<210> SEQ ID NO 134
<211> LENGTH: 383
<212> TYPE: PRT
<213> ORGANISM: Artificial sequence
<220> FEATURE:
<223> OTHER INFORMATION: Synthetic polypeptide

<400> SEQUENCE: 134

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Glu Pro Lys Ser Ser Asp Lys Thr His
145                 150                 155                 160

Thr Cys Pro Pro Cys Pro Ala Pro Glu Leu Leu Gly Gly Pro Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240
```

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Val Leu Asp Ser
            325                 330                 335

Asp Gly Ser Phe Phe Leu Tyr Ser Lys Leu Thr Val Asp Lys Ser Arg
                340                 345                 350

Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly Lys
        370                 375                 380

<210> SEQ ID NO 135
<211> LENGTH: 384
<212> TYPE: PRT
<213> ORGANISM: Artificial sequence
<220> FEATURE:
<223> OTHER INFORMATION: Synthetic polypeptide

<400> SEQUENCE: 135

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Leu Leu Glu Pro Lys Ser Ser Asp Lys Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
                180                 185                 190

Thr Pro Glu Val Thr Cys Val Val Val Asp Val Ser His Glu Asp Pro
            195                 200                 205

Glu Val Lys Phe Asn Trp Tyr Val Asp Gly Val Glu Val His Asn Ala
        210                 215                 220

```
Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
            245                 250                 255

Lys Cys Lys Val Ser Asn Lys Ala Leu Pro Ala Pro Ile Glu Lys Thr
        260                 265                 270

Ile Ser Lys Ala Lys Gly Gln Pro Arg Glu Pro Gln Val Tyr Thr Leu
    275                 280                 285

Pro Pro Ser Arg Asp Glu Leu Thr Lys Asn Gln Val Ser Leu Thr Cys
290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

<210> SEQ ID NO 136
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 136

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
130                 135                 140

Val Leu Gly Arg Thr Gly Leu Leu Ala Glu Pro Lys Ser Ser Asp Lys
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205
```

```
Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385

<210> SEQ ID NO 137
<211> LENGTH: 386
<212> TYPE: PRT
<213> ORGANISM: Artificial sequence
<220> FEATURE:
<223> OTHER INFORMATION: Synthetic polypeptide

<400> SEQUENCE: 137

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Gly Arg Thr Gly Leu Leu Ala Asp Glu Pro Lys Ser Ser Asp
145                 150                 155                 160

Lys Thr His Thr Cys Pro Pro Cys Pro Ala Pro Glu Leu Leu Gly Gly
                165                 170                 175
```

```
Pro Ser Val Phe Leu Phe Pro Pro Lys Pro Lys Asp Thr Leu Met Ile
            180                 185                 190

Ser Arg Thr Pro Glu Val Thr Cys Val Val Val Asp Val Ser His Glu
        195                 200                 205

Asp Pro Glu Val Lys Phe Asn Trp Tyr Val Asp Gly Val Glu Val His
    210                 215                 220

Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
                245                 250                 255

Glu Tyr Lys Cys Lys Val Ser Asn Lys Ala Leu Pro Ala Pro Ile Glu
            260                 265                 270

Lys Thr Ile Ser Lys Ala Lys Gly Gln Pro Arg Glu Pro Gln Val Tyr
        275                 280                 285

Thr Leu Pro Pro Ser Arg Asp Glu Leu Thr Lys Asn Gln Val Ser Leu
    290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Lys Leu Thr Val Asp
            340                 345                 350

Lys Ser Arg Trp Gln Gln Gly Asn Val Phe Ser Cys Ser Val Met His
        355                 360                 365

Glu Ala Leu His Asn His Tyr Thr Gln Lys Ser Leu Ser Leu Ser Pro
    370                 375                 380

Gly Lys
385

<210> SEQ ID NO 138
<211> LENGTH: 387
<212> TYPE: PRT
<213> ORGANISM: Artificial sequence
<220> FEATURE:
<223> OTHER INFORMATION: Synthetic polypeptide

<400> SEQUENCE: 138

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140
```

Val Leu Gly Arg Thr Gly Leu Leu Ala Asp Leu Glu Pro Lys Ser Ser
145                 150                 155                 160

Asp Lys Thr His Thr Cys Pro Pro Cys Pro Ala Pro Glu Leu Leu Gly
            165                 170                 175

Gly Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
            195                 200                 205

Glu Asp Pro Glu Val Lys Phe Asn Trp Tyr Val Asp Gly Val Glu Val
210                 215                 220

His Asn Ala Lys Thr Lys Pro Arg Glu Gln Tyr Asn Ser Thr Tyr
225                 230                 235                 240

Arg Val Val Ser Val Leu Thr Val Leu His Gln Asp Trp Leu Asn Gly
            245                 250                 255

Lys Glu Tyr Lys Cys Lys Val Ser Asn Lys Ala Leu Pro Ala Pro Ile
            260                 265                 270

Glu Lys Thr Ile Ser Lys Ala Lys Gly Gln Pro Arg Glu Pro Gln Val
            275                 280                 285

Tyr Thr Leu Pro Pro Ser Arg Asp Glu Leu Thr Lys Asn Gln Val Ser
290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
            325                 330                 335

Val Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
            355                 360                 365

His Glu Ala Leu His Asn His Tyr Thr Gln Lys Ser Leu Ser Leu Ser
370                 375                 380

Pro Gly Lys
385

<210> SEQ ID NO 139
<211> LENGTH: 388
<212> TYPE: PRT
<213> ORGANISM: Artificial sequence
<220> FEATURE:
<223> OTHER INFORMATION: Synthetic polypeptide

<400> SEQUENCE: 139

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
            50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
            85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Leu Leu Ala Asp Leu Leu Glu Pro Lys Ser
145                 150                 155                 160

Ser Asp Lys Thr His Thr Cys Pro Pro Cys Pro Ala Pro Glu Leu Leu
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gln Pro Arg Glu Pro Gln
        275                 280                 285

Val Tyr Thr Leu Pro Pro Ser Arg Asp Glu Leu Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly Lys
385

<210> SEQ ID NO 140
<211> LENGTH: 389
<212> TYPE: PRT
<213> ORGANISM: Artificial sequence
<220> FEATURE:
<223> OTHER INFORMATION: Synthetic polypeptide

<400> SEQUENCE: 140

Leu Gln Val Thr Val Pro Asp Lys Lys Val Ala Met Leu Phe Gln
1               5                   10                  15

Pro Thr Val Leu Arg Cys His Phe Ser Thr Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Gly Arg Thr Gly Leu Leu Ala Asp Leu Leu Pro Glu Pro Lys
145                 150                 155                 160

Ser Ser Asp Lys Thr His Thr Cys Pro Pro Cys Pro Ala Pro Glu Leu
                165                 170                 175

Leu Gly Gly Pro Ser Val Phe Leu Phe Pro Pro Lys Pro Lys Asp Thr
            180                 185                 190

Leu Met Ile Ser Arg Thr Pro Glu Val Thr Cys Val Val Val Asp Val
            195                 200                 205

Ser His Glu Asp Pro Glu Val Lys Phe Asn Trp Tyr Val Asp Gly Val
210                 215                 220

Glu Val His Asn Ala Lys Thr Lys Pro Arg Glu Glu Gln Tyr Asn Ser
225                 230                 235                 240

Thr Tyr Arg Val Val Ser Val Leu Thr Val Leu His Gln Asp Trp Leu
                245                 250                 255

Asn Gly Lys Glu Tyr Lys Cys Lys Val Ser Asn Lys Ala Leu Pro Ala
            260                 265                 270

Pro Ile Glu Lys Thr Ile Ser Lys Ala Lys Gly Gln Pro Arg Glu Pro
            275                 280                 285

Gln Val Tyr Thr Leu Pro Pro Ser Arg Asp Glu Leu Thr Lys Asn Gln
290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
            355                 360                 365

Val Met His Glu Ala Leu His Asn His Tyr Thr Gln Lys Ser Leu Ser
370                 375                 380

Leu Ser Pro Gly Lys
385

<210> SEQ ID NO 141
<211> LENGTH: 390
<212> TYPE: PRT
<213> ORGANISM: Artificial sequence
<220> FEATURE:
<223> OTHER INFORMATION: Synthetic polypeptide

<400> SEQUENCE: 141

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
 65                  70                  75                  80

Arg Val Val Ala Ser Lys Gln Gly Ser Thr Val Thr Leu Gly Asp Phe
                 85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Gly Arg Thr Gly Leu Leu Ala Asp Leu Leu Pro Ser Glu Pro
145                 150                 155                 160

Lys Ser Ser Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
    370                 375                 380

Ser Leu Ser Pro Gly Lys
385                 390

<210> SEQ ID NO 142
<211> LENGTH: 391
<212> TYPE: PRT
<213> ORGANISM: Artificial sequence
<220> FEATURE:
<223> OTHER INFORMATION: Synthetic polypeptide

<400> SEQUENCE: 142

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
         35                  40                  45

Ser Leu Gly Met Ser Ser Thr Arg Ala Gln Ser Leu Ser Lys Arg Asn
     50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                 85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Glu
145                 150                 155                 160

Pro Lys Ser Ser Asp Lys Thr His Thr Cys Pro Pro Cys Pro Ala Pro
                165                 170                 175

Glu Leu Leu Gly Gly Pro Ser Val Phe Leu Phe Pro Pro Lys Pro Lys
            180                 185                 190

Asp Thr Leu Met Ile Ser Arg Thr Pro Glu Val Thr Cys Val Val Val
        195                 200                 205

Asp Val Ser His Glu Asp Pro Glu Val Lys Phe Asn Trp Tyr Val Asp
210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285

Glu Pro Gln Val Tyr Thr Leu Pro Pro Ser Arg Asp Glu Leu Thr Lys
    290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
    370                 375                 380

Leu Ser Leu Ser Pro Gly Lys
385                 390

<210> SEQ ID NO 143
<211> LENGTH: 392
<212> TYPE: PRT
<213> ORGANISM: Artificial sequence
<220> FEATURE:
<223> OTHER INFORMATION: Synthetic polypeptide

<400> SEQUENCE: 143

```
Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65              70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Ala
145                 150                 155                 160

Glu Pro Lys Ser Ser Asp Lys Thr His Thr Cys Pro Pro Cys Pro Ala
                165                 170                 175

Pro Glu Leu Leu Gly Gly Pro Ser Val Phe Leu Phe Pro Pro Lys Pro
            180                 185                 190

Lys Asp Thr Leu Met Ile Ser Arg Thr Pro Glu Val Thr Cys Val Val
        195                 200                 205

Val Asp Val Ser His Glu Asp Pro Glu Val Lys Phe Asn Trp Tyr Val
    210                 215                 220

Asp Gly Val Glu Val His Asn Ala Lys Thr Lys Pro Arg Glu Glu Gln
225                 230                 235                 240

Tyr Asn Ser Thr Tyr Arg Val Val Ser Val Leu Thr Val Leu His Gln
                245                 250                 255

Asp Trp Leu Asn Gly Lys Glu Tyr Lys Cys Lys Val Ser Asn Lys Ala
            260                 265                 270

Leu Pro Ala Pro Ile Glu Lys Thr Ile Ser Lys Ala Lys Gly Gln Pro
        275                 280                 285

Arg Glu Pro Gln Val Tyr Thr Leu Pro Pro Ser Arg Asp Glu Leu Thr
    290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Val Leu Asp Ser Asp Gly Ser Phe Phe Leu Tyr
            340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
    370                 375                 380

Ser Leu Ser Leu Ser Pro Gly Lys
385                 390
```

<210> SEQ ID NO 144
<211> LENGTH: 393
<212> TYPE: PRT
<213> ORGANISM: Artificial sequence
<220> FEATURE:
<223> OTHER INFORMATION: Synthetic polypeptide

<400> SEQUENCE: 144

```
Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Ala
145                 150                 155                 160

Val Glu Pro Lys Ser Ser Asp Lys Thr His Thr Cys Pro Pro Cys Pro
                165                 170                 175

Ala Pro Glu Leu Leu Gly Gly Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
    290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
        355                 360                 365

Phe Ser Cys Ser Val Met His Glu Ala Leu His Asn His Tyr Thr Gln
```

```
              370                 375                 380
Lys Ser Leu Ser Leu Ser Pro Gly Lys
385                 390

<210> SEQ ID NO 145
<211> LENGTH: 394
<212> TYPE: PRT
<213> ORGANISM: Artificial sequence
<220> FEATURE:
<223> OTHER INFORMATION: Synthetic polypeptide

<400> SEQUENCE: 145

Leu Gln Val Thr Val Pro Asp Lys Lys Val Ala Met Leu Phe Gln
1               5                   10                  15

Pro Thr Val Leu Arg Cys His Phe Ser Thr Ser His Gln Pro Ala
                20                  25                  30

Val Val Gln Trp Lys Phe Lys Ser Tyr Cys Gln Asp Arg Met Gly Glu
                35                  40                  45

Ser Leu Gly Met Ser Ser Thr Arg Ala Gln Ser Leu Ser Lys Arg Asn
50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
                115                 120                 125

Thr Pro Asp Asp Leu Glu Gly Lys Asn Glu Asp Ser Val Glu Leu Leu
130                 135                 140

Val Leu Gly Arg Thr Gly Leu Leu Ala Asp Leu Leu Pro Ser Phe Ala
145                 150                 155                 160

Val Glu Glu Pro Lys Ser Ser Asp Lys Thr His Thr Cys Pro Pro Cys
                165                 170                 175

Pro Ala Pro Glu Leu Leu Gly Gly Pro Ser Val Phe Leu Phe Pro Pro
                180                 185                 190

Lys Pro Lys Asp Thr Leu Met Ile Ser Arg Thr Pro Glu Val Thr Cys
                195                 200                 205

Val Val Val Asp Val Ser His Glu Asp Pro Glu Val Lys Phe Asn Trp
210                 215                 220

Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
                245                 250                 255

His Gln Asp Trp Leu Asn Gly Lys Glu Tyr Lys Cys Lys Val Ser Asn
                260                 265                 270

Lys Ala Leu Pro Ala Pro Ile Glu Lys Thr Ile Ser Lys Ala Lys Gly
                275                 280                 285

Gln Pro Arg Glu Pro Gln Val Tyr Thr Leu Pro Pro Ser Arg Asp Glu
                290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
```

```
                340             345             350
Leu Tyr Ser Lys Leu Thr Val Asp Lys Ser Arg Trp Gln Gln Gly Asn
            355                 360                 365

Val Phe Ser Cys Ser Val Met His Glu Ala Leu His Asn His Tyr Thr
        370                 375                 380

Gln Lys Ser Leu Ser Leu Ser Pro Gly Lys
385                 390

<210> SEQ ID NO 146
<211> LENGTH: 395
<212> TYPE: PRT
<213> ORGANISM: Artificial sequence
<220> FEATURE:
<223> OTHER INFORMATION: Synthetic polypeptide

<400> SEQUENCE: 146

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Ala
145                 150                 155                 160

Val Glu Ile Glu Pro Lys Ser Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
        195                 200                 205

Cys Val Val Val Asp Val Ser His Glu Asp Pro Glu Val Lys Phe Asn
    210                 215                 220

Trp Tyr Val Asp Gly Val Glu Val His Asn Ala Lys Thr Lys Pro Arg
225                 230                 235                 240

Glu Glu Gln Tyr Asn Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
        275                 280                 285

Gly Gln Pro Arg Glu Pro Gln Val Tyr Thr Leu Pro Pro Ser Arg Asp
    290                 295                 300

Glu Leu Thr Lys Asn Gln Val Ser Leu Thr Cys Leu Val Lys Gly Phe
```

```
                305                 310                 315                 320
Tyr Pro Ser Asp Ile Ala Val Glu Trp Glu Ser Asn Gly Gln Pro Glu
                    325                 330                 335

Asn Asn Tyr Lys Thr Thr Pro Pro Val Leu Asp Ser Asp Gly Ser Phe
                    340                 345                 350

Phe Leu Tyr Ser Lys Leu Thr Val Asp Lys Ser Arg Trp Gln Gln Gly
                    355                 360                 365

Asn Val Phe Ser Cys Ser Val Met His Glu Ala Leu His Asn His Tyr
                    370                 375                 380

Thr Gln Lys Ser Leu Ser Leu Ser Pro Gly Lys
385                 390                 395

<210> SEQ ID NO 147
<211> LENGTH: 398
<212> TYPE: PRT
<213> ORGANISM: Artificial sequence
<220> FEATURE:
<223> OTHER INFORMATION: Synthetic polypeptide

<400> SEQUENCE: 147

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                    20                  25                  30

Val Val Gln Trp Lys Phe Lys Ser Tyr Cys Gln Asp Arg Met Gly Glu
                    35                  40                  45

Ser Leu Gly Met Ser Ser Thr Arg Ala Gln Ser Leu Ser Lys Arg Asn
                50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                    85                  90                  95

Tyr Arg Gly Arg Glu Ile Thr Ile Val His Asp Ala Asp Leu Gln Ile
                    100                 105                 110

Gly Lys Leu Met Trp Gly Asp Ser Gly Leu Tyr Tyr Cys Ile Ile Thr
                    115                 120                 125

Thr Pro Asp Asp Leu Glu Gly Lys Asn Glu Asp Ser Val Glu Leu Leu
                130                 135                 140

Val Leu Gly Arg Thr Gly Leu Leu Ala Asp Leu Leu Pro Ser Phe Ala
145                 150                 155                 160

Val Glu Ile Met Pro Glu Glu Pro Lys Ser Ser Asp Lys Thr His Thr
                    165                 170                 175

Cys Pro Pro Cys Pro Ala Pro Glu Leu Leu Gly Gly Pro Ser Val Phe
                    180                 185                 190

Leu Phe Pro Pro Lys Pro Lys Asp Thr Leu Met Ile Ser Arg Thr Pro
                    195                 200                 205

Glu Val Thr Cys Val Val Val Asp Val Ser His Glu Asp Pro Glu Val
                    210                 215                 220

Lys Phe Asn Trp Tyr Val Asp Gly Val Glu Val His Asn Ala Lys Thr
225                 230                 235                 240

Lys Pro Arg Glu Glu Gln Tyr Asn Ser Thr Tyr Arg Val Val Ser Val
                    245                 250                 255

Leu Thr Val Leu His Gln Asp Trp Leu Asn Gly Lys Glu Tyr Lys Cys
                    260                 265                 270

Lys Val Ser Asn Lys Ala Leu Pro Ala Pro Ile Glu Lys Thr Ile Ser
```

```
              275                 280                 285
Lys Ala Lys Gly Gln Pro Arg Glu Pro Gln Val Tyr Thr Leu Pro Pro
290                 295                 300

Ser Arg Asp Glu Leu Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
                340                 345                 350

Gly Ser Phe Phe Leu Tyr Ser Lys Leu Thr Val Asp Lys Ser Arg Trp
                355                 360                 365

Gln Gln Gly Asn Val Phe Ser Cys Ser Val Met His Glu Ala Leu His
370                 375                 380

Asn His Tyr Thr Gln Lys Ser Leu Ser Leu Ser Pro Gly Lys
385                 390                 395

<210> SEQ ID NO 148
<211> LENGTH: 397
<212> TYPE: PRT
<213> ORGANISM: Artificial sequence
<220> FEATURE:
<223> OTHER INFORMATION: Synthetic polypeptide

<400> SEQUENCE: 148

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
        130                 135                 140

Val Leu Gly Arg Thr Gly Leu Leu Ala Asp Leu Leu Pro Ser Phe Ala
145                 150                 155                 160

Val Glu Ile Met Pro Glu Pro Lys Ser Ser Asp Lys Thr His Thr Cys
                165                 170                 175

Pro Pro Cys Pro Ala Pro Glu Leu Leu Gly Gly Pro Ser Val Phe Leu
            180                 185                 190

Phe Pro Pro Lys Pro Lys Asp Thr Leu Met Ile Ser Arg Thr Pro Glu
        195                 200                 205

Val Thr Cys Val Val Val Asp Val Ser His Glu Asp Pro Glu Val Lys
        210                 215                 220

Phe Asn Trp Tyr Val Asp Gly Val Glu Val His Asn Ala Lys Thr Lys
225                 230                 235                 240

Pro Arg Glu Glu Gln Tyr Asn Ser Thr Tyr Arg Val Val Ser Val Leu
```

```
                       245                 250                 255
Thr Val Leu His Gln Asp Trp Leu Asn Gly Lys Glu Tyr Lys Cys Lys
                260                 265                 270

Val Ser Asn Lys Ala Leu Pro Ala Pro Ile Glu Lys Thr Ile Ser Lys
            275                 280                 285

Ala Lys Gly Gln Pro Arg Glu Pro Gln Val Tyr Thr Leu Pro Pro Ser
        290                 295                 300

Arg Asp Glu Leu Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Lys Leu Thr Val Asp Lys Ser Arg Trp Gln
        355                 360                 365

Gln Gly Asn Val Phe Ser Cys Ser Val Met His Glu Ala Leu His Asn
    370                 375                 380

His Tyr Thr Gln Lys Ser Leu Ser Leu Ser Pro Gly Lys
385                 390                 395

<210> SEQ ID NO 149
<211> LENGTH: 396
<212> TYPE: PRT
<213> ORGANISM: Artificial sequence
<220> FEATURE:
<223> OTHER INFORMATION: Synthetic polypeptide

<400> SEQUENCE: 149

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Gly Ala
145                 150                 155                 160

Val Glu Ile Met Glu Pro Lys Ser Ser Asp Lys Thr His Thr Cys Pro
                165                 170                 175

Pro Cys Pro Ala Pro Glu Leu Leu Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe
```

```
            210                 215                 220
Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
            275                 280                 285

Lys Gly Gln Pro Arg Glu Pro Gln Val Tyr Thr Leu Pro Pro Ser Arg
            290                 295                 300

Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
            355                 360                 365

Gly Asn Val Phe Ser Cys Ser Val Met His Glu Ala Leu His Asn His
370                 375                 380

Tyr Thr Gln Lys Ser Leu Ser Leu Ser Pro Gly Lys
385                 390                 395

<210> SEQ ID NO 150
<211> LENGTH: 399
<212> TYPE: PRT
<213> ORGANISM: Artificial sequence
<220> FEATURE:
<223> OTHER INFORMATION: Synthetic polypeptide

<400> SEQUENCE: 150

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
            130                 135                 140

Val Leu Gly Arg Thr Gly Leu Leu Ala Asp Leu Leu Pro Ser Phe Ala
145                 150                 155                 160

Val Glu Ile Met Pro Glu Trp Glu Pro Lys Ser Ser Asp Lys Thr His
                165                 170                 175

Thr Cys Pro Pro Cys Pro Ala Pro Glu Leu Leu Gly Gly Pro Ser Val
```

```
                180              185              190
Phe Leu Phe Pro Pro Lys Pro Lys Asp Thr Leu Met Ile Ser Arg Thr
            195              200              205

Pro Glu Val Thr Cys Val Val Asp Val Ser His Glu Asp Pro Glu
210              215              220

Val Lys Phe Asn Trp Tyr Val Asp Gly Val Glu Val His Asn Ala Lys
225              230              235              240

Thr Lys Pro Arg Glu Glu Gln Tyr Asn Ser Thr Tyr Arg Val Val Ser
                245              250              255

Val Leu Thr Val Leu His Gln Asp Trp Leu Asn Gly Lys Glu Tyr Lys
            260              265              270

Cys Lys Val Ser Asn Lys Ala Leu Pro Ala Pro Ile Glu Lys Thr Ile
            275              280              285

Ser Lys Ala Lys Gly Gln Pro Arg Glu Pro Gln Val Tyr Thr Leu Pro
        290              295              300

Pro Ser Arg Asp Glu Leu Thr Lys Asn Gln Val Ser Leu Thr Cys Leu
305              310              315              320

Val Lys Gly Phe Tyr Pro Ser Asp Ile Ala Val Glu Trp Glu Ser Asn
                325              330              335

Gly Gln Pro Glu Asn Asn Tyr Lys Thr Thr Pro Pro Val Leu Asp Ser
                340              345              350

Asp Gly Ser Phe Phe Leu Tyr Ser Lys Leu Thr Val Asp Lys Ser Arg
            355              360              365

Trp Gln Gln Gly Asn Val Phe Ser Cys Ser Val Met His Glu Ala Leu
        370              375              380

His Asn His Tyr Thr Gln Lys Ser Leu Ser Leu Ser Pro Gly Lys
385              390              395

<210> SEQ ID NO 151
<211> LENGTH: 400
<212> TYPE: PRT
<213> ORGANISM: Artificial sequence
<220> FEATURE:
<223> OTHER INFORMATION: Synthetic polypeptide

<400> SEQUENCE: 151

Leu Gln Val Thr Val Pro Asp Lys Lys Val Ala Met Leu Phe Gln
1               5                  10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Gly Arg Thr Gly Leu Leu Ala Asp Leu Leu Pro Ser Phe Ala
```

```
            145                 150                 155                 160
Val Glu Ile Met Pro Glu Trp Val Glu Pro Lys Ser Ser Asp Lys Thr
                165                 170                 175

His Thr Cys Pro Pro Cys Pro Ala Pro Glu Leu Leu Gly Gly Pro Ser
                180                 185                 190

Val Phe Leu Phe Pro Pro Lys Pro Lys Asp Thr Leu Met Ile Ser Arg
                195                 200                 205

Thr Pro Glu Val Thr Cys Val Val Val Asp Val Ser His Glu Asp Pro
        210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
                260                 265                 270

Lys Cys Lys Val Ser Asn Lys Ala Leu Pro Ala Pro Ile Glu Lys Thr
                275                 280                 285

Ile Ser Lys Ala Lys Gly Gln Pro Arg Glu Pro Gln Val Tyr Thr Leu
        290                 295                 300

Pro Pro Ser Arg Asp Glu Leu Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
                340                 345                 350

Ser Asp Gly Ser Phe Phe Leu Tyr Ser Lys Leu Thr Val Asp Lys Ser
        355                 360                 365

Arg Trp Gln Gln Gly Asn Val Phe Ser Cys Ser Val Met His Glu Ala
                370                 375                 380

Leu His Asn His Tyr Thr Gln Lys Ser Leu Ser Leu Ser Pro Gly Lys
385                 390                 395                 400

<210> SEQ ID NO 152
<211> LENGTH: 401
<212> TYPE: PRT
<213> ORGANISM: Artificial sequence
<220> FEATURE:
<223> OTHER INFORMATION: Synthetic polypeptide

<400> SEQUENCE: 152

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
```

```
                115                 120                 125
Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Phe Ala
145                 150                 155                 160

Val Glu Ile Met Pro Glu Trp Val Phe Glu Pro Lys Ser Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
                195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
                275                 280                 285

Thr Ile Ser Lys Ala Lys Gly Gln Pro Arg Glu Pro Gln Val Tyr Thr
            290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
                355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro Gly
385                 390                 395                 400

Lys

<210> SEQ ID NO 153
<211> LENGTH: 370
<212> TYPE: PRT
<213> ORGANISM: Artificial sequence
<220> FEATURE:
<223> OTHER INFORMATION: Synthetic polypeptide

<400> SEQUENCE: 153

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80
```

```
Gln Gly Ser Thr Val Thr Leu Gly Asp Phe Tyr Arg Gly Arg Glu Ile
                 85                  90                  95
Thr Ile Val His Asp Ala Asp Leu Gln Ile Gly Lys Leu Met Trp Gly
            100                 105                 110
Asp Ser Gly Leu Tyr Tyr Cys Ile Ile Thr Thr Pro Asp Asp Leu Glu
        115                 120                 125
Gly Lys Asn Glu Asp Ser Val Glu Leu Leu Glu Pro Lys Ser Ser Asp
130                 135                 140
Lys Thr His Thr Cys Pro Pro Cys Pro Ala Pro Glu Leu Leu Gly Gly
145                 150                 155                 160
Pro Ser Val Phe Leu Phe Pro Pro Lys Pro Lys Asp Thr Leu Met Ile
                165                 170                 175
Ser Arg Thr Pro Glu Val Thr Cys Val Val Val Asp Val Ser His Glu
            180                 185                 190
Asp Pro Glu Val Lys Phe Asn Trp Tyr Val Asp Gly Val Glu Val His
        195                 200                 205
Asn Ala Lys Thr Lys Pro Arg Glu Glu Gln Tyr Asn Ser Thr Tyr Arg
210                 215                 220
Val Val Ser Val Leu Thr Val Leu His Gln Asp Trp Leu Asn Gly Lys
225                 230                 235                 240
Glu Tyr Lys Cys Lys Val Ser Asn Lys Ala Leu Pro Ala Pro Ile Glu
                245                 250                 255
Lys Thr Ile Ser Lys Ala Lys Gly Gln Pro Arg Glu Pro Gln Val Tyr
            260                 265                 270
Thr Leu Pro Pro Ser Arg Asp Glu Leu Thr Lys Asn Gln Val Ser Leu
        275                 280                 285
Thr Cys Leu Val Lys Gly Phe Tyr Pro Ser Asp Ile Ala Val Glu Trp
290                 295                 300
Glu Ser Asn Gly Gln Pro Glu Asn Asn Tyr Lys Thr Thr Pro Pro Val
305                 310                 315                 320
Leu Asp Ser Asp Gly Ser Phe Phe Leu Tyr Ser Lys Leu Thr Val Asp
                325                 330                 335
Lys Ser Arg Trp Gln Gln Gly Asn Val Phe Ser Cys Ser Val Met His
            340                 345                 350
Glu Ala Leu His Asn His Tyr Thr Gln Lys Ser Leu Ser Leu Ser Pro
        355                 360                 365
Gly Lys
370

<210> SEQ ID NO 154
<211> LENGTH: 371
<212> TYPE: PRT
<213> ORGANISM: Artificial sequence
<220> FEATURE:
<223> OTHER INFORMATION: Synthetic polypeptide

<400> SEQUENCE: 154

Asp Lys Lys Lys Val Ala Met Leu Phe Gln Pro Thr Val Leu Arg Cys
1               5                  10                  15
His Phe Ser Thr Ser Ser His Gln Pro Ala Val Val Gln Trp Lys Phe
                20                  25                  30
Lys Ser Tyr Cys Gln Asp Arg Met Gly Glu Ser Leu Gly Met Ser Ser
            35                  40                  45
Thr Arg Ala Gln Ser Leu Ser Lys Arg Asn Leu Glu Trp Asp Pro Tyr
        50                  55                  60
```

```
Leu Asp Cys Leu Asp Ser Arg Thr Val Arg Val Ala Ser Lys
 65                  70                  75                  80

Gln Gly Ser Thr Val Thr Leu Gly Asp Phe Tyr Arg Gly Arg Glu Ile
                 85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Pro Asp Asp Leu Glu
            115                 120                 125

Gly Lys Asn Glu Asp Ser Val Glu Leu Leu Val Glu Pro Lys Ser Ser
130                 135                 140

Asp Lys Thr His Thr Cys Pro Pro Cys Pro Ala Pro Glu Leu Leu Gly
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Ile
                245                 250                 255

Glu Lys Thr Ile Ser Lys Ala Lys Gly Gln Pro Arg Glu Pro Gln Val
            260                 265                 270

Tyr Thr Leu Pro Pro Ser Arg Asp Glu Leu Thr Lys Asn Gln Val Ser
        275                 280                 285

Leu Thr Cys Leu Val Lys Gly Phe Tyr Pro Ser Asp Ile Ala Val Glu
290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
            340                 345                 350

His Glu Ala Leu His Asn His Tyr Thr Gln Lys Ser Leu Ser Leu Ser
        355                 360                 365

Pro Gly Lys
    370

<210> SEQ ID NO 155
<211> LENGTH: 372
<212> TYPE: PRT
<213> ORGANISM: Artificial sequence
<220> FEATURE:
<223> OTHER INFORMATION: Synthetic polypeptide

<400> SEQUENCE: 155

Asp Lys Lys Lys Val Ala Met Leu Phe Gln Pro Thr Val Leu Arg Cys
 1               5                  10                  15

His Phe Ser Thr Ser Ser His Gln Pro Ala Val Val Gln Trp Lys Phe
             20                  25                  30

Lys Ser Tyr Cys Gln Asp Arg Met Gly Glu Ser Leu Gly Met Ser Ser
         35                  40                  45
```

Thr Arg Ala Gln Ser Leu Ser Lys Arg Asn Leu Glu Trp Asp Pro Tyr
    50                  55                  60

Leu Asp Cys Leu Asp Ser Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Glu Pro Lys Ser
    130                 135                 140

Ser Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
                180                 185                 190

His Glu Asp Pro Glu Val Lys Phe Asn Trp Tyr Val Asp Gly Val Glu
            195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
                260                 265                 270

Val Tyr Thr Leu Pro Pro Ser Arg Asp Glu Leu Thr Lys Asn Gln Val
            275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
                340                 345                 350

Met His Glu Ala Leu His Asn His Tyr Thr Gln Lys Ser Leu Ser Leu
            355                 360                 365

Ser Pro Gly Lys
    370

<210> SEQ ID NO 156
<211> LENGTH: 373
<212> TYPE: PRT
<213> ORGANISM: Artificial sequence
<220> FEATURE:
<223> OTHER INFORMATION: Synthetic polypeptide

<400> SEQUENCE: 156

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
           35                  40                  45

Thr Arg Ala Gln Ser Leu Ser Lys Arg Asn Leu Glu Trp Asp Pro Tyr
        50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Glu Pro Lys
        130                 135                 140

Ser Ser Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn Gln
        275                 280                 285

Val Ser Leu Thr Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
        355                 360                 365

Leu Ser Pro Gly Lys
        370

<210> SEQ ID NO 157
<211> LENGTH: 374
<212> TYPE: PRT
<213> ORGANISM: Artificial sequence
<220> FEATURE:
<223> OTHER INFORMATION: Synthetic polypeptide

<400> SEQUENCE: 157

Asp Lys Lys Lys Val Ala Met Leu Phe Gln Pro Thr Val Leu Arg Cys
1               5                   10                  15

```
His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
 50                  55                  60

Leu Asp Cys Leu Asp Ser Arg Arg Thr Val Arg Val Val Ala Ser Lys
 65                  70                  75                  80

Gln Gly Ser Thr Val Thr Leu Gly Asp Phe Tyr Arg Gly Arg Glu Ile
                 85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Glu Pro
130                 135                 140

Lys Ser Ser Asp Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly Lys
    370

<210> SEQ ID NO 158
<211> LENGTH: 375
<212> TYPE: PRT
<213> ORGANISM: Artificial sequence
<220> FEATURE:
<223> OTHER INFORMATION: Synthetic polypeptide

<400> SEQUENCE: 158
```

-continued

```
Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Glu
    130                 135                 140

Pro Lys Ser Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375
```

<210> SEQ ID NO 159
<211> LENGTH: 376
<212> TYPE: PRT
<213> ORGANISM: Artificial sequence
<220> FEATURE:

<223> OTHER INFORMATION: Synthetic polypeptide

<400> SEQUENCE: 159

Asp Lys Lys Lys Val Ala Met Leu Phe Gln Pro Thr Val Leu Arg Cys
1               5                   10                  15
His Phe Ser Thr Ser Ser His Gln Pro Ala Val Val Gln Trp Lys Phe
                20                  25                  30
Lys Ser Tyr Cys Gln Asp Arg Met Gly Glu Ser Leu Gly Met Ser Ser
            35                  40                  45
Thr Arg Ala Gln Ser Leu Ser Lys Arg Asn Leu Glu Trp Asp Pro Tyr
        50                  55                  60
Leu Asp Cys Leu Asp Ser Arg Arg Thr Val Arg Val Ala Ser Lys
65                  70                  75                  80
Gln Gly Ser Thr Val Thr Leu Gly Asp Phe Tyr Arg Gly Arg Glu Ile
                85                  90                  95
Thr Ile Val His Asp Ala Asp Leu Gln Ile Gly Lys Leu Met Trp Gly
            100                 105                 110
Asp Ser Gly Leu Tyr Tyr Cys Ile Ile Thr Thr Pro Asp Asp Leu Glu
        115                 120                 125
Gly Lys Asn Glu Asp Ser Val Glu Leu Leu Val Leu Gly Arg Thr Gly
130                 135                 140
Glu Pro Lys Ser Ser Asp Lys Thr His Thr Cys Pro Pro Cys Pro Ala
145                 150                 155                 160
Pro Glu Leu Leu Gly Gly Pro Ser Val Phe Leu Phe Pro Pro Lys Pro
                165                 170                 175
Lys Asp Thr Leu Met Ile Ser Arg Thr Pro Glu Val Thr Cys Val Val
            180                 185                 190
Val Asp Val Ser His Glu Asp Pro Glu Val Lys Phe Asn Trp Tyr Val
        195                 200                 205
Asp Gly Val Glu Val His Asn Ala Lys Thr Lys Pro Arg Glu Glu Gln
210                 215                 220
Tyr Asn Ser Thr Tyr Arg Val Val Ser Val Leu Thr Val Leu His Gln
225                 230                 235                 240
Asp Trp Leu Asn Gly Lys Glu Tyr Lys Cys Lys Val Ser Asn Lys Ala
                245                 250                 255
Leu Pro Ala Pro Ile Glu Lys Thr Ile Ser Lys Ala Lys Gly Gln Pro
            260                 265                 270
Arg Glu Pro Gln Val Tyr Thr Leu Pro Pro Ser Arg Asp Glu Leu Thr
        275                 280                 285
Lys Asn Gln Val Ser Leu Thr Cys Leu Val Lys Gly Phe Tyr Pro Ser
290                 295                 300
Asp Ile Ala Val Glu Trp Glu Ser Asn Gly Gln Pro Glu Asn Asn Tyr
305                 310                 315                 320
Lys Thr Thr Pro Pro Val Leu Asp Ser Asp Gly Ser Phe Phe Leu Tyr
                325                 330                 335
Ser Lys Leu Thr Val Asp Lys Ser Arg Trp Gln Gln Gly Asn Val Phe
            340                 345                 350
Ser Cys Ser Val Met His Glu Ala Leu His Asn His Tyr Thr Gln Lys
        355                 360                 365
Ser Leu Ser Leu Ser Pro Gly Lys
370                 375

<210> SEQ ID NO 160
<211> LENGTH: 377

<212> TYPE: PRT
<213> ORGANISM: Artificial sequence
<220> FEATURE:
<223> OTHER INFORMATION: Synthetic polypeptide

<400> SEQUENCE: 160

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
            85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
    130                 135                 140

Leu Glu Pro Lys Ser Ser Asp Lys Thr His Thr Cys Pro Pro Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
            195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Asp Glu Leu
            275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
            325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
            355                 360                 365

Lys Ser Leu Ser Leu Ser Pro Gly Lys
    370                 375

<210> SEQ ID NO 161
<211> LENGTH: 378
<212> TYPE: PRT
<213> ORGANISM: Artificial sequence
<220> FEATURE:
<223> OTHER INFORMATION: Synthetic polypeptide

<400> SEQUENCE: 161

```
Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
    210                 215                 220

Glu Gln Tyr Asn Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Asp Glu
        275                 280                 285

Leu Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365
```

Gln Lys Ser Leu Ser Leu Ser Pro Gly Lys
       370                 375

<210> SEQ ID NO 162
<211> LENGTH: 379
<212> TYPE: PRT
<213> ORGANISM: Artificial sequence
<220> FEATURE:
<223> OTHER INFORMATION: Synthetic polypeptide

<400> SEQUENCE: 162

Asp Lys Lys Val Ala Met Leu Phe Gln Pro Thr Val Leu Arg Cys
1               5                   10                  15

His Phe Ser Thr Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Ala Ser Lys
65              70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Pro Asp Asp Leu Glu
            115                 120                 125

Gly Lys Asn Glu Asp Ser Val Glu Leu Leu Val Leu Gly Arg Thr Gly
        130                 135                 140

Leu Leu Ala Glu Pro Lys Ser Ser Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
        195                 200                 205

Trp Tyr Val Asp Gly Val Glu Val His Asn Ala Lys Thr Lys Pro Arg
210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Asp
        275                 280                 285

Glu Leu Thr Lys Asn Gln Val Ser Leu Thr Cys Leu Val Lys Gly Phe
290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
                355                 360                 365

Thr Gln Lys Ser Leu Ser Leu Ser Pro Gly Lys
    370                 375

<210> SEQ ID NO 163
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 163

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
                35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
                115                 120                 125

Gly Lys Asn Glu Asp Ser Val Glu Leu Leu Val Leu Gly Arg Thr Gly
                130                 135                 140

Leu Leu Ala Asp Glu Pro Lys Ser Ser Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
                180                 185                 190

Thr Cys Val Val Val Asp Val Ser His Glu Asp Pro Glu Val Lys Phe
                195                 200                 205

Asn Trp Tyr Val Asp Gly Val Glu Val His Asn Ala Lys Thr Lys Pro
                210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
                260                 265                 270

Lys Gly Gln Pro Arg Glu Pro Gln Val Tyr Thr Leu Pro Pro Ser Arg
                275                 280                 285

Asp Glu Leu Thr Lys Asn Gln Val Ser Leu Thr Cys Leu Val Lys Gly
                290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

```
Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
        370                 375                 380

<210> SEQ ID NO 164
<211> LENGTH: 381
<212> TYPE: PRT
<213> ORGANISM: Artificial sequence
<220> FEATURE:
<223> OTHER INFORMATION: Synthetic polypeptide

<400> SEQUENCE: 164

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
130                 135                 140

Leu Leu Ala Asp Leu Glu Pro Lys Ser Ser Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Asp Glu Leu Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320
```

```
Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
    370                 375                 380

<210> SEQ ID NO 165
<211> LENGTH: 382
<212> TYPE: PRT
<213> ORGANISM: Artificial sequence
<220> FEATURE:
<223> OTHER INFORMATION: Synthetic polypeptide

<400> SEQUENCE: 165

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Glu Pro Lys Ser Ser Asp Lys Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
        275                 280                 285

Ser Arg Asp Glu Leu Thr Lys Asn Gln Val Ser Leu Thr Cys Leu Val
    290                 295                 300
```

```
Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
                340                 345                 350

Gln Gln Gly Asn Val Phe Ser Cys Ser Val Met His Glu Ala Leu His
                355                 360                 365

Asn His Tyr Thr Gln Lys Ser Leu Ser Leu Ser Pro Gly Lys
            370                 375                 380

<210> SEQ ID NO 166
<211> LENGTH: 383
<212> TYPE: PRT
<213> ORGANISM: Artificial sequence
<220> FEATURE:
<223> OTHER INFORMATION: Synthetic polypeptide

<400> SEQUENCE: 166

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Glu Pro Lys Ser Ser Asp Lys Thr His
145                 150                 155                 160

Thr Cys Pro Pro Cys Pro Ala Pro Glu Leu Leu Gly Gly Pro Ser Val
                165                 170                 175

Phe Leu Phe Pro Pro Lys Pro Lys Asp Thr Leu Met Ile Ser Arg Thr
                180                 185                 190

Pro Glu Val Thr Cys Val Val Val Asp Val Ser His Glu Asp Pro Glu
            195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
                260                 265                 270

Ser Lys Ala Lys Gly Gln Pro Arg Glu Pro Gln Val Tyr Thr Leu Pro
            275                 280                 285
```

```
Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
370                 375                 380
```

<210> SEQ ID NO 167
<211> LENGTH: 384
<212> TYPE: PRT
<213> ORGANISM: Artificial sequence
<220> FEATURE:
<223> OTHER INFORMATION: Synthetic polypeptide

<400> SEQUENCE: 167

```
Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
130                 135                 140

Leu Leu Ala Asp Leu Leu Pro Ser Glu Pro Lys Ser Ser Asp Lys Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270
```

Ile Ser Lys Ala Lys Gly Gln Pro Arg Glu Pro Gln Val Tyr Thr Leu
            275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
            355                 360                 365

Leu His Asn His Tyr Thr Gln Lys Ser Leu Ser Leu Ser Pro Gly Lys
            370                 375                 380

<210> SEQ ID NO 168
<211> LENGTH: 385
<212> TYPE: PRT
<213> ORGANISM: Artificial sequence
<220> FEATURE:
<223> OTHER INFORMATION: Synthetic polypeptide

<400> SEQUENCE: 168

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
            85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
            130                 135                 140

Leu Leu Ala Asp Leu Leu Pro Ser Phe Glu Pro Lys Ser Ser Asp Lys
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
            195                 200                 205

Pro Glu Val Lys Phe Asn Trp Tyr Val Asp Gly Val Glu Val His Asn
            210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
            245                 250                 255

```
Tyr Lys Cys Lys Val Ser Asn Lys Ala Leu Pro Ala Pro Ile Glu Lys
                260                 265                 270

Thr Ile Ser Lys Ala Lys Gly Gln Pro Arg Glu Pro Gln Val Tyr Thr
        275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
385

<210> SEQ ID NO 169
<211> LENGTH: 386
<212> TYPE: PRT
<213> ORGANISM: Artificial sequence
<220> FEATURE:
<223> OTHER INFORMATION: Synthetic polypeptide

<400> SEQUENCE: 169

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Glu Pro Lys Ser Ser Asp
145                 150                 155                 160

Lys Thr His Thr Cys Pro Pro Cys Pro Ala Pro Glu Leu Leu Gly Gly
                165                 170                 175

Pro Ser Val Phe Leu Phe Pro Pro Lys Pro Lys Asp Thr Leu Met Ile
            180                 185                 190

Ser Arg Thr Pro Glu Val Thr Cys Val Val Val Asp Val Ser His Glu
        195                 200                 205

Asp Pro Glu Val Lys Phe Asn Trp Tyr Val Asp Gly Val Glu Val His
    210                 215                 220
```

```
Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
            245                 250                 255

Glu Tyr Lys Cys Lys Val Ser Asn Lys Ala Leu Pro Ala Pro Ile Glu
            260                 265                 270

Lys Thr Ile Ser Lys Ala Lys Gly Gln Pro Arg Glu Pro Gln Val Tyr
            275                 280                 285

Thr Leu Pro Pro Ser Arg Asp Glu Leu Thr Lys Asn Gln Val Ser Leu
        290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
            325                 330                 335

Leu Asp Ser Asp Gly Ser Phe Phe Leu Tyr Ser Lys Leu Thr Val Asp
            340                 345                 350

Lys Ser Arg Trp Gln Gln Gly Asn Val Phe Ser Cys Ser Val Met His
            355                 360                 365

Glu Ala Leu His Asn His Tyr Thr Gln Lys Ser Leu Ser Leu Ser Pro
370                 375                 380

Gly Lys
385

<210> SEQ ID NO 170
<211> LENGTH: 387
<212> TYPE: PRT
<213> ORGANISM: Artificial sequence
<220> FEATURE:
<223> OTHER INFORMATION: Synthetic polypeptide

<400> SEQUENCE: 170

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
            85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
            130                 135                 140

Leu Leu Ala Asp Leu Leu Pro Ser Phe Ala Val Glu Pro Lys Ser Ser
145                 150                 155                 160

Asp Lys Thr His Thr Cys Pro Pro Cys Pro Ala Pro Glu Leu Leu Gly
            165                 170                 175

Gly Pro Ser Val Phe Leu Phe Pro Pro Lys Pro Lys Asp Thr Leu Met
            180                 185                 190
```

```
Ile Ser Arg Thr Pro Glu Val Thr Cys Val Val Val Asp Val Ser His
        195                 200                 205

Glu Asp Pro Glu Val Lys Phe Asn Trp Tyr Val Asp Gly Val Glu Val
210                 215                 220

His Asn Ala Lys Thr Lys Pro Arg Glu Glu Gln Tyr Asn Ser Thr Tyr
225                 230                 235                 240

Arg Val Val Ser Val Leu Thr Val Leu His Gln Asp Trp Leu Asn Gly
                245                 250                 255

Lys Glu Tyr Lys Cys Lys Val Ser Asn Lys Ala Leu Pro Ala Pro Ile
                260                 265                 270

Glu Lys Thr Ile Ser Lys Ala Lys Gly Gln Pro Arg Glu Pro Gln Val
            275                 280                 285

Tyr Thr Leu Pro Pro Ser Arg Asp Glu Leu Thr Lys Asn Gln Val Ser
        290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Lys Leu Thr Val
                340                 345                 350

Asp Lys Ser Arg Trp Gln Gln Gly Asn Val Phe Ser Cys Ser Val Met
            355                 360                 365

His Glu Ala Leu His Asn His Tyr Thr Gln Lys Ser Leu Ser Leu Ser
        370                 375                 380

Pro Gly Lys
385

<210> SEQ ID NO 171
<211> LENGTH: 388
<212> TYPE: PRT
<213> ORGANISM: Artificial sequence
<220> FEATURE:
<223> OTHER INFORMATION: Synthetic polypeptide

<400> SEQUENCE: 171

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu Glu Pro Lys Ser
145                 150                 155                 160
```

```
Ser Asp Lys Thr His Thr Cys Pro Pro Cys Pro Ala Pro Glu Leu Leu
            165                 170                 175

Gly Gly Pro Ser Val Phe Leu Phe Pro Pro Lys Pro Lys Asp Thr Leu
        180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
        260                 265                 270

Ile Glu Lys Thr Ile Ser Lys Ala Lys Gly Gln Pro Arg Glu Pro Gln
        275                 280                 285

Val Tyr Thr Leu Pro Pro Ser Arg Asp Glu Leu Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
        340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly Lys
385

<210> SEQ ID NO 172
<211> LENGTH: 389
<212> TYPE: PRT
<213> ORGANISM: Artificial sequence
<220> FEATURE:
<223> OTHER INFORMATION: Synthetic polypeptide

<400> SEQUENCE: 172

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125
```

```
Gly Lys Asn Glu Asp Ser Val Glu Leu Val Leu Gly Arg Thr Gly
    130                 135                 140

Leu Leu Ala Asp Leu Leu Pro Ser Phe Ala Val Glu Ile Glu Pro Lys
145                 150                 155                 160

Ser Ser Asp Lys Thr His Thr Cys Pro Pro Cys Pro Ala Pro Glu Leu
                165                 170                 175

Leu Gly Gly Pro Ser Val Phe Leu Phe Pro Pro Lys Pro Lys Asp Thr
                180                 185                 190

Leu Met Ile Ser Arg Thr Pro Glu Val Thr Cys Val Val Val Asp Val
            195                 200                 205

Ser His Glu Asp Pro Glu Val Lys Phe Asn Trp Tyr Val Asp Gly Val
210                 215                 220

Glu Val His Asn Ala Lys Thr Lys Pro Arg Glu Glu Gln Tyr Asn Ser
225                 230                 235                 240

Thr Tyr Arg Val Val Ser Val Leu Thr Val Leu His Gln Asp Trp Leu
                245                 250                 255

Asn Gly Lys Glu Tyr Lys Cys Lys Val Ser Asn Lys Ala Leu Pro Ala
                260                 265                 270

Pro Ile Glu Lys Thr Ile Ser Lys Ala Lys Gly Gln Pro Arg Glu Pro
            275                 280                 285

Gln Val Tyr Thr Leu Pro Pro Ser Arg Asp Glu Leu Thr Lys Asn Gln
290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Lys Leu
                340                 345                 350

Thr Val Asp Lys Ser Arg Trp Gln Gln Gly Asn Val Phe Ser Cys Ser
            355                 360                 365

Val Met His Glu Ala Leu His Asn His Tyr Thr Gln Lys Ser Leu Ser
370                 375                 380

Leu Ser Pro Gly Lys
385

<210> SEQ ID NO 173
<211> LENGTH: 390
<212> TYPE: PRT
<213> ORGANISM: Artificial sequence
<220> FEATURE:
<223> OTHER INFORMATION: Synthetic polypeptide

<400> SEQUENCE: 173

Asp Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95
```

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
        130                 135                 140

Leu Leu Ala Asp Leu Leu Pro Ser Phe Ala Val Glu Ile Met Glu Pro
145                 150                 155                 160

Lys Ser Ser Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
            195                 200                 205

Val Ser His Glu Asp Pro Glu Val Lys Phe Asn Trp Tyr Val Asp Gly
        210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
            355                 360                 365

Ser Val Met His Glu Ala Leu His Asn His Tyr Thr Gln Lys Ser Leu
        370                 375                 380

Ser Leu Ser Pro Gly Lys
385                 390

<210> SEQ ID NO 174
<211> LENGTH: 391
<212> TYPE: PRT
<213> ORGANISM: Artificial sequence
<220> FEATURE:
<223> OTHER INFORMATION: Synthetic polypeptide

<400> SEQUENCE: 174

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

```
Leu Asp Cys Leu Asp Ser Arg Arg Thr Val Arg Val Ala Ser Lys
 65                  70                  75                  80

Gln Gly Ser Thr Val Thr Leu Gly Asp Phe Tyr Arg Gly Arg Glu Ile
                 85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Pro Asp Asp Leu Glu
        115                 120                 125

Gly Lys Asn Glu Asp Ser Val Glu Leu Leu Val Leu Gly Arg Thr Gly
130                 135                 140

Leu Leu Ala Asp Leu Leu Pro Ser Phe Ala Val Glu Ile Met Pro Glu
145                 150                 155                 160

Pro Lys Ser Ser Asp Lys Thr His Thr Cys Pro Pro Cys Pro Ala Pro
                165                 170                 175

Glu Leu Leu Gly Gly Pro Ser Val Phe Leu Phe Pro Pro Lys Pro Lys
            180                 185                 190

Asp Thr Leu Met Ile Ser Arg Thr Pro Glu Val Thr Cys Val Val Val
        195                 200                 205

Asp Val Ser His Glu Asp Pro Glu Val Lys Phe Asn Trp Tyr Val Asp
210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285

Glu Pro Gln Val Tyr Thr Leu Pro Pro Ser Arg Asp Glu Leu Thr Lys
290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
370                 375                 380

Leu Ser Leu Ser Pro Gly Lys
385                 390

<210> SEQ ID NO 175
<211> LENGTH: 392
<212> TYPE: PRT
<213> ORGANISM: Artificial sequence
<220> FEATURE:
<223> OTHER INFORMATION: Synthetic polypeptide

<400> SEQUENCE: 175

Asp Lys Lys Val Ala Met Leu Phe Gln Pro Thr Val Leu Arg Cys
 1               5                  10                  15

His Phe Thr Ser Ser His Gln Pro Ala Val Val Gln Trp Lys Phe
                20                  25                  30
```

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
 50                  55                  60

Leu Asp Cys Leu Asp Ser Arg Arg Thr Val Arg Val Ala Ser Lys
 65                  70                  75                  80

Gln Gly Ser Thr Val Thr Leu Gly Asp Phe Tyr Arg Gly Arg Glu Ile
                 85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
130                 135                 140

Leu Leu Ala Asp Leu Leu Pro Ser Phe Ala Val Glu Ile Met Pro Glu
145                 150                 155                 160

Glu Pro Lys Ser Ser Asp Lys Thr His Thr Cys Pro Pro Cys Pro Ala
                165                 170                 175

Pro Glu Leu Leu Gly Gly Pro Ser Val Phe Leu Phe Pro Pro Lys Pro
                180                 185                 190

Lys Asp Thr Leu Met Ile Ser Arg Thr Pro Glu Val Thr Cys Val Val
            195                 200                 205

Val Asp Val Ser His Glu Asp Pro Glu Val Lys Phe Asn Trp Tyr Val
            210                 215                 220

Asp Gly Val Glu Val His Asn Ala Lys Thr Lys Pro Arg Glu Glu Gln
225                 230                 235                 240

Tyr Asn Ser Thr Tyr Arg Val Val Ser Val Leu Thr Val Leu His Gln
                245                 250                 255

Asp Trp Leu Asn Gly Lys Glu Tyr Lys Cys Lys Val Ser Asn Lys Ala
            260                 265                 270

Leu Pro Ala Pro Ile Glu Lys Thr Ile Ser Lys Ala Lys Gly Gln Pro
            275                 280                 285

Arg Glu Pro Gln Val Tyr Thr Leu Pro Pro Ser Arg Asp Glu Leu Thr
290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Val Leu Asp Ser Asp Gly Ser Phe Phe Leu Tyr
            340                 345                 350

Ser Lys Leu Thr Val Asp Lys Ser Arg Trp Gln Gln Gly Asn Val Phe
            355                 360                 365

Ser Cys Ser Val Met His Glu Ala Leu His Asn His Tyr Thr Gln Lys
            370                 375                 380

Ser Leu Ser Leu Ser Pro Gly Lys
385                 390

<210> SEQ ID NO 176
<211> LENGTH: 393
<212> TYPE: PRT
<213> ORGANISM: Artificial sequence
<220> FEATURE:
<223> OTHER INFORMATION: Synthetic polypeptide

<400> SEQUENCE: 176

```
Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Gly Arg Thr Gly
        130                 135                 140

Leu Leu Ala Asp Leu Leu Pro Ser Phe Ala Val Glu Ile Met Pro Glu
145                 150                 155                 160

Trp Glu Pro Lys Ser Ser Asp Lys Thr His Thr Cys Pro Pro Cys Pro
                165                 170                 175

Ala Pro Glu Leu Leu Gly Gly Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
        355                 360                 365

Phe Ser Cys Ser Val Met His Glu Ala Leu His Asn His Tyr Thr Gln
370                 375                 380

Lys Ser Leu Ser Leu Ser Pro Gly Lys
385                 390
```

<210> SEQ ID NO 177
<211> LENGTH: 394
<212> TYPE: PRT

<213> ORGANISM: Artificial sequence
<220> FEATURE:
<223> OTHER INFORMATION: Synthetic polypeptide

<400> SEQUENCE: 177

```
Asp Lys Lys Lys Val Ala Met Leu Phe Gln Pro Thr Val Leu Arg Cys
1               5                  10                  15
His Phe Ser Thr Ser Ser His Gln Pro Ala Val Val Gln Trp Lys Phe
            20                  25                  30
Lys Ser Tyr Cys Gln Asp Arg Met Gly Glu Ser Leu Gly Met Ser Ser
        35                  40                  45
Thr Arg Ala Gln Ser Leu Ser Lys Arg Asn Leu Glu Trp Asp Pro Tyr
    50                  55                  60
Leu Asp Cys Leu Asp Ser Arg Arg Thr Val Arg Val Val Ala Ser Lys
65                  70                  75                  80
Gln Gly Ser Thr Val Thr Leu Gly Asp Phe Tyr Arg Gly Arg Glu Ile
                85                  90                  95
Thr Ile Val His Asp Ala Asp Leu Gln Ile Gly Lys Leu Met Trp Gly
            100                 105                 110
Asp Ser Gly Leu Tyr Tyr Cys Ile Ile Thr Thr Pro Asp Asp Leu Glu
        115                 120                 125
Gly Lys Asn Glu Asp Ser Val Glu Leu Leu Val Leu Gly Arg Thr Gly
    130                 135                 140
Leu Leu Ala Asp Leu Leu Pro Ser Phe Ala Val Glu Ile Met Pro Glu
145                 150                 155                 160
Trp Val Glu Pro Lys Ser Ser Asp Lys Thr His Thr Cys Pro Pro Cys
                165                 170                 175
Pro Ala Pro Glu Leu Leu Gly Gly Pro Ser Val Phe Leu Phe Pro Pro
            180                 185                 190
Lys Pro Lys Asp Thr Leu Met Ile Ser Arg Thr Pro Glu Val Thr Cys
        195                 200                 205
Val Val Val Asp Val Ser His Glu Asp Pro Glu Val Lys Phe Asn Trp
    210                 215                 220
Tyr Val Asp Gly Val Glu Val His Asn Ala Lys Thr Lys Pro Arg Glu
225                 230                 235                 240
Glu Gln Tyr Asn Ser Thr Tyr Arg Val Val Ser Val Leu Thr Val Leu
                245                 250                 255
His Gln Asp Trp Leu Asn Gly Lys Glu Tyr Lys Cys Lys Val Ser Asn
            260                 265                 270
Lys Ala Leu Pro Ala Pro Ile Glu Lys Thr Ile Ser Lys Ala Lys Gly
        275                 280                 285
Gln Pro Arg Glu Pro Gln Val Tyr Thr Leu Pro Pro Ser Arg Asp Glu
    290                 295                 300
Leu Thr Lys Asn Gln Val Ser Leu Thr Cys Leu Val Lys Gly Phe Tyr
305                 310                 315                 320
Pro Ser Asp Ile Ala Val Glu Trp Glu Ser Asn Gly Gln Pro Glu Asn
                325                 330                 335
Asn Tyr Lys Thr Thr Pro Pro Val Leu Asp Ser Asp Gly Ser Phe Phe
            340                 345                 350
Leu Tyr Ser Lys Leu Thr Val Asp Lys Ser Arg Trp Gln Gln Gly Asn
        355                 360                 365
Val Phe Ser Cys Ser Val Met His Glu Ala Leu His Asn His Tyr Thr
    370                 375                 380
Gln Lys Ser Leu Ser Leu Ser Pro Gly Lys
```

```
385                 390
```

<210> SEQ ID NO 178
<211> LENGTH: 395
<212> TYPE: PRT
<213> ORGANISM: Artificial sequence
<220> FEATURE:
<223> OTHER INFORMATION: Synthetic polypeptide

<400> SEQUENCE: 178

```
Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Gly Arg Thr Gly
    130                 135                 140

Leu Leu Ala Asp Leu Leu Pro Ser Phe Ala Val Glu Ile Met Pro Glu
145                 150                 155                 160

Trp Val Phe Glu Pro Lys Ser Ser Asp Lys Thr His Thr Cys Pro Pro
                165                 170                 175

Cys Pro Ala Pro Glu Leu Leu Gly Gly Pro Ser Val Phe Leu Phe Pro
            180                 185                 190

Pro Lys Pro Lys Asp Thr Leu Met Ile Ser Arg Thr Pro Glu Val Thr
        195                 200                 205

Cys Val Val Val Asp Val Ser His Glu Asp Pro Glu Val Lys Phe Asn
    210                 215                 220

Trp Tyr Val Asp Gly Val Glu Val His Asn Ala Lys Thr Lys Pro Arg
225                 230                 235                 240

Glu Glu Gln Tyr Asn Ser Thr Tyr Arg Val Val Ser Val Leu Thr Val
                245                 250                 255

Leu His Gln Asp Trp Leu Asn Gly Lys Glu Tyr Lys Cys Lys Val Ser
            260                 265                 270

Asn Lys Ala Leu Pro Ala Pro Ile Glu Lys Thr Ile Ser Lys Ala Lys
        275                 280                 285

Gly Gln Pro Arg Glu Pro Gln Val Tyr Thr Leu Pro Pro Ser Arg Asp
    290                 295                 300

Glu Leu Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
```

Asn Val Phe Ser Cys Ser Val Met His Glu Ala Leu His Asn His Tyr
            370                 375                 380

Thr Gln Lys Ser Leu Ser Leu Ser Pro Gly Lys
385                 390                 395

<210> SEQ ID NO 179
<211> LENGTH: 379
<212> TYPE: PRT
<213> ORGANISM: Artificial sequence
<220> FEATURE:
<223> OTHER INFORMATION: Synthetic polypeptide

<400> SEQUENCE: 179

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
130                 135                 140

Val Leu Glu Glu Pro Lys Ser Ser Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
        195                 200                 205

Trp Tyr Val Asp Gly Val Glu Val His Asn Ala Lys Thr Lys Pro Arg
    210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Asp
        275                 280                 285

Glu Leu Thr Lys Asn Gln Val Ser Leu Thr Cys Leu Val Lys Gly Phe
290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe

```
                    325                 330                 335
Phe Leu Tyr Ser Lys Leu Thr Val Asp Lys Ser Arg Trp Gln Gln Gly
                340                 345                 350
Asn Val Phe Ser Cys Ser Val Met His Glu Ala Leu His Asn His Tyr
            355                 360                 365
Thr Gln Lys Ser Leu Ser Leu Ser Pro Gly Lys
        370                 375

<210> SEQ ID NO 180
<211> LENGTH: 380
<212> TYPE: PRT
<213> ORGANISM: Artificial sequence
<220> FEATURE:
<223> OTHER INFORMATION: Synthetic polypeptide

<400> SEQUENCE: 180

Leu Gln Val Thr Val Pro Asp Lys Lys Lys Val Ala Met Leu Phe Gln
1               5                   10                  15
Pro Thr Val Leu Arg Cys His Phe Ser Thr Ser Ser His Gln Pro Ala
            20                  25                  30
Val Val Gln Trp Lys Phe Lys Ser Tyr Cys Gln Asp Arg Met Gly Glu
        35                  40                  45
Ser Leu Gly Met Ser Ser Thr Arg Ala Gln Ser Leu Ser Lys Arg Asn
    50                  55                  60
Leu Glu Trp Asp Pro Tyr Leu Asp Cys Leu Asp Ser Arg Arg Thr Val
65                  70                  75                  80
Arg Val Val Ala Ser Lys Gln Gly Ser Thr Val Thr Leu Gly Asp Phe
                85                  90                  95
Tyr Arg Gly Arg Glu Ile Thr Ile Val His Asp Ala Asp Leu Gln Ile
            100                 105                 110
Gly Lys Leu Met Trp Gly Asp Ser Gly Leu Tyr Tyr Cys Ile Ile Thr
        115                 120                 125
Thr Pro Asp Asp Leu Glu Gly Lys Asn Glu Asp Ser Val Glu Leu Leu
    130                 135                 140
Val Leu Glu Trp Glu Pro Lys Ser Ser Asp Lys Thr His Thr Cys Pro
145                 150                 155                 160
Pro Cys Pro Ala Pro Glu Leu Leu Gly Gly Pro Ser Val Phe Leu Phe
                165                 170                 175
Pro Pro Lys Pro Lys Asp Thr Leu Met Ile Ser Arg Thr Pro Glu Val
            180                 185                 190
Thr Cys Val Val Val Asp Val Ser His Glu Asp Pro Glu Val Lys Phe
        195                 200                 205
Asn Trp Tyr Val Asp Gly Val Glu Val His Asn Ala Lys Thr Lys Pro
    210                 215                 220
Arg Glu Glu Gln Tyr Asn Ser Thr Tyr Arg Val Val Ser Val Leu Thr
225                 230                 235                 240
Val Leu His Gln Asp Trp Leu Asn Gly Lys Glu Tyr Lys Cys Lys Val
                245                 250                 255
Ser Asn Lys Ala Leu Pro Ala Pro Ile Glu Lys Thr Ile Ser Lys Ala
            260                 265                 270
Lys Gly Gln Pro Arg Glu Pro Gln Val Tyr Thr Leu Pro Pro Ser Arg
        275                 280                 285
Asp Glu Leu Thr Lys Asn Gln Val Ser Leu Thr Cys Leu Val Lys Gly
    290                 295                 300
Phe Tyr Pro Ser Asp Ile Ala Val Glu Trp Glu Ser Asn Gly Gln Pro
```

```
305                 310                 315                 320
Glu Asn Asn Tyr Lys Thr Thr Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
            355                 360                 365

Tyr Thr Gln Lys Ser Leu Ser Leu Ser Pro Gly Lys
            370                 375                 380

<210> SEQ ID NO 181
<211> LENGTH: 396
<212> TYPE: PRT
<213> ORGANISM: Artificial sequence
<220> FEATURE:
<223> OTHER INFORMATION: Synthetic polypeptide

<400> SEQUENCE: 181

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Gly Arg Thr Gly Leu Leu Ala Asp Leu Leu Pro Ser Ala Ala
145                 150                 155                 160

Val Glu Ile Met Glu Pro Lys Ser Ser Asp Lys Thr His Thr Cys Pro
                165                 170                 175

Pro Cys Pro Ala Pro Glu Leu Leu Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
```

```
            290                 295                 300
Asp Glu Leu Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
        355                 360                 365

Gly Asn Val Phe Ser Cys Ser Val Met His Glu Ala Leu His Asn His
    370                 375                 380

Tyr Thr Gln Lys Ser Leu Ser Leu Ser Pro Gly Lys
385                 390                 395

<210> SEQ ID NO 182
<211> LENGTH: 382
<212> TYPE: PRT
<213> ORGANISM: Artificial sequence
<220> FEATURE:
<223> OTHER INFORMATION: Synthetic polypeptide

<400> SEQUENCE: 182

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
        50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
130                 135                 140

Val Leu Glu Trp Val Phe Glu Pro Lys Ser Ser Asp Lys Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
```

```
                  260                 265                 270
Lys Ala Lys Gly Gln Pro Arg Glu Pro Gln Val Tyr Thr Leu Pro Pro
            275                 280                 285

Ser Arg Asp Glu Leu Thr Lys Asn Gln Val Ser Leu Thr Cys Leu Val
        290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380

<210> SEQ ID NO 183
<211> LENGTH: 383
<212> TYPE: PRT
<213> ORGANISM: Artificial sequence
<220> FEATURE:
<223> OTHER INFORMATION: Synthetic polypeptide

<400> SEQUENCE: 183

Leu Gln Val Thr Val Pro Asp Lys Lys Lys Val Ala Met Leu Phe Gln
1               5                   10                  15

Pro Thr Val Leu Arg Cys His Phe Ser Thr Ser Ser His Gln Pro Ala
            20                  25                  30

Val Val Gln Trp Lys Phe Lys Ser Tyr Cys Gln Asp Arg Met Gly Glu
        35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
            100                 105                 110

Gly Lys Leu Met Trp Gly Asp Ser Gly Leu Tyr Tyr Cys Ile Ile Thr
        115                 120                 125

Thr Pro Asp Asp Leu Glu Gly Lys Asn Glu Asp Ser Val Glu Leu Leu
    130                 135                 140

Val Leu Glu Trp Val Phe Val Glu Pro Lys Ser Ser Asp Lys Thr His
145                 150                 155                 160

Thr Cys Pro Pro Cys Pro Ala Pro Glu Leu Leu Gly Gly Pro Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
```

```
                    245                 250                 255
Cys Lys Val Ser Asn Lys Ala Leu Pro Ala Pro Ile Glu Lys Thr Ile
                260                 265                 270

Ser Lys Ala Lys Gly Gln Pro Arg Glu Pro Gln Val Tyr Thr Leu Pro
                275                 280                 285

Pro Ser Arg Asp Glu Leu Thr Lys Asn Gln Val Ser Leu Thr Cys Leu
            290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
                340                 345                 350

Trp Gln Gln Gly Asn Val Phe Ser Cys Ser Val Met His Glu Ala Leu
                355                 360                 365

His Asn His Tyr Thr Gln Lys Ser Leu Ser Leu Ser Pro Gly Lys
                370                 375                 380

<210> SEQ ID NO 184
<211> LENGTH: 384
<212> TYPE: PRT
<213> ORGANISM: Artificial sequence
<220> FEATURE:
<223> OTHER INFORMATION: Synthetic polypeptide

<400> SEQUENCE: 184

Leu Gln Val Thr Val Pro Asp Lys Lys Val Ala Met Leu Phe Gln
1               5                   10                  15

Pro Thr Val Leu Arg Cys His Phe Ser Thr Ser Ser His Gln Pro Ala
                20                  25                  30

Val Val Gln Trp Lys Phe Lys Ser Tyr Cys Gln Asp Arg Met Gly Glu
            35                  40                  45

Ser Leu Gly Met Ser Ser Thr Arg Ala Gln Ser Leu Ser Lys Arg Asn
    50                  55                  60

Leu Glu Trp Asp Pro Tyr Leu Asp Cys Leu Asp Ser Arg Arg Thr Val
65                  70                  75                  80

Arg Val Val Ala Ser Lys Gln Gly Ser Thr Val Thr Leu Gly Asp Phe
                85                  90                  95

Tyr Arg Gly Arg Glu Ile Thr Ile Val His Asp Ala Asp Leu Gln Ile
                100                 105                 110

Gly Lys Leu Met Trp Gly Asp Ser Gly Leu Tyr Tyr Cys Ile Ile Thr
            115                 120                 125

Thr Pro Asp Asp Leu Glu Gly Lys Asn Glu Asp Ser Val Glu Leu Leu
    130                 135                 140

Val Leu Glu Trp Val Phe Val Gly Glu Pro Lys Ser Ser Asp Lys Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
```

```
                  225                 230                 235                 240
Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

<210> SEQ ID NO 185
<211> LENGTH: 373
<212> TYPE: PRT
<213> ORGANISM: Artificial sequence
<220> FEATURE:
<223> OTHER INFORMATION: Synthetic polypeptide

<400> SEQUENCE: 185

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Glu Glu Pro Lys
    130                 135                 140

Ser Ser Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
```

```
                    210                 215                 220
Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
                260                 265                 270

Gln Val Tyr Thr Leu Pro Pro Ser Arg Asp Glu Leu Thr Lys Asn Gln
            275                 280                 285

Val Ser Leu Thr Cys Leu Val Lys Gly Phe Tyr Pro Ser Asp Ile Ala
        290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
                340                 345                 350

Val Met His Glu Ala Leu His Asn His Tyr Thr Gln Lys Ser Leu Ser
            355                 360                 365

Leu Ser Pro Gly Lys
        370

<210> SEQ ID NO 186
<211> LENGTH: 374
<212> TYPE: PRT
<213> ORGANISM: Artificial sequence
<220> FEATURE:
<223> OTHER INFORMATION: Synthetic polypeptide

<400> SEQUENCE: 186

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Glu Trp Glu Pro
    130                 135                 140

Lys Ser Ser Asp Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
```

```
            195                 200                 205
Val Glu Val His Asn Ala Lys Thr Lys Pro Arg Glu Glu Gln Tyr Asn
210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
            245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly Lys
    370

<210> SEQ ID NO 187
<211> LENGTH: 375
<212> TYPE: PRT
<213> ORGANISM: Artificial sequence
<220> FEATURE:
<223> OTHER INFORMATION: Synthetic polypeptide

<400> SEQUENCE: 187

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
            85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Glu Trp Val Glu
130                 135                 140

Pro Lys Ser Ser Asp Lys Thr His Thr Cys Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
```

```
                    180                 185                 190
Asp Val Ser His Glu Asp Pro Glu Val Lys Phe Asn Trp Tyr Val Asp
            195                 200                 205

Gly Val Glu Val His Asn Ala Lys Thr Lys Pro Arg Glu Glu Gln Tyr
        210                 215                 220

Asn Ser Thr Tyr Arg Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 188
<211> LENGTH: 376
<212> TYPE: PRT
<213> ORGANISM: Artificial sequence
<220> FEATURE:
<223> OTHER INFORMATION: Synthetic polypeptide

<400> SEQUENCE: 188

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
            20                  25                  30

Lys Ser Tyr Cys Gln Asp Arg Met Gly Glu Ser Leu Gly Met Ser Ser
        35                  40                  45

Thr Arg Ala Gln Ser Leu Ser Lys Arg Asn Leu Glu Trp Asp Pro Tyr
    50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Glu Trp Val Phe
    130                 135                 140

Glu Pro Lys Ser Ser Asp Lys Thr His Thr Cys Pro Pro Cys Pro Ala
145                 150                 155                 160

Pro Glu Leu Leu Gly Gly Pro Ser Val Phe Leu Phe Pro Pro Lys Pro
```

```
                    165                 170                 175
Lys Asp Thr Leu Met Ile Ser Arg Thr Pro Glu Val Thr Cys Val Val
                180                 185                 190

Val Asp Val Ser His Glu Asp Pro Glu Val Lys Phe Asn Trp Tyr Val
                195                 200                 205

Asp Gly Val Glu Val His Asn Ala Lys Thr Lys Pro Arg Glu Glu Gln
            210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
                260                 265                 270

Arg Glu Pro Gln Val Tyr Thr Leu Pro Pro Ser Arg Asp Glu Leu Thr
                275                 280                 285

Lys Asn Gln Val Ser Leu Thr Cys Leu Val Lys Gly Phe Tyr Pro Ser
                290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
                340                 345                 350

Ser Cys Ser Val Met His Glu Ala Leu His Asn His Tyr Thr Gln Lys
                355                 360                 365

Ser Leu Ser Leu Ser Pro Gly Lys
                370                 375

<210> SEQ ID NO 189
<211> LENGTH: 377
<212> TYPE: PRT
<213> ORGANISM: Artificial sequence
<220> FEATURE:
<223> OTHER INFORMATION: Synthetic polypeptide

<400> SEQUENCE: 189

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
                100                 105                 110

Asp Ser Gly Leu Tyr Tyr Cys Ile Ile Thr Thr Pro Asp Asp Leu Glu
            115                 120                 125

Gly Lys Asn Glu Asp Ser Val Glu Leu Leu Val Leu Glu Trp Val Phe
130                 135                 140

Val Glu Pro Lys Ser Ser Asp Lys Thr His Thr Cys Pro Pro Cys Pro
```

```
                145                 150                 155                 160
Ala Pro Glu Leu Leu Gly Gly Pro Ser Val Phe Leu Phe Pro Pro Lys
                    165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Lys Phe Asn Trp Tyr
            195                 200                 205

Val Asp Gly Val Glu Val His Asn Ala Lys Thr Lys Pro Arg Glu Glu
        210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Asp Glu Leu
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
        355                 360                 365

Lys Ser Leu Ser Leu Ser Pro Gly Lys
    370                 375

<210> SEQ ID NO 190
<211> LENGTH: 378
<212> TYPE: PRT
<213> ORGANISM: Artificial sequence
<220> FEATURE:
<223> OTHER INFORMATION: Synthetic polypeptide

<400> SEQUENCE: 190

Asp Lys Lys Lys Val Ala Met Leu Phe Gln Pro Thr Val Leu Arg Cys
1               5                   10                  15

His Phe Ser Thr Ser Ser His Gln Pro Ala Val Val Gln Trp Lys Phe
                20                  25                  30

Lys Ser Tyr Cys Gln Asp Arg Met Gly Glu Ser Leu Gly Met Ser Ser
            35                  40                  45

Thr Arg Ala Gln Ser Leu Ser Lys Arg Asn Leu Glu Trp Asp Pro Tyr
        50                  55                  60

Leu Asp Cys Leu Asp Ser Arg Arg Thr Val Arg Val Val Ala Ser Lys
65                  70                  75                  80

Gln Gly Ser Thr Val Thr Leu Gly Asp Phe Tyr Arg Gly Arg Glu Ile
                85                  90                  95

Thr Ile Val His Asp Ala Asp Leu Gln Ile Gly Lys Leu Met Trp Gly
            100                 105                 110

Asp Ser Gly Leu Tyr Tyr Cys Ile Ile Thr Thr Pro Asp Asp Leu Glu
        115                 120                 125

Gly Lys Asn Glu Asp Ser Val Glu Leu Leu Val Leu Glu Trp Val Phe
```

```
                130             135             140
Val Gly Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
                180                 185                 190

Val Val Val Asp Val Ser His Glu Asp Pro Glu Val Lys Phe Asn Trp
            195                 200                 205

Tyr Val Asp Gly Val Glu Val His Asn Ala Lys Thr Lys Pro Arg Glu
        210                 215                 220

Glu Gln Tyr Asn Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
                260                 265                 270

Gln Pro Arg Glu Pro Gln Val Tyr Thr Leu Pro Pro Ser Arg Asp Glu
            275                 280                 285

Leu Thr Lys Asn Gln Val Ser Leu Thr Cys Leu Val Lys Gly Phe Tyr
        290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
                340                 345                 350

Val Phe Ser Cys Ser Val Met His Glu Ala Leu His Asn His Tyr Thr
            355                 360                 365

Gln Lys Ser Leu Ser Leu Ser Pro Gly Lys
        370                 375
```

POLYPEPTIDES AND USES THEREOF FOR TREATMENT OF AUTOIMMUNE DISORDERS AND INFECTION

FIELD OF THE INVENTION

The present invention relates to C1ORF32 protein, and its variants, fragments and fusion proteins thereof, pharmaceutical compositions comprising same and methods of use thereof for treatment of immune related disorders and infections.

BACKGROUND OF THE INVENTION

The balance between proinflammatory mechanisms and the dampening of excessive immune activation is important for treatment of infectious disease and also for treatment of autoimmune disease. The former benefits from an activated immune system while the latter requires reduce immune system activity. Thus, the immune system has the reciprocal tasks to protect the host against invading pathogens, but simultaneously to prevent damage resulting from unwanted reactions to self antigens.

The latter part is known as immune tolerance and performed by a complex set of interactive and complementary pathways, which regulate immune responses. T cells have the ability to react to a variety of antigens, both self and nonself. Therefore, there are many mechanisms that exist naturally to eliminate potentially self-reactive responses—this is known as natural tolerance. The main mechanism for eliminating potential auto-reactive T cells occurs in the thymus and is known as central tolerance. Some potentially autoreactive T cells escape central tolerance and, therefore, peripheral tolerance mechanisms also exist. Despite these mechanisms, some self-reactive T cells may 'escape' and be present in the repertoire; it is believed that their activation may lead to autoimmune disease.

Studies on therapeutic tolerance have attempted to induce and amplify potent physiological mechanisms of tolerance in order to eliminate or neutralize self-reactive T cells and prevent or treat autoimmune diseases. One way to induce tolerance is by manipulation of the interaction between costimulatory ligands and receptors on antigen presenting cells (APCs) and lymphocytes.

CTLA-4 is the most extensively studied costimulatory molecule which down-regulates immune responses. The attributes of immunosuppressive qualities and capacity to induce tolerance have made its recognition as a potential immuno-therapeutic agent for autoimmune mediated inflammatory disorders. Abatacept (commercial name: Orencia) is a fusion protein composed of the ECD (extracellular domain) of CTLA-4 fused to the Fc fragment of hIgG1. Abatacept is believed to induce costimulation blockade, which has been approved for treating patients with rheumatoid arthritis, by effectively interfering with the inflammatory cascade.

Induction of disease control with the current therapies, followed by progressive withdrawal in parallel with re-establishing immune tolerance, may be an attractive approach in the future of autoimmune therapies. Furthermore, due to their immune specificity, in the absence of global immunosuppression, such therapies should be safer.

T helper type 1 (Th1) cells are induced by IL-12 and produce IFN-γ, while T helper type 2 (Th2) cells secrete IL-4, IL-5 and IL-13. Th1 cells can mediate proinflammatory or cell-mediated immune responses, whereas Th2 cells mainly promote certain types of humoral immunity. Some immune related diseases, such as autoimmune reactions, inflammation, and infection, are characterized by a dysregulation of the pro-versus anti-inflammatory tendencies of the immune system, as well as an imbalance in the Th1 versus Th2 cytokine balance. During inflammation, induction of a shift in the balance from Th1 to Th2 protects the organism from systemic 'overshooting' with Th1/pro-inflammatory cytokines, by reducing the inflammatory tendencies of the immune system Immunomodulatory therapies that are associated with a Th1 to Th2 immune shift have protective effects in Th1-mediated autoimmune diseases, such as multiple sclerosis and rheumatoid arthritis. For example, Laquinimod, which has demonstrated efficacy in animal models of several autoimmune diseases including MS, shows immunomodulatory effects through Th1/Th2 shift, and does not lead to immunosuppression. Glatiramer acetate (Copaxone) also induces Th1/Th2 shift with decreased secretion of proinflammatory cytokines, and increased secretion of anti-inflammatory cytokines. Furthermore, GA-specific Th2 cells are able to migrate across the blood-brain barrier and cause in situ bystander suppression of autoaggressive Th1 T cells.

The balance between proinflammatory mechanisms and the dampening of excessive immune activation is also critical for successful clearance of a pathogen without harm to the host. Excessive immune activation may lead to autoimmune attacks, while too little immune activation will not result in clearance of the pathogen from the host. Chronic pathogens exploit co-inhibitory pathways to attenuate Ag-specific T cell immunity. Emerging data from a wide range of studies on acute and chronic infections support an important role for negative costimulatory receptors in controlling infection. Most notably, exhausted T cells, functionally impaired T cells which are present during chronic infection and are characterized by reduced proliferative and cytotoxic abilities, express high levels of multiple co-inhibitory receptors such as CTLA-4, PD-1, and LAGS (Crawford et al., Curr Opin Immunol. 2009; 21:179-186; Kaufmann et al., J Immunol 2009; 182:5891-5897, Sharpe et al., Nat Immunol 2007; 8:239-245). Furthermore, the exhausted phenotype can be reversed by blocking co-inhibitory pathways (Rivas et al., J Immunol. 2009; 183:4284-91; Golden-Mason et al., J Virol. 2009; 83:9122-30), thus allowing restoration of anti viral immune function, supporting therapeutic application of co-inhibitory blockade in viral infection.

One potentially promising strategy to control chronic infections such as human immunodeficiency virus, hepatitis B virus, and hepatitis C virus is therapeutic vaccination, which aims to reduce persisting virus by stimulating a patient's own antiviral immune responses. However, this approach has fallen short of expectations, because antiviral T cells generated during chronic infections often become functionally exhausted, as explained above, and thus do not respond properly to therapeutic vaccination. Therefore, it is necessary to restore T cell effector functions and effectively boost endogenous T-cell responses in order to develop therapeutic vaccines against chronic viral infections. Blocking the negative signaling pathways, PD-1 and CTLA-4, could restore the host immune system, enabling it to respond to further stimulation. Blockade of the PD-1/PD-L1 pathway, for example, is able to restore functional capabilities to exhausted CTLs (Hofmeyer et al, J. Biomed. & Biotech. Vol. 2011, Art. ID 451694). Combining therapeutic vaccination along with the blockade of inhibitory signals could synergistically enhance functional CD8(+) T-cell responses and improve viral control in chronically infected individuals, providing a promising strategy for the treatment of chronic viral infections. (Ha et al, Immunol Rev. 2008 June; 223: 317-33). Antibodies to PD-1 and CTLA-4 are currently in clinical trials in chronic hepatitis C, as promising candidates for combination with both prophylactic and therapeutic vaccines (Diepolder and Obst, Expert Rev Vaccines. 2010 March; 9(3):243-7).

The therapeutic potential of co-inhibition blockade for treating viral infection was extensively studied by blocking the PD-1/PD-L1. Blocking this pathway was shown to be efficacious in several animal models of infection including acute and chronic Simian immunodeficiency virus (SIV) infection in rhesus macaques (Valu et al., Nature 2009; 458:206-210) and in mouse model of chronic viral infection with lymphocytic choriomeningitis virus (LCMV) (Barber et al., Nature. 2006; 439:682-7).

Modulation of costimulatory pathway has also been proven effective in optimizing antiviral immunity by limiting the memory T cell response to its protective capacities (Teijaro et al., J Immunol. 2009: 182; 5430-5438). This has been demonstrated in models of influenza infection in which inhibiting CD28 costimulation with CTLA4-Ig suppressed primary responses in naive mice infected with influenza, but was remarkably curative for memory CD4 T cell-mediated secondary responses to influenza leading to improved clinical outcome and increased survival to influenza challenge. The curative effect of CTLA4-Ig on secondary responses was accompanied by inhibition of proliferation and egress of lymphoid naive and memory T cells, while leaving lung resident memory CD4 T cell responses intact thus maintaining enhanced and rapid lung viral clearance mediated by memory CD4 T cells, yet reducing lung immunopathology.

These data demonstrate an active and reversible role for molecules of the B7:CD28 family, PD-1, CTLA-4, and their ligands, in virus-specific T cell exhaustion associated with chronic viral infection and point to promising potential for immunotherapeutic interventions based on manipulation of these inhibitory networks.

Regulating costimulation using agonists and antagonists to various costimulatory proteins has been extensively studied as a strategy for treating autoimmune diseases, graft rejection, allergy and cancer. This field has been clinically pioneered by CTLA4-Ig (Abatacept, Orencia®) that is approved for treatment of RA, and by the anti-CTLA4 antibody (Ipilimumab, Yervoy®), recently approved for the treatment of melanoma. Other costimulation regulators are currently in advanced stages of clinical development including anti PD-1 antibody (MDX-1106) which is in development for treatment of advanced/metastatic clear-cell renal cell carcinoma (RCC) and anti-CD40L Antibody (BG9588, Antova®) for treatment of renal allograft transplantation. In addition, such agents are in clinical development for viral infections, for example the anti PD-1 Ab, MDX-1106, is being tested for treatment of hepatitis C. Another example is CP-675,206 (tremelimumab) and anti-CTLA4 Ab which is in a clinical trial in hepatitis C virus-infected patients with hepatocellular carcinoma.

B cells play a critical role in recognition of foreign antigens and subsequent production of antibodies in the specific humoral adaptive immune responses that provide protection against various types of infectious agents. B cells play a critical role in recognition of foreign antigens and they produce the antibodies necessary to provide protection against various type of infectious agents. T cell help to B cells is a pivotal process of adaptive immune responses. Follicular helper T (Tfh) cells are a subset of CD4+ T cells specialized in B cell help (reviewed by Crotty, Annu. Rev. Immunol. 29: 621-663, 2011). Tfh cells express the B cell homing chemokine receptor, CXCR5, which drives Tfh cell migration into B cell follicles within lymph nodes in a CXCL13-dependent manner. The requirement of Tfh cells for B cell help and T cell-dependent antibody responses, indicates that this cell type is of great importance for protective immunity against various types of infectious agents, as well as for rational vaccine design.

Tfh cells selectively express a wealth of surface proteins, which are involved in their selective localization (such as CXCR5) and in direct physical interactions with B cells to provide B cell help. Among the latter group are several members of the costimulatory proteins family which are highly expressed in Tfh cells, including the inducible co-stimulatory receptor ICOS, and the negative costimulators (inhibitory receptors) PD-1 and BTLA (Crotty, Annu. Rev. Immunol. 29: 621-663, 2011).

BRIEF SUMMARY OF THE INVENTION

The background art fails to provide therapies that target multiple cells and pathways involved in autoimmunity and inflammation, such as Th1, Th17, Th22, Th2, Tregs, or other cells that secrete, or influence other cells that secrete, inflammatory molecules such as cytokines, metalloproteases, chemokines and other molecules. The background art also does not teach such therapies that are targeted with regard to providing a balance between excessive immune activation and desirable pro-inflammatory immune activation, for the treatment of autoimmune diseases and infectious disease.

The present invention is of C1ORF32 protein, and its variants, fragments and fusion proteins thereof, pharmaceutical compositions comprising same and methods of use thereof for treatment of immune related disorders and infections.

With regard to treatment for immune related diseases, it should be noted that such diseases may optionally relate to any disease in which it is desirable to induce immune tolerance. With regard to treatment of infections, it should be noted that such diseases may optionally relate to any disease in which T cell exhaustion to a foreign pathogenic antigen plays a role.

According to at least some embodiments of the present invention, there are provided C1ORF32 polypeptides, as an isolated polypeptide, comprising an amino acid sequence of C1ORF32 IgV domain fragment, set forth in any one of SEQ ID NOs: 29, 30, 41-105, with the proviso that the amino acid sequence does not include the complete, exact sequence of SEQ ID NO: 35. Optionally, the isolated polypeptide has less than 90% identity with SEQ ID NO:35, optionally has less than 85% identity with SEQ ID NO:35 and optionally has less than 80% identity with SEQ ID NO:35. Also optionally and preferably, the isolated polypeptide consists essentially of the amino acid sequence as set forth in any one of SEQ ID NOs: 29, 30, 41-105, or optionally up to 95% identical thereof. It is further contemplated that optionally the C1ORF32 IgV domain fragment may be extended beyond the border delimited by the end of SEQ ID NO:35, as long as one or more of the above conditions regarding sequence identity are met. A further description of such fragments is provided with regard to Table 1 below.

Briefly, a sequence alignment and comparison is provided between SEQ ID NO:35 and SEQ ID NO:29, as an example of the above described inventive sequences:

```
Query:   1 LQVTVPDKKKVAMLFQPTVLRCHFSTSSHQPAVVQWKFKSYCQDRMGESLGMSSTRAQSL   60
           LQVTVPDKKKVAMLFQPTVLRCHFSTSSHQPAVVQWKFKSYCQDRMGESLGMSSTRAQSL
Sbjct:   1 LQVTVPDKKKVAMLFQPTVLRCHFSTSSHQPAVVQWKFKSYCQDRMGESLGMSSTRAQSL   60

Query:  61 SKRNLEWDPYLDCLDSRRTVRVVASKQGSTVTLGDFYRGREITIVHDADLQIGKLMWGDS  120
           SKRNLEWDPYLDCLDSRRTVRVVASKQGSTVTLGDFYRGREITIVHDADLQIGKLMWGDS
Sbjct:  61 SKRNLEWDPYLDCLDSRRTVRVVASKQGSTVTLGDFYRGREITIVHDADLQIGKLMWGDS  120

Query: 121GLYYCIITTPDDLEGKNEGSLGLLVLGRTGLLADLLPSFAVEIMPE               168
           GLYYCIITTPDDLEGKNEGKNEDSVELLVLG
Sbjct: 121GLYYCIITTPDDLEGKNEGKNEDSVELLVLG...................          147
```

For this non-limiting example, SEQ ID NO:29 is shorter than SEQ ID NO:35 but as noted above, for some inventive sequences, the inventive amino acid sequence is longer than SEQ ID NO:35, but still fulfills one or more of the above conditions regarding sequence identity. An equivalent difference exists between the inventive sequences and SEQ ID NO:36, such that the inventive sequences are as described above and herein, the proviso that the amino acid sequence does not include the complete, exact sequence of SEQ ID NO: 36. Optionally, the isolated polypeptide has less than 90% identity with SEQ ID NO:36, optionally has less than 85% identity with SEQ ID NO:36 and optionally has less than 80% identity with SEQ ID NO:36. It is further contemplated that optionally the C1ORF32 IgV domain fragment may be extended beyond the border delimited by the end of SEQ ID NO:36, as long as one or more of the above conditions regarding sequence identity are met.

According to at least some embodiments, there is provided an isolated polypeptide comprising a soluble C1ORF32 polypeptide or fragment or variant thereof, having an amino acid substitution preventing a cleavage of the C1ORF32 ECD (SEQ ID NO:14) between amino acids F and A at positions 179 and 180 of any of H19011_1_P8_V1 or H19011_1_P8 (Seq ID NOs: 4 or 5). Optionally, the amino acid substitution in the cleavage site of C1ORF32 ECD (SEQ ID NO:14) at positions 179 and 180 of any of H19011_1_P8_V1 or H19011_1_P8 (Seq ID NOs: 4 or 5) is selected from FA→GA; FA→AA; and FA→GG. Optionally and preferably, the polypeptide has an amino acid sequence as set forth in any one of SEQ ID NOs:45, 64, and 96.

According to at least some embodiments of the present invention, there are provided C1ORF32 polypeptides, optionally provided as fusion proteins containing a C1ORF32 polypeptide. C1ORF32 fusion polypeptides optionally have a first fusion partner comprising part of a C1ORF32 soluble polypeptide, or a sequence homologous thereto, and a second fusion partner composed of a heterologous sequence (respectively non-C1ORF32), fused together directly or indirectly via a peptide linker sequence or a chemical linker.

Optionally, the fusion protein comprises the polypeptide as described herein, fused to a heterologous sequence, directly or indirectly via a linker peptide, a polypeptide sequence or a chemical linker.

Optionally the heterologous sequence comprises at least a portion of an immunoglobulin constant domain. Also optionally, the constant domain comprises an immunoglobulin heavy chain constant region corresponding to an antibody isotype selected from the group consisting of an IgG1, IgG2, IgG3, IgG4, IgM, IgE, IgA and IgD.

Optionally, the immunoglobulin constant domain comprises the hinge, CH2 and CH3 regions of a human IgG immunoglobulin, selected from the group consisting of Cγ1, Cγ2, Cγ3 and Cγ4 chain.

Optionally, the fusion protein further comprises a domain that mediates dimerization or multimerization of the fusion protein to form homodimers, heterodimers, homomultimers, or heteromultimers. Optionally, the domain that mediates dimerization or multimerization is selected from the group consisting of one or more cysteines that are capable of forming an intermolecular disulfide bond with a cysteine on the partner fusion protein, a coiled-coil domain, an acid patch, a zinc finger domain, a calcium hand domain, a CHI region, a CL region, a leucine zipper domain, an SH2 (src homology 2) domain, an SH3 (src Homology 3) domain, a PTB (phosphotyrosine binding) domain, a WW domain, a PDZ domain, a 14-3-3 domain, a WD40 domain, an EH domain, a Lim domain, an isoleucine zipper domain, and a dimerization domain of a receptor dimer pair.

According to at least some embodiments of the present invention, there is provided a dimeric protein comprising a first and a second fusion protein, wherein the first and the second fusion proteins comprise the fusion protein as described herein and wherein the first and the second fusion proteins are bound to one another by covalent or noncovalent bonds to form a dimer.

According to at least some embodiments, the isolated polypeptide is at least 80, 90, 95, 96, 97, 98 or 99% homologous to a polypeptide set forth in any one of SEQ ID NOs: 29, 30, 41-105. The C1ORF32 polypeptide may be of any species of origin. In further embodiments, the C1ORF32 polypeptide is of murine, non-human primate or human origin.

Without wishing to be limited by a single hypothesis, according to at least some embodiments the C1ORF32 protein, which may optionally comprise a fusion protein, inhibits the inflammatory activity of Th1, Th17, Th22, or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs. Again without wishing to be limited by a single hypothesis, according to at least some embodiments the C1ORF32 protein can also increase the suppressive capacity of Tregs or the immunomodulatory activity of Th2 cells. The C1ORF32 fusion protein can also increase the production of anti-inflammatory molecules such as the cytokine IL-10.

Optionally, the fragment is of at least about 20 amino acids of the extracellular domain of C1ORF32, but no more than 169 amino acids of the extracellular domain, in order to fulfill the conditions regarding sequence identity as described with regard to SEQ ID NO:35 as described above. Optionally, the fragment is of at least about 21, 22, 23, 24, 25 and so forth amino acids of the extracellular domain of C1ORF32, but no more than 100, 101, 102 and so forth, up to 168 amino acids of the extracellular domain, as described above, optionally including any integral value between 20 and 169 amino acids in length, although as noted above, the inventive sequence may optionally have more amino acids than the ECD of SEQ ID NO:35. Optionally the polypeptide is attached to a detectable or therapeutic moiety.

According to at least some embodiments of the present invention, there is provided a method for prevention of damage to the myelin coat of neural cells in the central nervous system in MS (multiple sclerosis) patients comprising administering to a subject in need thereof a pharmaceutical composition comprising: a soluble molecule having the C1ORF32 polypeptide, selected from the group consisting of SEQ ID NOs: 29, 30, 41-105, or a fragment, variant, a homolog, a fusion protein or a conjugate thereof; optionally provided as a pharmaceutical composition. Optionally, the fragment is as described above.

Multiple sclerosis (MS) is a chronic, inflammatory, demyelinating disorder of the central nervous system (CNS), which involves autoimmune responses to myelin antigens. It is characterized by lesions within the CNS and demyelination is a key feature of these lesions. Autoreactive T cells are thought to initiate an autoimmune response directed against components of CNS myelin. The main targets of the autoimmune reactions are thought to be myelin basic protein (MBP), proteolipid protein (PLP) and myelin oligodendrocyte glycoprotein (MOG). Experimental autoimmune encephalomyelitis (EAE), an animal model of MS induced by immunization with myelin components in adjuvant, shows comparable neuronal pathology. Without wishing to be limited by a single hypothesis, studies in EAE have provided convincing evidence that T cells specific for self-antigens mediate pathology in these diseases.

According to at least some embodiments of the present invention, there is provided an isolated soluble C1ORF32 polypeptide, selected from the group consisting of SEQ ID NOs: 29, 30, 41-105, fragment, variant, or homolog thereof; optionally as a fusion protein or conjugate, wherein said polypeptide or said fusion protein or conjugate is used for anti-immune related condition immunotherapy for an immune related disorder and/or infection as described herein, optionally provided as a pharmaceutical composition.

Optionally treating comprises one or more of preventing, curing, managing, reversing, attenuating, alleviating, minimizing, suppressing, managing, or halting the deleterious effects of the above-described diseases.

Optionally, managing comprises reducing the severity of the disease, reducing the frequency of episodes of the disease, reducing the duration of such episodes, or reducing the severity of such episodes or a combination thereof.

In another embodiment, the C1ORF32 polypeptides, fragments or variants or homologs thereof, fusion proteins or conjugates comprising same, or pharmaceutical composition comprising same, can be used to treat patients who do not respond to TNF blockers.

According to at least some embodiments, the present invention provides a method for combining therapeutic vaccination with an antigen along with administration of the foregoing pharmaceutical composition for treatment of infection. According to at least some embodiments of the present invention, the antigen is a viral antigen, a bacterial antigen, fungal antigen and/or other parasite antigen.

According to at least some embodiments, the present invention further provides a method for combining the foregoing pharmaceutical composition, used as adjuvant, along with an antigen in a vaccine, in order to increase the immune response. According to at least some embodiments of the present invention, the antigen is a viral antigen, a bacterial antigen, fungal antigen, parasite antigen, and/or other pathogen's antigen.

DETAILED DESCRIPTION OF THE INVENTION

Figures 1, 2:
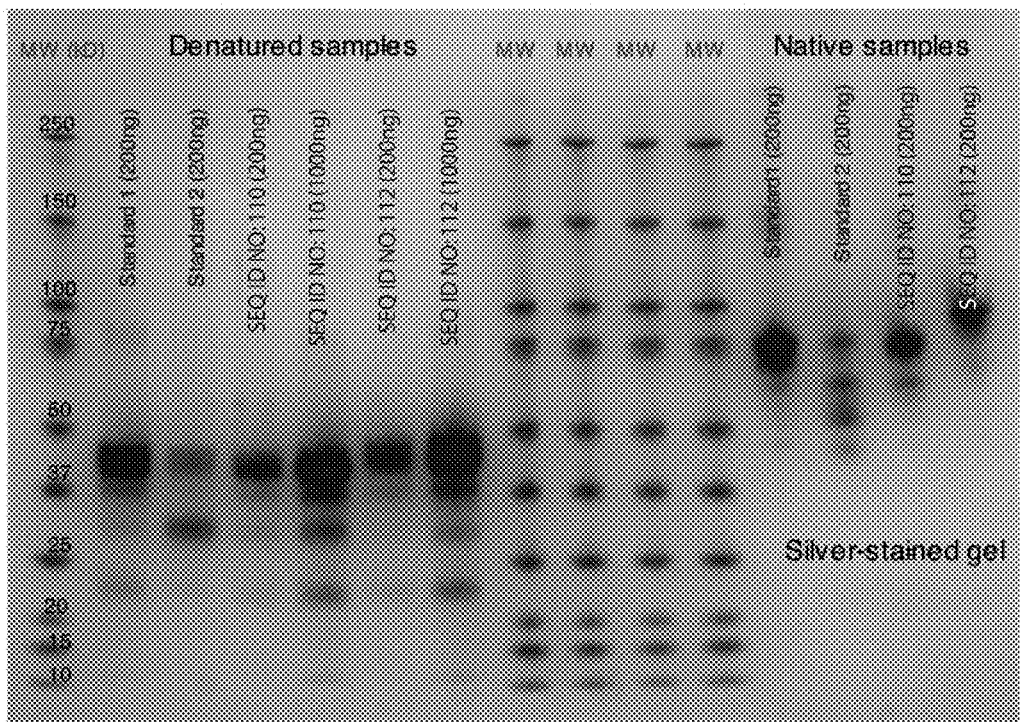
FIG. 1 shows a schematic drawing of a full length soluble C1ORF32 protein. Signal Peptide is shown in italic face font; two potential start points of IgV are shown in underlined italic and bold shape; IgV domain is in bold face font; amino acid region deleted in H19011_1_P9 (SEQ ID NO:6) as compared to the H19011_1_P8 (SEQ ID NO:4) is shown in dashed underline; the locations of the three SNPs (DS-VE→GSLG) is shown in double underlined italic and bold shape; the location of point mutations (FA→GA, FA→AA, FA→GG) is shown in bold and dashed underline. Transmembrane domain (TM) of H19011_1_P8 (SEQ ID NO:4) is shown in light font with dotted underline; in H19011_1_P9 (SEQ ID NO:6) the TM starts at amino acid residues "FVG . . . ", 2 amino acids downstream to the start point of the H19011_1_P8 (SEQ ID NO:4) transmembrane domain. Vertical bars represent five possible C-terminal end points of the soluble C1ORF32 proteins from position 1 on the left (end of IgV) to position 5 on the right (end of predicted ECD).
FIG. 2 shows SDS-PAGE results for produced proteins.

The present invention, in at least some embodiments, relates to any one of the C1ORF32 proteins, selected from the group consisting of SEQ ID NOs: 29, 30, 41-105, fragments, variants and homologs thereof and fusion proteins and conjugates containing same, and pharmaceutical compositions comprising same, and nucleic acid sequences encoding same, and the use thereof as a therapeutic agent for treatment of immune related disorder and/or infection, and/or optionally the corresponding DNAs or vectors or cells expressing same for use in immunotherapy.

In order that the present invention may be more readily understood, certain terms are first defined. Additional definitions are set forth throughout the detailed description.

As used herein the term "isolated" refers to a compound of interest (for example a polynucleotide or a polypeptide) that is in an environment different from that in which the compound naturally occurs e.g. separated from its natural milieu such as by concentrating a peptide to a concentration at which it is not found in nature. "Isolated" includes compounds that are within samples that are substantially enriched for the compound of interest and/or in which the compound of interest is partially or substantially purified.

An "immune cell" refers to any cell from the hemopoietic origin including but not limited to T cells, B cells, monocytes, dendritic cells, and macrophages.

As used herein, the term "polypeptide" refers to a chain of amino acids of any length, regardless of modification (e.g., phosphorylation or glycosylation).

The term "immune related disease (or disorder or condition)" as used herein should be understood to encompass any disease disorder or condition selected from the group including but not limited to autoimmune diseases, inflammatory disorders and immune disorders associated with graft transplantation rejection, such as acute and chronic rejection of organ transplantation, allogenic stem cell transplantation, autologous stem cell transplantation, bone marrow transplantation, and graft versus host disease.

As used herein the term "inflammatory disorders" and/or "inflammation", used interchangeably, includes inflammatory abnormalities characterized by disregulated immune response to harmful stimuli, such as pathogens, damaged cells, or irritants. Inflammatory disorders underlie a vast variety of human diseases. Non-immune diseases with etiological origins in inflammatory processes include atherosclerosis, and ischaemic heart disease. Examples of disorders associated with inflammation include: Chronic prostatitis, Glomerulonephritis, Hypersensitivities, Pelvic inflammatory disease, Reperfusion injury, Sarcoidosis, Vasculitis, Interstitial cystitis, normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, TNF receptor-associated periodic syndrome (TRAPSP), gingivitis, periodontitis, hepatitis, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

The term "autoimmune disease" as used herein should be understood to encompass any disease in which recognition of a "self" antigen (self-reactivity) is at least a part of the disease process. According to at least some embodiments of the invention, the autoimmune diseases should be understood to encompass any disease disorder or condition including one or more of, but not limited to, multiple sclerosis, rheumatoid arthritis; psoriatic arthritis, discoid lupus erythematosus, systemic lupus erythematosus (SLE); ulcerative colitis; Crohn's disease; benign lymphocytic angiitis, autoimmune lymphoproliferative syndrome, sarcoidosis, autoimmune thrombocytopenic purpura, idiopathic thrombocytopenic purpura, pure red cell aplasia, Sjogren's syndrome, rheumatic disease, polymyalgia rheumatica, mixed connective tissue disease, inflammatory rheumatism, degenerative rheumatism, extra-articular rheumatism, juvenile arthritis, juvenile rheumatoid arthritis, systemic juvenile idiopathic arthritis, arthritis uratica, muscular rheumatism, chronic polyarthritis, reactive arthritis, Reiter's syndrome, rheumatic fever, relapsing polychondritis, Raynaud's phenomenon, vasculitis, cryoglobulinemic vasculitis, ANCA-associated vasculitis, temporal arteritis, giant cell arteritis, Takayasu arteritis, Behcet's disease, antiphospholipid syndrome, myasthenia gravis, autoimmune haemolytic anaemia, Guillain-Barre syndrome, chronic immune polyneuropathy, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pernicious anaemia, pemphigus, pemphigus vulgaris, cirrhosis, primary biliary cirrhosis, idiopathic pulmonary fibrosis, myositis, dermatomyositis, juvenile dermatomyositis, polymyositis, fibromyositis, myogelosis, celiac disease, celiac sprue dermatitis, immunoglobulin A nephropathy, Henoch-Schonlein purpura, Evans syndrome, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, allergic asthma, allergy, primary biliary cirrhosis, Hashimoto's thyroiditis, fibromyalgia, chronic fatigue and immune dysfunction syndrome (CFIDS), primary myxedema, sympathetic ophthalmia, autoimmune inner ear disease, autoimmune uveitis, autoimmune chronic active hepatitis, collagen diseases, ankylosing spondylitis, periarthritis humeroscapularis, panarteritis nodosa, polyarteritis nodosa, chondrocalcinosis, Wegener's granulomatosis, microscopic polyangiitis, chronic urticaria, bullous skin disorders, pemphigoid, bullous pemphigoid, cicatricial pemphigoid, vitiligo, atopic eczema, eczema, chronic urticaria, autoimmune urticaria, normocomplementemic urticarial vasculitis, hypocomplementemic urticarial vasculitis, alopecia areata, alopecia universalis, alopecia totalis, Devic's disease, pernicious anemia, childhood autoimmune hemolytic anemia, idiopathic autoimmune hemolytic anemia, refractory or chronic Autoimmune Cytopenias, Prevention of development of Autoimmune Anti-Factor VIII Antibodies in Acquired Hemophilia A, Cold agglutinin disease, Neuromyelitis Optica, Stiff Person Syndrome, gingivitis, periodontitis, pancreatitis, myocarditis, gastritis, gout, gouty arthritis, idiopathic pericarditis, anti-synthetase syndrome, scleritis, macrophage activation syndrome, PAPA Syndrome, Blau's Syndrome, adult and juvenile Still's disease, cryopyrin associated periodic syndrome, Muckle-Wells syndrome, familial cold auto-inflammatory syndrome, neonatal onset multisystem inflammatory disease, chronic infantile neurologic cutaneous and articular syndrome, familial Mediterranean fever, Hyper IgD syndrome, Schnitzler's syndrome, autoimmune retinopathy, age-related macular degeneration, or TNF receptor-associated periodic syndrome (TRAPS).

As used herein, "multiple sclerosis" comprises multiple sclerosis or a related disease, and optionally refers to all types and stages of multiple sclerosis, including, but not limited to: benign multiple sclerosis, relapsing remitting multiple sclerosis, secondary progressive multiple sclerosis, primary progressive multiple sclerosis, progressive relapsing multiple sclerosis, chronic progressive multiple sclerosis, transitional/progressive multiple sclerosis, rapidly worsening multiple sclerosis, clinically-definite multiple sclerosis, malignant multiple sclerosis, also known as Marburg's Variant, and acute multiple sclerosis. Optionally, "conditions relating to multiple sclerosis" include, e.g., Devic's disease, also known as Neuromyelitis Optica; acute disseminated encephalomyelitis, acute demyelinating optic neuritis, demyelinative transverse myelitis, Miller-Fisher syndrome, encephalomyelradiculoneuropathy, acute demyelinative polyneuropathy, tumefactive multiple sclerosis and Balo's concentric sclerosis.

As used herein, "rheumatoid arthritis" comprises rheumatoid arthritis or a related disease and refers to all types and stages of rheumatoid arthritis, including, but not limited to: rheumatoid arthritis, gout and pseudo-gout, juvenile idiopathic arthritis, juvenile rheumatoid arthritis, Still's disease, ankylosing spondylitis, rheumatoid vasculitis. Optionally, conditions relating to rheumatoid arthritis include, e.g., osteoarthritis, sarcoidosis, Henoch-Schönlein purpura, Psoriatic arthritis, Reactive arthritis, Spondyloarthropathy, septic arthritis, Haemochromatosis, Hepatitis, vasculitis, Wegener's granulomatosis, Lyme disease, Familial Mediterranean fever, Hyperimmunoglobulinemia D with recurrent fever, TNF receptor associated periodic syndrome, and Enteropathic arthritis associated with inflammatory bowel disease.

As used herein, "Uveitis" refers to all types and stages of Uveitis, including, but not limited to: anterior uveitis (or iridocyclitis), intermediate uveitis (pars planitis), posterior uveitis (or chorioretinitis) and the panuveitic form.

As used herein, "inflammatory bowel disease" also refers to a related disease and refers to all types and stages of inflammatory bowel disease (IBD), including, but not limited to: Crohn's disease and ulcerative colitis (UC). Optionally, conditions relating to IBD include, e.g., Collagenous colitis, Lymphocytic colitis, Ischaemic colitis, Diversion colitis, Behçet's disease, Indeterminate colitis.

As used herein, "psoriasis" also refers to a related disease and refers to all types and stages of psoriasis, including, but not limited to: Nonpustular Psoriasis including Psoriasis vulgaris and Psoriatic erythroderma (erythrodermic psoriasis), Pustular psoriasis including Generalized pustular psoriasis (pustular psoriasis of von Zumbusch), Pustulosis palmaris et plantaris (persistent palmoplantar pustulosis, pustular psoriasis of the Barber type, pustular psoriasis of the extremities), Annular pustular psoriasis, Acrodermatitis continua, Impetigo herpetiformis. Optionally, conditions relating to psoriasis include, e.g., drug-induced psoriasis, Inverse psoriasis, Napkin psoriasis, Seborrheic-like psoriasis, Guttate psoriasis, Nail psoriasis, Psoriatic arthritis.

As used herein, "type 1 diabetes" refers to all types and stages of type 1 diabetes, including, but not limited to: insulin-dependent diabetes mellitus, idiopathic diabetes, juvenile type ldiabetes, maturity onset diabetes of the young, latent autoimmune diabetes in adults, gestational diabetes. Conditions relating to type 1 diabetes include, neuropathy including polyneuropathy, mononeuropathy, peripheral neuropathy and autonomicneuropathy; eye complications: glaucoma, cataracts, retinopathy.

As used herein, "Sjogren's syndrome" refers to all types and stages of Sjogren's syndrome, including, but not limited to: Primary Sjogren's syndrome and Secondary Sjogren's syndrome. Conditions relating to Sjogren's syndrome include connective tissue disease, such as rheumatoid arthritis, systemic lupus erythematosus, or scleroderma. Other complications include pneumonia, polmunary fibrosis, interstitial nephritis, inflammation of the tissue around the kidney's filters, glomerulonephritis, renal tubular acidosis, carpal tunnel syndrome, peripheral neuropathy, cranial neuropathy, primary biliary cirrhosis (PBC), cirrhosis, Inflammation in the esophagus, stomach, pancreas, and liver (including hepatitis), Polymyositis, Raynaud's phenomenon, Vasculitis, Autoimmune thyroid problems, lymphoma.

As used herein, "systemic lupus erythematosus", refers to all types and stages of systemic lupus erythematosus, including, but not limited to discoid lupus, lupus arthritis, lupus pneumonitis, lupus nephritis. Conditions relating to systemic lupus erythematosus include osteoarticular tuberculosis, antiphospholipid antibody syndrome, inflammation of various parts of the heart, such as pericarditis, myocarditis, and endocarditis, Lung and pleura inflammation, pleuritis, pleural effusion, chronic diffuse interstitial lung disease, pulmonary hypertension, pulmonary emboli, pulmonary hemorrhage, and shrinking lung syndrome, lupus headache, Guillain-Barré syndrome, aseptic meningitis, demyelinating syndrome, mononeuropathy, mononeuritis multiplex, myasthenia gravis, myelopathy, cranial neuropathy, polyneuropathy, vasculitis.

As used herein the term "infectious disorder and/or disease" and/or "infection", used interchangeably, includes any disorder, disease and/or condition caused by presence and/or growth of pathogenic biological agent in an individual host organism. As used herein the term "infection" comprises the disorder, disease and/or condition as above, exhibiting clinically evident illness (i.e., characteristic medical signs and/or symptoms of disease) and/or which is asymtomatic for much or all of it course. As used herein the term "infection" also comprises disorder, disease and/or condition caused by persistence of foreign antigen that lead to exhaustion T cell phenotype characterized by impaired functionality which is manifested as reduced proliferation and cytokine production. As used herein the term "infectious disorder and/or disease" and/or "infection", further includes any of the below listed infectious disorders, diseases and/or conditions, caused by a bacterial infection, viral infection, fungal infection and/or parasite infection.

As used herein the term "viral infection" comprises any infection caused by a virus, optionally including but not limited to Retroviridae (e.g., human immunodeficiency viruses, such as HIV-1 or HIV-2, acquired immune deficiency (AIDS) also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxviridae (variola virsues, vaccinia viruses, pox viruses); and Iridoviridae (e.g., African swine fever virus); and unclassified viruses (e.g., the etiological agents of Spongiform encephalopathies, the agent of delta hepatitides (thought to be a defective satellite of hepatitis B virus), the agents of non-A, non-B hepatitis (class 1—internally transmitted; class 2—parenterally transmitted (i.e., Hepatitis C); Norwalk and related viruses, and astroviruses) as well as Severe acute respiratory syndrome virus and respiratory syncytial virus (RSV).

As used herein the term "fungal infection" comprises any infection caused by a fungi, optionally including but not limited to *Cryptococcus neoformans, Histoplasma capsulatum, Coccidioides immitis, Blastomyces dermatitidis, Chlamydia trachomatis, Candida albicans*.

As used herein the term "parasite infection" comprises any infection caused by a parasite, optionally including but not limited to protozoa, such as *Amebae, Flagellates, Plasmodium falciparum, Toxoplasma gondii, Ciliates, Coccidia, Microsporidia, Sporozoa*; helminthes, Nematodes (Roundworms), Cestodes (Tapeworms), Trematodes (Flukes), Arthropods, and aberrant proteins known as prions.

An infectious disorder and/or disease caused by bacteria may optionally comprise one or more of Sepsis, septic shock, sinusitis, skin infections, pneumonia, bronchitis, meningitis, Bacterial vaginosis, Urinary tract infection (UCI), Bacterial gastroenteritis, Impetigo and erysipelas, Erysipelas, Cellulitis, anthrax, whooping cough, lyme disease, Brucellosis, enteritis, acute enteritis, Tetanus, diphtheria, Pseudomembranous colitis, Gas gangrene, Acute food poisoning, Anaerobic cellulitis, Nosocomial infections, Diarrhea, Meningitis in infants, Traveller's diarrhea, Hemorrhagic colitis, Hemolytic-uremic syndrome, Tularemia, Peptic ulcer, Gastric and Duodenal ulcers, Legionnaire's Disease, Pontiac fever, Leptospirosis, Listeriosis, Leprosy (Hansen's disease), Tuberculosis, Gonorrhea, Ophthalmia neonatorum, Septic arthritis, Meningococcal disease including meningitis, Waterhouse-Friderichsen syndrome, *Pseudomonas* infection, Rocky mountain spotted fever, Typhoid fever type *salmonellosis, Salmonellosis* with gastroenteritis and enterocolitis, Bacillary dysentery/Shigellosis, Coagulase-positive staphylococcal infections: Localized skin infections including Diffuse skin infection (Impetigo), Deep localized infections, Acute infective endocarditis, Septicemia, Necrotizing pneumonia, Toxinoses such as Toxic shock syndrome and Staphylococcal food poisoning, Cystitis, Endometritis, Otitis media, Streptococcal pharyngitis, Scarlet fever, Rheumatic fever, Puerperal fever, Necrotizing fasciitis, Cholera, Plague (including Bubonic plague and Pneumonic plague), as well as any infection caused by a bacteria selected from but not limited to *Helicobacter pyloris, Boreliai burgdorferi, Legionella pneumophilia, Mycobacteria* sps (e.g., *M. tuberculosis, M. avium, M. Intracellulare, M. kansaii, M gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp *Haemophilus influenzae, Bacillus antracis, corynebacterium diphtheriae, corynebacterium* sp., *Erysipelothrix rhusiopathiae, Clostridium perfringers, Clostridium tetani, Enterobacter erogenes, Klebsiella pneuomiae, Pasteurella multicoda, Bacteroides* sp., *Fusobacterium nucleatum, Sreptobacillus moniliformis, Treponema pallidium, Treponema pertenue, Leptospira*, and *Actinomeyces israelli*.

Non limiting examples of infectious disorder and/or disease caused by virus is selected from the group consisting of but not limited to acquired immune deficiency (AIDS), West Nile encephalitis, coronavirus infection, rhinovirus infection, influenza, dengue, hemorrhagic fever; an otological infection; severe acute respiratory syndrome (SARS), acute febrile pharyngitis, pharyngoconjunctival fever, epidemic keratoconjunctivitis, infantile gastroenteritis, infectious mononucleosis, Burkitt lymphoma, acute hepatitis, chronic hepatitis, hepatic cirrhosis, hepatocellular carcinoma, primary HSV-1 infection, (gingivostomatitis in children, tonsillitis & pharyngitis in adults, keratoconjunctivitis), latent HSV-1 infection (herpes labialis, cold sores), aseptic meningitis, Cytomegalovirus infection, Cytomegalic inclusion disease, Kaposi sarcoma, Castleman disease, primary effusion lymphoma, influenza, measles, encephalitis, postinfectious encephalomyelitis, Mumps, hyperplastic epithelial lesions (common, flat, plantar and anogenital warts, laryngeal papillomas, epidermodysplasia verruciformis), croup, pneumonia, bronchiolitis, Poliomyelitis, Rabies, bronchiolitis, pneumonia, German measles, congenital rubella, Hemorrhagic Fever, Chickenpox, Dengue, Ebola infection, Echovirus infection, EBV infection, Fifth Disease, Filovirus, Flavivirus, Hand, foot & mouth disease, Herpes Zoster Virus (Shingles), Human Papilloma Virus Associated Epidermal Lesions, Lassa Fever, Lymphocytic choriomeningitis, Parainfluenza Virus Infection, Paramyxovirus, Parvovirus B19 Infection, Picornavirus, Poxviruses infection, Rotavirus diarrhea, Rubella, Rubeola, Varicella, Variola infection.

An infectious disorder and/or disease caused by fungi optionally includes but is not limited to Allergic bronchopulmonary aspergillosis, *Aspergilloma, Aspergillosis, Basidiobolomycosis, Blastomycosis, Candidiasis, Chronic pulmonary aspergillosis, Chytridiomycosis, Coccidioidomycosis, Conidiobolomycosis*, Covered smut (barley), *Cryptococcosis, Dermatophyte, Dermatophytid, Dermatophytosis, Endothrix, Entomopathogenic fungus, Epizootic lymphangitis, Epizootic ulcerative syndrome, Esophageal candidiasis, Exothrix, Fungemia, Histoplasmosis, Lobomycosis, Massospora cicadina, Mycosis, Mycosphaerella fragariae, Myringomycosis, Paracoccidioidomycosis, Pathogenic fungi, Penicilliosis*, Thousand cankers disease, *Tinea, Zeaspora, Zygomycosis*. Non limiting examples of infectious disorder and/or disease caused by parasites is selected from the group consisting of but not limited to *Acanthamoeba, Amoebiasis, Ascariasis, Ancylostomiasis, Anisakiasis, Babesiosis, Balantidiasis, Baylisascariasis, Blastocystosis, Candiru*, Chagas disease, *Clonorchiasis, Cochliomyia, Coccidia*, Chinese Liver Fluke *Cryptosporidiosis, Dientamoebiasis, Diphyllobothriasis, Dioctophyme renalis* infection, *Dracunculiasis, Echinococcosis, Elephantiasis, Enterobiasis, Fascioliasis, Fasciolopsiasis, Filariasis, Giardiasis, Gnathostomiasis, Hymenolepiasis, Halzoun Syndrome, Isosporiasis, Katayama fever, Leishmaniasis, lymphatic filariasis, Malaria, Metagonimiasis, Myiasis, Onchocerciasis, Pediculosis*, Primary amoebic meningoencephalitis, Parasitic pneumonia, *Paragonimiasis*, Scabies, *Schistosomiasis*, Sleeping sickness, *Strongyloidiasis, Sparganosis, Rhinosporidiosis*, River blindness, *Taeniasis* (cause of Cysticercosis), *Toxocariasis, Toxoplasmosis, Trichinosis, Trichomoniasis, Trichuriasis, Trypanosomiasis*, Tapeworm infection.

A preferred example of infectious disease is a disease caused by any of hepatitis B, hepatitis C, infectious mononucleosis, EBV, cytomegalovirus, AIDS, HIV-1, HIV-2, tuberculosis, malaria and schistosomiasis.

As used herein, the term "vaccine" refers to a biological preparation that improves immunity to a particular disease, wherein the vaccine includes an antigen, such as weakened or killed forms of pathogen, its toxins or one of its surface proteins, against which immune responses are elicited. A vaccine typically includes an adjuvant as immune potentiator to stimulate the immune system. As used herein, the term "therapeutic vaccine" and/or "therapeutic vaccination" refers to a vaccine used to treat ongoing disease, such as infectious disease.

As used herein, the term "adjuvant" refers to an agent used to stimulate the immune system and increase the response to a vaccine, without having any specific antigenic effect in itself.

As used herein, a "costimulatory polypeptide" or "costimulatory molecule" is a polypeptide that, upon interaction with a cell-surface molecule on T cells, modulates T cell responses.

As used herein, a "costimulatory signaling" is the signaling activity resulting from the interaction between costimulatory polypeptides on antigen presenting cells and their receptors on T cells during antigen-specific T cell responses. Without wishing to be limited by a single hypothesis, the antigen-specific T cell response is believed to be mediated by two signals: 1) engagement of the T cell Receptor (TCR) with antigenic peptide presented in the context of MHC (signal 1), and 2) a second antigen-independent signal delivered by contact between different costimulatory receptor/ligand pairs (signal 2). Without wishing to be limited by a single hypothesis, this "second signal" is critical in determining the type of T cell response (activation vs inhibition) as well as the strength and duration of that response, and is regulated by both positive and negative signals from costimulatory molecules, such as the B7 family of proteins.

As used herein, the term "B7" polypeptide means a member of the B7 family of proteins that costimulate T cells including, but not limited to B7-1, B7-2, B7-DC, B7-H5, B7-H1, B7-H2, B7-H3, B7-H4, B7-H6, B7-S3 and biologically active fragments and/or variants thereof. Representative biologically active fragments include the extracellular domain or fragments of the extracellular domain that costimulate T cells.

As used herein, "inflammatory molecules" refers to molecules that induce inflammatory responses (directly or indirectly) including, but not limited to, cytokines and metalloproteases such as including, but not limited to, IL-1beta, TNF-alpha, TGF-beta, IFN-gamma, IL-17, IL-6, IL-23, IL-22, IL-21, and MMPs.

As used herein, the term "vaccine" refers to a biological preparation that improves immunity to a particular disease, wherein the vaccine includes an antigen, such as weakened or killed forms of pathogen, its toxins or one of its surface proteins, against which immune responses are elicited. A vaccine typically includes an adjuvant as immune potentiator to stimulate the immune system. As used herein, the term "therapeutic vaccine" and/or "therapeutic vaccination" refers to a vaccine used to treat ongoing disease, such as infectious disease.

As used herein, the term "adjuvant" refers to an agent used to stimulate the immune system and increase the response to a vaccine, without having any specific antigenic effect in itself.

As used herein, a "vector" is a replicon, such as a plasmid, phage, or cosmid, into which another DNA segment may be inserted so as to bring about the replication of the inserted segment. The vectors described herein can be expression vectors. As used herein, an "expression vector" is a vector that includes one or more expression control sequences As used herein, an "expression control sequence" is a DNA sequence that controls and regulates the transcription and/or translation of another DNA sequence.

"Operably linked" refers to an arrangement of elements wherein the components so described are configured so as to perform their usual or intended function. Thus, two different polypeptides operably linked together retain their respective biological functions while physically linked together.

As used herein, "valency" refers to the number of binding sites available per molecule.

As used herein, a "variant" polypeptide contains at least one amino acid sequence alteration as compared to the amino acid sequence of the corresponding wild-type polypeptide.

As used herein, "conservative" amino acid substitutions are substitutions wherein the substituted amino acid has similar structural or chemical properties. As used herein, the term "host cell" refers to prokaryotic and eukaryotic cells into which a recombinant vector can be introduced.

As used herein, "transformed" and "transfected" encompass the introduction of a nucleic acid (e.g. a vector) into a cell by a number of techniques known in the art.

As used herein, the terms "immunologic", "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. Without wishing to be limited by a single hypothesis, a cellular immune response is elicited by the presentation of polypeptide epitopes in association with Class I or Class II MHC molecules to activate antigen-specific CD4+ T helper cells and/or CD8+ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4+ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

As used herein, the term "C1ORF32" refers to the protein encoded by any one of the H19011_1_T8 (SEQ ID NO:1), H19011_1_T9 (SEQ ID NO:2) transcripts reported herein, particularly to proteins as set forth in any one of H19011_1_P8 (SEQ ID NO:4), H19011_1_P8_V1 (SEQ ID NO:5), H19011_1_P9 (SEQ ID NO:6) or H19011_1_P9_V1 (SEQ ID NO:34), variants and fragments thereof, which can have therapeutic effect on immune related disorder and/or infection.

Fragments of C1ORF32 Polypeptides

As used herein the term "soluble C1ORF32" or "soluble C1ORF32 proteins/molecules" refers to fragments of C1ORF32 that include some or all of the IgV domain of the C1ORF32 polypeptide, and lack some or all of the intracellular and/or transmembrane domains, wherein said fragments retain a biological activity of inhibition of T cell activation.

The soluble C1ORF32 molecules used in the methods of the invention may or may not include a signal (leader) peptide sequence.

Various fragments are given in Table 1 below. "N-term" refers to the N-terminus, so "first N-term" refers to the N-terminus Particular sequences of interest, according to at least some embodiments of the present invention, include but are not limited to SEQ ID NOs: 29, 30, 41-105, and/or 45, 64, or 96. It should be noted that one or more activities and/or functions ascribed herein to any of SEQ ID NOs: 29, 30, 41-105 are also applicable to any of SEQ ID NOs: 45, 64 or 96.

The below table describes a number of sequences with abbreviations, which are defined as follows. The terms "first N-term" and "second N-term" refer to the two potential start points of the IgV domain, as shown in FIG. 1. The terms "#1 option cut point" (and "#2 option cut point") refer to different possible C-terminal end points of the soluble protein—also as shown in FIG. 1. FIG. 1 shows five different possible C-terminal end points, which are as follows: the end of the IgV domain, #1 option cut point, #2 option cut point, the end of the produced protein, and the position before the start of the predicted TM (transmembrane region, which occurs two amino acids after the end of the produced protein). Reference to "+1" or "−1" from a reference point indicate one amino acid after or before that point, respectively, with larger numbers indicating a greater number of amino acids after or before that point as stated below.

The right-most column relates to the SEQ ID NO of the amino acid sequence fused to an Fc sequence (hIgG1 C220S—SEQ ID NO 115) to form a fusion protein; for example, the amino acid sequence having SEQ ID NO:14, given as fused the above Fc sequence, has SEQ ID NO:116 as a fusion protein.

TABLE 1 amino acid sequences discussed in the present application

| SEQ ID NO: | Amino acid sequence | Description | SEQ ID NO with Fc (hIgG1 C220s-SEQ ID 115) fusion |
|---|---|---|---|
| 14 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEGSLGLLVLGRTGLLADLLPSFAVEIM | residues 21-184 of H19011_1_P8 | 116 |
| 15 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEGSLGLLVLEWV | residues 21-169 of H19011_1_P9 | 117 |
| 19 | MDRVLLRWISLFWLTAMVEGLQVTVPDKKKVAM LFQPTVLRCHFSTSSHQPAVVQWKFKSYCQDRM GESLGMSSTRAQSLSKRNLEWDPYLDCLDSRRT VRVVASKQGSTVTLGDFYRGREITIVHDADLQI GKLMWGDSGLYYCIITTPDDLEGKNEDSVELLV LGRTGLLADLLPSFAVEIM | residues 1-184 of the sequence H19011_1_P8_V1 | 118 |
| 28 | MDRVLLRWISLFWLTAMVEGLQVTVPDKKKVAM LFQPTVLRCHFSTSSHQPAVVQWKFKSYCQDRM GESLGMSSTRAQSLSKRNLEWDPYLDCLDSRRT VRVVASKQGSTVTLGDFYRGREITIVHDADLQI GKLMWGDSGLYYCIITTPDDLEGKNEGSLGLLV LEW | residues 1-169 of H19011_1_P9 | 119 |
| 29 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLG | residues 21-167 of H19011_1_P8V1 | 120 |
| 30 | CHFSTSSHQPAVVQWKFKSYCQDRMGESLGMSS TRAQSLSKRNLEWDPYLDCLDSRRTVRVVASKQ GSTVTLGDFYRGREITIVHDADLQIGKLMWGDS GLYYC | residues 42-145 of (H19011_1_P8 from first C residue to last C residue) | 121 |
| 35 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSFAVEIM | H19011_1_P8V1_from_21_to_184 (first N-term to end of produced ECD -2 from end of predicted ECD) | 122 |
| 36 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLEWV | residues 21-169 of H19011_1_P9_V1 | 123 |
| 37 | MDRVLLRWISLFWLTAMVEGLQVTVPDKKKVAM LFQPTVLRCHFSTSSHQPAVVQWKFKSYCQDRM | residues 1-184 of H19011_1_P8 | 124 |

TABLE 1-continued amino acid sequences discussed in the present application

| SEQ ID NO: | Amino acid sequence | Description | SEQ ID NO with Fc (hIgG1 C220s-SEQ ID 115) fusion |
|---|---|---|---|
| | GESLGMSSTRAQSLSKRNLEWDPYLDCLDSRRT VRVVASKQGSTVTLGDFYRGREITIVHDADLQI GKLMWGDSGLYYCIITTPDDLEGKNEGSLGLLV LGRTGLLADLLPSFAVEIM | | |
| 40 | MDRVLLRWISLFWLTAMVEGLQVTVPDKKKVAM LFQPTVLRCHFSTSSHQPAVVQWKFKSYCQDRM GESLGMSSTRAQSLSKRNLEWDPYLDCLDSRRT VRVVASKQGSTVTLGDFYRGREITIVHDADLQI GKLMWGDSGLYYCIITTPDDLEGKNEDSVELLV LEWV | residues 1-169 of H19011_1_P9V1 | 125 |
| 41 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLG | residues 21-167 of H19011_1_P8V1 (first N-term to end of IgV) | 126 |
| 42 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELL | H19011_1_P8V1_from_21_to_164 (first N-term to -3 from end of IgV) | 127 |
| 43 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLV | H19011_1_P8V1_from_21_to_165 (first N-term to -2 from end of IgV) | 128 |
| 44 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVL | H19011_1_P8V1_from_21_to_166 (first N-term to -1 from end of IgV) | 129 |
| 45 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSGGVEIM | H19011_1_P8_V1_from_21_to_184 (first N-term to end of produced ECD with FA->GG mutation) | 130 |
| 46 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGR | H19011_1_P8_V1_from_21_to_168 (first N-term to +1 after end of IgV) | 131 |
| 47 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRT | H19011_1_P8_V1_from_21_to_169 (first N-term to +2 after end of IgV) | 132 |
| 48 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTG | H19011_1_P8_V1_from_21_to_170 (first N-term to +3 after end of IgV -3 before #1 option cut point) | 133 |
| 49 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGL | H19011_1_P8_V1_from_21_to_171 (first N-term to -2 before #1 option cut point) | 134 |
| 50 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLL | H19011_1_P8_V1_from_21_to_172 (first N-term to -1 before #1 option cut point) | 135 |

TABLE 1-continued amino acid sequences discussed in the present application

| SEQ ID NO: | Amino acid sequence | Description | SEQ ID NO with Fc (hIgG1 C220s-SEQ ID 115) fusion |
|---|---|---|---|
| 51 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLA | H19011_1_P8_V1_from_21_to_173 (first N-term to #1 option cut point) | 136 |
| 52 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLAD | H19011_1_P8_V1_from_21_to_174 (first N-term to +1 after #1 option cut point) | 137 |
| 53 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADL | H19011_1_P8_V1_from_21_to_175 (first N-term to +2 after #1 option cut point -3 before #2 option cut point) | 138 |
| 54 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLL | H19011_1_P8_V1_from_21_to_176 (first N-term to +3 after #1 option cut point -2 before #2 option cut point) | 139 |
| 55 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLP | H19011_1_P8_V1_from_1_to_1772 (first N-term to -1 before #2 option cut point) | 140 |
| 56 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPS | H19011_1_P8_V1_from_21_to_178 (first N-term to #2 option cut point | 141 |
| 57 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSF | H19011_1_P8_V1_from_21_to_179 (first N-term to +1 after #2 option cut point) | 142 |
| 58 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSFA | H19011_1_P8_V1_from_21_to_180 (first N-term to +2 after #2 option cut point) | 143 |
| 59 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSFAV | H19011_1_P8_V1_from_21_to_181 (first N-term to +3 after #2 option cut point -3 from end of produced ECD) | 144 |
| 60 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSFAVE | H19011_1_P8_V1_from_21_to_182 (first N-term to -2 from end of produced ECD) | 145 |
| 61 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSFAVEI | H19011_1_P8_V1_from_21_to_183 (first N-term to -1 from end of produced ECD -3 from end of predicted ECD) | 146 |
| 62 | LQVTVPDKKKVAMLFQPTVLRCHFSTSSHQPAV VQWKFKSYCQDRMGESLGMSSTRAQSLSKRNLE | H19011_1_P8_V1 from 21 to 186 (first N- | 147 |

TABLE 1-continued amino acid sequences discussed in the present application

| SEQ ID NO: | Amino acid sequence | Description | SEQ ID NO with Fc (hIgG1 C220s-SEQ ID 115) fusion |
|---|---|---|---|
| | WDPYLDCLDSRRTVRVVASKQGSTVTLGDFYRG REITIVHDADLQIGKLMWGDSGLYYCIITTPDD LEGKNEDSVELLVLGRTGLLADLLPSFAVEIMP E | term to end of predicted ECD) | |
| 63 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSFAVEIMP E | H19011_1_P8_V1_from_21_to_185 (first N-term to +1 after produced ECD -1 from end of predicted ECD) | 148 |
| 64 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSGAVEIM | H19011_1_P8_V1_from_21_to_184 (first N-term to end of produced ECD with FA->GA mutation) | 149 |
| 65 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSFAVEIMP EW | H19011_1_P8_V1_from_21_to_187 (first N-term to +3 after produced ECD +1 in predicted TM) | 150 |
| 66 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSFAVEIMP EWV | H19011_1_P8_V1_from_21_to_188 (first N-term to +2 in predicted TM) | 151 |
| 67 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLGRTGLLADLLPSFAVEIMP EWVF | H19011_1_P8_V1_from_21_to_189 (first N-term to +3 in predicted TM) | 152 |
| 68 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELL | H19011_1_P8_V1_from_27_to_164 (second N-term to -3 from end of IgV) | 153 |
| 69 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLV | H19011_1_P8_V1_from_27_to_165 (second N-term to -2 from end of IgV) | 154 |
| 70 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVL | H19011_1_P8_V1_from_27_to_166 (second N-term to -1 from end of IgV) | 155 |
| 71 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLG | H19011_1_P8_V1_from_27_to_167 (second N-term to end of IgV) | 156 |
| 72 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGR | H19011_1_P8_V1_from_27_to_168 (second N-term to +1 after end of IgV) | 157 |
| 73 | DKKKVAMLFQPTVLRCHFSTSSHQPAVVQWKFK SYCQDRMGESLGMSSTRAQSLSKRNLEWDPYLD | H19011_1_P8_V1_from_27_to_169 (second N- | 158 |

TABLE 1-continued amino acid sequences discussed in the present application

| SEQ ID NO: | Amino acid sequence | Description | SEQ ID NO with Fc (hIgG1 C220s-SEQ ID 115) fusion |
|---|---|---|---|
| | CLDSRRTVRVVASKQGSTVTLGDFYRGREITIV HDADLQIGKLMWGDSGLYYCIITTPDDLEGKNE DSVELLVLGRT | term to +2 after end of IgV) | |
| 74 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTG | H19011_1_P8_V1_from_27_to_170 (second N-term to +3 after end of IgV -3 before #1 option cut point) | 159 |
| 75 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGL | H19011_1_P8_V1_from_27_to_171 (second N-term to -2 before #1 option cut point) | 160 |
| 76 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLL | H19011_1_P8_V1_from_27_to_172 (second N-term to -1 before #1 option cut point) | 161 |
| 77 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLA | H19011_1_P8_V1_from_27_to_173 (second N-term to #1 option cut point) | 162 |
| 78 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLAD | H19011_1_P8_V1_from_27_to_174 (second N-term to +1 after #1 option cut point) | 163 |
| 79 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADL | H19011_1_P8_V1_from_7_to_1752 (second N-term to +2 after #1 option cut point -3 before #2 option cut point) | 164 |
| 80 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLL | H19011_1_P8_V1_from_27_to_176 (second N-term to +3 after #1 option cut point -2 before #2 option cut point) | 165 |
| 81 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLP | H19011_1_P8_V1_from_27_to_177 (second N-term to -1 before #2 option cut point) | 166 |
| 82 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPS | H19011_1_P8_V1_from_27_to_178 (second N-term to #2 option cut point) | 167 |
| 83 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSF | H19011_1_P8_V1_from_27_to_179 (second N-term to +1 after #2 option cut point) | 168 |
| 84 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFA | H19011_1_P8_V1_from_27_to_180 (second N-term to +2 after #2 option cut point) | 169 |

TABLE 1-continued amino acid sequences discussed in the present application

| SEQ ID NO: | Amino acid sequence | Description | SEQ ID NO with Fc (hIgG1 C220s-SEQ ID 115) fusion |
|---|---|---|---|
| 85 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFAV | H19011_1_P8_V1_from_27_to_181 (second N-term to +3 after #2 option cut point -3 from end of produced ECD) | 170 |
| 86 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFAVE | H19011_1_P8_V1_from_27_to_182 (second N-term to -2 from end of produced ECD) | 171 |
| 87 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFAVEI | H19011_1_P8_V1_from_27_to_183 (second N-term to -1 from end of produced ECD -3 from end of predicted ECD) | 172 |
| 88 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFAVEIM | H19011_1_P8_V1_from_27_to_184 (second N-term to end of produced ECD -2 from end of predicted ECD) | 173 |
| 89 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFAVEIMP | H19011_1_P8_V1_from_27_to_185 (second N-term to +1 after end of produced ECD -1 from end of predicted ECD) | 174 |
| 90 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFAVEIMPE | H19011_1_P8_V1_from_27_to_186 (second N-term to +2 after end of produced ECD end of predicted ECD) | 175 |
| 91 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFAVEIMPEW | H19011_1_P8_V1_from_27_to_187 (second N-term to +2 after end of produced ECD +1 in predicted TM) | 176 |
| 92 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFAVEIMPEWV | H19011_1_P8_V1_from_27_to_188 (second N-term to +2 in predicted TM) | 177 |
| 93 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLGRTGLLADLLPSFAVEIMPEWVF | H19011_1_P8_V1_from_27_to_189 (second N-term to +3 in predicted TM) | 178 |
| 94 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLE | H19011_1_P9_V1_from_21_to_167 (first N-term to -2 from end of predicted ECD) | 179 |
| 95 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLEW | H19011_1_P9_V1_from_21_to_1 (first N-term to -1 from end of predicted ECD) | 180 |
| 96 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG | H19011_1_P8_V1_from_21_to_184 (first N-term to end of | 181 |

TABLE 1-continued amino acid sequences discussed in the present application

| SEQ ID NO: | Amino acid sequence | Description | SEQ ID NO with Fc (hIgG1 C220s- SEQ ID 115) fusion |
|---|---|---|---|
| | REITIVHDADLQIGKLMWGDSGLYYCIITTPDD LEGKNEDSVELLVLGRTGLLADLLPSAAVEIM | produced ECD with FA- >AA mutation) | |
| 97 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLEWVF | H19011_1_P9_V1_from_21_to_170 (first N- term to +1 predicted TM) | 182 |
| 98 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLEWVFV | H19011_1_P9_V1_from_21_to_171 (first N- term to +2 predicted TM) | 183 |
| 99 | LQVTVPDKKKVAMLFQPTVLRCHFSTSSHQPAV VQWKFKSYCQDRMGESLGMSSTRAQSLSKRNLE WDPYLDCLDSRRTVRVVASKQGSTVTLGDFYRG REITIVHDADLQIGKLMWGDSGLYYCIITTPDD LEGKNEDSVELLVLEWVFVG | H19011_1_P9_V1_from_21_to_172 (first N- term to +3 predicted TM) | 184 |
| 100 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLE | H19011_1_P9_V1_from_27_to_167 (second N- term to -2 from end of predicted ECD) | 185 |
| 101 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLEW | H19011_1_P9_V1_from_27_to_168 (second N- term to -1 from end of predicted ECD) | 186 |
| 102 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLEWV | H19011_1_P9_V1_from_27_to_169 (second N- term to end of predicted ECD) | 187 |
| 103 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLEWVF | H19011_1_P9_V1_from_27_to_170 (second N- term to +1 predicted TM) | 188 |
| 104 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLEWVFV | H19011_1_P9_V1_from_27_to_171 (second N- term to +2 predicted TM) | 189 |
| 105 | DKKKVAMLFQPTVLRCHFSTSSHQPAVVQWKFK SYCQDRMGESLGMSSTRAQSLSKRNLEWDPYLD CLDSRRTVRVVASKQGSTVTLGDFYRGREITIV HDADLQIGKLMWGDSGLYYCIITTPDDLEGKNE DSVELLVLEWVFVG | H19011_1_P9_V1_from_27_to_172 (second N- term to +3 predicted TM) | 190 |

In particular, the fragments of the extracellular domain of C1ORF32 can include any sequence corresponding to any portion of or comprising the IgV domain of the extracellular domain of C1ORF32, having any sequence corresponding to residues of H19011_1_P8 (SEQ ID NO:4) starting from any position between 18 and 31 and ending at any position between 157 and 175 or corresponding to residues of H19011_1_P8_V1 (SEQ ID NO:5) starting from any position between 18 and 31 and ending at any position between 157 and 175, or corresponding to residues of H19011_1_P9 (SEQ ID NO:6) starting from any position between 18 and 31 and ending at any position between 159 and 172, or corresponding to residues of H19011_1_P9_V1 (SEQ ID NO:34) starting from any position between 18 and 31 and ending at any position between 159 and 172. The base sequences as given above are without a signal peptide.

The C1ORF32 proteins contain an immunoglobulin domain within the extracellular domain, the IgV domain (or V domain), which is related to the variable domain of antibodies. The IgV domain may be responsible for receptor binding, by analogy to the other B7 family members. The Ig domain of the extracellular domain includes one disulfide bond formed between intradomain cysteine residues, as is typical for this fold and may be important for structure-function. In SEQ ID NO: 4 these cysteines are located at residues 42 and 145.

In one embodiment, the first fusion partner is a soluble fragment of C1ORF32. Without wishing to be limited by a single hypothesis, it is believed that useful fragments are those that retain the ability to bind to their natural receptor or receptors and/or retain the ability to inhibit T cell activation. A C1ORF32 polypeptide that is a fragment of full-length C1ORF32 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural receptor(s) and/or of the ability to inhibit T cell activation as compared to full-length C1ORF32. Soluble C1ORF32 polypeptide fragments are fragments of C1ORF32 polypeptides that may be shed, secreted or otherwise extracted from the producing cells. In other embodiments, the soluble fragments of C1ORF32 polypeptides include fragments of the C1ORF32 extracellular domain that retain C1ORF32 biological activity, such as fragments that retain the ability to bind to their natural receptor or receptors and/or retain the ability to inhibit T cell activation. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both.

In some embodiments the extracellular domain is only the IgV domain as set forth in SEQ ID NO: 29, or fragments or variants thereof, or the region between the conserved cysteines of the IgV domain which are located at residues 42 and 145 of the full-length protein SEQ ID NO:4, corresponding to the sequence set forth in SEQ ID NO: 30: CHFSTSSHQPAVVQWKFKSYC-QDRMGESLGMSSTRAQSLSKRNLEWDPYLDCLD-SRR TVRVVASKQGSTVTLGDFYRGREITIVH-DADLQIGKLMWGDSGLYYC. In particular, the fragments of the IgV domain can include any sequence corresponding to residues of H19011_1_P8 (SEQ ID NO:4) starting from any position between 18 and 31 and ending at any position between 157 and 175 or corresponding to residues of H19011_1_P8_V1 (SEQ ID NO:5) starting from any position between 18 and 31 and ending at any position between 157 and 175, or corresponding to residues of H19011_1_P9 (SEQ ID NO:6) starting from any position between 18 and 31 and ending at any position between 159 and 172, or corresponding to residues of H19011_1_P9_V1 (SEQ ID NO:34) starting from any position between 18 and 31 and ending at any position between 159 and 172.

Generally, the C1ORF32 polypeptide fragments are expressed from nucleic acids that include sequences that encode a signal sequence. The signal sequence is generally cleaved from the immature polypeptide to produce the mature polypeptide lacking the signal sequence. The signal sequence of C1ORF32 can be replaced by the signal sequence of another polypeptide using standard molecule biology techniques to affect the expression levels, secretion, solubility, or other property of the polypeptide. The signal sequence that is used to replace the C1ORF32 signal sequence can be any known in the art.

In a further embodiment, the fusion protein includes the extracellular domain of C1ORF32, or a fragment thereof fused to an Ig Fc region. Recombinant IgC1ORF32 polypeptides, fragments or fusion proteins thereof fusion proteins can be prepared by fusing the coding region of the extracellular domain of C1ORF32 or a fragment thereof to the Fc region of human IgG1 or mouse IgG2a, as described previously (Chapoval, et al., Methods Mol. Med, 45:247-255 (2000)).

Variants of C1ORF32 Polypeptides

Useful variants of such C1ORF32 polypeptides include those that increase biological activity, as indicated by any of the assays described herein, or that increase half life or stability of the protein. Soluble C1ORF32 polypeptides and C1ORF32 fragments, or fusions thereof having C1ORF32 activity, can be engineered to increase biological activity. In a further embodiment, the C1ORF32 polypeptide or fusion protein has been modified with at least one amino acid substitution, deletion, or insertion that increases the binding of the molecule to an immune cell, for example a T cell, and transmits an inhibitory signal into the T cell. Other optional variants are those C1ORF32 polypetpides that are engineered to selectively bind to one type of T cell versus other immune cells. For example, the C1ORF32 polypeptide can be engineered to bind optionally to Tregs, Th0, Th1, Th17, Th2 or Th22 cells. Preferential binding refers to binding that is at least 10%, 20%, 30%, 40%, 50%, 60% f 70%, 80%, 90%, 95%, or greater for one type of cell over another type of cell. Still other variants of C1ORF32 can be engineered to have reduced binding to immune cells relative to wildtype C1ORF32. These variants can be used in combination with variants having stronger binding properties to modulate the immune response with a moderate impact. Also optionally, soluble C1ORF32 polypeptides and C1ORF32 fragments, or fusions thereof having C1ORF32 activity, can be engineered to have an increased half-life relative to wildtype. These variants typically are modified to resist enzymatic degradation. Exemplary modifications include modified amino acid residues and modified peptide bonds that resist enzymatic degradation. Various modifications to achieve this are known in the art.

Also optionally, variant C1ORF32 polypeptides can be engineered to prevent a cleavage of the full C1ORF32 ECD (SEQ ID NO:14) between amino acids F and A at positions 179 and 180 of H19011_1_P8_V1 or H19011_1_P8 (Seq ID NOs: 4 or 5). According to at least some embodiments of the present invention there is provided one or more amino acid insertions, deletions or substitutions that prevent the cleavage of the C1ORF32 polypeptides, fusion proteins, or fragments thereof. Suitable amino acid substitutions include conservative and non-conservative substitutions, as described above. According to at least some embodiments of the present invention the amino acid substitution in the cleavage site of C1ORF32 ECD at positions 179 and 180 of H19011_1_P8_V1 or H19011_1_P8 (Seq ID NOs: 4 or 5) is selected from but not limited to: FA→GA (as for example disclosed in SEQ ID NO:64); FA→AA (as for example disclosed in SEQ ID NO:96); and FA→GG (as for example disclosed in SEQ ID NO:45).

The terms "individual", "host", "subject", and "patient" are used interchangeably herein, and refer any human or nonhuman animal. The term "nonhuman animal" includes all vertebrates, e.g., mammals and non-mammals, such as nonhuman primates, sheep, dogs, cats, horses, cows chickens, amphibians, reptiles, etc.

Various aspects of the invention are described in further detail in the following subsections.

Nucleic Acids

A "nucleic acid fragment" or an "oligonucleotide" or a "polynucleotide" are used herein interchangeably to refer to a polymer of nucleic acid residues. A polynucleotide sequence of the present invention refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

Thus, the present invention encompasses nucleic acid sequences described hereinabove; fragments thereof, sequences hybridizable therewith, sequences homologous thereto [e.g., at least 90%, at least 95, 96, 97, 98 or 99% or more identical to the nucleic acid sequences set forth herein, sequences encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (i.e., which form a part of a polynucleotide sequence of the present invention), which include sequence regions unique to the polynucleotides of the present invention.

In cases where the polynucleotide sequences of the present invention encode previously unidentified polypeptides, the present invention also encompasses novel polypeptides or portions thereof, which are encoded by the isolated polynucleotide and respective nucleic acid fragments thereof described hereinabove and/or degenerative variants thereof.

Thus, the present invention also encompasses polypeptides encoded by the polynucleotide sequences of the present invention. The present invention also encompasses homologues of these polypeptides, such homologues can be at least 90%, at least 95, 96, 97, 98 or 99% or more homologous to the amino acid sequences set forth below, as can be determined using BlastP software of the National Center of Biotechnology Information (NCBI) using default parameters. Finally, the present invention also encompasses fragments of the above described polypeptides and polypeptides having mutations, such as deletions, insertions or substitutions of one or more amino acids, either naturally occurring or man induced, either randomly or in a targeted fashion.

As mentioned hereinabove, biomolecular sequences of the present invention can be efficiently utilized as tissue or pathological markers and as putative drugs or drug targets for treating or preventing a disease.

Oligonucleotides designed for carrying out the methods of the present invention for any of the sequences provided herein (designed as described above) can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Oligonucleotides used according to this aspect of the present invention are those having a length selected from a range of about 10 to about 200 bases preferably about 15 to about 150 bases, more preferably about 20 to about 100 bases, most preferably about 20 to about 50 bases.

The oligonucleotides of the present invention may comprise heterocyclic nucleosides consisting of purines and the pyrimidines bases, bonded in a 3' to 5' phosphodiester linkage.

Preferable oligonucleotides are those modified in either backbone, internucleoside linkages or bases, as is broadly described hereinunder. Such modifications can oftentimes facilitate oligonucleotide uptake and resistivity to intracellular conditions.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469, 863; 4,476,301; 5,023,243; 5,177,196; 5,188,897; 5,264, 423; 5,276,019; 5,278,302; 5,286,717; 5,321,131; 5,399, 676; 5,405,939; 5,453,496; 5,455,233; 5,466, 677; 5,476, 925; 5,519,126; 5,536,821; 5,541,306; 5,550,111; 5,563, 253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science and Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Another modification of the oligonucleotides of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No. 6,303,374.

It is not necessary for all positions in a given oligonucleotide molecule to be uniformly modified, and in fact more than one of the aforementioned modifications may be incorporated in a single compound or even at a single nucleoside within an oligonucleotide.

Peptides

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

Polypeptide products can be biochemically synthesized such as by employing standard solid phase techniques. Such methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of a polypeptide are desired, it can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

It will be appreciated that peptides identified according to the teachings of the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N (CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted by synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine Furthermore, the term "amino acid" includes both D- and L-amino acids.

Since the peptides of the present invention are preferably utilized in therapeutics which require the peptides to be in soluble form, the peptides of the present invention preferably include one or more non-natural or natural polar amino acids, including but not limited to serine and threonine which are capable of increasing peptide solubility due to their hydroxyl-containing side chain.

In cases where large amounts of the peptides of the present invention are desired, the peptides of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Expression Systems

To enable cellular expression of the polynucleotides of the present invention, a nucleic acid construct according to the present invention may be used, which includes at least a coding region of one of the above nucleic acid sequences, and further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining elements, or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptides of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Recombinant Expression Vectors and Host Cells

Another aspect of the invention pertains to vectors, preferably expression vectors, containing a nucleic acid encoding a protein of the invention, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked.

Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequences in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for production of variant proteins in prokaryotic or eukaryotic cells. For example, proteins of the invention can be expressed in bacterial cells such as *Escherichia coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase.

Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., Gene Expression Technology: Methods in Enzymology 185, Academic Press, San Diego, Calif. (1990) 60-89)—not accurate, pET11a-d have N terminal T7 tag.

One strategy to maximize recombinant protein expression in *E. coli* is to express the protein in a host bacterium with an impaired capacity to proteolytically cleave the recombinant protein. See, e.g., Gottesman, Gene Expression Technology: Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. Nucl. Acids Res. 20: 2111-2118). Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E. coli* tRNA genes.

In another embodiment, the expression vector encoding for the protein of the invention is a yeast expression vector. Examples of vectors for expression in yeast *Saccharomyces cerevisiae* include pYepSec1 (Baldari, et al., 1987. EMBO J. 6: 229-234), pMFa (Kurjan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

Alternatively, polypeptides of the present invention can be produced in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific;

Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

The present invention in at least some embodiments further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to mRNA encoding for protein of the invention. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, protein of the invention can be produced in bacterial cells such as *E. coli*, insect cells, yeast, plant or mammalian cells (such as Chinese hamster ovary cells (CHO) or COS or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding protein of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) protein of the invention. Accordingly, the present invention in at least some embodiments further provides methods for producing proteins of the invention using the host cells of the invention. In one embodiment, the method comprises culturing the host cell of the present invention (into which a recombinant expression vector encoding protein of the invention has been introduced) in a suitable medium such that the protein of the invention is produced. In another embodiment, the method further comprises isolating protein of the invention from the medium or the host cell.

For efficient production of the protein, it is preferable to place the nucleotide sequences encoding the protein of the invention under the control of expression control sequences optimized for expression in a desired host. For example, the sequences may include optimized transcriptional and/or translational regulatory sequences (such as altered Kozak sequences).

It should be noted, that according to at least some embodiments of the present invention the C1ORF32 polypeptides as described herein may optionally be isolated as naturally-occurring polypeptides, or from any source whether natural, synthetic, semi-synthetic or recombinant. Accordingly, the C1ORF32 proteins may be isolated as naturally-occurring proteins from any species, particularly mammalian, including bovine, ovine, porcine, murine, equine, and preferably human. Alternatively, the C1ORF32 proteins may be isolated as recombinant polypeptides that are expressed in prokaryote or eukaryote host cells, or isolated as a chemically synthesized polypeptide.

A skilled artisan can readily employ standard isolation methods to obtain isolated C1ORF32 proteins. The nature and degree of isolation will depend on the source and the intended use of the isolated molecules.

Fusion Proteins

According to at least some embodiments, C1ORF32 fusion polypeptides have a first fusion partner comprising all or a part of a C1ORF32 protein fused to a second polypeptide directly or via a linker peptide sequence or a chemical linker useful to connect the two proteins. The C1ORF32 polypeptide may or may not contain the native signal peptide. The C1ORF32 polypeptide may optionally be fused to a second polypeptide to form a fusion protein as described herein. The presence of the second polypeptide can alter the solubility, stability, affinity and/or valency of the C1ORF32 fusion polypeptide. As used herein, "valency" refers to the number of binding sites available per molecule. In one embodiment the second polypeptide is a polypeptide from a different source or different protein.

According to at least some embodiments, the C1ORF32 protein or fragment is selected for its activity for the treatment of immune related disorder and/or infection and/or according to one or more in vitro biological activities as described herein.

In one embodiment, the second polypeptide contains one or more domains of an immunoglobulin heavy chain constant region, preferably having an amino acid sequence corresponding to the hinge, CH2 and CH3 regions of a human immunoglobulin Cγ1, Cγ2, Cγ3 or Cγ4, chains or to the hinge, CH2 and CH3 regions of a murine immunoglobulin Cγ2a chain. SEQ ID NO: 20 provides exemplary sequence for the hinge, CH2 and CH3 regions of a human immunoglobulin Cγ1.

According to at least some embodiments, the fusion protein is a dimeric fusion protein. In an optional dimeric fusion protein, the dimer results from the covalent bonding of Cys residue in the hinge region of two of the Ig heavy chains that are the same Cys residues that are disulfide linked in dimerized normal Ig heavy chains. Such proteins are referred to as IgC1ORF32 polypeptides, fragments or fusion proteins thereof.

In one embodiment, the immunoglobulin constant domain may contain one or more amino acid insertions, deletions or substitutions that enhance binding to specific cell types, increase the bioavailablity, or increase the stability of the C1ORF32 polypeptides, fusion proteins, or fragments thereof. Suitable amino acid substitutions include conservative and non-conservative substitutions, as described above.

The fusion proteins optionally contain a domain that functions to dimerize or multimerize two or more fusion proteins. The peptide/polypeptide linker domain can either be a separate domain, or alternatively can be contained within one of the other domains (C1ORF32 polypeptide or second polypeptide) of the fusion protein. Similarly, the domain that functions to dimerize or multimerize the fusion proteins can either be a separate domain, or alternatively can be contained within one of the other domains (C1ORF32 polypeptide, second polypeptide or peptide/polypeptide linker domain) of the fusion protein. In one embodiment, the dimerization/multimerization domain and the peptide/polypeptide linker domain are the same. Further specific, illustrative and non-limiting examples of dimerization/multimerization domains and linkers are given below.

Fusion proteins disclosed herein according to at least some embodiments of the present invention are of formula I: N—R1-R2-R3-C wherein "N" represents the N-terminus of the fusion protein, "C" represents the C-terminus of the fusion protein. In the further embodiment, "R1" is a C1ORF32 polypeptide, "R2" is an optional peptide/polypeptide or chemical linker domain, and "R3" is a second polypeptide. Alternatively, R3 may be a C1ORF32 polypeptide and R1 may be a second polypeptide. Various non-limiting examples of linkers are described in greater detail below.

Optionally, the fusion protein comprises the C1ORF32 polypeptide fragments selected from the group consisting of SEQ ID NOs: 29, 30, 41-105, fused, optionally by a linker peptide of one or more amino acids (e.g. GS) to one or more "half-life extending moieties". A "half-life extending moiety" is any moiety, for example, a polypeptide, small molecule or polymer, that, when appended to protein, extends the in vivo half-life of that protein in the body of a subject (e.g., in the plasma of the subject). For example, a half-life extending moiety is, in an embodiment of the invention, polyethylene glycol (PEG), monomethoxy PEG (mPEG) or an immunoglobulin (Ig). In an embodiment of the invention, PEG is a 5, 10, 12, 20, 30, 40 or 50 kDa moiety or larger or comprises about 12000 ethylene glycol units (PEG12000).

The fusion protein may also optionally be prepared by chemical synthetic methods and the "join" effected chemically, either during synthesis or post-synthesis. Cross-linking and other such methods may optionally be used (optionally also with the above described genetic level fusion methods), as described for example in U.S. Pat. No. 5,547,853 to Wallner et al, which is hereby incorporated by reference as if fully set forth herein as a non-limiting example only.

According to the present invention, a fusion protein may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises the hinge, CH2 and CH3 domains. The Fc chain may optionally be a known or "wild type" Fc chain, or alternatively may be mutated or truncated. The Fc portion of the fusion protein may optionally be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al, Mol. Immun., 34(6):441-452 (1997), Swann, et al., Cur. Opin. Immun., 20:493-499 (2008), and Presta, Cur. Opin. Immun 20:460-470 (2008). In some embodiments the Fc region is the native IgG1, IgG2, or IgG4 Fc region. In some embodiments the Fc region is a hybrid, for example a chimeric consisting of IgG2/IgG4 Fc constant regions.

Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host or substuting the Asn at position 297), and IgG1 with altered pH-dependent binding to FcRn. The Fc region may include the entire hinge region, or less than the entire hinge region.

In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA)

Another embodiment includes IgG2-4 hybrids and IgG4 mutants that have reduced binding to FcR (Fc receptor) which increase their half life. Representative IgG2-4 hybrids and IgG4 mutants are described in Angal, S. et al., Molecular Immunology, 30(1):105-108 (1993); Mueller, J. et al., Molecular Immunology, 34(6): 441-452 (1997); and U.S. Pat. No. 6,982,323 to Wang et al. In some embodiments the IgG1 and/or IgG2 domain is deleted; for example, Angal et al. describe IgG1 and IgG2 having serine 241 replaced with a proline.

In a further embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., Cancer Res., 57(18):8882-90 (2007). Exemplary variants of human IgG1 Fc domains with reduced binding to CD32B and/or increased binding to CD16A contain F243L, R929P, Y300L, V3051 or P296L substitutions. These amino acid substitutions may be present in a human IgG1 Fc domain in any combination.

In one embodiment, the human IgG1 Fc domain variant contains a F243L, R929P and Y300L substitution. In another embodiment, the human IgG1 Fc domain variant contains a F243L, R929P, Y300L, V3051 and P296L substitution. In another embodiment, the human IgG1 Fc domain variant contains an N297A/Q substitution, as these mutations abolish FcγR binding. Non-limiting, illustrative, exemplary types of mutations are described in US Patent Application No. 20060034852, published on Feb. 16, 2006, hereby incorporated by reference as if fully set forth herein. The term "Fc chain" also optionally comprises any type of Fc fragment.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein include the following changes (given with regard to the Fc sequence nomenclature as given by Kabat, from Kabat E A et al: Sequences of Proteins of Immunological Interest. US Department of Health and Human Services, NIH, 1991): 220C→S; 233-238 ELLGGP→EAEGAP; 265D→A, preferably in combination with 434N→A; 297N→A (for example to block N-glycosylation); 318-322 EYKCK→AYACA; 330-331AP→SS; or a combination thereof (see for example M. Clark, "Chemical Immunol and Antibody Engineering", pp 1-31 for a description of these mutations and their effect). The construct for the Fc chain which features the above changes optionally and preferably comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, "Chemical Immunol and Antibody Engineering", pp 1-31). Substitution of 331proline for serine may block the ability to activate complement, which may optionally be considered an undesired function (see M. Clark, "Chemical Immunol and Antibody Engineering", pp 1-31). Changing 330 alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to another amino acid residue (e.g., serine), to avoid any type of covalent linkage (see M. Clark, "Chemical Immunol and Antibody Engineering", pp 1-31) or by deletion or truncation.

The above changes to residues 265 and 434 may optionally be implemented to reduce or block binding to the Fc receptor, which may optionally block undesired functionality of Fc related to its immune system functions (see "Binding site on Human IgG1 for Fc Receptors", Shields et al, Vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

In a further embodiment, the fusion protein includes the C1ORF32 fragment fused to an Ig Fc region. Recombinant Ig-C1ORF32 fragment polypeptides can be prepared by fusing the coding region of the C1ORF32 fragment to the Fc region of human IgG1 or mouse IgG2a, as described previously (Chapoval, et al., Methods Mol. Med, 45:247-255 (2000)). Optionally, C1ORF32 fusion protein, comprising an amino acid sequence of human C1ORF32 ECD fragment fused to murine or human immunoglobulin Fc. Optionally, said fusion protein comprises the amino acid sequence set forth in anyone of SEQ ID NOs: 29, 30, 41-105, and/or 45, 64, or 96, fused to human IgG1 Fc set forth in any one of SEQ ID NOs: 20, 21, 115. Optionally, the amino acid sequence of said fusion protein is set forth in SEQ ID NO: 39, 108-112, 116-190; optionally and preferably, the amino acid sequence is set forth in any of SEQ ID NOs:112, 120 or alternatively in any one of SEQ ID NOs:110, 136.

The aforementioned exemplary fusion proteins can incorporate any combination of the variants described herein. In another embodiment the terminal lysine of the aforementioned exemplary fusion proteins is deleted.

The disclosed fusion proteins can be isolated using standard molecular biology techniques. For example, an expression vector containing a DNA sequence encoding a C1ORF32 ECD fragments or fusion proteins thereof fusion protein is transfected into 293 cells by calcium phosphate precipitation and cultured in serum-free DMEM. The supernatant is collected at 72 h and the fusion protein is purified by Protein G, or preferably Protein A SEPHAROSE® columns (Pharmacia, Uppsala, Sweden). Optionally, a DNA sequence encoding a C1ORF32 fragments fusion protein is transfected into GPEx® retrovectors and expressed in CHO-S cells following four rounds of retrovector transduction. The protein is clarified from supernatants using protein A chromatography.

In another embodiment the second polypeptide may have a conjugation domain through which additional molecules can be bound to the C1ORF32 fragments fusion proteins. In one such embodiment, the conjugated molecule is capable of targeting the fusion protein to a particular organ or tissue; further specific, illustrative, non-limiting examples of such targeting domains and/or molecules are given below.

In another such embodiment the conjugated molecule is another immunomodulatory agent that can enhance or augment the effects of the C1ORF32 fusion protein. In another embodiment the conjugated molecule is Polyethylene Glycol (PEG).

Peptide or Polypeptide Linker Domain

The disclosed C1ORF32 fusion proteins optionally contain a peptide or polypeptide linker domain that separates the C1ORF32 polypeptide from the second polypeptide. In one embodiment, the linker domain contains the hinge region of an immunoglobulin. In a further embodiment, the hinge region is derived from a human immunoglobulin. Suitable human immunoglobulins that the hinge can be derived from include IgG, IgD and IgA. In a further embodiment, the hinge region is derived from human IgG. Amino acid sequences of immunoglobulin hinge regions and other domains are well known in the art. In one embodiment, C1ORF32 fusion polypeptides contain the hinge, CH2 and CH3 regions of a human immunoglobulin Cγ1 chain, optionally with the Cys at position 220 (according to full length human IgG1, position 5 in SEQ ID NO: 20) replaced with a Ser (SEQ ID NO: 115) having at least 85%, 90%, 95%, 99% or 100% sequence homology to amino acid sequence set forth in SEQ ID NO: 20:

EPKSCDKTHTCPPCPAPELLGGPSVFLEPPKPKDTLMISRTPEVTCVVVDVSHEDPEVKENNYVDGVEVHNAKT

KPREEQYNSTYRVVSVLTVLHQDWLNGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTVDKSRWQQGNVFSCSVMHEALHNHYT

QKSLSLSPGK

The hinge can be further shortened to remove amino acids 1, 2, 3, 4, 5, or combinations thereof of any one of SEQ ID NOs: 20 or 115. In one embodiment, amino acids 1-5 of any one of SEQ ID NOs: 20 or 115 are deleted.

In another embodiment, C1ORF32 fusion polypeptides contain the CH2 and CH3 regions of a human immunoglobulin Cγ1 chain having at least 85%, 90%, 95%, 99% or 100% sequence homology to amino acid sequence set forth in SEQ ID NO: 21:

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK

In another embodiment, the C1ORF32 fusion polypeptides contain the CH2 and CH3 regions of a murine immunoglobulin Cγ2a chain at least 85%, 90%, 95%, 99% or 100% sequence homology to amino acid sequence set forth in SEQ ID NO:31:

EPRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVT

LTCMVTDFMPEDIYVEWTNNGKTELNYKNTEPVLDSDGSYFMYSKLRVEK

KNWVERNSYSCSVVHEGLHNHHTTKSFSRTPGK.

In another embodiment, the linker domain contains a hinge region of an immunoglobulin as described above, and further includes one or more additional immunoglobulin domains.

Other suitable peptide/polypeptide linker domains include naturally occurring or non-naturally occurring peptides or polypeptides. Peptide linker sequences are at least 2 amino acids in length. Optionally the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently. Exemplary flexible peptides/polypeptides include, but are not limited to, the amino acid sequences Gly-Ser (SEQ ID NO: 24), Gly-Ser-Gly-Ser (SEQ ID NO: 25), Ala-Ser (SEQ ID NO:26), Gly-Gly-Gly-Ser (SEQ ID NO: 27), Gly4-Ser (SEQ ID NO: 106), (Gly4-Ser)2 (SEQ ID NO: 107), (Gly4-Ser)3 (SEQ ID NO: 32) and (Gly4-Ser)4 (SEQ ID NO: 33). Additional flexible peptide/polypeptide sequences are well known in the art. Other suitable peptide linker domains include helix forming linkers such as Ala-(Glu-Ala-Ala-Ala-Lys)n-Ala (n=1-5) (for n=1, SEQ ID NO:114 as a non-limiting example). Additional helix forming peptide/polypeptide sequences are well known in the art. Additional example of a cleavable linker is TEV-linker Gly Ser Glu Asn Leu Tyr Phe Gln Gly Ser Gly (SEQ ID NO:113). Non-limiting examples of C1ORF32 polypeptide fragments fused to Fc portion via a linker are depicted in SEQ ID NOs: 8 and 108-112.

Dimerization, Multimerization and Targeting Domains

The fusion proteins disclosed herein optionally contain a dimerization or multimerization domain that functions to dimerize or multimerize two or more fusion proteins. The domain that functions to dimerize or multimerize the fusion proteins can either be a separate domain, or alternatively can be contained within one of the other domains (C1ORF32 polypeptide, second polypeptide, or peptide/polypeptide linker domain) of the fusion protein.

Dimerization or multinierization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric. The second polypeptide "partner" in the C1ORF32 fusion polypeptides may be comprised of one or more other proteins, protein fragments or peptides as described herein, including but not limited to any immunoglobulin (Ig) protein or portion thereof, preferably the Fc region, or a portion of a biologically or chemically active protein such as the papillomavirus E7 gene product, melanoma-associated antigen p97), and HIV env protein (gp120). The "partner" is optionally selected to provide a soluble dimer/multimer and/or for one or more other biological activities as described herein.

A "dimerization domain" is formed by the association of at least two amino acid residues or of at least two peptides or polypeptides (which may have the same, or different, amino acid sequences). The peptides or polypeptides may interact with each other through covalent and/or non-covalent associations). Optional dimerization domains contain at least one cysteine that is capable of forming an intermolecular disulfide bond with a cysteine on the partner fusion protein. The dimerization domain can contain one or more cysteine residues such that disulfide bond(s) can form between the partner fusion proteins. In one embodiment, dimerization domains contain one, two or three to about ten cysteine residues. In a further embodiment, the dimerization domain is the hinge region of an immunoglobulin.

Additional exemplary dimerization domains can be any known in the art and include, but not limited to, coiled coils, acid patches, zinc fingers, calcium hands, a $C_H1$-$C_L$ pair, an "interface" with an engineered "knob" and/or "protruberance" as described in U.S. Pat. No. 5,821,333, leucine zippers (e.g., from jun and/or fos) (U.S. Pat. No. 5,932,448), and/or the yeast transcriptional activator GCN4, SH2 (src homology 2), SH3 (src Homology 3) (Vidal, et al, Biochemistry, 43, 7336-44 ((2004)), phosphotyrosine binding (PTB) (Zhou, et al., Nature, 378:584-592 (1995)), WW (Sudol, Prog, Biochys. MoL Bio., 65:113-132 (1996)), PDZ (Kim, et al., Nature, 378: 85-88 (1995); Komau, et al, Science, 269.1737-1740 (1995)) 14-3-3, WD40 (Hu5 et al., J Biol Chem., 273, 33489-33494 (1998)) EH, Lim, an isoleucine zipper, a receptor dimer pair (e.g., interleukin-8 receptor (IL-8R); and integrin heterodimers such as LFA-I and GPIIIb/IIIa), or the dimerization region(s) thereof, dimeric ligand polypeptides (e.g. nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF) (Arakawa, et al., J Biol. Chem., 269(45): 27833-27839 (1994) and Radziejewski, et al., Biochem., 32(48): 1350 (1993)) and can also be variants of these domains in which the affinity is altered. The polypeptide pairs can be identified by methods known in the art, including yeast two hybrid screens. Yeast two hybrid screens are described in U.S. Pat. Nos. 5,283,173 and 6,562,576. Affinities between a pair of interacting domains can be determined using methods known in the art, including as described in Katahira, et at, J. Biol Chem, 277, 9242-9246 (2002)). Alternatively, a library of peptide sequences can be screened for heterodimerization, for example, using the methods described in WO 01/00814. Useful methods for protein-protein interactions are also described in U.S. Pat. No. 6,790,624.

A "multimerization domain" is a domain that causes three or more peptides or polypeptides to interact with each other through covalent and/or non-covalent association(s). Suitable multimerization domains include, but are not limited to, coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, Ile, Leu, Met, Tyr, Phe and Trp. "Mainly hydrophobic" means that at least 50% of the residues must be selected from the mentioned hydrophobic amino acids.

The coiled coil domain may be derived from laminin. In the extracellular space, the heterotrimeric coiled coil protein laminin plays an important role in the formation of basement membranes. Apparently, the multifunctional oligomeric structure is required for laminin function. Coiled coil domains may also be derived from the thrombospondins in which three (TSP-I and TSP-2) or five (TSP-3, TSP-4 and TSP-5) chains are connected, or from COMP (COMPcc) (Guo, et at., EMBO J, 1998, 17: 5265-5272) which folds into a parallel five-stranded coiled coil (Malashkevich, et al., Science, 274: 761-765 (1996)). Additional non limiting examples of coiled-coil domains derived from other proteins, and other domains that mediate polypeptide multimerization are known in the art such as the vasodialator-stimulated phosphoprotein (VASP) domain, matrilin-1 (CMP), viral fusion peptides, soluble NSF (N-ethylmaleimide-sensitive factor) Attachment Protein receptor (SNARE) complexes, leucine-rich repeats, certain tRNA synthetases, are suitable for use in the disclosed fusion proteins.

In another embodiment, C1ORF32 polypeptides, fusion proteins, or fragments thereof can be induced to form multimers by binding to a second multivalent polypeptide, such as an antibody. Antibodies suitable for use to multimerize C1ORF32 polypeptides, fusion proteins, or fragments thereof include, but are not limited to, IgM antibodies and cross-linked, multivalent IgG, IgA, IgD, or IgE complexes.

Dimerization or multimerization can occur between or among two or more fusion proteins through dimerization or multimerization domains, including those described above. Alternatively, dimerization or multimerization of fusion proteins can occur by chemical crosslinking. Fusion protein dimers can be homodimers or heterodimers. Fusion protein multimers can be homomultimers or heteromultimers. Fusion protein dimers as disclosed herein are of formula N—R1-R2-R3-C N—R4-R5-R6-C or, alternatively, are of formula N—R1-R2-R3-C C—R4-R5-R6-N wherein the fusion proteins of the dimer provided by formula II are defined as being in a parallel orientation and the fusion proteins of the dimer provided by formula III are defined as being in an antiparallel orientation. Parallel and antiparallel dimers are also referred to as cis and trans dimers, respectively. "N" and "C" represent the N- and C-termini of the fusion protein, respectively. The fusion protein constituents "R1", "R2" and "R3" are as defined above with respect to formula I. With respect to both formula II and formula III, "R4" is a C1ORF32 polypeptide or a second polypeptide, "R5" is an optional peptide/polypeptide linker domain, and "R6" is a C1ORF32 polypeptide or a second polypeptide, wherein "R6" is a C1ORF32 polypeptide when "R4" is a second polypeptide, and "R6'" is a second polypeptide when "R4" is a C1ORF32 polypeptide. In one embodiment, "R1" is a C1ORF32 polypeptide, "R4" is also a C1ORF32 polypeptide, and "R3" and "R6" are both second polypeptides.

Fusion protein dimers of formula II are defined as homodimers when "R1"="R4", "R2"="R5" and "R3"="R6" Similarly, fusion protein dimers of formula III are defined as homodimers when "R1"="R6", "R2"="R5" and "R3"="R4". Fusion protein dimers are defined as heterodimers when these conditions are not met for any reason. For example, heterodimers may contain domain orientations that meet these conditions (i.e., for a dimer according to formula II, "R1" and "R4" are both C1ORF32 polypeptides, "R2" and "R5" are both peptide/polypeptide linker domains and "R3" and "R6" are both second polypeptides), however the species of one or more of these domains is not identical. For example, although "R3" and "R6" may both be C1ORF32 polypeptides, one polypeptide may contain a wild-type C1ORF32 amino acid sequence while the other polypeptide may be a variant C1ORF32 polypeptide. An exemplary variant C1ORF32 polypeptide is C1ORF32 polypeptide that has been modified to have increased or decreased binding to a target cell, increased activity on immune cells, increased or decreased half life or stability. Dimers of fusion proteins that contain either a CHI or CL region of an immunoglobulin as part of the polypeptide linker domain preferably form heterodimers wherein one fusion protein of the dimer contains a CHI region and the other fusion protein of the dimer contains a CL region.

Fusion proteins can also be used to form multimers. As with dimers, multimers may be parallel multimers, in which all fusion proteins of the multimer are aligned in the same orientation with respect to their N- and C-termini. Multimers may be antiparallel multimers, in which the fusion proteins of the multimer are alternatively aligned in opposite orientations with respect to their N- and C-termini. Multimers (parallel or antiparallel) can be either homomultimers or heteromultimers. The fusion protein is optionally produced in dimeric form; more preferably, the fusion is performed at the genetic level as described below, by joining polynucleotide sequences corresponding to the two (or more) proteins, portions of proteins and/or peptides, such that a joined or fused protein is produced by a cell according to the joined polynucleotide sequence. A description of preparation for such fusion proteins is described with regard to U.S. Pat. No. 5,851,795 to Linsley et al, which is hereby incorporated by reference as if fully set forth herein as a non-limiting example only.

Targeting Domains

The C1ORF32 polypeptides and fusion proteins can contain a targeting domain to target the molecule to specific sites in the body. Optional targeting domains target the molecule to areas of inflammation. Exemplary targeting domains are antibodies, or antigen binding fragments thereof that are specific for inflamed tissue or to a proinflammatory cytokine including but not limited to IL17, IL-4, IL-6, IL-12, IL-21, IL-22, and IL-23. In the case of neurological disorders such as Multiple Sclerosis, the targeting domain may target the molecule to the CNS or may bind to VCAM-I on the vascular epithelium. Additional targeting domains can be peptide aptamers specific for a proinflammatory molecule. In other embodiments, the C1ORF32 fusion protein can include a binding partner specific for a polypeptide displayed on the surface of an immune cell, for example a T cell. In still other embodiments, the targeting domain specifically targets activated immune cells. Optional immune cells that are targeted include Th0, Th1, Th 17, Th2 and Th22 T cells, other cells that secrete, or cause other cells to secrete inflammatory molecules including, but not limited to, IL-1beta, TNF-alpha, TGF-beta, IFN-gamma, IL-17, IL-6, IL-23, IL-22, IL-21, and MMPs, and Tregs. For example, a targeting domain for Tregs may bind specifically to CD25. The above changes are intended as illustrations only of optional changes and are not meant to be limiting in any way. Furthermore, the above explanation is provided for descriptive purposes only, without wishing to be bound by a single hypothesis.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric. The second polypeptide "partner" in the C1ORF32 fusion polypeptides may be comprised of one or more other proteins, protein fragments or peptides as described herein, including but not limited to any immunoglobulin (Ig) protein or portion thereof, preferably the Fc region, or a portion of a biologically or chemically active protein such as the papillomavirus E7 gene product, melanoma-associated antigen p97), and HIV env protein (gp120). The "partner" is optionally selected to provide a soluble dimer/multimer and/or for one or more other biological activities as described herein.

Addition of Groups

If a protein according to the present invention is a linear molecule, it is possible to place various functional groups at various points on the linear molecule which are susceptible to or suitable for chemical modification. Functional groups can be added to the termini of linear forms of the protein according to at least some embodiments of the invention. In some embodiments, the functional groups improve the activity of the protein with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions according to at least some embodiments of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. (Ditter et al., J. Pharm. Sci. 57:783 (1968); Ditter et al., J. Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—

CO—, sec-butyl-O—CO—, t-butyl-O—CO—, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —$NH_2$, —$NHR_2$ and —$NR_2R_3$) or ester (i.e. the hydroxyl group at the C-terminus is replaced with —$OR_2$). $R_2$ and $R_3$ are optionally independently an aliphatic, substituted aliphatic, benzyl, substituted benzyl, aryl or a substituted aryl group. In addition, taken together with the nitrogen atom, $R_2$ and $R_3$ can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —$NH_2$, —$NHCH_3$, —$N(CH_3)_2$, —NH(ethyl), —N(ethyl)$_2$, —N(methyl) (ethyl), —NH(benzyl), —N(C1-C4 alkyl)(benzyl), —NH (phenyl), —N(C1-C4 alkyl) (phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to preferred embodiments of the present invention, one or more peptidomimetics are selected such that the composition at least substantially retains its physiological activity as compared to the native protein according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, Tetrahedron Lett. 26:647-650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S, 3S)-methyl-phenylalanine, (2S, 3R)-methyl-phenylalanine, (2R, 3S)-methyl-phenylalanine and (2R, 3R)-methyl-phenylalanine (Kazmierski and Hruby, Tetrahedron Lett. (1991)).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

Protein Chemical Modifications

In the present invention any part of a protein according to at least some embodiments of the invention may optionally be chemically modified, i.e. changed by addition of functional groups. For example the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Altered Glycosylation

Proteins according to at least some embodiments of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins according to at least some embodiments of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on proteins according to at least some embodiments of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Methods of Treatment

As used herein "therapeutic agent" is any one of the C1ORF32 proteins and polypeptides fragments according to at least some embodiments of the present invention, and/or fusion proteins and/or multimeric proteins comprising same, and/or nucleic acid sequence or fragments thereof encoding same.

As mentioned herein above, the therapeutic agents can be used to treat immune related disorders as recited herein, and/or autoimmune disorders as recited herein, and/or infectious disorders as recited herein, and/or for blocking and/or promoting immune costimulation mediated by the C1ORF32 polypeptides in a subject.

According to an additional aspect of the present invention the therapeutic agents can be used to prevent pathologic inhibition of T cell activity, such as that directed against chronic infections; and/or prevent pathologic stimulation of T cell activity, such as that directed against autoantigens in autoimmune diseases. For example, these molecules can be administered to cells in culture, in vitro or ex vivo, or to human subjects, e.g., in vivo, to treat, prevent and to diagnose a variety of disorders. Preferred subjects include human patients, having disorders mediated by cells expressing the C1ORF32 protein, and cells that possess C1ORF32 activity.

According to an additional aspect of the present invention the therapeutic agents can be used to inhibit T cell activation, as can be manifested for example by T cell proliferation and cytokine secretion.

Thus, according to an additional aspect of the present invention there is provided a method of treating immune related disorders as recited herein, and/or autoimmune disorders as recited herein, and/or infectious disorders as recited herein, and/or for blocking or promoting immune stimulation mediated by the C1ORF32 polypeptide in a subject by administering to a subject in need thereof an effective amount of any one of the therapeutic agents and/or a pharmaceutical composition comprising any of the therapeutic agents and further comprising a pharmaceutically acceptable diluent or carrier.

The subject according to the present invention is a mammal, preferably a human which is diagnosed with one of the disease, disorder or conditions described hereinabove, or alternatively is predisposed to at least one infectious disorder, and/or immune related disorder.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder. "Mammal" for purposes of treatment refers to any animal classified as a mammal, including humans, domestic and farm animals, and zoo, sports, or pet animals, such as dogs, horses, cats, cows, etc. Preferably, the mammal is human.

As used herein the term "treating" refers to preventing, delaying the onset of, curing, reversing, attenuating, alleviating, minimizing, suppressing or halting the deleterious effects of the above-described diseases, disorders or conditions. It also includes managing the disease as described above. By "manage" it is meant reducing the severity of the disease, reducing the frequency of episodes of the disease, reducing the duration of such episodes, reducing the severity of such episodes and the like.

Treating, according to the present invention, can be effected by specifically upregulating the amount and/or the expression of at least one of the polypeptides of the present invention in the subject.

Optionally, upregulation may be effected by administering to the subject at least one of the polypeptides of the present invention (e.g., recombinant or synthetic) or an active portion thereof, as described herein. However, since the bioavailability of large polypeptides may potentially be relatively small due to high degradation rate and low penetration rate, administration of polypeptides is preferably confined to small peptide fragments (e.g., about 100 amino acids). The polypeptide or peptide may optionally be administered in as part of a pharmaceutical composition, described in more detail below.

It will be appreciated that treatment of the above-described diseases according to at least some embodiments of the present invention may be combined with other treatment methods known in the art (i.e., combination therapy), as described herein.

Immune System Related Disease Treatment

The therapeutic agents and/or a pharmaceutical composition comprising same, as recited herein, according to at least some embodiments of the present invention can also be used in combination with one or more of the following agents to regulate an immune response: soluble gp39 (also known as CD40 ligand (CD40L), CD154, T-BAM, TRAP), soluble CD29, soluble CD40, soluble CD80 (e.g. ATCC 68627), soluble CD86, soluble CD28 (e.g. 68628), soluble CD56, soluble Thy-1, soluble CD3, soluble TCR, soluble VLA-4, soluble VCAM-1, soluble LECAM-1, soluble ELAM-1, soluble CD44, antibodies reactive with gp39 (e.g. ATCC HB-10916, ATCC HB-12055 and ATCC HB-12056), antibodies reactive with CD40 (e.g. ATCC HB-9110), antibodies reactive with B7 (e.g. ATCC HB-253, ATCC CRL-2223, ATCC CRL-2226, ATCC HB-301, ATCC HB-11341, etc), antibodies reactive with CD28 (e.g. ATCC HB-11944 or mAb 9.3), antibodies reactive with LFA-1 (e.g. ATCC HB-9579 and ATCC TIB-213), antibodies reactive with LFA-2, antibodies reactive with IL-2, antibodies reactive with IL-12, antibodies reactive with IFN-gamma, antibodies reactive with CD2, antibodies reactive with CD48, antibodies reactive with any ICAM (e.g., ICAM-1 (ATCC CRL-2252), ICAM-2 and ICAM-3), antibodies reactive with CTLA4 (e.g. ATCC HB-304), antibodies reactive with Thy-1, antibodies reactive with CD56, antibodies reactive with CD3, antibodies reactive with CD29, antibodies reactive with TCR, antibodies reactive with VLA-4, antibodies reactive with VCAM-1, antibodies reactive with LECAM-1, antibodies reactive with ELAM-1, antibodies reactive with CD44; L104EA29YIg, CD80 monoclonal antibodies (mAbs), CD86 mAbs, gp39 mAbs, CD40 mAbs, CD28 mAbs; anti-LFA1 mAbs, antibodies or other agents targeting mechanisms of the immune system such as CD52 (alemtuzumab), CD25 (daclizumab), VLA-4 (natalizumab), CD20 (rituximab), IL2R (daclizumab) and MS4A1 (ocrelizumab); novel oral immunomodulating agents have shown to prevent lymphocyte recirculation from lymphoid organs such as fingolimod (FTY720) or leading to lymphocyte depletion such as mylinax (oral cladribine) or teriflunomide; and agents that prevent immunoactivation such as panaclar (dimethyl fumarate BG-12) or laquinimod (ABR216062). Other combinations will be readily appreciated and understood by persons skilled in the art. In some embodiments, the therapeutic agents can be used to attenuate or reverse the activity of a pro-inflammatory drug, and/or limit the adverse effects of such drugs.

As persons skilled in the art will readily understand, the combination can include the therapeutic agents and/or a pharmaceutical composition comprising same, according to at least some embodiments of the invention and one other immunosuppressive agent; the therapeutic agents and/or a pharmaceutical composition comprising same, as recited herein, with two other immunosuppressive agents, the therapeutic agents and/or a pharmaceutical composition comprising same, as recited herein, with three other immunosuppressive agents, etc. The determination of the optimal combination and dosages can be determined and optimized using methods well known in the art.

The therapeutic agent according to the present invention and one or more other therapeutic agents can be administered in either order or simultaneously.

The invention also encompasses the use of the therapeutic agents and/or a pharmaceutical composition comprising same according to at least some embodiments of the invention in combination with other pharmaceutical agents to treat immune system diseases. For example, autoimmune disease may be treated with molecules according to at least some embodiments of the invention in conjunction with, immunosuppressants such as corticosteroids, cyclosporin, cyclophosphamide, prednisone, azathioprine, methotrexate, rapamycin, tacrolimus, biological agents such as TNF-alpha blockers or antagonists, immunosuppressive agents (e.g., antibodies against other lymphocyte surface markers (e.g., CD40, alpha-4 integrin) or against cytokines), other fusion proteins (e.g., CTLA-4-Ig (Orencia®), TNFR-Ig (Enbrel®)), TNF-alpha blockers such as Enbrel, Remicade, Cimzia and Humira, cyclophosphamide (CTX) (i.e. Endoxan®, Cytoxan®, Neosar®, Procytox®, Revimmune™), methotrexate (MTX) (i.e. Rheumatrex®, Trexall®), belimumab (i.e. Benlysta®), or other immunosuppressive drugs (e.g., cyclosporin A, FK506-like compounds, rapamycin compounds, or steroids), anti-proliferatives, cytotoxic agents, or other compounds that may assist in immunosuppression. or any other biological agent targeting any inflammatory cytokine, nonsteroidal antiinflammatory drugs/Cox-2 inhibitors, hydroxychloroquine, sulphasalazopryine, gold salts, etanercept, infliximab, mycophenolate mofetil, basiliximab, atacicept, rituximab, cytoxan, interferon beta-1a, interferon beta-1b, glatiramer acetate, mitoxantrone hydrochloride, anakinra and/or other biologics and/or intravenous immunoglobulin (IVIG). Non-limiting examples of such known therapeutics include interferons, such as IFN-beta-1a (REBIF®. AVONEX® and CINNOVEX®) and IFN-beta-1b (BETASERON®, EXTAVIA®, BETAFERON®, ZIFERON®); glatiramer acetate (COPAXONE®), a polypeptide; natalizumab (TYSABRI®); and mitoxantrone (NOVANTRONE®), a cytotoxic agent.

Thus, treatment of multiple sclerosis using the agents according to at least some embodiments of the present invention may be combined with, for example, any known therapeutic agent or method for treating multiple sclerosis. Non-limiting examples of such known therapeutic agent or method for treating multiple sclerosis include interferon class, IFN-beta-1a (REBIF®. AVONEX® and CINNOVEX®) and IFN-beta-1b (BETASERON®, EXTAVIA®, BETAFERON®, ZIFERON®); glatiramer acetate (COPAXONE®), a polypeptide; natalizumab (TYSABRI®); and mitoxantrone (NOVANTRONE®), a cytotoxic agent, Fampridine (AMPYRA®). Other drugs include corticosteroids, methotrexate, cyclophosphamide, azathioprine, and intravenous immunoglobulin (IVIG), inosine, Ocrelizumab (R1594), Mylinax (Caldribine), alemtuzumab (Campath), daclizumab (Zenapax), Panaclar/dimethyl fumarate (BG-12), Teriflunomide (HMR1726), fingolimod (FTY720), laquinimod (ABR216062), as well as Haematopoietic stem cell transplantation, Neurovax, Rituximab (Rituxan) BCG vaccine, low dose naltrexone, helminthic therapy, angioplasty, venous stents, and alternative therapy, such as vitamin D, polyunsaturated fats, medical marijuana.

Thus, treatment of rheumatoid arthritis, using the agents according to at least some embodiments of the present invention may be combined with, for example, any known therapeutic agent or method for treating rheumatoid arthritis. Non-limiting examples of such known therapeutic agents or methods for treating rheumatoid arthritis include glucocorticoids, nonsteroidal anti-inflammatory drug (NSAID) such as salicylates, or cyclooxygenase-2 inhibitors, ibuprofen and naproxen, diclofenac, indometacin, etodolac Disease-modifying antirheumatic drugs (DMARDs)-Oral DMARDs: Auranofin (Ridaura), Azathioprine (Imuran), Cyclosporine (Sandimmune, Gengraf, Neoral, generic), D-Penicillamine (Cuprimine), Hydroxychloroquine (Plaquenil), IM gold Gold sodium thiomalate (Myochrysine) Aurothioglucose (Solganal), Leflunomide (Arava), Methotrexate (Rheumatrex), Minocycline (Minocin), Staphylococcal protein A immunoadsorption (Prosorba column), Sulfasalazine (Azulfidine). Biologic DMARDs: TNF-α blockers including Adalimumab (Humira), Etanercept (Enbrel), Infliximab (Remicade), golimumab (Simponi), certolizumab pegol (Cimzia), and other Biological DMARDs, such as Anakinra (Kineret), Rituximab (Rituxan), Tocilizumab (Actemra), CD28 inhibitor including Abatacept (Orencia) and Belatacept.

Thus, treatment of IBD, using the agents according to at least some embodiments of the present invention may be combined with, for example, any known therapeutic agent or method for treating IBD. Non-limiting examples of such known therapeutic agents or methods for treating IBD include immunosuppression to control the symptom, such as prednisone, Mesalazine (including Asacol, Pentasa, Lialda, Aspiro), azathioprine (Imuran), methotrexate, or 6-mercaptopurine, steroids, Ondansetron, TNF-α blockers (including infliximab, adalimumab golimumab, certolizumab pegol), Orencia (abatacept), ustekinumab (Stelara®), Briakinumab (ABT-874), Certolizumab pegol (Cimzia®), ITF2357 (givinostat), Natalizumab (Tysabri), Firategrast (SB-683699), Remicade (infliximab), vedolizumab (MLN0002), other drugs including GSK1605786 CCX282-B (Traficet-EN), AJM300, Stelara (ustekinumab), Semapimod (CNI-1493) tasocitinib (CP-690550), LMW Heparin MMX, Budesonide MMX, Simponi (golimumab), MultiStem®, Gardasil HPV vaccine, Epaxal Berna (virosomal hepatitis A vaccine), surgery, such as bowel resection, strictureplasty or a temporary or permanent colostomy or ileostomy; antifungal drugs such as nystatin (a broad spectrum gut antifungal) and either itraconazole (Sporanox) or fluconazole (Diflucan); alternative medicine, prebiotics and probiotics, *cannabis*, Helminthic therapy or ova of the *Trichuris suis* helminth.

Thus, treatment of psoriasis, using the agents according to at least some embodiments of the present invention may be combined with, for example, any known therapeutic agent or method for treating psoriasis. Non-limiting examples of such known therapeutics for treating psoriasis include topical agents, typically used for mild disease, phototherapy for moderate disease, and systemic agents for severe disease. Non-limiting examples of topical agents: bath solutions and moisturizers, mineral oil, and petroleum jelly; ointment and creams containing coal tar, dithranol (anthralin), corticosteroids like desoximetasone (Topicort), Betamethasone, fluocinonide, vitamin D3 analogues (for example, calcipotriol), and retinoids. Non-limiting examples of phototherapy: sunlight; wavelengths of 311-313 nm, psoralen and ultraviolet A phototherapy (PUVA). Non-limiting examples of systemic agents: Biologics, such as interleukin antagonists, TNF-α blockers including antibodies such as infliximab (Remicade), adalimumab (Humira), golimumab, certolizumab pegol, and recombinant TNF-α decoy receptor, etanercept (Enbrel); drugs that target T cells, such as efalizumab (Xannelim/Raptiva), alefacept (Ameviv), dendritic cells such Efalizumab; monoclonal antibodies (MAbs) targeting cytokines, including anti-IL-12/IL-23 (ustekinumab (brand name Stelara)) and anti-Interleukin-17; Briakinumab (ABT-874); small molecules, including but not limited to ISA247; Immunosuppressants, such as methotrexate, cyclosporine; vitamin A and retinoids (synthetic forms of vitamin A); and alternative therapy, such as changes in diet and lifestyle, fasting periods, low energy diets and vegetarian diets, diets supplemented with fish oil rich in Vitamin A and Vitamin D (such as cod liver oil), Fish oils rich in the two omega-3 fatty acids eicosapentaenoic acid (EPA) and docosahexaenoic acid (DHA) and contain Vitamin E Ichthyotherapy, Hypnotherapy, *cannabis*.

Thus, treatment of type 1 diabetes, using the agents according to at least some embodiments of the present invention may be combined with, for example, any known therapeutic agent or method for treating type 1 diabetes. Non-limiting examples of such known therapeutics for treating type 1 diabetes include insulin, insulin analogs, islet transplantation, stem cell therapy including PROCHYMAL®, non-insulin therapies such as i1-1beta inhibitors including Anakinra (Kineret®), Abatacept (Orencia®), Diamyd, alefacept (Ameviv®), Otelixizumab, DiaPep277 (Hsp60 derived peptide), Alpha 1-Antitrypsin, Prednisone, azathioprine, Ciclosporin, E1-INT (an injectable islet neogenesis therapy comprising an epidermal growth factor analog and a gastrin analog), statins including Zocor®, Simlup®, Simcard®, Simvacor®, Sitagliptin (dipeptidyl peptidase (DPP-4) inhibitor), Anti-CD3 mAb (e.g., Teplizumab); CTLA4-Ig (abatacept), Anti IL-1Beta (Canakinumab), Anti-CD20 mAb (e.g, rituximab).

Thus, treatment of uveitis, using the agents according to at least some embodiments of the present invention may be combined with, for example, any known therapeutic agent or method for treating uveitis. Non-limiting examples of such known therapeutics for treating uveitis include corticosteroids, topical cycloplegics, such as atropine or homatropine, or injection of PSTTA (posterior subtenon triamcinolone acetate), antimetabolite medications, such as methotrexate, TNF-α blockers (including infliximab, adalimumab, etanercept, golimumab, certolizumab pegol).

Thus, treatment for Sjogren's syndrome, using the agents according to at least some embodiments of the present invention may be combined with, for example, any known therapeutic agent or method for treating for Sjogren's syndrome. Non-limiting examples of such known therapeutics for treating for Sjogren's syndrome include Cyclosporine, pilocarpine (Salagen) and cevimeline (Evoxac), Hydroxychloroquine (Plaquenil), cortisone (prednisone and others) and/or azathioprine (Imuran) or cyclophosphamide (Cytoxan), Dexamethasone, Thalidomide, Dehydroepiandrosterone, NGX267, Rebamipide, FID 114657, Etanercept, Raptiva, Belimumab, MabThera (rituximab); Anakinra, intravenous immune globulin (IVIG), Allogeneic Mesenchymal Stem Cells (AlloMSC), Automatic neuro-electrostimulation by "Saliwell Crown".

Thus, treatment for systemic lupus erythematosus, using the agents according to at least some embodiments of the present invention may be combined with, for example, any known therapeutic agent or method for treating for systemic lupus erythematosus. Non-limiting examples of such known therapeutics for treating for systemic lupus erythematosus include corticosteroids and Disease-modifying antirheumatic drugs (DMARDs), commonly anti-malarial drugs such as plaquenil and immunosuppressants (e.g. methotrexate and azathioprine) Hydroxychloroquine, cytotoxic drugs (e.g., cyclophosphamide and mycophenolate), Hydroxychloroquine (HCQ), Benlysta (belimumab), nonsteroidal anti-inflammatory drugs, Prednisone, Cellcept, Prograf, Atacicept, Lupuzor, Intravenous Immunoglobulins (IVIGs), CellCept (mycophenolate mofetil), Orencia, CTLA4-IgG4m (RG2077), rituximab, Ocrelizumab, Epratuzumab, CNTO 136, Sifalimumab (MEDI-545), A-623 (formerly AMG 623), AMG 557, Rontalizumab, paquinimod (ABR-215757), LY2127399, CEP-33457, Dehydroepiandrosterone, Levothyroxine, abetimus sodium (LJP 394), Memantine, Opiates, Rapamycin, Renal transplantation, stem cell transplantation.

The therapeutic agents and/or a pharmaceutical composition comprising same, as recited herein, according to at least some embodiments of the invention, may be administered as the sole active ingredient or together with other drugs in immunomodulating regimens or other anti-inflammatory agents e.g. for the treatment or prevention of allo- or xenograft acute or chronic rejection or inflammatory or autoimmune disorders, or to induce tolerance.

For example, it may be used in combination with a calcineurin inhibitor, e.g. cyclosporin A or FK506; an immunosuppressive macrolide, e.g. rapamycine or a derivative thereof; e.g. 40-0-(2-hydroxy)ethyl-rapamycin, a lymphocyte homing agent, e.g. FTY720 or an analog thereof, corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands; or other immunomodulatory compounds, e.g. CTLA4-Ig (abatacept, ORENCIA® or belatacept), CD28-Ig, B7-H4-Ig, or other costimulatory agents, or adhesion molecule inhibitors, e.g. mAbs or low molecular weight inhibitors including LFA-1 antagonists, Selectin antagonists and VLA-4 antagonists.

Where the therapeutic agents and/or a pharmaceutical composition comprising same, as recited herein, according to at least some embodiments of the invention are administered in conjunction with other immunosuppressive/immunomodulatory or anti-inflammatory therapy, e.g. as herein above specified, dosages of the co-administered immunosuppressant, immunomodulatory or anti-inflammatory compound will of course vary depending on the type of co-drug employed, e.g. whether it is a steroid or a cyclosporin, on the specific drug employed, on the condition being treated and so forth.

According to at least some embodiments of the present invention, there is provided use of a combination of the therapeutic agents and/or a pharmaceutical composition comprising same, as recited herein, and a known therapeutic agent effective for treating infection.

The therapeutic agents and/or a pharmaceutical composition comprising same, as recited herein, can be administered in combination with one or more additional therapeutic agents used for treatment of bacterial infections, including, but not limited to, antibiotics including Aminoglycosides, Carbapenems, Cephalosporins, Macrolides, Lincosamides, Nitrofurans, penicillins, Polypeptides, Quinolones, Sulfonamides, Tetracyclines, drugs against mycobacteria including but not limited to Clofazimine, Cycloserine, Cycloserine, Rifabutin, Rifapentine, Streptomycin and other antibacterial drugs such as Chloramphenicol, Fosfomycin, Metronidazole, Mupirocin, and Tinidazole.

The therapeutic agents and/or a pharmaceutical composition comprising same, as recited herein, can be administered in combination with one or more additional therapeutic agents used for treatment of viral infections, including, but not limited to, antiviral drugs such as oseltamivir (brand name Tamiflu) and zanamivir (brand name Relenza) Arbidol—adamantane derivatives (Amantadine, Rimantadine)—neuraminidase inhibitors (Oseltamivir, Laninamivir, Peramivir, Zanamivir) nucleotide analog reverse transcriptase inhibitor including Purine analogue guanine (Aciclovir#/Valaciclovir, Ganciclovir/Valganciclovir, Penciclovir/Famciclovir) and adenine (Vidarabine), Pyrimidine analogue, uridine (Idoxuridine, Trifluridine, Edoxudine), thymine (Brivudine), cytosine (Cytarabine); Foscarnet; Nucleoside analogues/NARTIs: Entecavir, Lamivudine, Telbivudine, Clevudine; Nucleotide analogues/NtRTIs: Adefovir, Tenofovir; Nucleic acid inhibitors such as Cidofovir; InterferonInterferon alfa-2b, Peginterferon alfa-2a; Ribavirin#/Taribavirin; antiretroviral drugs including zidovudine, lamivudine, abacavir, lopinavir, ritonavir, tenofovir/emtricitabine, efavirenz each of them alone or a various combinations, gp41 (Enfuvirtide), Raltegravir, protease inhibitors such as Fosamprenavir, Lopinavir and Atazanavir, Methisazone, Docosanol, Fomivirsen, Tromantadine.

The therapeutic agents and/or a pharmaceutical composition comprising same, as recited herein, can be administered in combination with one or more additional therapeutic agents used for treatment of fungal infections, including, but not limited to, antifungal drugs of the Polyene antifungals, Imidazole, triazole, and thiazole antifungals, Allylamines, Echinocandins or other anti fungal drugs.

Alternatively or additionally, an upregulating method may optionally be effected by specifically upregulating the amount (optionally expression) in the subject of at least one of the polypeptides of the present invention or active portions thereof.

As is mentioned hereinabove and in the Examples section which follows, the biomolecular sequences of this aspect of the present invention may be used as valuable therapeutic tools in the treatment of diseases, disorders or conditions in which altered activity or expression of the wild-type gene product (known protein) is known to contribute to disease, disorder or condition onset or progression. For example, in case a disease is caused by overexpression of a membrane bound-receptor, a soluble variant thereof may be used as an antagonist which competes with the receptor for binding the ligand, to thereby terminate signaling from the receptor.

According to at least some embodiments, immune cells, preferably T cells, can be contacted in vivo or ex vivo with the therapeutic agents to modulate immune responses. The T cells contacted with the therapeutic agents can be any cell which expresses the T cell receptor, including $\alpha/\beta$ and $\gamma/\delta$ T cell receptors. T-cells include all cells which express CD3, including T-cell subsets which also express CD4 and CDS. T-cells include both naive and memory cells and effector cells such as CTL. T-cells also include cells such as Th1, Tc1, Th2, Tc2, Th3, Th17, Th22, Treg, and Tr1 cells. T-cells also include NKT-cells and similar unique classes of the T-cell lineage.

In a further embodiment, the additional therapeutic agent functions to inhibit or reduce T cell activation through a separate pathway. In one such embodiment, the additional therapeutic agent is a CTL A-4 fusion protein, such as CTLA-4-Ig (abatacept). CTLA-4-Ig fusion proteins compete with the co-stimulatory receptor, CD28, on T cells for binding to CD80/CD86 (B7-1/B7-2) on antigen presenting cells, and thus function to inhibit T cell activation. In another embodiment, the additional therapeutic agent is a CTLA-4-Ig fusion protein known as belatacept. Belatacept contains two amino acid substitutions (L104E and A29Y) that markedly increase its avidity to CD86 in vivo. In another embodiment, the additional therapeutic agent is Maxy-4.

In another embodiment, the second therapeutic agent is cyclophosphamide (CTX). Cyclophosphamide (the generic name for Endoxan®, Cytoxan®, Neosar®, Procytox®, Revimmune™), also known as cytophosphane, is a nitrogen mustard alkylating agent from the oxazophorines group. It is used to treat various types of cancer and some autoimmune disorders. In a further embodiment, IgC1ORF32 polypeptides, fragments or fusion proteins thereof and CTX are coadministered in effective amount to prevent or treat a chronic autoimmune disease or disorder such as Systemic lupus erythematosus (SLE). Cyclophosphamide (CTX) is the primary drug used for diffuse proliferative glomerulonephritis in patients with renal lupus. In some embodiments the combination therapy is administered in an effective amount to reduce the blood or serum levels of anti-double stranded DNA (anti-ds DNA) auto antibodies and/or to reduce proteinuria in a patient in need thereof.

In another embodiment, the second therapeutic is Tysabri or another therapeutic for MS. In a further embodiment, IgC1ORF32 polypeptides, fragments or fusion proteins thereof is cycled with Tysabri or used during a drug holiday in order to allow less frequent dosing with the second therapeutic and reduce the risk of side effects such as PML and to prevent resistance to the second therapeutic.

In another embodiment, the second therapeutic agent preferentially treats chronic inflammation, whereby the treatment regimen targets both acute and chronic inflammation. In a further embodiment the second therapeutic is a TNF-alpha blocker.

In another embodiment, the second therapeutic agent is a small molecule that inhibits or reduces differentiation, proliferation, activity, and/or cytokine production and/or secretion by Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs. In another embodiment, the second therapeutic agent is a small molecule that interacts with Tregs, enhances Treg activity, promotes or enhances IL-10 secretion by Tregs, increases the number of Tregs, increases the suppressive capacity of Tregs, or combinations thereof.

Typically useful small molecules are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Small molecules comprise functional groups necessary for structural interaction with proteins, particularly hydrogen bonding, and typically include at least an amine, carbonyl, hydroxyl or carboxyl group, preferably at least two of the functional chemical groups. The small molecules often comprise cyclical carbon or heterocyclic structures and/or aromatic or polyaromatic structures substituted with one or more of the above functional groups. Small molecules also include biomolecules including peptides, saccharides, fatty acids, steroids, purines, pyrimidines, derivatives, structural analogs or combinations thereof. In one embodiment, the small molecule is retinoic acid or a derivative thereof. The examples below demonstrate that retinoic acid inhibits or reduces differentiation and/or activity of ThI 7 cells. In a further embodiment, the compositions are used in combination or succession with compounds that increase Treg activity or production. Exemplary Treg enhancing agents include but are not limited to glucocorticoid fluticasone, salmeteroal, antibodies to IL-12, IFN-gamma, and IL-4; vitamin D3, and dexamethasone, and combinations thereof. Antibodies to other proinflammatory molecules can also be used in combination or alternation with the disclosed C1ORF32 polypeptide selected from the group consisting of SEQ ID NOs: 29, 30, 41-105, or a fragment, variant, a homolog, a fusion protein or a conjugate thereof. Preferred antibodies bind to IL-6, IL-23, IL-22 or IL-21.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art. The language "FK506-Hke compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. Preferably, the language "rapamycin compound" as used herein does not include FK506-like compounds.

Other suitable therapeutics include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5 (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clmdanac, oxepinac, felbmac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fiuosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolones prednisone, beclomethasone dipropionate, triamcinolone, and mixtures thereof.

Methods of Therapeutic Use

The C1ORF32 polypeptides, fragments or fusion proteins thereof are useful as therapeutic agents. According to at least some embodiments, immune cells, preferably T cells, can be contacted in vivo or ex vivo with C1ORF32 fusion polypeptides to decrease or inhibit immune responses including, but not limited to inflammation. According to at least some other embodiments, immune cells, preferably T cells, can be contacted in vivo or ex vivo with C1ORF32 fusion polypeptides to decrease or inhibit T cell exhaustion, optionally in combination with another therapeutic agent. In both cases, preferably the costimulatory pathway is modulated to achieve a desired immune system balance.

In either case, the T cells contacted with C1ORF32 fusion polypeptides can be any cell which expresses the T cell receptor, including $\alpha/\beta$ and $\gamma/\delta$ T cell receptors. T-cells include all cells which express CD3, including T-cell subsets which also express CD4 and CDS. T-cells include both naive and memory cells and effector cells such as CTL. T-cells also include cells such as Th1, Tc1, Th2, Tc2, Th3, Th17, Th22, Treg, and Tr1 cells. T-cells also include NKT-cells and similar unique classes of the T-cell lineage. For example the compositions can be used to modulate Th1, Th17, Th22, or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs. The compositions can also be used to increase or promote the activity of Tregs, increase the production of cytokines such as IL-10 from Tregs, increase the differentiation of Tregs, increase the number of Tregs, or increase the survival of Tregs. The compositions can also be used to increase or promote the activity of Th2 cells, increase the production of cytokines such as IL-10 or IL-4 from Th2 cells, increase the differentiation of Th2 cells, increase the number of Th2 cells, or increase the survival of Th2 cells.

Although the below discussion applies generally to the reversal of T cell exhaustion, preferably for treatment of such exhaustion memory T cells are treated. Optionally, additionally or alternatively, treatment of T cell exhaustion encompasses the modulation of cytokine secretion, or other cells that secrete, or cause other cells to secrete, inflammatory molecules, including, but not limited to, IL-2, TNF-alpha, IFN-gamma, 15 Granzyme B and MMPs or modulate the expression of molecules of the costimulatory/coinhibitory-family including, but not limited to PD-1, Tim3, CTLA4 and LAGS.

In some embodiments, the disclosed C1ORF32 polypeptide, selected from the group consisting of SEQ ID NOs: 29, 30, 41-105, or a fragment, variant, a homolog, a fusion protein or a conjugate thereof, are administered in combination with a second therapeutic. Combination therapies may be useful in immune modulation. In some embodiments, C1ORF32 polypeptide, selected from the group consisting of SEQ ID NOs: 29, 30, 41-105, or a fragment, variant, a homolog, a fusion protein or a conjugate thereof, can be used to attenuate or reverse the activity of a proinflammatory drug, and/or limit the adverse effects of such drugs. Other immune cells that can be treated with the disclosed C1ORF32 polypeptides, fragments or fusion thereof include T cell precursors, antigen presenting cells such as dendritic cells and monocytes or their precursors, B cells or combinations thereof. The C1ORF32 compositions can be used to modulate the production of antibodies by B cells by contacting the B cells with an effective amount of the C1ORF32 composition to inhibit or reduce antibody production by the B cell relative to a control. The C1ORF32 compositions can also modulate the production of cytokines by the B cells.

Methods of Treating Inflammatory Responses

The C1ORF32 polypeptides, fragments or fusion proteins thereof, selected from the group consisting of SEQ ID NOs: 29, 30, 41-105, or a fragment, variant, a homolog, a fusion protein or a conjugate thereof, according to at least some embodiments of the present invention inhibit T cell activation, as manifested by T cell proliferation and cytokine secretion. Specifically, the proteins inhibit T Th1 and Th17 responses, while promoting Th2 responses.

The C1ORF32 polypeptides, fragments or fusion proteins thereof, selected from the group consisting of SEQ ID NOs: 29, 30, 41-105, or a fragment, variant, a homolog, a fusion protein or a conjugate thereof, according to at least some embodiments of the present invention are potentially used for therapy of diseases that require down-regulation of costimulatory pathways and or such that require downregulation of Th1 and/or Th17 responses.

A further embodiment provides methods for treating or alleviating one or more symptoms of inflammation. In a further embodiment, the compositions and methods disclosed are useful for treating chronic and persistent inflammation. Inflammation in general can be treated using the disclosed C1ORF32 polypeptides or fragment or fusions thereof.

According to at least some embodiments of the present invention, there is provided use of an isolated C1ORF32 polypeptide as described herein or a fusion protein comprising an isolated C1ORF32 polypeptide as described herein, optionally in a pharmaceutical composition comprising a pharmaceutically acceptable diluent or carrier, for treatment of an immune related disorder and/or infection.

An immune response including inflammation can be inhibited or reduced in a subject, preferably a human, by administering an effective amount of C1ORF32 polypeptide selected from the group consisting of SEQ ID NOs: 29, 30, 41-105, or a fragment, variant, a homolog, a fusion protein or a conjugate thereof, to inhibit or reduce the biological activity of an immune cell or to reduce the amounts of proinflammatory molecules at a site of inflammation. Exemplary proinflammatory molecules include, but are not limited to, IL-1beta, TNF-alpha, TGF-beta, IFN-gamma, IL-17, IL-6, IL-23, IL-22, IL-21, and MMPs. Th1 and Th17 are exemplary T cells that can be targeted for inhibition by C1ORF32 polypeptide selected from the group consisting of SEQ ID NOs: 29, 30, 41-105, or a fragment, variant, a homolog, a fusion protein or a conjugate thereof, to inhibit or reduce inflammation.

Without wishing to be limited by a single hypothesis for this biological mechanism or any other biological mechanism described herein, the C1ORF32 polypeptides, fragments or fusion proteins thereof are useful for treating inflammation by any or all of the following: inhibiting or reducing differentiation of Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs; inhibiting or reducing activity of ThI, Th 17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs; inhibiting or reducing the Th1 and/or Th17 pathways; inhibiting or reducing cytokine production and/or secretion by Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6 IL-23, IL-22, IL-21, and MMPs; inhibiting or reducing proliferation of Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs.

Additionally, C1ORF32 polypeptide selected from the group consisting of SEQ ID NOs: 29, 30, 41-105, or a fragment, variant, a homolog, a fusion protein or a conjugate thereof can also enhance Th2 immune responses. C1ORF32 polypeptide selected from the group consisting of SEQ ID NOs: 29, 30, 41-105, or a fragment, variant, a homolog, a fusion protein or a conjugate thereof can also act directly on Th2 cells to promote or enhance production of IL-4, IL-5 or IL-10, or to increase the number of Th2 cells, resulting in inhibition of Th1 and/or Th17, and in immune modulation via a Th1/Th2 shift.

Additionally, C1ORF32 polypeptide selected from the group consisting of SEQ ID NOs: 29, 30, 41-105, or a fragment, variant, a homolog, a fusion protein or a conjugate thereof can cause Tregs to have an enhanced suppressive effect on an immune response. Tregs can suppress differentiation, proliferation, activity, and/or cytokine production and/or secretion by Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs. For example, C1ORF32 polypeptide selected from the group consisting of SEQ ID NOs: 29, 30, 41-105, or a fragment, variant, a homolog, a fusion protein or a conjugate thereof can cause Tregs to have an enhanced suppressive effect on Th1 and/or Th17 cells to reduce the level of IFN-gamma and IL-17 produced, respectively. C1ORF32polypeptide selected from the group consisting of SEQ ID NOs: 29, 30, 41-105, or a fragment, variant, a homolog, a fusion protein or a conjugate thereof can also act directly on Tregs to promote or enhance production of IL-10 to suppress the Th1 and/or Th17 pathway, and/or to increase the number of Tregs.

Additionally, C1ORF32 polypeptide selected from the group consisting of SEQ ID NOs: 29, 30, 41-105, or a fragment, variant, a homolog, a fusion protein or a conjugate thereof can cause Th2 to have an enhanced modulatory effect on an immune response. Th2 cells can modulate differentiation, proliferation, activity, and/or cytokine production and/or secretion by Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs. For example, C1ORF32 polypeptide selected from the group consisting of SEQ ID NOs: 29, 30, 41-105, or a fragment, variant, a homolog, a fusion protein or a conjugate thereof can cause Th2 cells to have an enhanced modulatory effect on Th1 and/or Th17 cells to reduce the level of IFN-gamma and IL-17 produced, respectively. C1ORF32 polypeptide selected from the group consisting of SEQ ID NOs: 29, 30, 41-105, or a fragment, variant, a homolog, a fusion protein or a conjugate thereof can also act directly on Th2 cells to promote or enhance production of IL-10 to suppress the Th1 and/or Th17 pathway, and/or to increase the number of Th2 cells.

Without wishing to be limited by a single hypothesis, it is believed that C1ORF32 polypeptide selected from the group consisting of SEQ ID NOs: 29, 30, 41-105, or a fragment, variant, a homolog, a fusion protein or a conjugate thereof acts at multiple points in multiple T cell pathways. For example, polypeptide selected from the group consisting of SEQ ID NOs: 29, 30, 41-105, or a fragment, variant, a homolog, a fusion protein or a conjugate thereof can inhibit the differentiation of naive T cells into either Th1 or Th17 cells. Alternatively, polypeptide selected from the group consisting of SEQ ID NOs: 29, 30, 41-105, or a fragment, variant, a homolog, a fusion protein or a conjugate thereof can interact with Th1 cells or Th17 cells, or both to inhibit or reduce the production of proinflammatory molecules.

Additionally, C1ORF32 polypeptide selected from the group consisting of SEQ ID NOs: 29, 30, 41-105, or a fragment, variant, a homolog, a fusion protein or a conjugate thereof may increase the differentiation of and/or promote Th2 responses resulting in an immunomodulatory effect on the Th1 and/or Th17 pathways to reduce the level of INF-gamma and/or IL-17 produced. C1ORF32 polypeptide selected from the group consisting of SEQ ID NOs: 29, 30, 41-105, or a fragment, variant, a homolog, a fusion protein or a conjugate thereof enhances the production of IL-10 from cells such as Th2 and/or Tregs, which in turn inhibits the activity of Th1 and/or Th17 cells.

Additionally, C1ORF32 polypeptide selected from the group consisting of SEQ ID NOs: 29, 30, 41-105, or a fragment, variant, a homolog, a fusion protein or a conjugate thereof can affect Tregs to have an enhanced suppressive effect on Th1 and/or Th17 pathways to reduce the level of INF-gamma and/or IL-17 produced. Additionally, C1ORF32 polypeptide selected from the group consisting of SEQ ID NOs: 29, 30, 41-105, or a fragment, variant, a homolog, a fusion protein or a conjugate thereof can enhance the production of IL-10 which inhibits the activity of Th1 and/or Th17 cells.

Inhibition of Th1 Responses a. Inhibition of Th1 Development

One method for inhibiting or reducing inflammation includes administering an effective amount of a C1ORF32 polypeptide selected from the group consisting of SEQ ID NOs: 29, 30, 41-105, or a fragment, variant, a homolog, a fusion protein or a conjugate thereof to inhibit Th1 development in a subject in need thereof. Inflammation can be inhibited or reduced by blocking naive T cells from differentiating into Th1 cells by administering C1ORF32 polypeptide selected from the group consisting of SEQ ID NOs:

29, 30, 41-105, or a fragment, variant, a homolog, a fusion protein or a conjugate thereof. In one embodiment, the C1ORF32 polypeptide selected from the group consisting of SEQ ID NOs: 29, 30, 41-105, or a fragment, variant, a homolog, a fusion protein or a conjugate thereof may inhibit or reduce proliferation of Th1 cells. C1ORF32 polypeptide selected from the group consisting of SEQ ID NOs: 29, 30, 41-105, or a fragment, variant, a homolog, a fusion protein or a conjugate thereof may also reduce naive T cells from differentiating into Th1 cells, by blocking antigen presenting cell maturation. Alternatively, C1ORF32 polypeptide selected from the group consisting of SEQ ID NOs: 29, 30, 41-105, or a fragment, variant, a homolog, a fusion protein or a conjugate thereof increase the differentiation of Th2 cells and thereby reduce the number of Th1 cells in a subject. By restricting the number of Th1 cells that can develop in the subject, the amount of proinflammatory molecules such as INF-gamma can be reduced or contained. INF-gamma stimulates the production or release of other proinflammatory molecules including IL-1beta, TNF-alpha, and MMPs. Thus, by controlling the number of Th1 cells in a subject, the levels of these other proinflammatory molecules can be controlled, thereby reducing inflammatory responses.

b. Inhibition of Proinflammatory Molecules

Another embodiment provides a method of inhibiting or reducing inflammation in a subject by administering to the subject an effective amount of a C1ORF32 polypeptide selected from the group consisting of SEQ ID NOs: 29, 30, 41-105, or a fragment, variant, a homolog, a fusion protein or a conjugate thereof to inhibit or reduce production of proinflammatory molecules by Th1 cells.

Exemplary proinflammatory molecules produced by Th1 cells includes IFN-gamma. In this embodiment the C1ORF32 polypeptide selected from the group consisting of SEQ ID NOs: 29, 30, 41-105, or a fragment, variant, a homolog, a fusion protein or a conjugate thereof can interact directly with the Th1 cell and inhibit or reduce IFN-gamma production by the Th1 cells. In this embodiment, the amount of proinflammatory molecules is regulated rather than the population of Th1 cells.

Inhibition of Th17 Responses a. Inhibition of Th17 Development

Inflammation can also be inhibited or reduced in a subject by administering an effective amount of a C1ORF32 polypeptide selected from the group consisting of SEQ ID NOs: 29, 30, 41-105, or a fragment, variant, a homolog, a fusion protein or a conjugate thereof, to inhibit or block naive T cells from developing into Th17 cells. In one embodiment, the C1ORF32 polypeptide selected from the group consisting of SEQ ID NOs: 29, 30, 41-105, or a fragment, variant, a homolog, a fusion protein or a conjugate thereof increases the suppressive activity of Tregs on the differentiation of naive T cells into Th17 cells by an amount sufficient to reduce the number of Th17 cells in a subject. Alternatively, the C1ORF32 polypeptide selected from the group consisting of SEQ ID NOs: 29, 30, 41-105, or a fragment, variant, a homolog, a fusion protein or a conjugate thereof inhibits or reduces proliferation of Th17 cells. C1ORF32 polypeptide selected from the group consisting of SEQ ID NOs: 29, 30, 41-105, or a fragment, variant, a homolog, a fusion protein or a conjugate thereof may also reduce naive T cells from differentiating into Th17 cells, by blocking antigen presenting cell maturation. By reducing the population of Th17 cells in a subject, the amount of IL-17 can be reduced, as well as IL-22 and IL-21. IL-17 is a proinflammatory cytokine that causes increases in other proinflammatory molecules such as IL-1beta, TNF-alpha, and MMPs. Thus, by reducing the amount of IL-17 these other proinflammatory molecules can be reduced, thereby reducing or inhibiting inflammation.

b. Inhibition of IL-17 Production

Still another embodiment provides a method for treating inflammation in a subject by administering an effective amount of C1ORF32 polypeptide selected from the group consisting of SEQ ID NOs: 29, 30, 41-105, or a fragment, variant, a homolog, a fusion protein or a conjugate thereof, to inhibit production of IL-17 by Th17 cells, as well as IL-22 and IL-21. In this embodiment, the C1ORF32 polypeptide selected from the group consisting of SEQ ID NOs: 29, 30, 41-105, or a fragment, variant, a homolog, a fusion protein or a conjugate thereof can act directly on Th17 cells, for example by binding to Th17 cells resulting in inhibition of IL-17 (or IL-22 and IL-21) production by those Th17 cells. As noted above, inhibition or reduction of IL-17 (and IL-22 or IL-21) leads to the reduction of other proinflammatory molecules, thereby reducing or inhibiting inflammation.

Inhibiting Th1 and Th17 Responses

The disclosed C1ORF32 polypeptide selected from the group consisting of SEQ ID NOs: 29, 30, 41-105, or a fragment, variant, a homolog, a fusion protein or a conjugate thereof can be used to inhibit both the Th1 and Th17 pathways simultaneously. Using one anti-inflammatory agent to inhibit two separate pathways provides more robust inhibition or reduction of the immune response.

Promoting Th2 Responses and IL-10 production.

Inflammation can also be treated by administering C1ORF32 polypeptide selected from the group consisting of SEQ ID NOs: 29, 30, 41-105, or a fragment, variant, a homolog, a fusion protein or a conjugate thereof to a subject in an amount effective to enhance Th2 responses, and the suppressive activity of IL-10 producing cells, and to enhance suppressive or modulatory activity on the Th1 and/or Th17 pathways. In this embodiment the disclosed C1ORF32 polypeptide selected from the group consisting of SEQ ID NOs: 29, 30, 41-105, or a fragment, variant, a homolog, a fusion protein or a conjugate thereof cause an increased suppressive effect on IFN-gamma and/or IL-17 production. Another embodiment provides a method for treating inflammation by administering an effective amount of C1ORF32 polypeptide selected from the group consisting of SEQ ID NOs: 29, 30, 41-105, or a fragment, variant, a homolog, a fusion protein or a conjugate thereof to increase production of IL-10 by Th2, Tregs or other immune cells.

Increased production of IL-10 results in the decreased production of IL-17 by Th17 cells and deceased production of IFN-gamma by Th1 cells. In this embodiment, the C1ORF32 polypeptide selected from the group consisting of SEQ ID NOs: 29, 30, 41-105, or a fragment, variant, a homolog, a fusion protein or a conjugate thereof can interact directly with immune cells to increase IL-10 production.

Still another embodiment provides a method for treating inflammation by administering an effective amount of C1ORF32 polypeptide selected from the group consisting of SEQ ID NOs: 29, 30, 41-105, or a fragment, variant, a homolog, a fusion protein or a conjugate thereof to inhibit or interfere with the Th1 pathway and Th17 pathway, and to enhance the suppressive effect on the Th1 and/or Th17 pathways by Th2 cells.

The C1ORF32 polypeptide selected from the group consisting of SEQ ID NOs: 29, 30, 41-105, or a fragment, variant, a homolog, a fusion protein or a conjugate thereof can also be administered to a subject in an amount effective to increase Th2 cell populations or numbers.

IL-10 production can be increased relative to a control by contacting Th2 cells, Tregs or other immune cells with an effective amount of C1ORF32 polypeptide selected from the group consisting of SEQ ID NOs: 29, 30, 41-105, or a fragment, variant, a homolog, a fusion protein or a conjugate thereof having C1ORF32 activity. The increase can occur in vitro or in vivo.

Inflammatory Disease to be Treated

Representative inflammatory or autoimmune diseases and disorders that may be treated using C1ORF32 polypeptide selected from the group consisting of SEQ ID NOs: 29, 30, 41-105, or a fragment, variant, a homolog, a fusion protein or a conjugate thereof include, but are not limited to multiple sclerosis, rheumatoid arthritis, type I diabetes, psoriasis, systemic lupus erythematosus, inflammatory bowel disease, uveitis, and Sjogren's syndrome.

C1ORF32 polypeptide selected from the group consisting of SEQ ID NOs: 29, 30, 41-105, or a fragment, variant, a homolog, a fusion protein or a conjugate thereof acts at multiple points in the inflammatory pathway master regulator to control the expression and/or activity of effectory cytokines such as IFN-gamma and TNF-alpha. Therefore, the C1ORF32 compositions described herein are particularly useful for treating patients that do not respond to TNF-alpha blockers such as Enbrel, Remicade, Cimzia and Humira, or where TNF-alpha blockers are not safe or effective. In addition, because of its activity as a master regulator in the inflammatory pathway, the C1ORF32 compositions disclosed are particularly useful for treating chronic and persistent inflammation.

In a further embodiment, the C1ORF32 compositions described herein are used to treat relapsing and/or remitting multiple sclerosis.

Inhibition of Epitope Spreading

Epitope spreading refers to the ability of B and T cell immune response to diversify both at the level of specificity, from a single determinant to many sites on an auto antigen, and at the level of V gene usage (Monneaux, F. et al., Arthritis & amp; Rheumatism, 46(6): 1430-1438 (2002). Epitope spreading is not restricted to systemic autoimmune disease. It has been described in T cell dependent organ specific diseases such as Diabetes mellitus type 1 and multiple sclerosis in humans, and EAE induced experimental animals with a variety of myelin proteins.

Epitope spreading involves the acquired recognition of new epitopes in the same self molecule as well as epitopes residing in proteins that are associated in the same macromolecular complex. Epitope spreading can be assessed by measuring delayed-type hypersensitivity (DTH) responses, methods of which are known in the art.

One embodiment provides a method for inhibiting or reducing epitope spreading in a subject by administering to the subject an effective amount of C1ORF32 polypeptide selected from the group consisting of SEQ ID NOs: 29, 30, 41-105, or a fragment, variant, a homolog, a fusion protein or a conjugate thereof. In a further embodiment the C1ORF32 polypeptide selected from the group consisting of SEQ ID NOs: 29, 30, 41-105, or a fragment, variant, a homolog, a fusion protein or a conjugate thereof inhibits epitope spreading in individuals with multiple sclerosis. Preferably, the C1ORF32 polypeptide selected from the group consisting of SEQ ID NOs: 29, 30, 41-105, or a fragment, variant, a homolog, a fusion protein or a conjugate thereof inhibits or blocks multiple points of the inflammation pathway.

Yet another embodiment provides a method for inhibiting or reducing epitope spreading in subjects with multiple sclerosis by administering to a subject an effective amount of C1ORF32 polypeptide selected from the group consisting of SEQ ID NOs: 29, 30, 41-105, or a fragment, variant, a homolog, a fusion protein or a conjugate thereof to inhibit or reduce differentiation of, proliferation of, activity of, and/or cytokine production and/or secretion by Th1, Th17, Th22, and/or other cells that secrete, or cause other cells to secrete, inflammatory molecules, including, but not limited to, IL-1beta, TNF-alpha, TGF-beta, IFN-gamma, IL-17, IL-6, IL-23, IL-22, IL-21, and MMPs. Another embodiment provides a method for treating multiple sclerosis by administering to a subject an effective amount of C1ORF32 polypeptide selected from the group consisting of SEQ ID NOs: 29, 30, 41-105, or a fragment, variant, a homolog, a fusion protein or a conjugate thereof to interact with Tregs, enhance Treg activity, promote or enhances IL-10 secretion by Tregs, increase the number of Tregs, increase the suppressive capacity of Tregs, or combinations thereof. Another embodiment provides a method for treating multiple sclerosis by administering to a subject an effective amount of C1ORF32 polypeptide selected from the group consisting of SEQ ID NOs: 29, 30, 41-105, or a fragment, variant, a homolog, a fusion protein or a conjugate thereof to interact with Th2 cells, enhance Th2 activity, promote or enhance IL-10 secretion by Th2 cells, increase the number of Th2 cells, increase the modulatory capacity of Th2 cells, or combinations thereof.

Induction of Immune Tolerance

In one embodiment, the present invention provides a method for inducing or re-establishing immune tolerance in a subject by administering to the subject an effective amount of C1ORF32 polypeptide selected from the group consisting of SEQ ID NOs: 29, 30, 41-105, or a fragment, variant, a homolog, a fusion protein or a conjugate thereof. In a further embodiment the C1ORF32 polypeptide selected from the group consisting of SEQ ID NOs: 29, 30, 41-105, or a fragment, variant, a homolog, a fusion protein or a conjugate thereof induces tolerance in individuals with immune related diseases. In a specific embodiment the C1ORF32 polypeptide, fragment or fusion protein thereof induces tolerance in individuals with multiple sclerosis or any other immune related disease as described herein. Preferably, the C1ORF32 polypeptide selected from the group consisting of SEQ ID NOs: 29, 30, 41-105, or a fragment, variant, a homolog, a fusion protein or a conjugate thereof inhibits or blocks multiple points of the inflammation pathway. In another specific embodiment, the C1ORF32 polypeptide selected from the group consisting of SEQ ID NOs: 29, 30, 41-105, or a fragment, variant, a homolog, a fusion protein or a conjugate thereof induces tolerance in individuals with rheumatoid arthritis. Another embodiment provides a method for treating immune related diseases by administering to a subject an effective amount of C1ORF32 polypeptide selected from the group consisting of SEQ ID NOs: 29, 30, 41-105, or a fragment, variant, a homolog, a fusion protein or a conjugate thereof to induce immune tolerance by interacting with Tregs, enhancing Treg activity, increasing the number of Tregs, increase the suppressive capacity of Tregs, or combinations thereof. Another embodiment provides a method for treating immune related diseases by administering to a subject an effective amount of C1ORF32 polypeptide selected from the group consisting of SEQ ID NOs: 29, 30, 41-105, or a fragment, variant, a homolog, a fusion protein or a conjugate thereof to promote or enhance IL-10 secretion by immune cells.

Use of the Therapeutic Agents According to at Least Some Embodiments of the Invention for Adoptive Immunotherapy:

One of the cardinal features of some models of tolerance is that once the tolerance state has been established, it can be perpetuated to naive recipients by the adoptive transfer of donor-specific regulatory cells. Such adoptive transfer studies have also addressed the capacity of T-cell subpopulations and non-T cells to transfer tolerance. Such tolerance can be induced by blocking costimulation or upon engagement of a co-inhibitory B7 with its counter receptor. This approach, that have been successfully applied in animals and is evaluated in clinical trials in humans, (Scalapino K J and Daikh D I. PLoS One. 2009; 4(6):e6031; Riley et al., Immunity. 2009; 30(5): 656-665) provides a promising treatment option for autoimmune disorders and transplantation. Therapeutic agents according to at least some embodiments of the invention, are used for_for adoptive immunotherapy. Thus, in at least some embodiments, the invention provides methods for in vivo or ex vivo tolerance induction, comprising administering effective amount of the therapeutic agent according to at least some embodiments, to a patient or to leukocytes isolated from the patient, in order to induce differentiation of tolerogenic regulatory cells; followed by ex-vivo enrichment and expansion of said cells and reinfusion of the tolerogenic regulatory cells to said patient.

Alternatively, immune responses can be enhanced in a patient by removing immune cells from the patient, contacting immune cells in vitro with an agent that inhibits C1ORF32 activity, and/or which inhibits the interaction of C1ORF32 with its natural binding partners, and reintroducing the in vitro stimulated immune cells into the patient. In another embodiment, a method of modulating immune responses involves isolating immune cells from a patient, transfecting them with a nucleic acid molecule encoding a form of C1ORF32, such that the cells express all or a portion of the C1ORF32 polypeptide according to various embodiments of the present invention on their surface, and reintroducing the transfected cells into the patient. The transfected cells have the capacity to modulate immune responses in the patient.

Pharmaceutical Compositions

The present invention, in some embodiments, features a pharmaceutical composition comprising a therapeutically effective amount of a therapeutic agent according to the present invention. According to the present invention the therapeutic agent could be any one of soluble C1ORF32 polypeptide selected from the group consisting of SEQ ID NOs: 29, 30, 41-105, or a fragment, variant, a homolog, a fusion protein or a conjugate thereof or a corresponding nucleic acid sequence encoding. The pharmaceutical composition according to the present invention is further used for the treatment of immune related disorder and/or infection as described herein.

The therapeutic agents of the present invention can be provided to the subject alone, or as part of a pharmaceutical composition where they are mixed with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., soluble C1ORF32 polypeptide selected from the group consisting of SEQ ID NOs: 29, 30, 41-105, or a fragment, variant, a homolog, a fusion protein or a conjugate thereof or a corresponding nucleic acid sequence encoding. The pharmaceutical compounds according to at least some embodiments of the present invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the present invention also may include one or more pharmaceutically acceptable anti-oxidants. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. A pharmaceutical composition according to at least some embodiments of the present invention also may include additives such as detergents and solubilizing agents (e.g., TWEEN 20 (polysorbate-20), TWEEN 80 (polysorbate-80)) and preservatives (e.g., Thimersol, benzyl alcohol) and bulking substances (e.g., lactose, mannitol).

Examples of suitable aqueous and nonaqueous carriers that may be employed in the pharmaceutical compositions according to at least some embodiments of the present invention include water, buffered saline of various buffer content (e.g., Tris-HCl, acetate, phosphate), pH and ionic strength, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the present invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about I percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the present invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intraperitoneal, intravenous (IV) and intradermal), transdermal (either passively or using iontophoresis or electroporation), transmucosal (e.g., sublingual administration, nasal, vaginal, rectal, or sublingual), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion or using bioerodible inserts, and can be formulated in dosage forms appropriate for each route of administration. In a specific embodiment, a protein, a therapeutic agent or a pharmaceutical composition according to at least some embodiments of the present invention can be administered intraperitoneally or intravenously.

Compositions of the present invention can be delivered to the lungs while inhaling and traverse across the lung epithelial lining to the blood stream when delivered either as an aerosol or spray dried particles having an aerodynamic diameter of less than about 5 microns. A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. For the polypeptide compositions disclosed herein and nucleic acids encoding the same, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For polypeptide compositions, generally dosage levels of 0.0001 to 100 mg/kg of body weight daily are administered to mammals and more usually 0.001 to 20 mg/kg. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Generally, for intravenous injection or infusion, dosage may be lower. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Optionally the polypeptide formulation may be administered in an amount between 0.0001 to 100 mg/kg weight of the patient/day, preferably between 0.001 to 20.0 mg/kg/day, according to any suitable timing regimen. A therapeutic composition according to at least some embodiments according to at least some embodiments of the present invention can be administered, for example, three times a day, twice a day, once a day, three times weekly, twice weekly or once weekly, once every two weeks or 3, 4, 5, 6, 7 or 8 weeks. Moreover, the composition can be administered over a short or long period of time (e.g., 1 week, 1 month, 1 year, 5 years).

Alternatively, therapeutic agent can be administered as a sustained release formulation, in which case less frequent administration is required. Dosage and frequency vary depending on the half-life of the therapeutic agent in the patient. In general, the half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of C1ORF32 soluble protein polypeptide selected from the group consisting of SEQ ID NOs: 29, 30, 41-105, or a fragment, variant, a homolog, a fusion protein or a conjugate thereof, preferably results in a decrease in severity of disease symptoms, an increase in frequency and duration of disease symptom-free periods, an increase in lifepan, disease remission, or a prevention or reduction of impairment or disability due to the disease affliction.

One of ordinary skill in the art would be able to determine a therapeutically effective amount based on such factors as the subject's size, the severity of the subject's symptoms, and the particular composition or route of administration selected.

In certain embodiments, the polypeptide compositions are administered locally, for example by injection directly into a site to be treated. Typically, the injection causes an increased localized concentration of the polypeptide compositions which is greater than that which can be achieved by systemic administration. For example, in the case of a neurological disorder like Multiple Sclerosis, the protein may be administered locally to a site near the CNS. In another example, as in the case of an arthritic disorder like Rheumatoid Arthritis, the protein may be administered locally to the synovium in the affected joint. The polypeptide compositions can be combined with a matrix as described above to assist in creating a increased localized concentration of the polypeptide compositions by reducing the passive diffusion of the polypeptides out of the site to be treated.

Pharmaceutical compositions of the present invention may be administered with medical devices known in the art.

For example, in an optional embodiment, a pharmaceutical composition according to at least some embodiments of the present invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in an optional embodiment, a therapeutic composition according to at least some embodiments of the present invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, C1ORF32 polypeptide selected from the group consisting of SEQ ID NOs: 29, 30, 41-105, or a fragment, variant, a homolog, a fusion protein or a conjugate thereof according to at least some embodiments of the present invention can be formulated to ensure proper distribution in vivo. For example, the blood-brain barrier (BBB) excludes many highly hydrophilic compounds. To ensure that the therapeutic compounds according to at least some embodiments of the present invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun 153:1038); antibodies (P. G. Bloeman et al. (1995) 1-BBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Formulations for Parenteral Administration

In a further embodiment, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., water soluble antioxidants such as ascorbic acid, sodium metabisulfite, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, alpha-tocopherol; and metal chelating agents, such as citric acid, ethylenediamine tetraacetic acid (EDTA), sorbitol, tartaric acid, phosphoric acid), and preservatives (e.g., Thimersol, benzyl alcohol) and bulking substances (e.g., lactose, mannitol). Examples of non-aqueous solvents or vehicles are ethanol, propylene glycol, polyethylene glycol, vegetable oils, such as olive oil and corn oil, gelatin, and injectable organic esters such as ethyl oleate. The formulations may be freeze dried (lyophilized) or vacuum dried and redissolved/resuspended immediately before use. The formulation may be sterilized by, for example, filtration through a bacteria retaining filter, by incorporating sterilizing agents into the compositions, by irradiating the compositions, or by heating thecompositions.

Formulations for Topical Administration

C1ORF32 polypeptide selected from the group consisting of SEQ ID NOs: 29, 30, 41-105, or a fragment, variant, a homolog, a fusion protein or a conjugate thereof, nucleic acids, and vectors disclosed herein can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers.

Controlled Delivery Polymeric Matrices

C1ORF32 polypeptide selected from the group consisting of SEQ ID NOs: 29, 30, 41-105, or a fragment, variant, a homolog, a fusion protein or a conjugate thereof, nucleic acids, and vectors disclosed herein may also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of polypeptides or nucleic acids encoding the polypeptides, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl Polymer ScL, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

Diagnostic Uses of C1ORF32

Soluble polypeptides according to at least some embodiments of the present invention may also be modified with a label capable of providing a detectable signal, either directly or indirectly, including, but not limited to, radioisotopes and fluorescent compounds. Such labeled polypeptides can be used for various uses, including but not limited to, prognosis, prediction, screening, early diagnosis, determination of progression, therapy selection and treatment monitoring of disease and/or an indicative condition, as detailed above.

According to at least some embodiments, the present invention provides a method for imaging an organ or tissue, the method comprising: (a) administering to a subject in need of such imaging, a labeled polypeptide; and (b) detecting the labeled polypeptide to determine where the labeled polypeptide is concentrated in the subject. When used in imaging applications, the labeled polypeptides according to at least some embodiments of the present invention typically have an imaging agent covalently or noncovalently attached thereto. Suitable imaging agents include, but are not limited to, radionuclides, detectable tags, fluorophores, fluorescent proteins, enzymatic proteins, and the like. One of skill in the art will be familiar with other methods for attaching imaging agents to polypeptides. For example, the imaging agent can be attached via site-specific conjugation, e.g., covalent attachment of the imaging agent to a peptide linker such as a polyarginine moiety having five to seven arginines present at the carboxyl-terminus of and Fc fusion molecule. The imaging agent can also be directly attached via non-site specific conjugation, e.g., covalent attachment of the imaging agent to primary amine groups present in the polypeptide. One of skill in the art will appreciate that an imaging agent can also be bound to a protein via noncovalent interactions (e.g., ionic bonds, hydrophobic interactions, hydrogen bonds, Van der Waals forces, dipole-dipole bonds, etc.).

In certain instances, the polypeptide is radiolabeled with a radionuclide by directly attaching the radionuclide to the polypeptide. In certain other instances, the radionuclide is bound to a chelating agent or chelating agent-linker attached to the polypeptide. Suitable radionuclides for direct conjugation include, without limitation, 18 F, 124 I, 125 I, 131 I, and mixtures thereof. Suitable radionuclides for use with a chelating agent include, without limitation, 47 Sc, 64 Cu, 67 Cu, 89 Sr, 86 Y, 87 Y, 90 Y, 105 Rh, 111 Ag, 111 In, 117m Sn, 149 Pm, 153 Sm, 166 Ho, 177 Lu, 186 Re, 188 Re, 211 At, 212 Bi, and mixtures thereof. Preferably, the radionuclide bound to a chelating agent is 64 Cu, 90 Y, 111 In, or mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to polypeptides of the present invention. In particular, attachment can be conveniently accomplished using, for example, commercially available bifunctional linking groups (generally heterobifunctional linking groups) that can be attached to a functional group present in a non-interfering position on the polypeptide and then further linked to a radionuclide, chelating agent, or chelating agent-linker.

Non-limiting examples of fluorophores or fluorescent dyes suitable for use as imaging agents include Alexa Fluor® dyes (Invitrogen Corp.; Carlsbad, Calif.), fluorescein, fluorescein isothiocyanate (FITC), Oregon Green™; rhodamine, Texas red, tetrarhodamine isothiocynate (TRITC), CyDye™ fluors (e.g., Cy2, Cy3, Cy5), and the like.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al., Mol. Microbiol., 55:1767-1781 (2005), the GFP variant described in Crameri et al., Nat. Biotechnol., 14:315-319 (1996), the cerulean fluorescent proteins described in Rizzo et al., Nat. Biotechnol, 22:445 (2004) and Tsien, Annu. Rev. Biochem., 67:509 (1998), and the yellow fluorescent protein described in Nagai et al., Nat. Biotechnol., 20:87-90 (2002). DsRed variants are described in, e.g., Shaner et al., Nat. Biotechnol., 22:1567-1572 (2004), and include mStrawberry, mCherry, morange, mBanana, mHoneydew, and mTangerine. Additional DsRed variants are described in, e.g., Wang et al., Proc. Natl. Acad. Sci. U.S.A., 101:16745-16749 (2004) and include mRaspberry and mPlum. Further examples of DsRed variants include mRFPmars described in Fischer et al., FEBS Lett., 577:227-232 (2004) and mRFPruby described in Fischer et al., FEBS Lett., 580:2495-2502 (2006).

In other embodiments, the imaging agent that is bound to a polypeptide according to at least some embodiments of the present invention comprises a detectable tag such as, for example, biotin, avidin, streptavidin, or neutravidin. In further embodiments, the imaging agent comprises an enzymatic protein including, but not limited to, luciferase, chloramphenicol acetyltransferase, β-galactosidase, β-glucuronidase, horseradish peroxidase, xylanase, alkaline phosphatase, and the like.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled polypeptide of the present invention. Positron emission tomography (PET) is another suitable technique for detecting radiation in a subject. Miniature and flexible radiation detectors intended for medical use are produced by Intra-Medical LLC (Santa Monica, Calif.). Magnetic Resonance Imaging (MRI) or any other imaging technique known to one of skill in the art is also suitable for detecting the radioactive emissions of radionuclides. Regardless of the method or device used, such detection is aimed at determining where the labeled polypeptide is concentrated in a subject, with such concentration being an indicator of disease activity.

Non-invasive fluorescence imaging of animals and humans can also provide in vivo diagnostic information and be used in a wide variety of clinical specialties. For instance, techniques have been developed over the years for simple ocular observations following UV excitation to sophisticated spectroscopic imaging using advanced equipment (see, e.g., Andersson-Engels et al., Phys. Med. Biol., 42:815-824 (1997)). Specific devices or methods known in the art for the in vivo detection of fluorescence, e.g., from fluorophores or fluorescent proteins, include, but are not limited to, in vivo near-infrared fluorescence (see, e.g., Frangioni, Curr. Opin. Chem. Biol., 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al., IEEE Transactions on Biomedical Engineering, 48:1034-1041 (2001), and the like.

Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

The present invention is further illustrated by the below examples related to C1ORF32 antigen, its domains and expression data as well as prophetic examples describing the manufacture of fully human antibodies thereto. This information and examples is illustrative and should not be construed as further limiting. The contents of all figures and all references, patents and published patent applications cited throughout this application are expressly incorporated herein by reference.

EXAMPLES

Example 1

Design and Production of Mutated C1ORF32 ECD Polypeptides

This Example relates to production of ECD fragments.
Materials and Methods
C1ORF32-P8-ECD-mFC Production in CHO Cells:

To produce C1ORF32-P8-ECD-mFC in CHO cells, retrovector constructs containing cDNA that code for the protein were transduced into CHO cells, and 3-4 rounds of transductions were carried out. Cell pool of the last transduction was grown in shake flasks by fed-batch production. Medium was harvested at 12-14 days when cell viability dropped to ~50%.

The harvested medium was clarified by depth filtration followed by 0.2 μm filter, and the clarified material was subjected to Protein A chromatography. The eluate, pH ~3.7, was incubated with mixing for 60 minutes at room temperature to facilitate viral inactivation, neutralized to pH ~7.2 and filtered through a 0.2 μm filter. Finally, the solution was buffer exchanged to PBS pH 7.2, concentrated to the desired protein concentration and filtered.

Results

SDS-PAGE analysis, under non-reducing conditions, of C1ORF32-P8-V1-ECD-mFC produced in CHO cells, as described below, revealed three main bands: the expected MW of ~100 kD, a band at MW of ~75 kD, and a third one at MW of ~55 kD. SDS-PAGE analysis in reduced conditions revealed two main bands—one at the expected MW of ~50 kD and an additional of ~30 kD.

Western Blot analyses using anti-C1ORF32-P8-V1-ECD and anti-mFc demonstrated the presence of mainly three protein species: the intact full-size dimer consisting of two chains each with an C1ORF32 ECD and a Fc (homodimer); a one-arm cleaved dimer consisting of one chain with an C1ORF32 ECD and a Fc and second chain with mainly the Fc (heterodimer); and a two-armed cleaved dimer composed of two chains with mainly the Fc (fully cleaved dimer).

N-terminal sequencing revealed a major cleavage site towards the C-terminus of the C1ORF32 ECD between amino acids F and A at positions 179 and 180 of H19011_1_P8_V1 or H19011_1_P8 (Seq ID NOs: 4 or 5). To prevent this cleavage the amino acids F and A at positions 179 and 180 of H19011_1_P8_V1 or H19011_1_P8 (SEQ ID NOs: 4 or 5) were mutated as follows: FA→GA, FA→AA, and FA→GG. The resulted C1ORF32 ECD fragments are represented by, for example, SEQ ID NOs: 64, 96, and 45, respectively.

Example 2

Production of Fc-Fused C1ORF32 Proteins

The Fc-fused C1ORF32 ECD proteins were produced as follows:

Fc-fused C1ORF32 ECD (SEQ ID NO:108), corresponds to C1ORF32 ECD without signal peptide (SEQ ID NO: 64) fused to mouse mIgG2a Fc (SEQ ID NO: 31) via GS_TEV_linker_SG (SEQ ID NO:113).

Fc-fused C1ORF32 ECD-Delta DLLPSFAVEIM (SEQ ID NO:110) corresponds to C1ORF32 ECD-Delta DLLPSFAVEIM fragment without signal peptide (SEQ ID NO:51) fused to mouse mIgG2a Fc (SEQ ID NO: 31) via GS_TEV_linker_SG (SEQ ID NO:113).

C1ORF32 ECD-Delta RTGLLADLLPSFAVEIM (SEQ ID NO:112) corresponds to C1ORF32 ECD-Delta RTGLLADLLPSFAVEIM fragment without signal peptide (SEQ ID. NO:29) fused to mouse mIgG2a Fc (SEQ ID NO: 31) via GS_TEV_linker_SG [(SEQ ID NO:113).

All the fused proteins were produced using two service providers; Catalent and ExcellGene, each using its own production protocol as described below:

Production by Catalent (Middleton, Wis., USA): Codon-optimized cDNA sequences encoding C1ORF32 ECD (SEQ ID NO:108), Fc-fused C1ORF32 ECD-Delta DLLPSFAVEIM (SEQ ID NO:110), and C1ORF32 ECD-Delta RTGLLADLLPSFAVEIM (SEQ ID NO:112) were produced at Catalent in CHO cells, in pIRESpuro3 vector.

The cDNA sequence of the insert was verified by Catalent and was used to construct GPEx® retrovectors, followed by four rounds of retrovector transduction into Catalent's "in-house" CHO-S cell line. A pooled population was produced and expanded and gene copy index was 2.7. Cell culture supernatants were analyzed by Catalent's Fc ELISA assay and relative productivity of the 4× transduced pool was 28 µg/ml.

The protein was produced in 5 L wave bioreactor, and purified according to their in-house process. The level of purity was estimated at >95%, by SDS PAGE and Coomassie staining (data not shown). The concentration of purified protein was measured by absorbance at A280 nm, and estimated at 1.60 mg/ml (using an absorbance coefficient of 1.28 mg/ml). Endotoxin levels were tested, and estimated at 0.25-0.5 EU/ml. A total of ~400 mg were obtained from ~10 L of cell pool.

Production by ExcellGene (Valais, Switzerland): Codon-optimized cDNA sequences encoding C1ORF32 ECD (SEQ ID NO:108), Fc-fused C1ORF32 ECD-Delta DLLPSFAVEIM (SEQ ID NO:110), and C1ORF32 ECD-Delta RTGLLADLLPSFAVEIM (SEQ ID NO:112) were synthesized and subcloned into ExcellGene's proprietary expression vector (pXLG6), designed for high yield transient gene expression vectors. Expression vectors were then transiently-transfected into Exellgene's CHOExpress™ host cells, and cells were cultured for 12-14 days in TubeSpin50® bioreactors. Viability was determined daily, and productivity was assessed at the end of the culture by Western Blot analysis. A second transient transfection was then performed, and the resultant cells were cultured in 1-2 L to obtain the required amount of protein. Culture supernatants were clarified and purified on Protein A columns. Purified proteins were analyzed by a standard SDS-PAGE gel under standard conditions, for which results are shown in FIG. 2, and concentration was determined by A280. Proteins were tested for bioburden and endotoxin. In FIG. 2, lane 12 relates to the protein having the sequence of SEQ ID NO:110, while lane 13 relates to the protein having the sequence of SEQ ID NO:112.

Example 3

The Effect of Fc-Fused C1ORF32 ECD (SEQ ID NO:108), Fc-Fused C1ORF32 ECD-Delta DLLPSFAVEIM (SEQ ID NO:110), and C1ORF32 ECD-Delta RTGLLADLLPSFAVEIM (SEQ ID NO:112) on TCR-Mediated Activation of Mouse CD4 T Cells The effect of Fc-fused C1ORF32 ECD (SEQ ID NO:108), Fc-fused C1ORF32 ECD-Delta DLLPSFAVEIM (SEQ ID NO:110), and C1ORF32 ECD-Delta RTGLLADLLPSFAVEIM (SEQ ID NO:112) on TCR-mediated activation of mouse T cells, was evaluated by testing their effect on IFNγ secretion and on the expression of the activation marker CD69 in CD4+CD25-purified T cells.

Methods

Mouse CD4 T Cells Isolation.

CD4+CD25− T cells were isolated from pools of spleens and lymph nodes of BALB/C mice by one step negative selection using T cell isolation Kit (Miltenyi Cat#130-093-227) according to the manufacturer's instructions. The purity obtained was >95%. The cells used in the functional assays, CD4+ T cells, were untouched CD4+CD25− cells, which include CD4+CD62L$^{high}$ naive T cells (85-90% of bulk CD4 population) and CD4+CD62L$^{low}$ memory cells.

Activation of Mouse CD4 T Cells

Anti-CD3 mAb (clone 145-2C11) alone or together with Fc-fused C1ORF32 ECD (SEQ ID NO:108), Fc-fused C1ORF32 ECD-Delta DLLPSFAVEIM (SEQ ID NO:110), and C1ORF32 ECD-Delta RTGLLADLLPSFAVEIM (SEQ ID NO:112) or with control mIgG2a (BioXCell Cat. #BE0085) were co-immobilized at the stated concentrations on 96-well flat bottom tissue culture plates (Sigma, Cat. #92096), overnight at 4° C. Wells were washed 3 times with PBS and plated with 1×10$^5$ CD4+ T cells per well at 37° C. Culture supernatants were collected 48h post stimulation and analyzed for IFNγ secretion using mouse IFNγ ELISA kit (R&D Systems). The effect of immobilized Fc-fused C1ORF32 ECD (SEQ ID NO:108), Fc-fused C1ORF32 ECD-Delta DLLPSFAVEIM (SEQ ID NO:110), and C1ORF32 ECD-Delta RTGLLADLLPSFAVEIM (SEQ ID NO:112) (10 µg/ml) on the activation marker CD69 was analyzed by FACS, 48 h post simulations with plate bound anti-CD3.

Results

Effect of Fc-Fused C1ORF32 ECD (SEQ ID NO:108), Fc-Fused C1ORF32 ECD-Delta DLLPSFAVEIM (SEQ ID NO:110), and C1ORF32 ECD-Delta RTGLLADLLPSFAVEIM (SEQ ID NO:112) on Mouse CD4 T Cells IFNγ Secretion In order to evaluate the effect of Fc-fused C1ORF32 ECD (SEQ ID NO:108), Fc-fused C1ORF32 ECD-Delta DLL- PSFAVEIM (SEQ ID NO:110), and C1ORF32 ECD-Delta RTGLLADLLPSFAVEIM (SEQ ID NO:112) on CD4 T cell response, titrated amounts of the respective Fc-fusion C1ORF32 ECD protein or control mIgG2a were immobilized on 96-well plates together with anti-CD3 mAb, and IFNγ secretion from CD4+ T cells was analyzed. Cells were activated for 48 hrs using full RPMI containing 10% FBS, 1 mM sodium pyruvate, 100 IU/ml Pen-Strep (without 2-ME). The results presented in FIG. 3 indicate potent inhibitory effect Fc-fused C1ORF32 ECD (SEQ ID NO:108), Fc-fused C1ORF32 ECD-Delta DLLPSFAVEIM (SEQ ID NO:110), and C1ORF32 ECD-Delta RTGLLADLLPSFAVEIM (SEQ ID NO:112) on CD4 T cells IFN-γ secretion.

Effect of Fc-Fused C1ORF32 ECD (SEQ ID NO:108), Fc-Fused C1ORF32 ECD-Delta DLLPSFAVEIM (SEQ ID NO:110), and C1ORF32 ECD-Delta RTGLLADLLPSFAVEIM (SEQ ID NO:112) on the Early Activation Marker CD69

Figure 3:
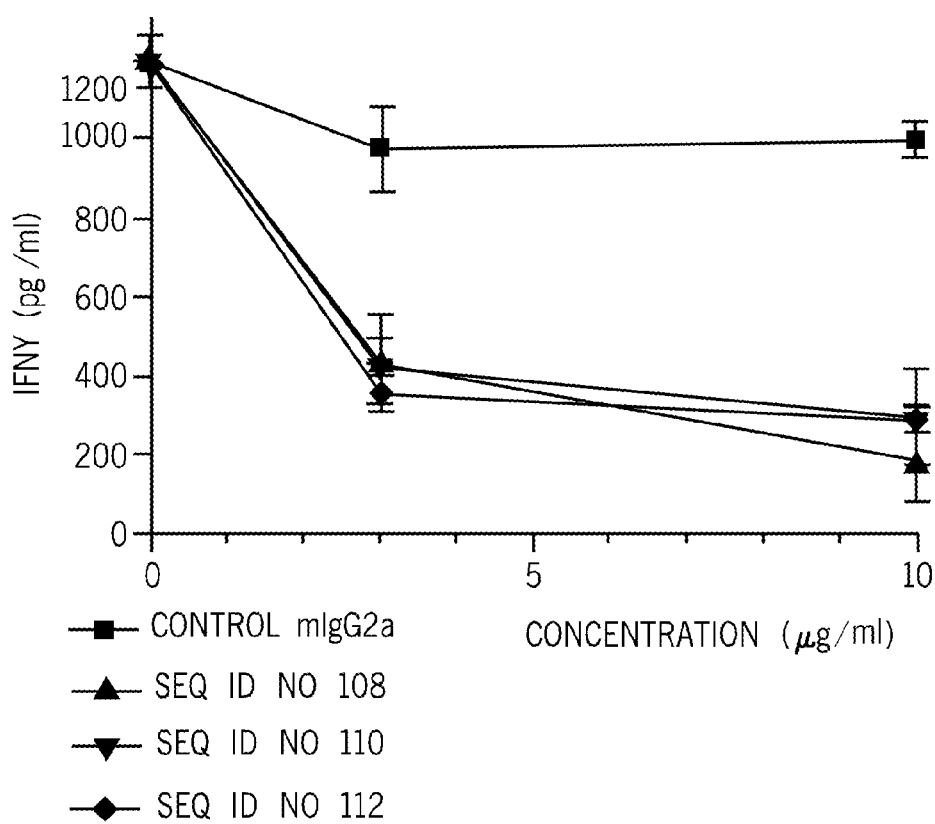
FIG. 3 shows inhibitory effect of Fc-fused C1ORF32 ECD (SEQ ID NO:108), Fc-fused C1ORF32 ECD-Delta DLLPSFAVEIM (SEQ ID NO:110), and C1ORF32 ECD-Delta RTGLLADLLPSFAVEIM (SEQ ID NO:112) on mouse CD4+ T cell IFNγ secretion. Purified CD4+CD25− T cells, 1×10$^5$ per well, were stimulated with anti-CD3 mAb (2 ug/mL) in the presence of test proteins or control mouse IgG2a at 0, 3 and 10 μg/ml. Culture supernatants were collected 48 hrs post stimulation and analyzed using mouse IFNγ ELISA kit. Results are shown as Mean±SD of four wells per point (Student's t-test, ***P<0.001, compared with control mouse IgG2a).
Figure 4:
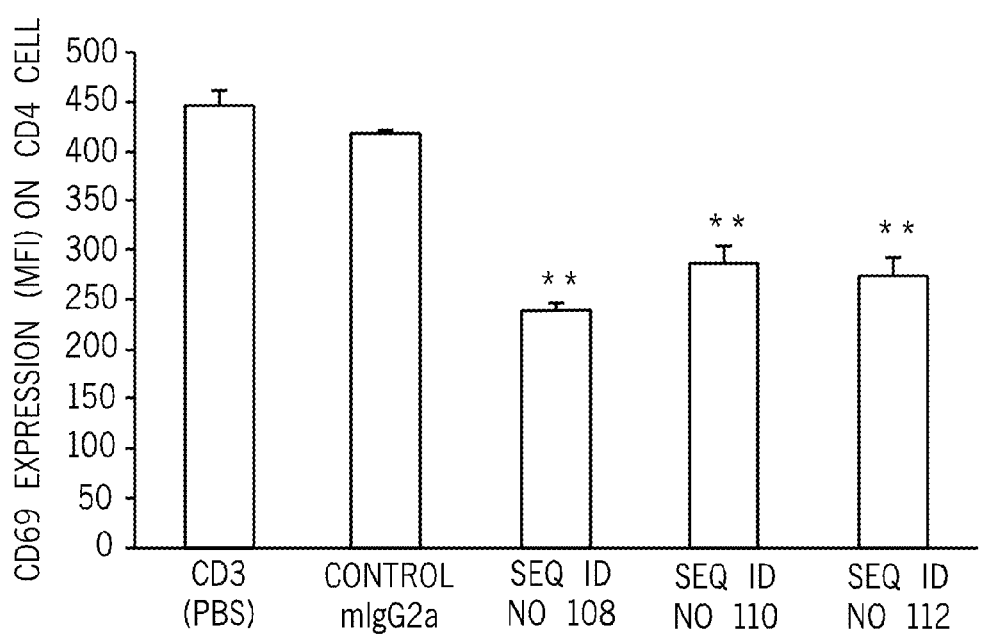
FIG. 4 shows inhibitory effect of Fc-fused C1ORF32 ECD (SEQ ID NO:108), Fc-fused C1ORF32 ECD-Delta DLLPSFAVEIM (SEQ ID NO:110), and C1ORF32 ECD-Delta RTGLLADLLPSFAVEIM (SEQ ID NO:112) on expression of the early TCR activation marker, CD69. 1×10$^5$ CD4+CD25− T cells were stimulated with plate bound anti-CD3 (2 μg/ml) together with test proteins or control mIgG2a (10 μg/ml). Cells were analyzed at 48 hrs for the expression CD69 by flow cytometry (**; P value<0.001 compare to control mIgG2A, student's T test).

In order to evaluate the effect of Fc-fused C1ORF32 ECD (SEQ ID NO:108), Fc-fused C1ORF32 ECD-Delta DLLPSFAVEIM (SEQ ID NO:110), and C1ORF32 ECD-Delta RTGLLADLLPSFAVEIM (SEQ ID NO:112) on the early activation marker CD69, an experiment similar to that described in FIG. 3 herein was carried out, using 10 ug/ml of Fc-fused C1ORF32 ECD (SEQ ID NO:108), Fc-fused C1ORF32 ECD-Delta DLLPSFAVEIM (SEQ ID NO:110), or C1ORF32 ECD-Delta RTGLLADLLPSFAVEIM (SEQ ID NO:112), respectively. All Fc-fused C1ORF32 ECD proteins tested had a suppressive effect on early activation markers CD69 at 48h post stimulation as manifested in a reduction of CD69 upregulation upon stimulation, as shown in FIG. 4.

Conclusion

Immobilized Fc-fused C1ORF32 ECD (SEQ ID NO:108), Fc-fused C1ORF32 ECD-Delta DLLPSFAVEIM (SEQ ID NO:110), or C1ORF32 ECD-Delta RTGLLADLLPSFAVEIM (SEQ ID NO:112) inhibit CD4 T cell activation to a similar extent as manifested by reduced IFNγ secretion and CD69 expression compare to control Ig upon TCR stimulation.

Example 4

The Effect of Fc-Fused C1ORF32 ECD (SEQ ID NO:108), Fc-Fused C1ORF32 ECD-Delta DLLPSFAVEIM (SEQ ID NO:110), or C1ORF32 ECD-Delta RTGLLADLLPSFAVEIM (SEQ ID NO:112) on Naïve CD4+ T Cell Proliferation Procedure:

Naive CD4+ T cells were isolated from spleens of DO11.10 mice (Jackson) via automax sort: CD4-negative sort (Miltenyi Cat#130-095-248), including anti-CD25 (Miltenyi Cat#130-091-072) in the negative sort cocktail, followed by CD62L-positive sort (Miltenyi Cat #130-049-701). Balb/c total splenocytes were also collected from one mouse, and irradiated with 3000 rads to serve as antigen presenting cells (APCs) for the D011.10 CD4+ T cells. Naive CD4+ T cells were cultured at $2.5 \times 10^5$ cells per well in flat-bottom 96-well plates with irradiated APCs at a ratio of 1:1 (APCs to T cells) in 200 ul of HL-1 medium, and activated with 2 ug/ml OVA323-339 in the presence of one of Fc-fused C1ORF32 ECD (SEQ ID NO:108), (produced in CHO-S and in CHO-DG44 as detailed in Example 2) Fc-fused C1ORF32 ECD-Delta DLLPSFAVEIM (SEQ ID NO:110), (produced in CHO-DG44 as detailed in Example 2) and or C1ORF32 ECD-Delta RTGLLADLLPSFAVEIM (SEQ ID NO:112) (produced in CHO-S and in CHO-DG44 as detailed in Example 3) or Isotype control Ig (mIgG2a, BioXCell Cat. # BE0085) at the indicated concentrations (0.1-10 ug/ml). The cells were pulsed with 1 uCi of tritiated-thymidine at 24 hours, and harvested at 72 hours.

Figure 5:
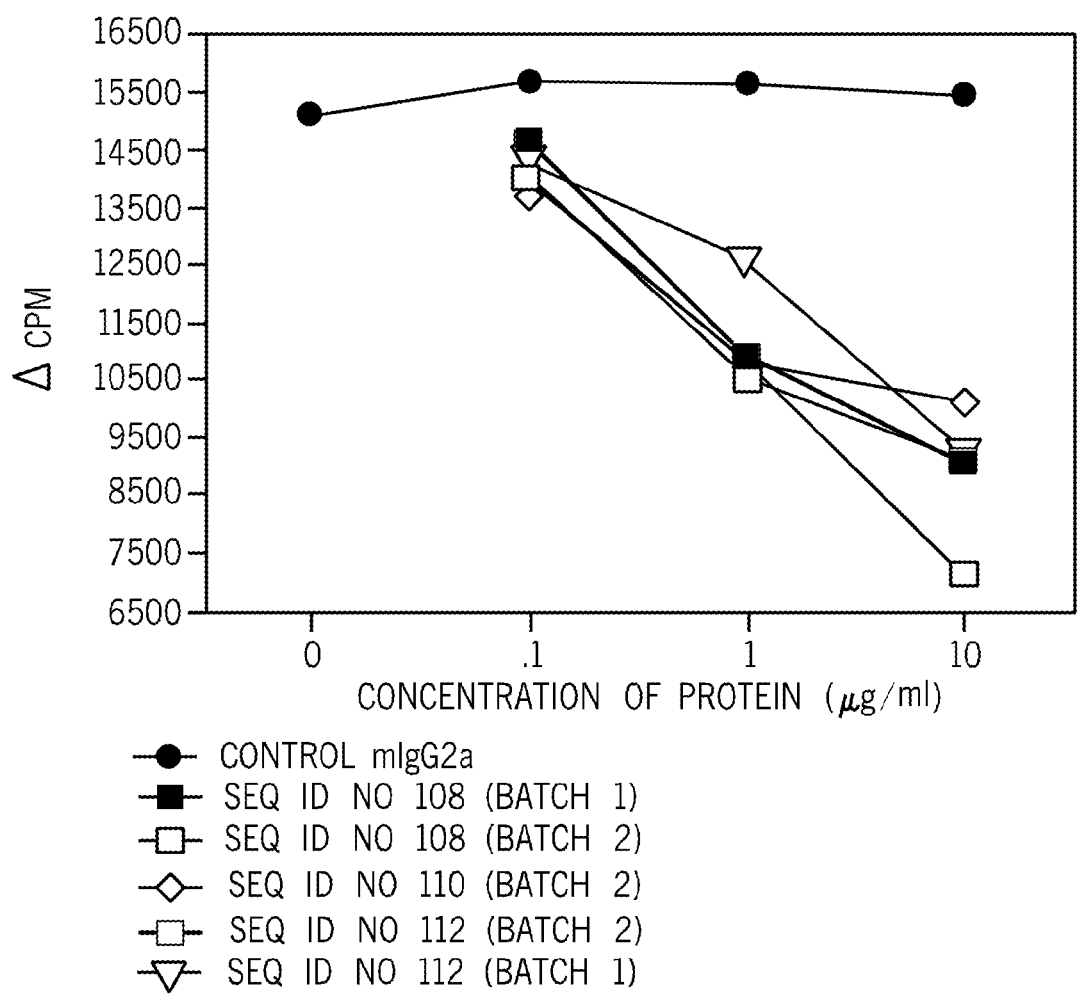
FIG. 5 shows inhibitory effect of Fc-fused C1ORF32 ECD (SEQ ID NO:108), (two different batches produced in CHO-S And in CHO-DG44), Fc-fused C1ORF32 ECD-Delta DLLPSFAVEIM (SEQ ID NO:110), and C1ORF32 ECD-Delta RTGLLADLLPSFAVEIM (SEQ ID NO:112) (two different batches produced in CHO-S And in CHO-DG44) on naive T cell proliferation. No inhibition was observed with the IgG2a isotype control.

Results and Conclusions:

As demonstrated in FIG. 5, the Fc-fused C1ORF32 ECD (SEQ ID NO:108), as well as Fc-fused C1ORF32 ECD-Delta DLLPSFAVEIM (SEQ ID NO:110), or C1ORF32 ECD-Delta RTGLLADLLPSFAVEIM (SEQ ID NO:112) inhibit T cell proliferation in response to OVA323-339 activation in a dose dependent manner A slightly reduced activity (approximately 3 fold) was achieved by the proteins produced in CHO-DG44 versus those produced in CHO-S. These differences reflect batch to batch variation of these proteins.

Example 5

The Effect of Fc-Fused C1ORF32 ECD (SEQ ID NO:108), Fc-Fused C1ORF32 ECD-Delta DLLPSFAVEIM (SEQ ID NO:110), or C1ORF32 ECD-Delta RTGLLADLLPSFAVEIM (SEQ ID NO:112) on Autoimmune Disease or Infectious Disease in a Subject A plurality of animals, having a disease model appropriate for testing of the autoimmune disease, receives each of the above described Fc-fused ECD proteins in a plurality of doses. A dose dependent response is seen.

Similarly, a plurality of animals infected with an infectious disease in which T cell exhaustion is exhibited (for example through chronic viral infection) and receives each of the above Fc-fused ECD proteins in a plurality of doses, in combination with an pharmaceutical agent in a pharmaceutically effective amount against the infectious agent. A dose dependent response is seen.

Example 6

Effect of C1ORF32 Protein Fragments and/or Fusion Proteins on Activation of Naïve CD4+ T Cells with Anti-CD3/Anti-CD28 Coated Beads Naive CD4+ T cells are isolated from 5 SJL (Harlan, Israel) mice via automax sort. Beads are coated with anti-CD3 (0.5 ug/ml; clone 2C11) and anti-CD28 (2 ug/ml; clone 37.51 eBioscience) following manufacturer's protocol (Dynabeads M-450 Epoxy Cat. 140.11, Invitrogen), and with increasing concentrations of any one of the C1ORF32 protein fragments and/or fusion proteins thereof (0.1-10 ug/ml). The total amount of protein used for beads coating with any one of the C1ORF32 protein fragments and/or fusion proteins thereof is completed to 10 ug/ml with Control Ig. Naive CD4+ T cells ($0.5 \times 10^6$/well) are activated with the coated beads at a ratio of 1:2 (beads to T cells). The cells are pulsed with 1 uCi of tritiated-thymidine after 24 hours, and harvested after 72.

The ability of any one of the C1ORF32 protein fragments and/or fusion proteins thereof to inhibitor T cell proliferation and elicit its effect in a dose dependent manner is checked. An appropriate response is seen.

Example 7

Dose Response Effect of C1ORF32 Protein Fragments and/or Fusion Proteins Thereof on Mouse CD4+ T Cell Activation with Plate Bound Anti-CD3, as Manifested in Cytokine Production and Expression of the Activation Marker CD69

Untouched CD4+CD25− T cells are isolated from pools of spleen and lymph node cells of BALB/C mice by negative selection using CD4+CD62L+ T cell isolation Kit (Miltenyi Cat#130-093-227) according to the manufacturer's instructions. The desired purity obtained is >95%.

Tissue culture 96-well plates are coated overnight at 4° C. with 2 ug/ml anti-CD3 mAb (clone 145-2C11) in the presence of any one of the C1ORF32 protein fragments and/or fusion proteins thereof at 1, 5 and 10 µg/ml. Control mIgG2a (Clone C1.18.4 from BioXCell; Cat#BE0085) is added to each well in order to complete a total protein concentration of 12 µg/ml per well. Wells are plated with $1 \times 10^5$ CD4+ CD25− T cells per well. At 48 hrs post stimulation, culture supernatants are collected and analyzed using mouse IFNγ ELISA kit, and cells are analyzed for expression of the activation marker CD69 by flow cytometry.

The inhibitory effects of any one of the C1ORF32 protein fragments and/or fusion proteins thereof on CD4 T cell activation is demonstrated by reduced IFNγ secretion and reduced expression of CD69 upon TCR stimulation, compared to control mIgG2a and CTLA4-Ig.

Example 8

The Effect of C1ORF32 Protein Fragments and/or Fusion Proteins Thereof on CD4+ T Cell Differentiation In Vitro.

To test the ability of any one of the C1ORF32 protein fragments and/or fusion proteins thereof to inhibit CD4+ T cell differentiation, naïve CD4+ T cells are isolated from DO11.10 mice, which are transgenic for a T cell receptor (TCR) that is specific for OVA323-339 peptide. Using DO11.10 T cells enables studying both polyclonal (anti-CD3/anti-CD28 mAbs) and peptide-specific responses on the same population of CD4+ T cells. Naïve CD4+ T cells are isolated from DO11.10 mice and activated in culture in the presence of anti-CD3/anti-CD28 coated beads or OVA323-339 peptide plus irradiated BALB/c splenocytes, in the presence of any one of the C1ORF32 protein fragments and/or fusion proteins thereof, control Ig, or B7-H4 Ig. The cells are activated in the presence of Th driving conditions as follows: Th0 cell− (IL-2), Th1 cell− (IL-2+IL-12), Th2 cell− (IL-2+IL-4), or Th17 cell− (TGF-β+IL-6+IL-23+anti-IL-2). The effects on T cell differentiation and Th-specific responses are assessed by measuring cell proliferation and subtype specific cytokine production: IL-4, IL-5, IL-10, IL-17, IFN-γ. An appropriate response is seen.

Example 9

Assessment of the Effect of any One of the C1ORF32 Protein Fragments and/or Fusion Proteins Thereof on Human T Cells Activation The effect of any one of the C1ORF32 protein fragments and/or fusion proteins thereof on human T cell response is tested by two different in vitro assays using purified human T cells. In the first assay, human T cells are activated by anti-CD3 and anti-CD28 coated beads, and in the other assay, activation is carried out using anti-CD3 and anti-CD28 antibodies in the presence of autologous, irradiated PBMCs. The regulatory activity of any one of the C1ORF32 protein fragments and/or fusion proteins thereof on human T cell activation, is evaluated by measuring cell proliferation and cytokine release.

Study I—Activation of Human T Cells with Anti-CD3 and Anti-CD28-Coated Beads is Inhibited by Fusion Proteins Naïve CD4+ T cells are isolated from 4 healthy human donors and activated with anti-CD3 mAb/anti-CD28 mAb coated beads in the presence of control mIgG2a, or any one of the C1ORF32 protein fragments and/or fusion proteins thereof. Two side-by-side culture sets are set up; one culture being pulsed at 24 hours with tritiated-thymidine and harvested at 72 hours while the second plate is harvested at 96 hours for cytokine production via LiquiChip.

Study II—Activation of Human T Cells with Irradiated Autologous PBMCs is Inhibited by Fusion Proteins Total PBMCs are isolated from fresh blood of healthy human donors using ficoll gradient. $10 \times 10^6$ total PBMCs are resuspended in Ex-Vivo 20 medium, and irradiated at 3000rad. These cells are used to activate the isolated T cells in vitro, by presenting the anti-CD3, anti-CD28 and either of the test proteins. The rest of PBMCs are used for isolation of T cells using CD4+ T cell Isolation Kit II from Miltenyi.

For activation, $5 \times 10^5$ isolated T cells are cultured in the presence of $5 \times 10^5$ autologous irradiate PBMCs. Anti-CD3 (0.5 µg/ml), anti-CD28 (2 µg/ml) and either of any one of the C1ORF32 protein fragments and/or fusion proteins thereof or control Ig (mIgG2a) are added in a soluble form. The cultures are pulsed with 1 uCi of triated thymidine at 24 hrs, and proliferation is measured at 72 hours.

Example 10

The Effect of any One of the C1ORF32 Protein Fragments Upon Ectopic Expression in APC-Like Cells, on Human T Cell Responses The effects of any one of the C1ORF32 protein fragments on human T cell responses are evaluated following their ectopic expression in 'T cell stimulator' cells: a murine thymoma cell line, Bw5147, which are engineered to express membrane-bound anti-human CD3 antibody fragments, that can trigger the TCR-complex on human T cells, with or without co-expression of putative costimulatory or coinhibitory ligands.

Codon-optimized cDNAs encoding any one of the C1ORF32 protein fragments are gene-synthesized and directionally cloned into a retroviral vector pCJK2 via Sfi-I sites. Monocistronic expression constructs are generated. The constructs are validated by agarose gel electrophoresis and were expressed in Bw5147 cells displaying high levels of membrane bound anti-CD3 antibody (Bw-3/2) (Leitner et al., 2010). As negative control Bw5147 cells transduced with "empty" vector (pCJK2) are used. In addition, Bw-3/2 cells expressing costimulatory molecules (ICOSL and CD70) and Bw-3/2-cells expressing coinhibitory molecules (B7-H3 and B7-H1/PD-L1) are also used as controls. Homogenously high expression of the stimulating membrane-bound anti-CD3 antibody is confirmed by FACS using a DyLight-649 anti-mouse IgG (H+L) antibody that reacts with the murine single chain antibody expressed on the stimulator cells. Presence and high level transcription of expression monocistronic constructs in the respective stimulator cells is confirmed by qPCR.

T cells are purified from buffy coats or heparinised blood derived from healthy volunteer donors and the mononuclear fraction is obtained by standard density centrifugation using Ficoll-Paque (GE-Healthcare). Untouched bulk human T cells are obtained through MACS-depletion of CD11b, CD14, CD16, CD19, CD33 and MHC-class II-bearing cells with the respective biotinylated mAb in conjunction with paramagnetic streptavidin beads (Leitner et al., 2009). Purified CD8 T cells and CD4 T cells are obtained by adding biotinylated CD4 and CD8 mAb to the pools. Naïve CD4 T cells are isolated using the Naïve CD4+ T cell Isolation Kit II (Miltenyi Biotec). Following isolation, cells are analyzed for purity by FACS, and samples with sufficient purity (>90%) were used for the experiments.

The stimulator cells are harvested, counted, irradiated (2×3000 rad) and seeded in flat-bottom 96-well plates (20000 cells/well). Liquid nitrogen stored MACS-purified T cells are thawed, counted and added to the wells at 100.000 cells per well; total volume was 200 µl/well. Triplicate wells are set up for each condition. Following 48 hours of co-culture, $^3$H-thymidine (final concentration of 0.025 mCi; PerkinElmer/NewEngland Nuclear Corporation, Wellesley, Mass.) are added to the wells. Following further culturing for 18 hours, the plates were harvested on filter-plates and incorporation of $^3$H-Thymidine was determined as described in Pfistershammer et al., 2004. In addition, a series of experiments with MACS-purified T cell subsets (CD8 T cells, CD4 T cells, and naïve CD45RA-positive CD4 T cells) are performed. Additional controls in all experiments include wells with stimulator cells alone to assess the cells microscopically and also to determine basal $^3$H-Thymidine incorporation of the stimulator cell w/o T cells. Results with stimulator cells that quickly disintegrated following irradiation are excluded from the analysis.

Results show the effect of stimulator cells expressing any one of the C1ORF32 protein fragments on the proliferation of human bulk T cells, CD4+ T cells, CD8+ T cells, or naïve CD4 CD45RA+ T cells, compared to cells expressing control costimulatory molecules (ICOSL and CD70), which results in a consistent and pronounced stimulation of proliferation of all cell subtypes, and compared to cells expressing control coinhibitory molecules (B7-H3 and B7-H1/PD-L1), which results in a mild inhibition of proliferation of different T cell subtypes.

Example 11

Characterizing the Target Cells for any One of the C1ORF32 Protein Fragments Proteins by Determining their Binding Profile to Immune Cells Splenocytes from DO11.10 mice (transgenic mice in which all of the CD4+ T cells express a T cell receptor that is specific for OVA323-339 peptide) are activated in the presence of OVA323-339 peptide, and cells are collected at t=0, 6, 12, 24, and 48 hours following initial activation to determine which cell type is expressing a receptor for any one of the C1ORF32 protein fragments over time. Cells are then co-stained for CD3, CD4, CD8, B220, CD19, CD11b, and CD11c.

Example 12

Assessment of the Effect of any One of the C1ORF32 Protein Fragments and/or Fusion Proteins Thereof on the Ability of B Cells to Class-Switch and Secrete Antibody Resting B cells are isolated from unprimed C57BL/6 mice and activated in vitro in the presence of anti-CD40 plus (i) no exogenous cytokine, (ii) IL-4, or (iii) IFN-γ. The cell cultures receive control Ig (mIgG2a), anti-CD86 mAb (as a positive control for increased Ig production), or any one of any one of the C1ORF32 protein fragments and/or fusion proteins thereof, at the time of culture set up, and are cultured for 5 days. Any one of the C1ORF32 protein fragments and/or fusion proteins thereof are tested at three concentrations each. At the end of culture, supernatants are tested for the presence of IgM, IgG1, and IgG2a via ELISA. If there appears to be an alteration in the ability of the B cells to class-switch to one isotype of antibody versus another, then the number of B cells that have class switched is determined via ELISPOT. If there is an alteration in the number of antibody producing cells, then it is determined if there is an alteration in the level of γ1- and γ2a-sterile transcripts versus the mature transcripts for IgG1 and IgG2a. An appropriate response is seen.

Assessment of the Therapeutic Effect of any One of the C1ORF32 Protein Fragments and/or Fusion Proteins Thereof for Treatment of Autoimmune Diseases Example 13

Efficacy of any One of the C1ORF32 Protein Fragments and/or Fusion Proteins Thereof in Mouse R-EAE Model of Multiple Sclerosis The therapeutic effect of any one of the C1ORF32 protein fragments and/or fusion proteins thereof for treatment of autoimmune diseases is tested in a mouse model of Multiple Sclerosis; Relapsing Remitting Experimental Autoimmune Encephalomyelitis (R-EAE):

Female SJL mice 6 weeks old are purchased from Harlan and maintained in the CCM facility for 1 week prior to beginning the experiment. Mice are randomly assigned into groups of 10 animals and primed with 50 µg PLP139-151/CFA on day 0. Mice receive 6 i.p. injections of 100 ug/dose of any one of the C1ORF32 protein fragments and/or fusion proteins thereof, mIgG2a isotype control, or CTLA4-Ig (mouse ECD fused to mouse IgG2a Fc) as positive control. Treatments begin at the time of onset of disease remission and are given 3 times per week for 2 weeks. Mice are followed for disease symptoms. On day 35, (during the peak of the disease relapse) 5 mice of each group are assayed for DTH (delayed type hypersensitivity) response to disease inducing epitope (PLP139-151) and to relapse-associated myelin epitope (PLP178-191) via injection of 10 µg of PLP139-151 in one ear and PLP178-191 into the opposite ear. The level of ear swelling is assayed at 24 hours post challenge.

The decrease in disease severity of R-EAE-induced mice upon treatment with any one of the C1ORF32 protein fragments and/or fusion proteins thereof, in a therapeutic mode is tested and compared to the level of inhibition of CTLA4-Ig.

In addition, inhibition of DTH responses to the disease inducing epitope (PLP139-151) and to relapse-associated epitope (PLP178-191). in R0EAE mice treated with any one of the C1ORF32 protein fragments and/or fusion proteins thereof is tested.

To test the dose dependency of the efficacy of any one of the C1ORF32 protein fragments and/or fusion proteins thereof as well as its mode of action in the PLP-induced R-EAE model, disease is induced as described above and mice are treated from onset of disease remission with 100, 30 or 10 ug/dose of any one of the C1ORF32 protein fragments and/or fusion proteins thereof, 3 times per week over two weeks. The ability of C1ORF32 protein fragments and/or fusion proteins thereof to decrease the level of disease severity in a dose dependent manner, as well as the ability to inhibit DTH responses to spread epitopes PLP178-191 and MBP84-104, to inhibit proliferation as well as reduction in IFNγ, IL-17, IL-4 and IL-10 release is tested.

The beneficial effect of any one of the C1ORF32 protein fragments and/or fusion proteins thereof in the R-EAE model on reduction in the infiltration of immune cells to the CNS is also tested.

Example 14

Efficacy of any of the C1ORF32 Protein Fragments and/or Fusion Proteins Thereof in Mouse CIA Models of Rheumatoid Arthritis Any one of the C1ORF32 protein fragments and/or fusion proteins thereof is tested in mouse model of collagen-induced arthritis (CIA) which is a model of rheumatoid arthritis. Male DBA/1 mice are housed in groups of 8-10, and maintained at 21° C.±2° C. on a 12h light/dark cycle with food and water ad libitum. Arthritis is induced by immunisation with type II collagen emulsified in complete Freund's adjuvant. Mice are monitored on a daily basis for signs of arthritis. On the appearance of arthritis (day 1) treatment with any one of the C1ORF32 protein fragments and/or fusion proteins thereof, mIgG2a isotype control or CTLA4-Ig (mouse ECD fused to mouse IgG2a Fc) as positive control (100 ug/dose, each) is initiated and given 3 times per week for 10 days. Hind footpad swelling is measured (using microcalipers), as well as the number and degree of joint involvement in all four limbs. This yields two measurements, clinical score and footpad thickness that can be used for statistical assessment.

At the end of the treatment period mice are bled and sacrificed. For histological analysis, paws are removed at post mortem, fixed in buffered formalin (10% v/v), then decalcified in EDTA in buffered formalin (5.5% w/v). The tissues are then embedded in paraffin, sectioned and stained with haematoxylin and eosin. The scoring system is as follows: 0=normal; 1=synovitis but cartilage loss and bone erosions absent or limited to discrete foci; 2=synovitis and significant erosions present but normal joint architecture intact; 3=synovitis, extensive erosions, joint architecture disrupted.

The ability of the treatment of mice with established CIA with any one of the C1ORF32 protein fragments and/or fusion proteins thereof to result in potent reduction of clinical score, paw swelling and histological damage is tested and compared to the efficacy obtained with CTLA4-Ig.

Effect of any of the C1ORF32 Protein Fragments and/or Fusion Proteins Thereof on Tolerance Induction in Transfer Model of CIA To further understand the effect of any one of the C1ORF32 protein fragments and/or fusion proteins thereof on immune regulation, the ability of these proteins to induce tolerance in a transfer model of arthritis is analyzed.

In brief, spleen and LN cells from arthritic DBA/1 mice treated for 10 days with any one of the C1ORF32 protein fragments and/or fusion proteins thereof or control Ig2a are removed and injected i.p into T-cell deficient C.B-17 SCID recipients. The mice then receive an injection of 100 μg type II collagen (without CFA), necessary for successful transfer of arthritis. Arthritis is then monitored in the SCID mice. Histology is performed and anti-collagen antibody levels are measured to determine that the C1ORF32 protein fragments and/or fusion proteins thereof treatment confers long-term disease protection.

Example 15

Assessment of the Effect of any One of C1ORF32 Protein Fragments and/or Fusion Proteins Thereof in a Viral Infection Model of TMEV Theiler's murine encephalomyelitis virus (TMEV) is a natural endemic pathogen of mice that causes an induced demyelinating disease (TMEV-IDD) in susceptible strains of mice (SJL/J, H-2KS) that resembles the primary progressive form of MS (Munz et al., Nat Rev Immunol 2009; 9:246-58). TMEV infection results in a life-long persistent virus infection of the CNS leading to development of a chronic T cell-mediated autoimmune demyelinating disease triggered via de novo activation of CD4 T cell responses to endogenous myelin epitopes in the inflamed CNS (i.e. epitope spreading) (Miller et al., Nat Med 1997; 3:1133-6; Katz-Levy et al., J Clin Invest 1999; 104:599-610).

SJL mice clear the majority of the virus within 21 days post infection, however a latent viral infection is maintained and infect microglia, astrocytes, and neurons. Disease symptoms are manifested around day 25-30 post infection.

The effect of treatment with any one of C1ORF32 protein fragments and/or fusion proteins thereof on acute and chronic phases of viral infection is studied in the TMEV-IDD model by assessment of viral clearance and disease severity.

Method:

Female SJL/J mice (5-6 weeks) are infected with TMEV by intracranial inoculation in the right cerebral hemisphere of $3\times10^7$ plaque forming units (PFU) of the BeAn strain 8386 of TMEV in 30 ul serum-free medium. From day 2 post infection mice are treated with Control Ig, or any one of C1ORF32 protein fragments and/or fusion proteins thereof, at 100 ug/dose each; 3 doses/week for 2 weeks.

Mice are followed for clinical scoring. On day 7 and day 14 post infection (after 3 and 6 treatments respectively) brains and spinal cords are collected from 5 mice in each treatment group for plaque assays. The tissues are weighted so that the ratio of PFU/mg of CNS tissue could be calculated after the plaque assay is completed.

TMEV Plaque Assay:

Brains and spinal cords of mice treated with Control Ig (mouse IgG2a), or with any one of C1ORF32 protein fragments and/or fusion proteins thereof are collected at days 7 and 14 post-infection from non-perfused anesthetized mice. The Brains and spinal cords are weighed, and homogenized. CNS homogenates are serially diluted in DMEM and added to tissue culture-treated plates of confluent BHK-21 cells for 1 h incubation at room temperature, with periodic gentle rocking.

A media/agar solution is mixed 1:1 (volume:volume), added to cells and allowed to solidify at room temperature. The plates are then cultured at 34 deg C. for 5 days. At the end of culture, 1 ml of formalin is added and incubated at room temperature for 1 h to fix the BHK monolayer. The formalin is poured off into a waste container, and the agar is removed from the plates. Plaques are visualized by staining with crystal violet for 5 min, and plates are gently rinsed with diH2O. To determine PFU/ml homogenate, the number of plaques on each plate is multiplied by the dilution factor of the homogenate and divided by the amount of homogenate added per plate. The PFU/ml is divided by the weight of the tissue to calculate PFU/mg tissue.

Example 16

Assessment of the Effect of any One of C1ORF32 Protein Fragments and/or Fusion Proteins Thereof on Primary and Secondary Immune Response to Viral Infection in a Mouse Model of Influenza To test the effect of any one of C1ORF32 protein fragments and/or fusion proteins thereof on primary and secondary immune responses to viral infection, BALB/c naïve mice (for primary immune responses) and 'HA-memory mice', is used, as well as 'polyclonal flu-memory mice' (to assess secondary responses mediated by memory CD4 T cells), which are generated as detailed in Teijaro et al., J Immunol. 2009: 182; 5430-5438, and described below.

To obtain 'HA-memory mice', first HA-specific memory CD4 T cells are generated, naive CD4 T cells are purified from spleens of HA-TCR mice [BALB/c-HA mice which express transgenic T cell receptor (TCR) specific for influenza hemagglutinin (HA) peptide (110-119)] and primed in vitro by culture with 5.0 microg/ml HA peptide and mitomycin C-treated, T-depleted BALB/c splenocytes as APCs for 3 days at 37° C. The resultant activated HA-specific effector cells are transferred into congenic BALB/c (Thy1.1) hosts ($5\times10^6$ cells/mouse) to yield "HA-memory mice" with a stable population of HA-specific memory CD4 T cells.

To obtain 'polyclonal-memory mice', first polyclonal influenza-specific memory CD4 T cells are generated, by infecting BALB/c mice intranasally with a sublethal dose of PR8 influenza, CD4 T cells are isolated 2-4 months postinfection, and the frequency of influenza-specific memory CD4 T cells is determined by ELISPOT. CD4 T cells from previously primed mice are transferred into BALB/c hosts to generate "polyclonal flu-memory" mice with a full complement of endogenous T cells.

Primary and secondary responses to influenza virus are tested by infecting naïve BALB/c mice or BALB/c-HA memory mice and BALB/c 'polyclonal flu-memory mice' with sublethal or lethal doses of PR8 influenza virus by intranasal administration.

Mice are treated with any one of C1ORF32 protein fragments and/or fusion proteins thereof or with mIgG2a control before and following influenza challenge. Weight loss and mortality will be monitored daily. Six days after the challenge, viral content in the bronchoalveolar lavage (BAL) is analyzed by collecting lavage liquid and testing the supernatant for viral content by determining the tissue culture infectious dose 50% (TCID50) in MDCK cells. In addition, lung tissue histopathology is performed.

To test the effect of any one of C1ORF32 protein fragments and/or fusion proteins thereof on T cell expansion BALB/c or BALB/c-HA memory mice or BALB/c 'polyclonal flu-memory mice' are infected as above and administered with BrdU (1 mg/dose) on days 3, 4 and 5 post infection. On day 6, spleen and lung are harvested and BrdU incorporation is estimated. Cytokine production by lung memory CD4 T cells during influenza challenge is also studied in HA-specific memory CD4 T cells stimulated in vitro with HA peptide in the presence of any one of C1ORF32 protein fragments and/or fusion proteins thereof or IgG2a for 18 hours.

Example 17

Assessment of the Effect of any One of C1ORF32 Protein Fragments and/or Fusion Proteins Thereof on Primary and Secondary CD8 T Cell Response to Viral Infection in a Mouse Model of Influenza The effect of any one of C1ORF32 protein fragments and/or fusion proteins thereof on primary CD8 T cell responses to influenza virus is studied according to methods as described in the literature (Hendriks et al., J Immunol 2005; 175; 1665-1676; Bertram et al., J Immunol. 2004; 172:981-8) using C57BL/6 mice infected with influenza A HKx31 by intranasal or intraperitoneal administration. Any one of C1ORF32 protein fragments and/or fusion proteins thereof or mIgG2a control is administered during priming Animal weight loss and mortality is monitored daily. To follow virus-specific CD8+ T cells, MHC H-2Db tetramers loaded with the major CD8 T cell epitope, the $NP_{366-374}$ peptide are used. Virus-specific H-$2D^b$/NP366-374+CD8+ T cells in the lung, draining lymph nodes, and spleen are expected to reach a peak around day 8-10 post infection and decline thereafter to only 1.5% virus-specific CD8 T cells (Hendriks et al J Immunol 2005; 175; 1665-1676; Bertram et al., J Immunol. 2002; 168:3777-85; Bertram et a., J Immunol. 2004; 172:981-8). Thus, mice are sacrificed at days 8 and 21 post infection, and virus-specific CD8 T cell numbers is evaluated in the lung, draining lymph nodes and spleen. Viral clearance is assessed. CD8 T cell responses are evaluated in spleen cell suspensions, and include intracellular IFN-γ staining and CTL activity, as previously described (Bertram et a., J Immunol. 2004; 172:981-8) and detailed below.

Cells are surface-stained with FITC-conjugated anti-mouse CD62L, PE-conjugated anti-mouse CD8 to measure CD8+ activated T cells (or anti-mouse CD4 to follow CD4+ cells). In addition to these Abs, allophycocyanin-labeled tetramers consisting of murine class I MHC molecule H-$2D^b$, $\beta_2$-microglobulin, and influenza NP peptide, $NP_{366-374}$ are used to measure influenza-specific CD8 T cells. For intracellular IFN-γ staining, cell suspensions are restimulated in culture medium for 6 h at 37° C. with 1 μM NP366-374 peptide and GolgiStop (BD PharMingen, San Diego, Calif.). Cells are then harvested, resuspended in PBS/2% FCS/azide, and surface stained with PE-anti-CD8 and FITC-anti-CD62L as described above. After surface staining, cells will be fixed in Cytofix/Cytoperm solution (BD PharMingen) and then stained with allophycocyanin-conjugated antimouse IFN-γ diluted in 1× perm/wash solution (BD PharMingen). Samples are analyzed by Flow Cytometry.

For cytotoxicity assays (CTL responses) splenocytes from influenza-infected mice are incubated for 2 h at 37° C. to remove adherent cells. Serial 3-fold dilutions of effectors are assayed for anti-influenza $NP_{366-374}$-specific CTL activity against $^{51}$Cr-labeled EL4 cells pulsed with 50 μM $NP_{366-374}$ peptide for 6 h as described by Bertram et al 2002 and Bertram et al 2004.

At 3 weeks postinfection, some mice are rechallenged with the serologically distinct influenza A/PR8/34 (PR8), which shares the NP gene with influenza A HKx31, but differs in hemagglutinin and neuraminidase, so that neutralizing Abs do not limit the secondary CTL response. Mice are sacrificed at days 5 & 7 following virus rechallenge, and virus-specific CD8 T cell numbers is evaluated in the lung, draining lymph nodes and spleen as described by Hendriks et al and Bertram et al (Hendriks et al., J Immunol 2005;

175; 1665-1676; Bertram et al., J Immunol. 2004; 172:981-8) and detailed above. Secondary CD8 T cell responses, including intracellular IFN-γ staining and CTL activity, are evaluated in spleen cell suspensions of mice at days 5 & 7 following virus rechallenge, as described above.

To determine the effect of any one of C1ORF32 protein fragments and/or fusion proteins thereof on expansion and accumulation of memory CD8+ T cells during the secondary response, adoptive transfer experiments are performed, according to methods previously described (Hendriks et al., J Immunol 2005; 175; 1665-1676; Bertram et al., J Immunol. 2004; 172:981-8): mice are immunized with influenza influenza A HKx31. Twenty-one days later, T cells are purified from spleens on mouse T cell enrichment immunocolumns (Cedarlane Laboratories, Hornsby, Ontario, Canada) and labeled with CFSE (alternatively Thy1.1 congenic mice are used as recipients). Equal numbers of tetramer-positive T cells are injected through the tail vein of recipient mice. Mice are rechallenged with influenza virus as described above, and 7 days later splenocytes are evaluated for donor virus-specific CD8 T cells, as detailed above.

Example 18

Assessment of Protein Expression in Exhausted T Cells, and the Binding and Effect of any One of C1ORF32 Protein Fragments and/or Fusion Proteins Thereof on Reversing Exhausted T Cell Phenotype Memory CD8 T-cell differentiation proceeds along distinct pathways after an acute versus a chronic viral infection (Klenerman and HillNat Immunol 6, 873-879, 2005). Memory CD8 T cells generated after an acute viral infection are highly functional and constitute an important component of protective immunity. In contrast, chronic infections are often characterized by varying degrees of functional impairment of virus-specific T-cell responses, and this defect is a principal reason for the inability of the host to eliminate the persisting pathogen. Although functional effector T cells are initially generated during the early stages of infection, they gradually lose function during the course of the chronic infection leading to exhausted phenotype characterized by impaired T cell functionality.

Study I. The Effect of any One of C1ORF32 Protein Fragments and/or Fusion Proteins Thereof on Clearance of Viral Infection and on T Cell Functions During Acute and Chronic Viral Infection.

The effect of any one of C1ORF32 protein fragments and/or fusion proteins thereof on acute and chronic viral infection is evaluated in a mouse model of infection with LCMV (lymphocytic chroriomeningitis virus) according to methodology described by Wherry et al J. Virol. 77: 4911-4927, 2003 and Barber et al Nature, 2006, and detailed below.

Two LCMV strains that can cause either acute or chronic infections in adult mice are used; the Armstrong strain which is cleared within a week, and the clone 13 strain which establishes a persistent infection that can last for months. As these two strains differ in only two amino acids, preserving all known T cell epitopes, it is possible to track the same CD8 T cell responses after an acute or chronic viral infection. In contrast to the highly robust memory CD8 T cells generated after an acute Armstrong infection, LCMV-specific CD8 T cells become exhausted during a persistent clone 13 infection (Wherry et al J. Virol. 77: 4911-4927, 2003; Barber et al., Nature. 2006; 439:682-7).

Mice are infected with $2\times10^5$ PFU of Armstrong strain of LCMV intraperitoneally to initiate acute infection or $2\times10^6$ PFU of C1-13 intravenously to initiate chronic infection. Mice are treated i.p. with any one of C1ORF32 protein fragments and/or fusion proteins thereof or with mIgG2a control, and with specific anti-C1ORF32 protein-antibody, or an isotype control.

The mice are monitored for numbers of virus specific CD8 T cells in the spleen, using virus-specific MHC tetramer epitopes, such as $D^bNP_{396-404}$ and $D^bGP_{33-41}$ which differ in acute or chronic infections. CD8 T cell functional assays, such as intracellular cytokines levels and CTL activity, are carried out as described by Wherry et al J. Virol. 77: 4911-4927, 2003, and similarly to those described in Example 40. Additional assays include production by splenocytes after stimulation with virus specific epitopes; and assessment of viral titers in the serum and in the spleen, liver, lung and kidney (Wherry et al J. Virol. 77: 4911-4927, 2003; Barber et al., Nature. 2006; 439:682-7).

Study II. Assessment of C1ORF32 Protein Expression on Exhausted T Cells and Binding of any One of C1ORF32 Protein Fragments and/or Fusion Proteins Thereof to Exhausted T Cells in Order to Evaluate Regulation of these Proteins or their Counterpart Receptors During Exhaustion of T Cells:

T cells are isolated from mice with chronic LCMV infection induced with C1-13 strain. The cells are co-stained with fluorescently labeled anti-PD-1 Ab as positive control (PD-1 is highly expressed by exhausted T cells) and biotinylated C1ORF32 protein fragments and/or fusion proteins thereof or biotinylated anti-C1ORF32 protein antibodies, and respective isotype control. Binding is detected by FACS analysis using fluorescently labeled streptavidin.

Example 19

Assessment of any One of C1ORF32 Protein Fragments Expression in Follicular Helper T (Tfh) Cells and the Binding of Ig Fusion Proteins to Tfh Cells Follicular helper T (Tfh) cells are a subset of CD4+ T cells specialized in B cell help (reviewed by Crotty, Annu. Rev. Immunol. 29: 621-663, 2011). Tfh cells migrate into B cell follicles within lymph nodes, and interact with cognate B cells at the T cell-B cell border and subsequently induce germinal center B cell differentiation and germinal center formation within the follicle (Reviewed by Crotty, Annu. Rev. Immunol. 29: 621-663, 2011). The requirement of Tfh cells for B cell help and T cell-dependent antibody responses, indicates that this cell type is of great importance for protective immunity against various types of infectious agents, as well as for rational vaccine design.

Tfh cells are readily identifiable at the peak of the CD4+ T cell response to an acute lymphocytic choriomeningitis virus (LCMV) infection as $CXCR5^{hi}SLAM^{lo}BTLA^{hi}PD1^{hi}Bcl6^+$ virus-specific CD4+ T cells (Choi et al 2011, Immunity 34: 932-946). T cells are isolated from mice with acute LCMV infection induced with $2\times10^5$ PFU of Armstrong strain of LCMV administered intraperitoneally. The cells are co-stained with fluorescently labeled antibodies for markers of Tfh (CXCR5, PD1, BTLA, Bcl6) which are highly expressed by Tfh cells, and biotinylated C1ORF32 protein fragments and/or fusion proteins thereof or biotinylated antibodies specific for C1ORF32 proteins, and respective isotype controls. Binding of Fc fused protein or antibody is detected by FACS analysis using fluorescently labeled streptavidin. An appropriate response is seen.

Example 20

Assessment of the Effect of any One of C1ORF32 Protein Fragments and/or Fusion Proteins Thereof on Follicular Helper T (Tfh) Cells Generation and Activity In order to investigate the effect of any one of C1ORF32 protein fragments and/or fusion proteins thereof on Tfh differentiation and development of B cell immunity in vivo, C57BL/6 are treated with any one of C1ORF32 protein fragments and/or fusion proteins thereof and an isotype control throughout the course of an acute viral infection with Armstrong strain of LCMV (lymphocytic choriomeningitis virus). Tfh differentiation and Bcl6 protein expression is assessed by FACS analysis as described by Eto et al 2011 (PLoS One 6: e17739). Splenocytes are analyzed 8 days following LCMV infection, Tfh generation) (CD44$^{hi}$CXCR5$^{hi}$SLAM$^{lo}$) and Bcl6 expression is evaluated by FACS analysis. In addition, the effect of any one of C1ORF32 protein fragments and/or fusion proteins thereof on antigen-specific B cell responses is evaluated as described by Eto et al 2011 (PLoS One 6: e17739), including titers of anti-LCMV IgG in the serum at 8 days following LCMV infection, and quantitation by FACS analysis of plasma cell (CD138$^+$IgD$^-$) development at 8 days post-infection, gated on CD19+ splenocytes.

Example 21

The Effect of any One of C1ORF32 Protein Fragments and/or Fusion Proteins Thereof in Modulation of Type 1 Diabetes in Nod Mice, CD28-KO NOD, and B7-2-KO NOD The effect of any one of C1ORF32 protein fragments and/or fusion proteins thereof is studied in a widely used mouse model of type 1 diabetes: nonobese diabetic (NOD) mice which develop spontaneous In NOD mice, spontaneous insulitis, the hallmark pathologic lesion, evolves through several characteristic stages that begin with peri-insulitis and end with with invading and destructive insulitis and overt diabetes. Peri-insulitis is first observed at 3-4 wk of age, invading insulitis at 8-10 wk, and destructive insulitis appears just before the onset of clinical diabetes, with the earliest cases at 10-12 wk. At 20 wk of age, 70-80% of female NOD mice become diabetic (Ansari et al 2003 J. Exp. Med. 198: 63-69).

Two KO mice: CD-28-KO NOD mice and B7-1/B7-2 double KO NOD mice, —which develop accelerated diabetes (Lenschow et al 1996 Immunity 5: 285-293; Salomon et al 2000 Immunity 12: 431-440), are also used.

Study I: NOD mice are treated with any one of C1ORF32 protein fragments and/or fusion proteins thereof early and late phases during the evolution of diabetes, before or after disease onset, to examine the effects of these compounds on disease pathogenesis and to demonstrate that such treatment reduces disease onset and ameliorates pathogenesis. To study the effect on insulitis, blood glucose levels are measured 3 times/week, for up to 25 weeks (Ansari et al 2003 J. Exp. Med. 198: 63-69).

Mechanism of disease modification and mode of action is studied by experimental evaluation of individual immune cell types: pancreas, pancreatic LNs and spleen will be harvested to obtain Tregs, Th subtypes and CD8 T cells, DCs and B cells. Effect on cytokines secretion from cells isolated from pancreas, pancreatic LN and spleen is analysed, focused on IFNg, IL-17, IL-4, IL-10 and TGFb. Upon effect of the tested compounds, the mechanism of disease modification is studied by examination of individual immune cell types (including Tregs, Th subtypes and CD8 T cells, DCs and B cells); cytokines (IFNg, IL-17, IL-4, IL-10 and TGFb) and histology. Histologycal analysis of the pancreas is carried out to compare the onset of insulitis, and the lymphocyte infiltration.

Study II—The effect of any one of C1ORF32 protein fragments and/or fusion proteins thereof in modulation of Type 1 Diabetes in Adoptive transfer model To further investigate the mode of action of the Ig fusion proteins, an adoptive transfer model of diabetes is used. T cells from diabetic or prediabetic NOD donors are transfered to NOD SCID recipient mice. These mice are monitored for development of diabetes. The urine glucose and blood glucose, and assess histology of the pancreas, and T cell responses are monitored as described in the previous example.

Study III—Diabetes is also induced by the transfer of activated CD4+CD62L+CD25− BDC2.5 T cells (transgenic for TCR recognizing islet specific peptide 1040-p31 activated by incubation with 1040-p31) to NOD recipients. Mice are treated with any one of C1ORF32 protein fragments and/or fusion proteins thereof, control mIgG2a or positive control. Treatments begin 1 day following transfer. Mice are followed for glucose levels 10-28 days post transfer (Bour-Jordan et al., J Clin Invest. 2004; 114(7):979-87).

Seven days post treatment pancreas, spleen, pancreatic LN and peripheral lymph node cells are extracted and examined for different immune cell populations. In addition, recall responses are measured by testing ex-vivo proliferation and cytokine secretion in response to p31 peptide.

C1ORF32 protein fragments and/or fusion proteins thereof prevent or reduce disease onset or the severity thereof in the above studies.

Example 22

The Effect of any One of C1ORF32 Protein Fragments and/or Fusion Proteins Thereof in Lupus Mouse Models Study I: The lupus-prone mouse model, (NZB×NZW)F1 (B/W) is used. Cyclophosphamide (CTX) is the primary drug used for diffuse proliferative glomerulonephritis in patients with renal lupus, Daikh and Wofsy reported that combination treatment with CTX and CTLA4-Ig was more effective than either agent alone in reducing renal disease and prolonging survival of NZB/NZW F1 lupus mice with advanced nephritis (Daikh and Wofsy, J Immunol, 166(5): 2913-6 (2001)). In the proof-of-concept study, treatments with any one of C1ORF32 protein fragments and/or fusion proteins thereof and CTX either alone or in combination are tested.

Blood samples are collected 3 days before the protein treatment and then every other week during and after treatments for plasma anti-dsDNA autoantibody analysis by ELISA. Glomerulonephritis is evaluated by histological analysis of kidneys. Proteinuria is measured by testing fresh urine samples using urinalysis dipsticks.

C1ORF32 protein fragments and/or fusion proteins thereof have a beneficial effect in at least ameliorating lupus nephtiris.

Study II: The NZM2410-derived B6.Sle1.Sle2.Sle3 mouse model of SLE is used. NZM2410 is a recombinant inbred strain produced from NZB and NZW that develops a highly penetrant lupus-like disease with an earlier onset of disease (Blenman et al 2006 Lab. Invest. 86: 1136-1148). The effect of any one of C1ORF32 protein fragments and/or fusion proteins thereof is studied in this model by assessment of proteinuria and autoantibodies as described above.

Study III: An induced lupus model is used. This model is based on chronic graft-vs-host (cGVH) disease induced by the transfer of Ia-incompatible spleen cells from one normal mouse strain (such as B6.C-H2(bm12)/KhEg (bm12)) to another (such as C57BL/6), which causes an autoimmune syndrome resembling systemic lupus erythematosus (SLE), including anti-double-stranded DNA (anti-dsDNA) autoantibodies and immune complex-type proliferative glomerulonephritis (Appleby et al Clin. Exp. Immunol. 1989 78: 449-453); Eisenberg and Choudhury 2004 Methods Mol. Med. 102:273-284).

Lupus is induced in this model following injection of spleen cells from bm12 mice into C57BL/6 recipients. The effect any one of C1ORF32 protein fragments and/or fusion proteins thereof is studied in this model by assessment of proteinuria and autoantibodies as described above. T cell and responses B cell responses will also be evaluated.

Study IV: The MRL/lpr lupus prone mouse model is used. The effect of any one of C1ORF32 protein fragments and/or fusion proteins thereof is studied in this model by assessment of proteinuria and autoantibodies as described above.

Example 23

The Effect of any of C1ORF32 Protein Fragments and/or Fusion Proteins Thereof in the Control of Intestinal Inflammation An adoptive transfer mouse model of colitis in mice is used, whereby Transfer of CD45RB$^{high}$-CD4+ naïve T cells from BALB/c mice to syngeneic SCID mice leads to the development of an IBD-like syndrome by 6-10 wks after T cell reconstitution, similar to human Crohn's disease.

SCID mice are reconstituted by i.p. injection of syngeneic CD45RB$^{high}$-CD4+ T cells either alone or cotransferred with syngeneic CD45RB$^{low}$-CD4+ or CD25+CD4+ cells ($4 \times 10^5$/mouse of each cell population) (Liu et al., J Immunol. 2001; 167(3): 1830-8). Colitic SCID mice, reconstituted with syngeneic CD45RB$^{high}$CD4+ T cells from spleen of normal mice, are treated i.p. with any one of C1ORF32 protein fragments and/or fusion proteins thereof or Ig isotype control, twice a week starting at the beginning of T cell transfer up to 8 wk. All mice are monitored weekly for weight, soft stool or diarrhea, and rectal prolapse. All mice are sacrificed 8 wk after T cell transfer or when they exhibit a loss of 20% of original body weight. Colonic tissues are collected for histologic and cytologic examinations. C1ORF32 protein fragments and/or fusion proteins thereof have a beneficial effect in at least ameliorating inflammatory bowel disease.

Example 24

The Effect of any One of C1ORF32 Protein Fragments and/or Fusion Proteins Thereof in Mouse Model of Psoriasis Study I: Establishment of Psoriasis SCID Xenograft Model.

Human psoriasis plaques are transplanted on to the SCID mice. Shave biopsies (2.5_2.5 cm) are taken from patients with generalized plaque psoriasis involving 5-10% of the total skin that did not receive any systemic treatment for psoriasis or phototherapy for 6 months and did not receive any topical preparations other than emollients for 6 weeks. The biopsies are obtained from active plaques located on the thigh or arm. Each piece of biopsy is divided into four equal parts of approximately 1 cm2 size. Each piece is transplanted to a separate mouse.

Under general anesthesia, a graft bed of approximately 1 cm2 is created on the shaved area of the back of a 7- to 8-week-old CB17 SCID mouse by removing a full-thickness skin sample, keeping the vessel plexus intact on the fascia covering the underlying back muscles. The partial thickness human skin obtained by shave biopsy is then orthotopically transferred onto the graft bed. Nexaband, a liquid veterinary bandage (Veterinary Products Laboratories, Phoenix, Ariz.) is used to attach the human skin to the mouse skin and an antibiotic ointment (bacitracin) is applied. Mice are treated intraperitoneally three times per week for 4 weeks with any one of C1ORF32 protein fragments and/or fusion proteins thereof, isotype control or CTLA4-Ig (positive control).

Punch biopsies (2 mm) are obtained on day 0 (before treatment) and day 28 (after treatment) of the study period. Biopsies are snap frozen and cryosections for histopathological and immunohistochemical studies. Therapeutic efficacy is determined by comparing pre- and post treatment data: (i) rete peg lengths to determine the effect on epidermal thickness and (ii) the level of lymphomononuclear cell infiltrates to determine the effect on inflammatory cellular infiltrates. (Raychaudhuri et al. 2008, J Invest Dermatol.; 128(8):1969-76; Boehncke et al., 1999 Arch Dermatol Res 291:104-6).

C1ORF32 protein fragments and/or fusion proteins thereof have a beneficial effect in at least ameliorating psoriasis.

Study II: The Effect of any One of C1ORF32 Protein Fragments and/or Fusion Proteins Thereof in Psoriasis and Colitis Model by Adoptive Transfer of CD45RBhi CD4+ T Cells in SCID Mice Immunocompromised mice are injected intraveneously (i.v.) with 0.3_10$^6$ CD4+CD45RBhi cells. On the day following the adoptive transfer of cells, mice are injected intraperitoneally (i.p.) with 10 microg of staphylococcal enterotoxin B (Davenport et al., Int Immunopharmacol. 2002 April; 2(5):653-72). Recipient mice are treated with any one of C1ORF32 protein fragments and/or fusion proteins thereof, isotype control or CTLA4-Ig (positive control). Mice are evaluated once a week for 8 weeks for weight loss and presence of skin lesions.

Example 25

The Effect of any One of C1ORF32 Protein Fragments and/or Fusion Proteins Thereof in Modulating Transplant Rejection Study I: THE EFFECT OF any one of C1ORF32 protein fragments and/or fusion proteins thereof IN A MODEL OF ALLOGENEIC ISLET TRANSPLANTATION IN DIABETIC MICE. To test the effect of any one of C1ORF32 protein fragments and/or fusion proteins thereof on transplant rejection, a model of allogeneic islet transplantation is used. Diabetes is induced in C57BL/6 mice by treatment with streptozotocin. Seven days later, the mice are transplanted under the kidney capsule with pancreatic islets which are isolated from BALB/c donor mice. Recipient mice are treated with any one of C1ORF32 protein fragments and/or fusion proteins thereof or with mIgG2a as a negative control. Tolerance with ECDI-fixed donor splenocytes is used as the positive control for successful modulation islet graft rejection. Recipient mice are monitored for blood glucose levels as a measure of graft acceptance/rejection (Luo et al., PNAS, Sep. 23, 2008_vol. 105_no. 38_14527-14532).

Study II: The Effect of any One of C1ORF32 Protein Fragments and/or Fusion Proteins Thereof In The HYA-Model of Skin Graft Rejection.

In humans and certain strains of laboratory mice, male tissue is recognized as non-self and destroyed by the female immune system via recognition of histocompatibility-Y chromosome encoded antigens (Hya). Male tissue destruction is thought to be accomplished by cytotoxic T lymphocytes in a helper-dependent manner To test the effect of any one of C1ORF32 protein fragments and/or fusion proteins thereof on transplantation, the Hya model system is used, in which female C57BL/6 mice receive tail skin grafts from male C57BL/6 donors.

In this study, female C57BL/6 mice are engrafted with orthotopic split-thickness tail skin from age matched male C57BL/6 mice. The mice are treated with any one of C1ORF32 protein fragments and/or fusion proteins thereof, isotype control mIgG2a Immunodominant Hya-encoded CD4 epitope (Dby) attached to female splenic leukocytes (Dby-SP) serve as positive control for successful modulation of graft rejection (Martin et al., J Immunol. 2010 Sep. 15; 185(6): 3326-3336). Skin grafts are scored daily for edema, pigment loss and hair loss. Rejection is defined as complete hair loss and more than 80% pigment loss. In addition, T cell recall responses of cells isolated from spleens and draining lymph nodes at different time points are studied in response to CD4 specific epitope (Dby), CD8 epitopes (Uty and Smcy) or irrelevant peptide (OVA 323-339) while anti CD3 stimulation is used as positive control for prolifereation and cytokine secretion.

Study III: The effect of any one of C1ORF32 protein fragments and/or fusion proteins thereof on graft rejection is studied in a murine model of syngeneic bone marrow cells transplantation using the Hya model system described above. Male hematopoietic cells expressing the CD45.1 marker are transplanted to female host mice which express the CD45.2 congenic marker. Female hosts are treated with any one of C1ORF32 protein fragments and/or fusion proteins thereof or with isotype control mIgG2a. The female hosts are followed over time and the presence of CD45.1+ cells is monitored.

Example 26

The Effect of C1ORF32 Protein Fragments and/or Fusion Proteins Thereof in Treatment of Alopecia Areata To induce alopecia areata (AA), lesional skin from C3H/HeJ mice that had developed spontaneous AA lesions is grafted onto the back of non-affected C3H/HeJ mice, as described previously (McElwee et al., 1998). Briefly, up to six grafts ~1-1.5 cm in diameter are aseptically removed from each donor by pinch cutting. The grafts are placed in sterile PBS while the recipient mice are prepared for transplantation. Recipient mice are anestized and a circular pice of skin ~1.5 cm in diameter is aseptically removed from the dorsal anto-posterior midline and replaced with a donor skin graft. The graft is oriented 180° from normal in order to have the hair growing in opposite direction to the recipient hair for easy identification. Four to seven weeks after grafting the recipients develop initial hair loss. Recipient mice are treated with any one of C1ORF32 protein fragments and/or fusion proteins thereof, isotype control or CTLA4-Ig (positive control). Morphological changes are examined and documented daily. Photographs are taken before treatment, and once per week during and after treatment. After completion of treatment, all mice are anesthetized, their dorsal skin is shaved and animals are sacrificed by cervical dislocation. Skin samples are taken for histopathological examination and immunohistochemistry.

It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination. It will also be appreciated by persons skilled in the art that the present invention is not limited by what has been particularly shown and described hereinabove.

What is claimed is:

1. An isolated polypeptide, consisting of an amino acid sequence set forth in any one of SEQ ID NOs: 29, 42-43, 64, 68, 69, 71-87, 89, and 91-105.

2. A fusion protein comprising the polypeptide according to claim 1, fused to a heterologous sequence, directly or indirectly via a linker peptide, a polypeptide sequence or a chemical linker.

3. The fusion protein of claim 2, wherein the heterologous sequence comprises at least a portion of an immunoglobulin constant domain.

4. The fusion protein of claim 3, comprising an immunoglobulin heavy chain constant domain corresponding to an antibody isotype selected from the group consisting of an IgG1, IgG2, IgG3, IgG4, IgM, IgE, IgA and IgD.

5. The fusion protein of claim 4, wherein the immunoglobulin constant domain comprises the hinge, CH2 and CH3 regions of a human IgG immunoglobulin, selected from the group consisting of Cγ1, Cγ2, Cγ3 and Cγ4 chain.

6. The fusion protein of claim 2, further comprising a domain that mediates dimerization or multimerization of the fusion protein to form homodimers, heterodimers, homomultimers, or heteromultimers.

7. The fusion protein of claim 6, wherein the domain that mediates dimerization or multimerization is selected from the group consisting of one or more cysteines that are capable of forming an intermolecular disulfide bond with a cysteine on the partner fusion protein, a coiled-coil domain, an acid patch, a zinc finger domain, a calcium hand domain, a CHI region, a CL region, a leucine zipper domain, an SH2 (src homology 2) domain, an SH3 (src Homology 3) domain, a PTB (phosphotyrosine binding) domain, a WW domain, a PDZ domain, a 14-3-3 domain, a WD40 domain, an EH domain, a Lim domain, an isoleucine zipper domain, and a dimerization domain of a receptor dimer pair.

8. The fusion protein of claim 7, comprising an Ig Fc domain set forth in any one of SEQ ID NOs: 20, 21, 31 or 115.

9. The fusion protein of claim 8, wherein said fusion protein consists of the amino acid sequence set forth in any one of SEQ ID NOs: 29, 42-43, 64, 68, 69, 71-87, 89, and 91-105, fused to human IgG1 Fc domain set forth in any one of SEQ ID NOs: 20, 21, and 115.

10. The fusion protein of claim 9, wherein the amino acid sequence of said fusion protein is set forth in any one of SEQ ID NO: 39, 108-112, and 116-190.

11. The fusion protein of claim 10, wherein the amino acid sequence of said fusion protein is set forth in any one of SEQ ID NOs:112, 120, 110, and 136.

12. A dimeric protein comprising a first and a second fusion protein, wherein the first and the second fusion proteins comprise the fusion protein of claim 2, wherein the first and the second fusion proteins are bound to one another by covalent or noncovalent bonds to form a dimer.

13. A pharmaceutical composition comprising the polypeptide of claim 1, or a fusion protein comprising same, and a pharmaceutically acceptable diluent or carrier, adapted for treatment of any one of an autoimmune disease, graft vs host disease or transplant rejection.

14. A method for treating an immune related disorder in a subject in need thereof, comprising administering to the subject an effective amount of the polypeptide of claim 1 or a fusion protein comprising same, or pharmaceutical composition comprising same, wherein the immune related disorder is selected from the group consisting of an autoimmune disease, graft vs host disease and a transplant rejection.

15. The method of claim 14, wherein administering an effective amount of the polypeptide, or the fusion protein, or the pharmaceutical composition comprising same to the subject inhibits or reduces differentiation of, proliferation of, activity of, and/or cytokine production and/or secretion by an immune cell selected from the group consisting of Th1, Th17, and/or Th22; and/or inhibits or reduces differentiation of, proliferation of, activity of, and/or cytokine production and/or secretion by Th1, Th17 and/or Th22 cells; and/or enhances the suppressive or immunomodulatory effect of Tregs and/or Th2 cells on Th1 or Th17 cells; and/or promotes or enhances IL-10 production; and/or increases cell numbers or increases populations of any of Tregs and/or Th2 cells; and/or inhibits the Th1 and/or Th17 pathways and enhances the activity of Tregs and/or Th2 cells on the Th1 and Th17 pathways and/or to promote or enhance IL-10 secretion.

16. The method of claim 14, wherein the polypeptide, or the fusion protein, or the pharmaceutical composition comprising same is administered in an effective amount for reducing proinflammatory molecule production in a subject.

17. The method according to claim 14 further comprising administering a second therapeutic agent effective for treatment of said immune related disorder.

18. The method according to claim 14, wherein graft transplantation rejection is selected from the group consisting of acute and chronic rejection of organ transplantation, allogeneic stem cell transplantation, autologous stem cell transplantation, bone marrow transplantation, and graft versus host disease.

19. The method according to claim 14, wherein the autoimmune disease is selected from the group consisting of multiple sclerosis, rheumatoid arthritis; psoriatic arthritis, discoid lupus erythematosus, systemic lupus erythematosus (SLE); ulcerative colitis; Crohn's disease; benign lymphocytic angiitis, autoimmune lymphoproliferative syndrome, sarcoidosis, autoimmune thrombocytopenic purpura, idiopathic thrombocytopenic purpura, pure red cell aplasia, Sjogren's syndrome, rheumatic disease, polymyalgia rheumatica, inflammatory rheumatism, degenerative rheumatism, extra-articular rheumatism, juvenile arthritis, juvenile rheumatoid arthritis, systemic juvenile idiopathic arthritis, muscular rheumatism, chronic polyarthritis, reactive arthritis, Reiter's syndrome, rheumatic fever, relapsing polychondritis, Raynaud's phenomenon, vasculitis, ANCA-associated vasculitis, temporal arteritis, giant cell arteritis, Takayasu arteritis, Behcet's disease, antiphospholipid syndrome, myasthenia gravis, autoimmune haemolytic anaemia, Guillain-Barre syndrome, chronic immune polyneuropathy, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pernicious anaemia, pemphigus, pemphigus vulgaris, cirrhosis, primary biliary cirrhosis, idiopathic pulmonary fibrosis, myositis, dermatomyositis, juvenile dermatomyositis, polymyositis, celiac disease, celiac sprue dermatitis, immunoglobulin A nephropathy, Henoch-Schonlein purpura, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, primary biliary cirrhosis, Hashimoto's thyroiditis, primary myxedema, sympathetic ophthalmia, autoimmune inner ear disease, autoimmune uveitis, autoimmune chronic active hepatitis, ankylosing spondylitis, panarteritis nodosa, polyarteritis nodosa, Wegener's granulomatosis, microscopic polyangiitis, bullous skin disorders, pemphigoid, bullous pemphigoid, cicatricial pemphigoid, vitiligo, atopic eczema, eczema, chronic urticaria, autoimmune urticaria, hypocomplementemic urticarial vasculitis, alopecia areata, alopecia universalis, alopecia totalis, Devic's disease, pernicious anemia, childhood autoimmune hemolytic anemia, idiopathic autoimmune hemolytic anemia, refractory or chronic Autoimmune Cytopenias, Prevention of development of Autoimmune Anti-Factor VIII Antibodies in Acquired Hemophilia A, Cold agglutinin disease, Neuromyelitis Optica, idiopathic pericarditis, anti-synthetase syndrome, PAPA Syndrome, adult and juvenile Still's disease, cryopyrin associated periodic syndrome, Muckle-Wells syndrome, Schnitzler's syndrome, autoimmune retinopathy, and age-related macular degeneration.

20. The method according to claim 19, wherein the treating comprises treatment of the autoimmune disease without global immunosuppression.

21. The method of claim 19, wherein the subject did not previously respond to treatment with TNF blockers.

* * * * *